US007855271B2

(12) United States Patent
Jiang et al.

(10) Patent No.: US 7,855,271 B2
(45) Date of Patent: *Dec. 21, 2010

(54) COMPOSITIONS AND METHODS FOR THE THERAPY AND DIAGNOSIS OF BREAST CANCER

(75) Inventors: Yuqiu Jiang, San Diego, CA (US); Davin C Dillon, Menlo Park, CA (US); Jennifer L Mitcham, Redmond, WA (US); Jiangchun Xu, San Diego, CA (US); Susan L Harlocker, Foster City, CA (US)

(73) Assignee: Corixa Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/930,080

(22) Filed: Oct. 30, 2007

(65) Prior Publication Data

US 2008/0206250 A1 Aug. 28, 2008

Related U.S. Application Data

(63) Continuation of application No. 11/226,869, filed on Sep. 13, 2005, now abandoned, which is a continuation of application No. 10/124,805, filed on Apr. 15, 2002, now Pat. No. 6,969,518, which is a continuation-in-part of application No. 10/076,622, filed on Feb. 13, 2002, now Pat. No. 6,958,361, which is a continuation-in-part of application No. 10/007,805, filed on Dec. 7, 2001, now Pat. No. 7,598,226, which is a continuation-in-part of application No. 09/834,759, filed on Apr. 13, 2001, now Pat. No. 6,680,197, which is a continuation-in-part of application No. 09/620,405, filed on Jul. 20, 2000, now Pat. No. 6,528,054, which is a continuation-in-part of application No. 09/604,287, filed on Jun. 22, 2000, now Pat. No. 6,586,572, which is a continuation-in-part of application No. 09/590,751, filed on Jun. 8, 2000, now Pat. No. 6,756,477, which is a continuation-in-part of application No. 09/551,621, filed on Apr. 17, 2000, now Pat. No. 6,844,325.

(51) Int. Cl.
*C07K 14/00* (2006.01)

(52) U.S. Cl. .................................... 530/350; 424/184.1

(58) Field of Classification Search ................. 530/350; 424/184.1
See application file for complete search history.

(56) References Cited

U.S. PATENT DOCUMENTS

| | | | | |
|---|---|---|---|---|
| 4,962,187 | A | 10/1990 | Pant | 530/350 |
| 5,215,926 | A | 6/1993 | Etchells, III et al. | 436/501 |
| 5,240,856 | A | 8/1993 | Goffe et al. | 435/299 |
| 5,478,556 | A | 12/1995 | Elliott et al. | 424/852 |
| 5,668,267 | A | 9/1997 | Watson et al. | 536/23.5 |
| 5,843,435 | A | 12/1998 | Slavin | 424/93.71 |
| 5,855,889 | A | 1/1999 | Watson et al. | 424/185.1 |
| 5,861,381 | A | 1/1999 | Chambon et al. | 514/44 |
| 5,891,857 | A | 4/1999 | Holt et al. | 514/44 |
| 5,922,836 | A | 7/1999 | Watson et al. | 530/300 |
| 5,968,754 | A | 10/1999 | Watson et al. | 435/7.23 |
| 5,981,731 | A | 11/1999 | Monia | 536/24.5 |
| 5,986,170 | A | 11/1999 | Subjeck | 800/2 |
| 6,004,756 | A | 12/1999 | Watson et al. | 435/6 |
| 6,150,168 | A | 11/2000 | Woo et al. | 435/440 |
| 6,153,386 | A | 11/2000 | Lalouel et al. | 435/6 |
| 6,387,697 | B1 | 5/2002 | Yuqiu et al. | 435/325 |
| 6,518,237 | B1 | 2/2003 | Yuqiu et al. | 514/2 |
| 6,528,054 | B1 | 3/2003 | Jiang et al. | 424/130.1 |
| 6,573,368 | B2 | 6/2003 | Yuqiu et al. | 536/23.1 |
| 6,579,973 | B1 * | 6/2003 | Yuqiu et al. | 424/185.1 |
| 6,586,572 | B2 * | 7/2003 | Jiang et al. | 530/350 |
| 6,590,076 | B1 * | 7/2003 | Yuqiu et al. | 530/350 |
| 6,680,197 | B2 | 1/2004 | Jiang et al. | 435/325 |
| 6,756,477 | B1 | 6/2004 | Jiang et al. | 530/350 |
| 6,844,325 | B2 | 1/2005 | Jiang et al. | 514/44 |
| 6,958,361 | B2 | 10/2005 | Houghton et al. | 514/885 |
| 6,969,518 | B2 | 11/2005 | Houghton et al. | 424/138.1 |
| 2002/0009738 | A1 | 1/2002 | Houghton et al. | 435/6 |
| 2002/0150581 | A1 | 10/2002 | Jiang et al. | 424/155.1 |

(Continued)

FOREIGN PATENT DOCUMENTS

CA 2226901 A1 7/1998

(Continued)

OTHER PUBLICATIONS

MPSRCH search result, 2009, us-11.930.080.475.rup. Result 4, pp. 1-2.*

(Continued)

*Primary Examiner*—Larry R. Helms
*Assistant Examiner*—Minh-Tam Davis
(74) *Attorney, Agent, or Firm*—Seed IP Law Group PLLC

(57) ABSTRACT

Compositions and methods for the therapy and diagnosis of cancer, particularly breast cancer, are disclosed. Illustrative compositions comprise one or more breast tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly breast cancer.

6 Claims, 2 Drawing Sheets

U.S. PATENT DOCUMENTS

2003/0170631 A1 9/2003 Houghton et al. .............. 435/6

FOREIGN PATENT DOCUMENTS

| | | |
|---|---|---|
| CA | 2226910 A1 | 10/1998 |
| CA | 2284642 A1 | 10/1998 |
| WO | WO 89/06280 | 7/1989 |
| WO | WO 91/16116 | 10/1991 |
| WO | WO 91/16629 | 10/1991 |
| WO | WO 92/07243 | 4/1992 |
| WO | WO 96/29430 | 9/1996 |
| WO | WO 97/02280 | 1/1997 |
| WO | WO 97/22349 | 6/1997 |
| WO | WO 97/25426 | 7/1997 |
| WO | WO 97/25431 | 7/1997 |
| WO | WO 98/04742 | 2/1998 |
| WO | WO 98/21331 | 5/1998 |
| WO | WO 98/24928 | 6/1998 |
| WO | WO 98/33915 | 8/1998 |
| WO | WO 98/45328 | 10/1998 |
| WO | WO 98/54963 | 12/1998 |
| WO | WO 99/09155 | 2/1999 |
| WO | WO 99/14230 | 3/1999 |
| WO | WO 00/08210 | 2/2000 |
| WO | WO 00/37643 | 6/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |
| WO | WO 01/51628 | 7/2001 |
| WO | WO 01/57270 | 8/2001 |
| WO | WO 01/75171 | 10/2001 |
| WO | WO 01/79286 | 10/2001 |
| WO | WO 02/059377 | 8/2002 |
| WO | WO 02/083956 | 10/2002 |

OTHER PUBLICATIONS

MPSRCH search result, 2009, us-11.930.080.475.oligo.rai. Result 40, p. 1.*

MPSRCH search result, 2009, us-11.930.080.474.n2poligo.rai. Result 40, pp. 1-2.*

Bowie (Science, 1990, 257:1306-1310).*

Burgess et al ( J of Cell Bio. 111:2129-2138, 1990).*

Lazar et al (Molecular and Cellular Biology, 1988, 8:1247-1252).*

Kirkin et al, APMIS, 1998, 106: 665-679.*

Holmes (Exp. Opin.Invest. Drugs, 2001, 10(3):511-519).*

Roitt et al, 1998, (Immunology, 4th ed, Mosby, London, p. 7.7-7.8).*

Roger, I et al, 1988, Bioscience Reports, 8(4): 359-368.*

Banki et al, 1994, JBC, 269 (4): 2847-51.*

Bost et al, 1988, Immunol Investigation, 17 (6&7): 577-586).*

Alberts et al. Mol. Biol. Cell, 3rd ed., p. 455, 1994.

Anderson and Seilhamer, "A comparison of selected MRNA and protein abundances in human liver", *Electrophoresis* 18: 533-537, 1997.

Anderson, W.F., "Human gene therapy," *Nature* 392(Suppl):25-30, Apr. 30, 1998.

Bodey, B. et al., "Failure of Cancer Vaccines: The Significant Limitation of the Approach to Immunotherapy," *Anticancer Research* 20:2665-2676, 2000.

Boon, T., "Toward a Genetic Analysis of Tumor Rejection Antigens", *Adv. Cancer Res.* 58: 177-210, 1992.

Bork, P., "Powers and Pitfalls in Sequence Analysis: The 70% Hurdle", *Genome Research* 10(4): 398-400, Apr. 2000.

Burmer, G.C. et al., "Frequency and Spectrum of c-Ki-*ras* Mutations in Human Sporadic Colon Carcinoma, Carcinomas Arising in Ulcerative Colitis, and Pancreatic Adenocarcinoma," *Environmental Health Perspectives* 93:27-31, 1991.

Buskens, C. et al., "Adenocarcinomas of the Gastro-Esophageal Junction: A Comparative Study of the Gastric Cardia and the Esophagus with Respect to Cyclooxygenase-2 Expression," *Digestive Disease Week Abstracts and Itinerary Planner*, Abstract No. 850, 2003.

Cameron, E.R., "Recent Advances in Transgenic Technology," *Molecular Biotechnology* 7: 253-265, 1997.

Chang and Shu, "Current status of adoptive immunotherapy of cancer," *Critical Reviews in Oncology/Hematology* 22(3):213-228, Apr. 1996.

Cheever and Chen, "Therapy with cultured T cells: principles revisited," *Immunological Reviews*, 157: 177-194, 1997.

Cheever et al., "Potential uses of interleukin 2 in cancer therapy," *Immunobiol.* 172:365-382, 1986.

Cheli et al., *Clin Chem.* 44(4): 765-72, 1998.

Chen et al., "T-cells for tumor therapy can be obtained from antigen-loaded sponge implants," *Cancer Research* 54(4):1065-1070, Feb. 15, 1994.

Cole et al., "Characterization of the functional specificity of a cloned T-cell receptor heterodimer recognizing the MART-1 melanoma antigen," *Cancer Research*, 55:748-752, Feb. 15, 1995.

Conner et al., "Trk receptor alterations in Alzheimer's disease," *Mol Brain Res.* 42: 1-17, 1996.

Curti, B.D., "Physical barriers to drug delivery in tumors", *Critical Reviews in Oncology/Hematology* 14: 29-39, 1993.

Dermer., *Bio/Technol.* 12: 320, 1994.

Doerks, T. et al., "Protein annotation: detective work for function prediction", *Trends in Genetics* 14(6): 248-250, Jun. 1998.

Durrant L., "Cancer vaccines," *Anti-Cancer Drugs* 8:727-733, 1997.

Eshhar Z., "Tumor-specific T-bodies: toward clinical application," *Cancer Immunol Immnother* 45:131-136, 1997.

Ezzell, C., "Cancer 'Vaccines': An Idea Whose Time Has Come?" *The Journal of NIH Research* 7: 46-49, Jan. 1995.

Freshney, Cult. Animal Cells, A Manual of Basic Technique, Alan R. Lisc. Inc. p. 4, 1983.

Fu et al., "Translational regulation of human p53 gene expression," *EMBO J.* 15: 4392-4401, 1996.

Gardner, R.L. et al., "Reflections on the biology of embryonic stem (ES) cells," *Int. J. Dev. Biol.* 41: 235-243, 1997.

Gaubin et al., J Immunol. 1999, 162(5): 2631-8.

GenBank Accession No. AA398925, Apr. 25, 1997.

GenBank Accession No. AA864891, Feb. 20, 1998.

GenBank Accession No. AI9511189. (First appeared in GenBank-NCBI on Aug. 19, 1999).

GenBank Accession No. B15703. (First appeared in GenBank-NCBI on Jun. 4, 1998).

GenBank Accession No. B17512. (First appeared in GenBank-NCBI on Jun. 4, 1998).

GenBank Accession No. X88318. (First appeared in GenBank-NCBI on Jul. 19, 1996).

GenBank Accession No. XP_035844. (First appeared in GenBank-NCBI on Jul. 16, 2001).

GenBank Accession No. AAK27325, Mar. 28, 2001.

GenBank Accession No. AC036170, Apr. 9, 2000.

GenBank Accession No. AC069200, May 24, 2000.

GenBank Accession No. AF269087, Mar. 28, 2001.

GenBank Accession No. AI687645, May 27, 1999.

GenBank Accession No. AL157387, Feb. 18, 2000.

GenBank Accession No. AL359312, Dec. 7, 2001.

GenBank Accession No. AQ280806, Nov. 22, 1998.

GenBank Database, Accession No. AA219147, Feb. 7, 1997.

GenBank Database, Accession No. AI272025, Nov. 17, 1998.

GenBank Database, Accession No. AL049911, Oct. 22, 1999.

Geneseq (Derwent) Database Accession No. V84525 (Dec. 10, 1998).

Geneseq (Derwent) Database, Accession No. AAV41453, Oct. 12, 1998.

Geneseq (Derwent) Database, Accession No. V90219, 1998.

Geneseq Database (Derwent), Accession No. AAA59007, Nov. 7, 2000.

Geneseq Database (Derwent), Accession No. AAA59008, Nov. 7, 2000.

Geneseq Database (Derwent), Accession No. AAA59009, Nov. 7, 2000.

Geneseq Database (Derwent), Accession No. AAA59010, Nov. 7, 2000.
Geneseq Database (Derwent), Accession No. AAA59011, Nov. 7, 2000.
Geneseq Database (Derwent), Accession No. AAA59012, Nov. 7, 2000.
Geneseq Database (Derwent), Accession No. AAA59013, Nov. 7, 2000.
Geneseq Database (Derwent), Accession No. AAA59014, Nov. 7, 2000.
Geneseq Database (Derwent), Accession No. AAA59015, Nov. 7, 2000.
Geneseq Database (Derwent), Accession No. AAB07638, Nov. 7, 2000.
Geneseq Database (Derwent), Accession No. AAB07639, Nov. 7, 2000.
Geneseq Database (Derwent), Accession No. AAB07640, Nov. 7, 2000.
Geneseq Database (Derwent), Accession No. AAB07641, Nov. 7, 2000.
Geneseq Database (Derwent), Accession No. AAB07642, Nov. 7, 2000.
Geneseq Database (Derwent), Accession No. AAB63900, Mar. 26, 2001.
Geneseq Database (Derwent), Accession No. AAB63901, Mar. 26, 2001.
Geneseq Database (Derwent), Accession No. AAB63903, Mar. 26, 2001.
Geneseq Database (Derwent), Accession No. AAB63905, Mar. 26, 2001.
Geneseq Database (Derwent), Accession No. AAB63906, Mar. 26, 2001.
Geneseq Database (Derwent), Accession No. AAB63907, Mar. 26, 2001.
Geneseq Database (Derwent), Accession No. AAB63909, Mar. 26, 2001.
Geneseq Database (Derwent), Accession No. AAB63911, Mar. 26, 2001.
Geneseq Database (Derwent), Accession No. AAB63913, Mar. 26, 2001.
Geneseq Database (Derwent), Accession No. AAB63915, Mar. 26, 2001.
Geneseq Database (Derwent), Accession No. AAB63916, Mar. 26, 2001.
Geneseq Database (Derwent), Accession No. AAB63917, Mar. 26, 2001.
Geneseq Database (Derwent), Accession No. AAB63918, Mar. 26, 2001.
Geneseq Database (Derwent), Accession No. AAB63919, Mar. 26, 2001.
Geneseq Database (Derwent), Accession No. AAB63922, Mar. 26, 2001.
Geneseq Database (Derwent), Accession No. AAB63925, Mar. 26, 2001.
Geneseq Database (Derwent), Accession No. AAB63926, Mar. 26, 2001.
Geneseq Database (Derwent), Accession No. AAB63929, Mar. 26, 2001.
Geneseq Database (Derwent), Accession No. AAB63931, Mar. 26, 2001.
Geneseq Database (Derwent), Accession No. AAB63933, Mar. 26, 2001.
Geneseq Database (Derwent), Accession No. AAB63935, Mar. 26, 2001.
Geneseq Database (Derwent), Accession No. AAB63938, Mar. 26, 2001.
Geneseq Database (Derwent), Accession No. AAB63939, Mar. 26, 2001.
Geneseq Database (Derwent), Accession No. AAB63942, Mar. 26, 2001.
Geneseq Database (Derwent), Accession No. AAB63943, Mar. 26, 2001.
Geneseq Database (Derwent), Accession No. AAB63945, Mar. 26, 2001.
Geneseq Database (Derwent), Accession No. AAB63965, Mar. 26, 2001.
Geneseq Database (Derwent), Accession No. AAB84701, Sep. 17, 2001.
Geneseq Database (Derwent), Accession No. AAB84702, Sep. 17, 2001.
Geneseq Database (Derwent), Accession No. AAD06847, Aug. 6, 2001.
Geneseq Database (Derwent), Accession No. AAF22978, Mar. 26, 2001.
Geneseq Database (Derwent), Accession No. AAF22993, Mar. 26, 2001.
Geneseq Database (Derwent), Accession No. AAH28489, Sep. 17, 2001.
Geneseq Database (Derwent), Accession No. AAI03961, Oct. 9, 2001.
Geneseq Database (Derwent), Accession No. AAL25059, Dec. 7, 2001.
Geneseq Database (Derwent), Accession No. AAM05199, Oct. 9, 2001.
Geneseq Database (Derwent), Accession No. AAZ91768, Jun. 1, 2000.
Geneseq Database (Derwent), Accession No. ABJ05537, Nov. 14, 2002.
Geneseq Database (Derwent), Accession No. ABT07694, Nov. 14, 2002.
Gillies and Wesolowski, "Antigen binding and biological activities of engineered mutant chimeric antibodies with human tumor specificities", *Hum Antibod. Hybridomas* 1(1): 47-54, 1990.
Goto, Y. et al., "A Novel Human Insulinoma-associated cDNA, IA-1, Encodes a Protein with 'Zinc-finger' DNA-binding Motifs," *The Journal of Biological Chemistry* 267(21):15252-15257, Jul. 25, 1992.
Greenbaum et al, Genome Biology 4(9): 117.1-117.8), 2003.
Gura, T., "Systems for identifying New Drugs Are Often Faulty," *Science* 278:1041-1042, Nov. 7, 1997.
Hammer, R.E. et al., "Spontaneous Inflammatory Disease in Transgenic Rats Expressing HLA-B27 and Human $\beta_2$m: An Animal Model of HLA-B27-Associated Human Disorders," *Cell* 63: 1099-1112, 1990.
Hartwell, L.H. et al., "Integrating Genetic Approaches into the Discovery of Anticancer Drugs," *Science* 278:1064-1068, Nov. 7, 1997.
Hell et al, "Hodgkin Cells Accumulate mRNA for *bcl-2," Laboratory Investigation* 73:492-496, 1995.
Hwu et al., "In vivo antitumor activity of T cells redirected with chimeric antibody/T-cell receptor genes," *Cancer Research*, 55:3369-3373, Aug. 1, 1995.
Jäger et al., "Identification of a tissue-specific putative transcription factor in breast tissue by serological screening of a breast cancer library," *Cancer Research* 61(5):2055-2061, Mar. 1, 2001.
Jain, R.K., "Barriers to Drug Delivery in Solid Tumors", *Scientific American* 271(1): 58-65, Jul. 1994.
Jiang, Y. et al., "Discovery of differentially expressed genes in human breast cancer using subtracted cDNA libraries and cDNA microarrays," *Oncogene* 21:2270-2282, 2002.
Kaiser, J., "First Pass at Cancer Genome Reveals Complex Landscape," *Science* 313:1370, Sep. 8, 2006.
Kang, D.-C. et al., "Reciprocal subtraction differential RNA display: An efficient and rapid procedure for isolating differentially expressed gene sequences," *Proc. Natl. Acad. Sci. USA* 95:13788-13793, Nov. 1998.
Kawakami et al., *Cancer Science* 95(10): 784-791, Oct. 2004.
Kirkin, A.F. et al., "Melanoma-associated antigens recognized by cytotoxic T lymphocytes," *APMIS* 106:665-679, 1998.
Lee, K.-H. et al., "Increased Vaccine-Specific T Cell Frequency After Peptide-Based Vaccination Correlates with Increased Susceptibility to in Vitro Stimulation But Does Not Lead to Tumor Regression," *Journal of Immunology* 163:6292-6300, 1999.
Lewin, B, ed., 1983, Genes, John Wiley & Sons, New York, pp. 72-74.

Lucas, S. et al., "Identification of a New *MAGE* Gene with Tumor-specific Expression by Representational Difference Analysis," *Cancer Research* 58:743-752, Feb. 15, 1998.
McClean et al., *Eur. J. Cancer* 29A(16): 2243-2248, 1993.
Montesano, R., "Genetic Alteration in Esophageal Cancer and Their Relevance to Etiology and Pathogenesis: A Review," *International Journal of Cancer* 69(3):225-235, 1996.
Moutsopoulos et al., *Molecular Medicine* 6(3): 141-151, 2000.
MPSRCH search report, 2006, pp. 1-3.
Mullins, J.J. et al., "Transgenesis in Nonmurine Species," *Hypertension* 22: 630-633, 1993.
Nyberg, K. et al., "Workshop on long-term follow-up of participants in human gene transfer research," *Mol. Ther.* 10(6): 976-980, Dec. 2004.
Porter-Jordan and Lippman, "Overview of the biologic markers of breast cancer," *Breast Cancer* 8:(1):73-100, Feb. 1994.
Prilliman et al., "HLA-B15 peptide ligands are preferentially anchored at their c termini," *The Journal of Immunology* 62(12):7277-7284, Jun. 15, 1999.
Russel and Barton, "Structural Features can be Unconserved in Proteins with Similar Folds. An Analysis of Side-chain to Side-chain Contacts Secondary Structure and Accessability", *J. Mol. Biol.* 244: 332-350, 1994.
Schmid S et al, "Expression of AMPA Receptor Subunit Flip/Flop Splice Variants in the Rat Auditory Brainstem and Inferior Colliculus," *Journal of Comparative Neurology*, 430(2): 160-171, 2001.
Schweinfest, C.W. et al., "Subtraction Hybridization cDNA Libraries From Colon Carcinoma and Hepatic Cancer," *Genetic Analysis, Techniques and Applications* 7(3):64-70, May 1990.
Shantz. et al., *J. Biochem. Cell Biol.* 31: 107-122, 1999.
Skolnick and Fetrow, "From genes to protein structure and function: novel applications of computational approaches in the genomic era", *Trends in Biotechnology* 18: 34-39, Jan. 2000.
Smith, K.R., "Gene transfer in higher animals: theoretical considerations and key concepts," *Journal of Biotechnology* 99: 1-22, 2002.
Smith, R.T., "Cancer and the Immune System," *Clinical Immunology* 41(4):841-849, Aug. 1994.
Spitler, L.E., "Cancer Vaccines: The Interferon Analogy", *Cancer Biotherapy* 10(1): 1-3, 1995.
Stratagene 1991 product catalog, Prime-ItTM Random Labeling Kit, catalog No. 300387, p. 66.
Sulston et al., "Toward a complete human genome sequence," *Genome Research* 8(11):1097-1108, 1998.
Tao et al., *J. Immunol.* 143(8): 2595-2601, 1989.
Thompson, T.N., "Optimization of Metabolic Stability as a Goal of Modern Drug Design," *Medicinal Research Reviews* 21(5): 412-449, 2001.
Wang et al., *J Immunol* 161(7): 3598-3606, 1998.
Watson et al., Methods of Creating Recombinant DNA Molecules, (Recombinant DNA Second Edition, pp. 63-77) 1994.
Wei et al., "Protection against mammary tumor growth by vaccination with full-length, modified human ErbB-2 DNA," *Int. J. Cancer* 81:748-754, 1999.
White et al., "Antibody-Targeted Immunotherapy for Treatment of Malignancy," *Ann Rev Med* 52: 125-145, 2001.
Wright et al., Genome Biology vol. 2(7): research0025.1-0025.18, Jul. 2001.
Xie, H. et al., "IA-2, a Transmembrane Protein Tyrosine Phosphatase, Is Expressed in Human Lung Cancer Cell Lines with Neuroendocrine Phenotype," *Cancer Research* 56:2742-2744, Jun. 15, 1996.
Xu, J. et al., "Identification of Differentially Expressed Genes in Human Prostate Cancer Using Subtraction and Microarray," *Cancer Research* 60:1677-1682, Mar. 15, 2000.
Xu, J. et al., "Identification of differentially expressed genes in human breast tumor using subtraction and microarray," *Proceedings of the American Association for Cancer Research. Annual Meeting* 40:319, Abstract #2115, 1999.
Yokota, J et al., "Altered expression of the retinoblastoma (RB) gene in small-cell carcinoma of the lung," *Oncogene* 3: 471-475, 1988.
Zehentner, B.K. et al., "Application of a Multigene Reverse Transcription-PCR Assay for Detection of Mammaglobin and Complementary Transcribed Genes in Breast Cancer Lymph Nodes," *Clinical Chemistry* 48(8):1225-1231, 2002.

* cited by examiner

SYN18C6 NORTHERN BLOT

D207 B726P-specific CTL Clone 1-9Arecognize HTB 21
a breast tumor cell line that expresses HLA-B*1501 and B726P

COMPOSITIONS AND METHODS FOR THE THERAPY AND DIAGNOSIS OF BREAST CANCER

STATEMENT REGARDING SEQUENCE LISTING

The Sequence Listing associated with this application is provided in text format in lieu of a paper copy, and is hereby incorporated by reference into the specification. The name of the text file containing the Sequence Listing is 210121_470C21_SEQUENCE_LISTING.txt. The text file is 501 KB, was created on Oct. 30, 2007, and is being submitted electronically via EFS-Web, concurrent with the filing of the specification.

TECHNICAL FIELD OF THE INVENTION

The present invention relates generally to therapy and diagnosis of cancer, such as breast cancer. The invention is more specifically related to polypeptides, comprising at least a portion of a breast tumor protein, and to polynucleotides encoding such polypeptides. Such polypeptides and polynucleotides are useful in pharmaceutical compositions, e.g., vaccines, and other compositions for the diagnosis and treatment of breast cancer.

BACKGROUND OF THE INVENTION

1. Field of the Invention

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

2. Description of the Related Art

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73-100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

In one aspect, the present invention provides polynucleotide compositions comprising a sequence selected from the group consisting of:

(a) sequences provided in SEQ ID NO:1-61, 63-175, 178, 180, 182-468, 474, 476, 477, 479, 482, 484, 486, 489-492, 504-506, 510-513, 520-533, 548-550, 564, 566-569, and 576;

(b) complements of the sequences provided in SEQ ID NO:1-61, 63-175, 178, 180, 182-468, 474, 476, 477, 479, 482, 484, 486, 489-492, 504-506, 510-513, 520-533, 548-550, 564, 566-569, and 576;

(c) sequences consisting of at least 20 contiguous residues of a sequence provided in SEQ ID NO:1-61, 63-175, 178, 180, 182-468, 474, 476, 477, 479, 482, 484, 486, 489-492, 504-506, 510-513, 520-533, 548-550, 564, 566-569, and 576;

(d) sequences that hybridize to a sequence provided in SEQ ID NO:1-61, 63-175, 178, 180, 182-468, 474, 476, 477, 479, 482, 484, 486, 489-492, 504-506, 510-513, 520-533, 548-550, 564, 566-569, and 576, under moderately stringent conditions;

(e) sequences having at least 75% identity to a sequence of SEQ ID NO:1-61, 63-175, 178, 180, 182-468, 474, 476, 477, 479, 482, 484, 486, 489-492, 504-506, 510-513, 520-533, 548-550, 564, 566-569, and 576;

(f) sequences having at least 90% identity to a sequence of SEQ ID NO:1-61, 63-175, 178, 180, 182-468, 474, 476, 477, 479, 482, 484, 486, 489-492, 504-506, 510-513, 520-533, 548-550, 564, 566-569, and 576; and (g) degenerate variants of a sequence provided in SEQ ID NO:1-61, 63-175, 178, 180, 182-468, 474, 476, 477, 479, 482, 484, 486, 489-492, 504-506, 510-513, 520-533, 548-550, 564, 566-569, and 576.

In one preferred embodiment, the polynucleotide compositions of the invention are expressed in at least about 20%, more preferably in at least about 30%, and most preferably in at least about 50% of breast tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NO:62, 176, 179, 181, 469-473, 475, 478, 483, 485, 487, 488, 493-503, 507-509, 514-519, 534-547, 551-553, 565, 570-573, and 577-627.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NO:62, 176, 179, 181, 469-473, 475, 478, 483, 485, 487, 488, 493-503, 507-509, 514-519, 534-547, 551-553, 565, 570-573, and 577-627 or a polypeptide sequence encoded by a polynucleotide sequence set forth in SEQ ID NO:1-61, 63-175, 178, 180, 182-468, 474, 476, 477, 479, 482, 484, 486, 489-492, 504-506, 510-513, 520-533, 548-550, 564, 566-569, and 576.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof, and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

The present invention further provides, in other aspects, fusion proteins that comprise at least one polypeptide as described above, as well as polynucleotides encoding such fusion proteins. Exemplary fusion proteins according to the present invention comprise a first amino acid portion and a second amino acid portion wherein the first amino acid portion includes 9 or more contiguous amino acids from mammaglobin as depicted by amino acids 1-93 of SEQ ID NO:493 (SEQ ID NO:503); wherein the second amino acid portion includes 9 or more contiguous amino acids from B726P as depicted by SEQ ID NO:475, SEQ ID NO:469, or SEQ ID NO:176; and wherein the first amino acid portion is connected to either the amino terminal or carboxy-terminal end of the second amino acid portion.

Still further embodiments of the present invention provide fusion proteins wherein said first amino acid portion is selected from the group consisting of: IDELKECFLNQTDETLSNVE (SEQ ID NO:496; amino acids 59-78 of SEQ ID NO:493); TTNAIDELKECFLNQ (SEQ ID NO:497; amino acids 55-69 of SEQ ID NO:493); SQHCYAGSGCPLLENVISKTI (SEQ ID NO:498; amino acids 13-33 of SEQ ID NO:493); EYKELLQEFIDDNATTNAID (SEQ ID NO:499; amino acids 41-60 of SEQ ID NO:493); KLLMVLMLA (SEQ ID NO:500; amino acids 2-10 of SEQ ID NO:493); QEFIDDNATTNAI (SEQ ID NO:501; amino acids 47-59 of SEQ ID NO:493); LKECFLNQTDETL (SEQ ID NO:502; amino acids 62-74 of SEQ ID NO:493), and any one of the amino acid sequences set forth in SEQ ID NO:578-593.

Alternative embodiments provide fusion proteins wherein the second amino acid portion includes 9 or more contiguous amino acids encoded by (1) the combined upstream and downstream open reading frame (ORF) of B726P as depicted in SEQ ID NO:475; (2) the upstream ORF of B726P as depicted in SEQ ID NO:469; and (3) the downstream ORF of B726P as depicted in SEQ ID NO:176. Fusion proteins according to the present invention may also comprise a second amino acid portion that includes 9 or more contiguous amino acids from the amino acid sequence depicted by amino acids 1-129 of SEQ ID NO:475. Still additional exemplary fusion proteins are depicted herein by SEQ ID NO:493, SEQ ID NO:494, and SEQ ID NO:495.

Fusion proteins are provided wherein the mammaglobin amino acid portion is connected to the amino-terminus of the B726P amino acid portion while other fusion proteins are provided wherein the mammaglobin amino acid portion is connected to the carboxy-terminus of the B726P amino acid portion. The connection between the mammaglobin amino acid portion and the B726P portion may be a covalent bond. Additionally, a stretch of amino acids either unrelated or related to either mammaglobin and/or B726P may be incorporated between or either amino- or carboxy-terminal to either the mammaglobin and/or B726P amino acid portion.

The present invention also provides isolated polynucleotides that encode any of the fusion proteins that are specifically disclosed herein as well as those fusion proteins that may be accomplished with routine experimentation by the ordinarily skilled artisan.

Within further aspects, the present invention provides methods for stimulating an immune response in a patient, preferably a T cell response in a human patient, comprising administering a pharmaceutical composition described herein. The patient may be afflicted with breast cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably a breast cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

Figure 1:
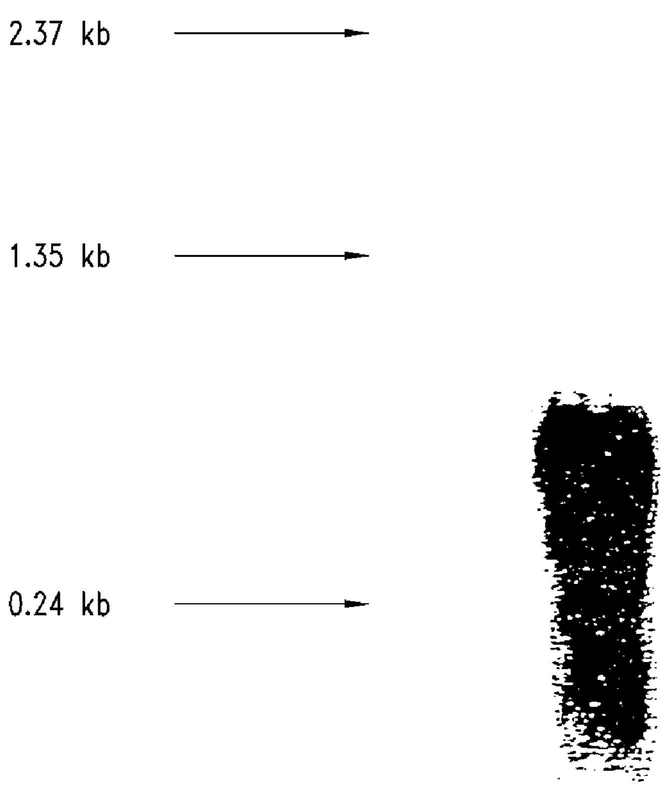
FIG. 1 shows the results of a Northern blot of the clone SYN18C6 (SEQ ID NO:40).

SEQ ID NO:1 is the determined cDNA sequence of JBT2.

SEQ ID NO:2 is the determined cDNA sequence of JBT6.

SEQ ID NO:3 is the determined cDNA sequence of JBT7.

SEQ ID NO:4 is the determined cDNA sequence of JBT10.

SEQ ID NO:5 is the determined cDNA sequence of JBT13.

SEQ ID NO:6 is the determined cDNA sequence of JBT14.

SEQ ID NO:7 is the determined cDNA sequence of JBT15.

SEQ ID NO:8 is the determined cDNA sequence of JBT16.

SEQ ID NO:9 is the determined cDNA sequence of JBT17.

SEQ ID NO:10 is the determined cDNA sequence of JBT22.

SEQ ID NO:11 is the determined cDNA sequence of JBT25.

SEQ ID NO:12 is the determined cDNA sequence of JBT28.

SEQ ID NO:13 is the determined cDNA sequence of JBT32.

SEQ ID NO:14 is the determined cDNA sequence of JBT33.

SEQ ID NO:15 is the determined cDNA sequence of JBT34.

SEQ ID NO:16 is the determined cDNA sequence of JBT36.

SEQ ID NO:17 is the determined cDNA sequence of JBT37.

SEQ ID NO:18 is the determined cDNA sequence of JBT51.

SEQ ID NO:19 is the determined cDNA sequence of JBTT1.

SEQ ID NO:20 is the determined cDNA sequence of JBTT7.

SEQ ID NO:21 is the determined cDNA sequence of JBTT11.

SEQ ID NO:22 is the determined cDNA sequence of JBTT14.

SEQ ID NO:23 is the determined cDNA sequence of JBTT18.

SEQ ID NO:24 is the determined cDNA sequence of JBTT19.

SEQ ID NO:25 is the determined cDNA sequence of JBTT20.

SEQ ID NO:26 is the determined cDNA sequence of JBTT21.

SEQ ID NO:27 is the determined cDNA sequence of JBTT22.

SEQ ID NO:28 is the determined cDNA sequence of JBTT28.

SEQ ID NO:29 is the determined cDNA sequence of JBTT29.

SEQ ID NO:30 is the determined cDNA sequence of JBTT33.

SEQ ID NO:31 is the determined cDNA sequence of JBTT37.

SEQ ID NO:32 is the determined cDNA sequence of JBTT38.

SEQ ID NO:33 is the determined cDNA sequence of JBTT47.

SEQ ID NO:34 is the determined cDNA sequence of JBTT48.

SEQ ID NO:35 is the determined cDNA sequence of JBTT50.

SEQ ID NO:36 is the determined cDNA sequence of JBTT51.

SEQ ID NO:37 is the determined cDNA sequence of JBTT52.

SEQ ID NO:38 is the determined cDNA sequence of JBTT54.

SEQ ID NO:39 is the determined cDNA sequence of SYN17F4.

SEQ ID NO:40 is the determined cDNA sequence of SYN18C6 (also known as B709P).

SEQ ID NO:41 is the determined cDNA sequence of SYN19A2.

SEQ ID NO:42 is the determined cDNA sequence of SYN19C8.

SEQ ID NO:43 is the determined cDNA sequence of SYN20A12.

SEQ ID NO:44 is the determined cDNA sequence of SYN20G6.

SEQ ID NO:45 is the determined cDNA sequence of SYN20G6-2.

SEQ ID NO:46 is the determined cDNA sequence of SYN21B9.

SEQ ID NO:47 is the determined cDNA sequence of SYN21B9-2.

SEQ ID NO:48 is the determined cDNA sequence of SYN21C10.

SEQ ID NO:49 is the determined cDNA sequence of SYN21G10.

SEQ ID NO:50 is the determined cDNA sequence of SYN21G10-2.

SEQ ID NO:51 is the determined cDNA sequence of SYN21G11.

SEQ ID NO:52 is the determined cDNA sequence of SYN21G11-2.

SEQ ID NO:53 is the determined cDNA sequence of SYN21H8.

SEQ ID NO:54 is the determined cDNA sequence of SYN22A10.

SEQ ID NO:55 is the determined cDNA sequence of SYN22A10-2.

SEQ ID NO:56 is the determined cDNA sequence of SYN22A12.

SEQ ID NO:57 is the determined cDNA sequence of SYN22A2 (also referred to as B718P).

SEQ ID NO:58 is the determined cDNA sequence of SYN22B4.

SEQ ID NO:59 is the determined cDNA sequence of SYN22C2.

SEQ ID NO:60 is the determined cDNA sequence of SYN22E10.

SEQ ID NO:61 is the determined cDNA sequence of SYN22F2.

SEQ ID NO:62 is a predicted amino acid sequence for SYN18C6 (also known as B709P).

SEQ ID NO:63 is the determined cDNA sequence of B723P.

SEQ ID NO:64 is the determined cDNA sequence for B724P.

SEQ ID NO:65 is the determined cDNA sequence of B770P.

SEQ ID NO:66 is the determined cDNA sequence of B716P.

SEQ ID NO:67 is the determined cDNA sequence of B725P.

SEQ ID NO:68 is the determined cDNA sequence of B717P.

SEQ ID NO:69 is the determined cDNA sequence of B771P.

SEQ ID NO:70 is the determined cDNA sequence of B722P.

SEQ ID NO:71 is the determined cDNA sequence of B726P.

SEQ ID NO:72 is the determined cDNA sequence of B727P.

SEQ ID NO:73 is the determined cDNA sequence of B728P.

SEQ ID NO:74-87 are the determined cDNA sequences of isolated clones which show homology to known sequences.

SEQ ID NO:88 is the determined cDNA sequence of 13053.

SEQ ID NO:89 is the determined cDNA sequence of 13057.

SEQ ID NO:90 is the determined cDNA sequence of 13059.

SEQ ID NO:91 is the determined cDNA sequence of 13065.

SEQ ID NO:92 is the determined cDNA sequence of 13067.

SEQ ID NO:93 is the determined cDNA sequence of 13068.

SEQ ID NO:94 is the determined cDNA sequence of 13071.

SEQ ID NO:95 is the determined cDNA sequence of 13072.

SEQ ID NO:96 is the determined cDNA sequence of 13073.

SEQ ID NO:97 is the determined cDNA sequence of 13075.

SEQ ID NO:98 is the determined cDNA sequence of 13078.

SEQ ID NO:99 is the determined cDNA sequence of 13079.

SEQ ID NO:100 is the determined cDNA sequence of 13081.

SEQ ID NO:101 is the determined cDNA sequence of 13082.

SEQ ID NO:102 is the determined cDNA sequence of 13092.

SEQ ID NO:103 is the determined cDNA sequence of 13097.

SEQ ID NO:104 is the determined cDNA sequence of 13101.

SEQ ID NO:105 is the determined cDNA sequence of 13102.

SEQ ID NO:106 is the determined cDNA sequence of 13119.

SEQ ID NO:107 is the determined cDNA sequence of 13131.

SEQ ID NO:108 is the determined cDNA sequence of 13133.

SEQ ID NO:109 is the determined cDNA sequence of 13135.

SEQ ID NO:110 is the determined cDNA sequence of 13139.

SEQ ID NO:111 is the determined cDNA sequence of 13140.

SEQ ID NO:112 is the determined cDNA sequence of 13146.

SEQ ID NO:113 is the determined cDNA sequence of 13147.

SEQ ID NO:114 is the determined cDNA sequence of 13148.

SEQ ID NO:115 is the determined cDNA sequence of 13149.

SEQ ID NO:116 is the determined cDNA sequence of 13151.

SEQ ID NO:117 is the determined cDNA sequence of 13051

SEQ ID NO:118 is the determined cDNA sequence of 13052

SEQ ID NO:119 is the determined cDNA sequence of 13055

SEQ ID NO:120 is the determined cDNA sequence of 13058

SEQ ID NO:121 is the determined cDNA sequence of 13062

SEQ ID NO:122 is the determined cDNA sequence of 13064

SEQ ID NO:123 is the determined cDNA sequence of 13080

SEQ ID NO:124 is the determined cDNA sequence of 13093

SEQ ID NO:125 is the determined cDNA sequence of 13094

SEQ ID NO:126 is the determined cDNA sequence of 13095

SEQ ID NO:127 is the determined cDNA sequence of 13096

SEQ ID NO:128 is the determined cDNA sequence of 13099

SEQ ID NO:129 is the determined cDNA sequence of 13100

SEQ ID NO:130 is the determined cDNA sequence of 13103

SEQ ID NO:131 is the determined cDNA sequence of 13106

SEQ ID NO:132 is the determined cDNA sequence of 13107

SEQ ID NO:133 is the determined cDNA sequence of 13108

SEQ ID NO:134 is the determined cDNA sequence of 13121

SEQ ID NO:135 is the determined cDNA sequence of 13126

SEQ ID NO:136 is the determined cDNA sequence of 13129

SEQ ID NO:137 is the determined cDNA sequence of 13130

SEQ ID NO:138 is the determined cDNA sequence of 13134

SEQ ID NO:139 is the determined cDNA sequence of 13141

SEQ ID NO:140 is the determined cDNA sequence of 13142

SEQ ID NO:141 is the determined cDNA sequence of 14376

SEQ ID NO:142 is the determined cDNA sequence of 14377

SEQ ID NO:143 is the determined cDNA sequence of 14383

SEQ ID NO:144 is the determined cDNA sequence of 14384

SEQ ID NO:145 is the determined cDNA sequence of 14387

SEQ ID NO:146 is the determined cDNA sequence of 14392

SEQ ID NO:147 is the determined cDNA sequence of 14394

SEQ ID NO:148 is the determined cDNA sequence of 14398

SEQ ID NO:149 is the determined cDNA sequence of 14401

SEQ ID NO:150 is the determined cDNA sequence of 14402

SEQ ID NO:151 is the determined cDNA sequence of 14405

SEQ ID NO:152 is the determined cDNA sequence of 14409

SEQ ID NO:153 is the determined cDNA sequence of 14412

SEQ ID NO:154 is the determined cDNA sequence of 14414

SEQ ID NO:155 is the determined cDNA sequence of 14415

SEQ ID NO:156 is the determined cDNA sequence of 14416

SEQ ID NO:157 is the determined cDNA sequence of 14419

SEQ ID NO:158 is the determined cDNA sequence of 14426

SEQ ID NO:159 is the determined cDNA sequence of 14427

SEQ ID NO:160 is the determined cDNA sequence of 14375

SEQ ID NO:161 is the determined cDNA sequence of 14378

SEQ ID NO:162 is the determined cDNA sequence of 14379

SEQ ID NO:163 is the determined cDNA sequence of 14380

SEQ ID NO:164 is the determined cDNA sequence of 14381

SEQ ID NO:165 is the determined cDNA sequence of 14382

SEQ ID NO:166 is the determined cDNA sequence of 14388

SEQ ID NO:167 is the determined cDNA sequence of 14399

SEQ ID NO:168 is the determined cDNA sequence of 14406

SEQ ID NO:169 is the determined cDNA sequence of 14407

SEQ ID NO:170 is the determined cDNA sequence of 14408

SEQ ID NO:171 is the determined cDNA sequence of 14417

SEQ ID NO:172 is the determined cDNA sequence of 14418

SEQ ID NO:173 is the determined cDNA sequence of 14423

SEQ ID NO:174 is the determined cDNA sequence of 14424

SEQ ID NO:175 is the determined cDNA sequence of B726P-20

SEQ ID NO:176 is the predicted amino acid sequence of B726P-20 (also referred to as B726P downstream ORF)

SEQ ID NO:177 is a PCR primer

SEQ ID NO:178 is the determined cDNA sequence of B726P-74

SEQ ID NO:179 is the predicted amino acid sequence of B726P-74

SEQ ID NO:180 is the determined cDNA sequence of B726P-79

SEQ ID NO:181 is the predicted amino acid sequence of B726P-79

SEQ ID NO:182 is the determined cDNA sequence of 19439.1, showing homology to the mammaglobin gene SEQ ID NO:183 is the determined cDNA sequence of 19407.1, showing homology to the human keratin gene SEQ ID NO:184 is the determined cDNA sequence of 19428.1, showing homology to human chromosome 17 clone SEQ ID NO:185 is the determined cDNA sequence of B808P (19408), showing no significant homology to any known gene SEQ ID NO:186 is the determined cDNA sequence of 19460.1, showing no significant homology to any known gene SEQ ID NO:187 is the determined cDNA sequence of 19419.1, showing homology to Ig kappa light chain SEQ ID NO:188 is the determined cDNA sequence of 19411.1, showing homology to human alpha-1 collagen SEQ ID NO:189 is the determined cDNA sequence of 19420.1, showing homology to mus musculus proteinase-3

SEQ ID NO:190 is the determined cDNA sequence of 19432.1, showing homology to human high motility group box SEQ ID NO:191 is the determined cDNA sequence of 19412.1, showing homology to the human plasminogen activator gene SEQ ID NO:192 is the determined cDNA sequence of 19415.1, showing homology to mitogen activated protein kinase SEQ ID NO:193 is the determined cDNA sequence of 19409.1, showing homology to the chondroitin sulfate proteoglycan protein SEQ ID NO:194 is the determined cDNA sequence of 19406.1, showing no significant homology to any known gene SEQ ID NO:195 is the determined cDNA sequence of 19421.1, showing homology to human fibronectin SEQ ID NO:196 is the determined cDNA sequence of 19426.1, showing homology to the retinoic acid receptor responder 3

SEQ ID NO:197 is the determined cDNA sequence of 19425.1, showing homology to MyD88 mRNA SEQ ID NO:198 is the determined cDNA sequence of 19424.1, showing homology to peptide transporter (TAP-1) mRNA SEQ ID NO:199 is the determined cDNA sequence of 19429.1, showing no significant homology to any known gene SEQ ID NO:200 is the determined cDNA sequence of 19435.1, showing homology to human polymorphic epithelial mucin SEQ ID NO:201 is the determined cDNA sequence of B813P (19434.1), showing homology to human GATA-3 transcription factor SEQ ID NO:202 is the determined cDNA sequence of 19461.1, showing homology to the human AP-2 gene SEQ ID NO:203 is the determined cDNA sequence of 19450.1, showing homology to DNA binding regulatory factor SEQ ID NO:204 is the determined cDNA sequence of 19451.1, showing homology to Na/H exchange regulatory co-factor SEQ ID NO:205 is the determined cDNA sequence of 19462.1, showing no significant homology to any known gene SEQ ID NO:206 is the determined cDNA sequence of 19455.1, showing homology to human mRNA for histone HAS.Z SEQ ID NO:207 is the determined cDNA sequence of 19459.1, showing homology to PAC clone 179N16

SEQ ID NO:208 is the determined cDNA sequence of 19464.1, showing no significant homology to any known gene SEQ ID NO:209 is the determined cDNA sequence of 19414.1, showing homology to lipophilin B SEQ ID NO:210 is the determined cDNA sequence of 19413.1, showing homology to chromosome 17 clone hRPK.209_J__20

SEQ ID NO:211 is the determined cDNA sequence of 19416.1, showing no significant homology to any known gene SEQ ID NO:212 is the determined cDNA sequence of 19437.1, showing homology to human clone 24976 mRNA SEQ ID NO:213 is the determined cDNA sequence of 19449.1, showing homology to mouse DNA for PG-M core protein SEQ ID NO:214 is the determined cDNA sequence of 19446.1, showing no significant homology to any known gene SEQ ID NO:215 is the determined cDNA sequence of 19452.1, showing no significant homology to any known gene SEQ ID NO:216 is the determined cDNA sequence of 19483.1, showing no significant homology to any known gene SEQ ID NO:217 is the determined cDNA sequence of 19526.1, showing homology to human lipophilin C SEQ ID NO:218 is the determined cDNA sequence of 19484.1, showing homology to the secreted cement gland protein XAG-2

SEQ ID NO:219 is the determined cDNA sequence of 19470.1, showing no significant homology to any known gene SEQ ID NO:220 is the determined cDNA sequence of 19469.1, showing homology to the human HLA-DM gene SEQ ID NO:221 is the determined cDNA sequence of 19482.1, showing homology to the human pS2 protein gene SEQ ID NO:222 is the determined cDNA sequence of B805P (19468.1), showing no significant homology to any known gene SEQ ID NO:223 is the determined cDNA sequence of 19467.1, showing homology to human thrombospondin mRNA SEQ ID NO:224 is the determined cDNA sequence of 19498.1, showing homology to the CDC2 gene involved in cell cycle control SEQ ID NO:225 is the determined cDNA sequence of 19506.1, showing homology to human cDNA for TREB protein SEQ ID NO:226 is the determined cDNA sequence of B806P (19505.1), showing no significant homology to any known gene SEQ ID NO:227 is the determined cDNA sequence of 19486.1, showing homology to type I epidermal keratin SEQ ID NO:228 is the determined cDNA sequence of 19510.1, showing homology to glucose transporter for glycoprotein SEQ ID NO:229 is the determined cDNA sequence of 19512.1, showing homology to the human lysyl hydroxylase gene SEQ ID NO:230 is the determined cDNA sequence of 19511.1, showing homology to human palimotoyl-protein thioesterase SEQ ID NO:231 is the determined cDNA sequence of 19508.1, showing homology to human alpha enolase SEQ ID NO:232 is the determined cDNA sequence of B807P (19509.1), showing no significant homology to any known gene SEQ ID NO:233 is the determined cDNA sequence of B809P (19520.1), showing homology to clone 102D24 on chromosome 11q13.31

SEQ ID NO:234 is the determined cDNA sequence of 19507.1, showing homology toprosome beta-subunit SEQ ID NO:235 is the determined cDNA sequence of 19525.1, showing homology to human pro-urokinase precursor SEQ ID NO:236 is the determined cDNA sequence of 19513.1, showing no significant homology to any known gene SEQ ID NO:237 is the determined cDNA sequence of 19517.1, showing homology to human PAC 128M19 clone SEQ ID NO:238 is the determined cDNA sequence of 19564.1, showing homology to human cytochrome P450-10B SEQ ID NO:239 is the determined cDNA sequence of 19553.1, showing homology to human GABA-A receptor pi subunit SEQ ID NO:240 is the determined cDNA sequence of B811P (19575.1), showing no significant homology to any known gene SEQ ID NO:241 is the determined cDNA sequence of B810P (19560.1), showing no significant homology to any known gene SEQ ID NO:242 is the determined cDNA sequence of 19588.1, showing homology to aortic carboxypetidase-like protein SEQ ID NO:243 is the determined cDNA sequence of 19551.1, showing homology to human BCL-1 gene SEQ ID NO:244 is the determined cDNA sequence of 19567.1, showing homology to human proteasome-related mRNA SEQ ID NO:245 is the determined cDNA sequence of B803P (19583.1), showing no significant homology to any known gene SEQ ID NO:246 is the determined cDNA sequence of B812P (19587.1), showing no significant homology to any known gene SEQ ID NO:247 is the determined cDNA sequence of B802P (19392.2), showing homology to human chromosome 17

SEQ ID NO:248 is the determined cDNA sequence of 19393.2, showing homology to human nicein B2 chain SEQ ID NO:249 is the determined cDNA sequence of 19398.2, human MHC class II DQ alpha mRNA SEQ ID NO:250 is the determined cDNA sequence of B804P (19399.2), showing homology to human Xp22 BAC GSHB-184P 14

SEQ ID NO:251 is the determined cDNA sequence of 19401.2, showing homology to human ikB kinase-b gene SEQ ID NO:252 is the determined cDNA sequence of 20266, showing no significant homology to any known gene SEQ ID NO:253 is the determined cDNA sequence of B826P (20270), showing no significant homology to any known gene SEQ ID NO:254 is the determined cDNA sequence of 20274, showing no significant homology to any known gene SEQ ID NO:255 is the determined cDNA sequence of 20276, showing no significant homology to any known gene SEQ ID NO:256 is the determined cDNA sequence of 20277, showing no significant homology to any known gene SEQ ID NO:257 is the determined cDNA sequence of B823P (20280), showing no significant homology to any known gene SEQ ID NO:258 is the determined cDNA sequence of B821P (20281), showing no significant homology to any known gene SEQ ID NO:259 is the determined cDNA sequence of B824P (20294), showing no significant homology to any known gene SEQ ID NO:260 is the determined cDNA sequence of 20303, showing no significant homology to any known gene SEQ ID NO:261 is the determined cDNA sequence of B820P (20310), showing no significant homology to any known gene SEQ ID NO:262 is the determined cDNA sequence of B825P (20336), showing no significant homology to any known gene SEQ ID NO:263 is the determined cDNA sequence of B827P (20341), showing no significant homology to any known gene SEQ ID NO:264 is the determined cDNA sequence of 20941, showing no significant homology to any known gene SEQ ID NO:265 is the determined cDNA sequence of 20954, showing no significant homology to any known gene SEQ ID NO:266 is the determined cDNA sequence of 20961, showing no significant homology to any known gene SEQ ID NO:267 is the determined cDNA sequence of 20965, showing no significant homology to any known gene SEQ ID NO:268 is the determined cDNA sequence of 20975, showing no significant homology to any known gene SEQ ID NO:269 is the determined cDNA sequence of 20261, showing homology to Human p120 catenin SEQ ID NO:270 is the determined cDNA sequence of B822P (20262), showing homology to Human membrane glycoprotein 4F2

SEQ ID NO:271 is the determined cDNA sequence of 20265, showing homology to Human Na, K-ATPase Alpha 1

SEQ ID NO:272 is the determined cDNA sequence of 20267, showing homology to Human heart HS 90, partial cds SEQ ID NO:273 is the determined cDNA sequence of 20268, showing homology to Human mRNA GPI-anchored protein p137

SEQ ID NO:274 is the determined cDNA sequence of 20271, showing homology to Human cleavage stimulation factor 77 kDa subunit SEQ ID NO:275 is the determined cDNA sequence of 20272, showing homology to Human p190-B SEQ ID NO:276 is the determined cDNA sequence of 20273, showing homology to Human ribophorin SEQ ID NO:277 is the determined cDNA sequence of 20278, showing homology to Human ornithine amino transferase SEQ ID NO:278 is the determined cDNA sequence of 20279, showing homology to Human S-adenosylmethionine synthetase SEQ ID NO:279 is the determined cDNA sequence of 20293, showing homology to Human x inactivation transcript SEQ ID NO:280 is the determined cDNA sequence of 20300, showing homology to Human cytochrome p450

SEQ ID NO:281 is the determined cDNA sequence of 20305, showing homology to Human elongation factor-1 alpha SEQ ID NO:282 is the determined cDNA sequence of 20306, showing homology to Human epithelial ets protein SEQ ID NO:283 is the determined cDNA sequence of 20307, showing homology to Human signal transducer mRNA SEQ ID NO:284 is the determined cDNA sequence of 20313, showing homology to Human GABA-A receptor pi subunit mRNA SEQ ID NO:285 is the determined cDNA sequence of 20317, showing homology to Human tyrosine phosphatase SEQ ID NO:286 is the determined cDNA sequence of 20318, showing homology to Human cathepsine B proteinase SEQ ID NO:287 is the determined cDNA sequence of 20320, showing homology to Human 2-phosphopyruvate-hydratase-alpha-enolase SEQ ID NO:288 is the determined cDNA sequence of 20321, showing homology to Human E-cadherin SEQ ID NO:289 is the determined cDNA sequence of 20322, showing homology to Human hsp86

SEQ ID NO:290 is the determined cDNA sequence of B828P (20326), showing homology to Human x inactivation transcript SEQ ID NO:291 is the determined cDNA sequence of 20333, showing homology to Human chromatin regulator, SMARCA5

SEQ ID NO:292 is the determined cDNA sequence of 20335, showing homology to Human sphingolipid activator protein 1

SEQ ID NO:293 is the determined cDNA sequence of 20337, showing homology to Human hepatocyte growth factor activator inhibitor type 2

SEQ ID NO:294 is the determined cDNA sequence of 20338, showing homology to Human cell adhesion molecule CD44

SEQ ID NO:295 is the determined cDNA sequence of 20340, showing homology to Human nuclear factor (erythroid-derived)-like 1

SEQ ID NO:296 is the determined cDNA sequence of 20938, showing homology to Human vinculin mRNA SEQ ID NO:297 is the determined cDNA sequence of 20939, showing homology to Human elongation factor EF-1-alpha SEQ ID NO:298 is the determined cDNA sequence of 20940, showing homology to Human nestin gene SEQ ID NO:299 is the determined cDNA sequence of 20942, showing homology to Human pancreatic ribonuclease SEQ ID NO:300 is the determined cDNA sequence of 20943, showing homology to Human transcobalamin 1

SEQ ID NO:301 is the determined cDNA sequence of 20944, showing homology to Human beta-tubulin SEQ ID NO:302 is the determined cDNA sequence of 20946, showing homology to Human HS1 protein SEQ ID NO:303 is the determined cDNA sequence of 20947, showing homology to Human cathepsin B SEQ ID NO:304 is the determined cDNA sequence of 20948, showing homology to Human testis enhanced gene transcript SEQ ID NO:305 is the determined cDNA sequence of 20949, showing homology to Human elongation factor EF-1-alpha SEQ ID NO:306 is the determined cDNA sequence of 20950, showing homology to Human ADP-ribosylation factor 3

SEQ ID NO:307 is the determined cDNA sequence of 20951, showing homology to Human IFP53 or WRS for tryptophanyl-tRNA synthetase SEQ ID NO:308 is the determined cDNA sequence of 20952, showing homology to Human cyclin-dependent protein kinase SEQ ID NO:309 is the determined cDNA sequence of 20957, showing homology to Human alpha-tubulin isoform 1

SEQ ID NO:310 is the determined cDNA sequence of 20959, showing homology to Human tyrosine phosphatase-61 bp deletion SEQ ID NO:311 is the determined cDNA sequence of 20966, showing homology to Human tyrosine phosphatase SEQ ID NO:312 is the determined cDNA sequence of B830P (20976), showing homology to Human nuclear factor NF 45

SEQ ID NO:313 is the determined cDNA sequence of B829P (20977), showing homology to Human delta-6 fatty acid desaturase SEQ ID NO:314 is the determined cDNA sequence of 20978, showing homology to Human nuclear aconitase SEQ ID NO:315 is the determined cDNA sequence of clone 23176.

SEQ ID NO:316 is the determined cDNA sequence of clone 23140.

SEQ ID NO:317 is the determined cDNA sequence of clone 23166.

SEQ ID NO:318 is the determined cDNA sequence of clone 23167.

SEQ ID NO:319 is the determined cDNA sequence of clone 23177.

SEQ ID NO:320 is the determined cDNA sequence of clone 23217.

SEQ ID NO:321 is the determined cDNA sequence of clone 23169.

SEQ ID NO:322 is the determined cDNA sequence of clone 23160.

SEQ ID NO:323 is the determined cDNA sequence of clone 23182.

SEQ ID NO:324 is the determined cDNA sequence of clone 23232.

SEQ ID NO:325 is the determined cDNA sequence of clone 23203.

SEQ ID NO:326 is the determined cDNA sequence of clone 23198.

SEQ ID NO:327 is the determined cDNA sequence of clone 23224.

SEQ ID NO:328 is the determined cDNA sequence of clone 23142.

SEQ ID NO:329 is the determined cDNA sequence of clone 23138.

SEQ ID NO:330 is the determined cDNA sequence of clone 23147.

SEQ ID NO:331 is the determined cDNA sequence of clone 23148.

SEQ ID NO:332 is the determined cDNA sequence of clone 23149.

SEQ ID NO:333 is the determined cDNA sequence of clone 23172.

SEQ ID NO:334 is the determined cDNA sequence of clone 23158.

SEQ ID NO:335 is the determined cDNA sequence of clone 23156.

SEQ ID NO:336 is the determined cDNA sequence of clone 23221.

SEQ ID NO:337 is the determined cDNA sequence of clone 23223.

SEQ ID NO:338 is the determined cDNA sequence of clone 23155.

SEQ ID NO:339 is the determined cDNA sequence of clone 23225.

SEQ ID NO:340 is the determined cDNA sequence of clone 23226.

SEQ ID NO:341 is the determined cDNA sequence of clone 23228.

SEQ ID NO:342 is the determined cDNA sequence of clone 23229.

SEQ ID NO:343 is the determined cDNA sequence of clone 23231.

SEQ ID NO:344 is the determined cDNA sequence of clone 23154.

SEQ ID NO:345 is the determined cDNA sequence of clone 23157.

SEQ ID NO:346 is the determined cDNA sequence of clone 23153.

SEQ ID NO:347 is the determined cDNA sequence of clone 23159.

SEQ ID NO:348 is the determined cDNA sequence of clone 23152.

SEQ ID NO:349 is the determined cDNA sequence of clone 23161.

SEQ ID NO:350 is the determined cDNA sequence of clone 23162.

SEQ ID NO:351 is the determined cDNA sequence of clone 23163.

SEQ ID NO:352 is the determined cDNA sequence of clone 23164.

SEQ ID NO:353 is the determined cDNA sequence of clone 23165.

SEQ ID NO:354 is the determined cDNA sequence of clone 23151.

SEQ ID NO:355 is the determined cDNA sequence of clone 23150.

SEQ ID NO:356 is the determined cDNA sequence of clone 23168.

SEQ ID NO:357 is the determined cDNA sequence of clone 23146.

SEQ ID NO:358 is the determined cDNA sequence of clone 23170.

SEQ ID NO:359 is the determined cDNA sequence of clone 23171.

SEQ ID NO:360 is the determined cDNA sequence of clone 23145.

SEQ ID NO:361 is the determined cDNA sequence of clone 23174.

SEQ ID NO:362 is the determined cDNA sequence of clone 23175.

SEQ ID NO:363 is the determined cDNA sequence of clone 23144.

SEQ ID NO:364 is the determined cDNA sequence of clone 23178.

SEQ ID NO:365 is the determined cDNA sequence of clone 23179.

SEQ ID NO:366 is the determined cDNA sequence of clone 23180.

SEQ ID NO:367 is the determined cDNA sequence of clone 23181.

SEQ ID NO:368 is the determined cDNA sequence of clone 23143

SEQ ID NO:369 is the determined cDNA sequence of clone 23183.

SEQ ID NO:370 is the determined cDNA sequence of clone 23184.

SEQ ID NO:371 is the determined cDNA sequence of clone 23185.

SEQ ID NO:372 is the determined cDNA sequence of clone 23186.

SEQ ID NO:373 is the determined cDNA sequence of clone 23187.

SEQ ID NO:374 is the determined cDNA sequence of clone 23190.

SEQ ID NO:375 is the determined cDNA sequence of clone 23189.

SEQ ID NO:376 is the determined cDNA sequence of clone 23202.

SEQ ID NO:378 is the determined cDNA sequence of clone 23191.

SEQ ID NO:379 is the determined cDNA sequence of clone 23188.

SEQ ID NO:380 is the determined cDNA sequence of clone 23194.

SEQ ID NO:381 is the determined cDNA sequence of clone 23196.

SEQ ID NO:382 is the determined cDNA sequence of clone 23195.

SEQ ID NO:383 is the determined cDNA sequence of clone 23193.

SEQ ID NO:384 is the determined cDNA sequence of clone 23199.

SEQ ID NO:385 is the determined cDNA sequence of clone 23200.

SEQ ID NO:386 is the determined cDNA sequence of clone 23192.

SEQ ID NO:387 is the determined cDNA sequence of clone 23201.

SEQ ID NO:388 is the determined cDNA sequence of clone 23141.

SEQ ID NO:389 is the determined cDNA sequence of clone 23139.

SEQ ID NO:390 is the determined cDNA sequence of clone 23204.

SEQ ID NO:391 is the determined cDNA sequence of clone 23205.

SEQ ID NO:392 is the determined cDNA sequence of clone 23206.

SEQ ID NO:393 is the determined cDNA sequence of clone 23207.

SEQ ID NO:394 is the determined cDNA sequence of clone 23208.

SEQ ID NO:395 is the determined cDNA sequence of clone 23209.

SEQ ID NO:396 is the determined cDNA sequence of clone 23210.

SEQ ID NO:397 is the determined cDNA sequence of clone 23211.

SEQ ID NO:398 is the determined cDNA sequence of clone 23212.

SEQ ID NO:399 is the determined cDNA sequence of clone 23214.

SEQ ID NO:400 is the determined cDNA sequence of clone 23215.

SEQ ID NO:401 is the determined cDNA sequence of clone 23216.

SEQ ID NO:402 is the determined cDNA sequence of clone 23137.

SEQ ID NO:403 is the determined cDNA sequence of clone 23218.

SEQ ID NO:404 is the determined cDNA sequence of clone 23220.

SEQ ID NO:405 is the determined cDNA sequence of clone 19462.

SEQ ID NO:406 is the determined cDNA sequence of clone 19430.

SEQ ID NO:407 is the determined cDNA sequence of clone 19407.

SEQ ID NO:408 is the determined cDNA sequence of clone 19448.

SEQ ID NO:409 is the determined cDNA sequence of clone 19447.

SEQ ID NO:410 is the determined cDNA sequence of clone 19426.

SEQ ID NO:411 is the determined cDNA sequence of clone 19441.

SEQ ID NO:412 is the determined cDNA sequence of clone 19454.

SEQ ID NO:413 is the determined cDNA sequence of clone 19463.

SEQ ID NO:414 is the determined cDNA sequence of clone 19419.

SEQ ID NO:415 is the determined cDNA sequence of clone 19434.

SEQ ID NO:416 is the determined extended cDNA sequence of B820P.

SEQ ID NO:417 is the determined extended cDNA sequence of B821P.

SEQ ID NO:418 is the determined extended cDNA sequence of B822P.

SEQ ID NO:419 is the determined extended cDNA sequence of B823P.

SEQ ID NO:420 is the determined extended cDNA sequence of B824P.

SEQ ID NO:421 is the determined extended cDNA sequence of B825P.

SEQ ID NO:422 is the determined extended cDNA sequence of B826P.

SEQ ID NO:423 is the determined extended cDNA sequence of B827P.

SEQ ID NO:424 is the determined extended cDNA sequence of B828P.

SEQ ID NO:425 is the determined extended cDNA sequence of B829P.

SEQ ID NO:426 is the determined extended cDNA sequence of B830P.

SEQ ID NO:427 is the determined cDNA sequence of clone 266B4.

SEQ ID NO:428 is the determined cDNA sequence of clone 22892.

SEQ ID NO:429 is the determined cDNA sequence of clone 266G3.

SEQ ID NO:430 is the determined cDNA sequence of clone 22890.

SEQ ID NO:431 is the determined cDNA sequence of clone 264B4.

SEQ ID NO:432 is the determined cDNA sequence of clone 22883.

SEQ ID NO:433 is the determined cDNA sequence of clone 22882.

SEQ ID NO:434 is the determined cDNA sequence of clone 22880.

SEQ ID NO:435 is the determined cDNA sequence of clone 263G1.

SEQ ID NO:436 is the determined cDNA sequence of clone 263G6.

SEQ ID NO:437 is the determined cDNA sequence of clone 262B2.

SEQ ID NO:438 is the determined cDNA sequence of clone 262B6.

SEQ ID NO:439 is the determined cDNA sequence of clone 22869.

SEQ ID NO:440 is the determined cDNA sequence of clone 21374.

SEQ ID NO:441 is the determined cDNA sequence of clone 21362.

SEQ ID NO:442 is the determined cDNA sequence of clone 21349.

SEQ ID NO:443 is the determined cDNA sequence of clone 21309.

SEQ ID NO:444 is the determined cDNA sequence of clone 21097.

SEQ ID NO:445 is the determined cDNA sequence of clone 21096.

SEQ ID NO:446 is the determined cDNA sequence of clone 21094.

SEQ ID NO:447 is the determined cDNA sequence of clone 21093.

SEQ ID NO:448 is the determined cDNA sequence of clone 21091.

SEQ ID NO:449 is the determined cDNA sequence of clone 21089.

SEQ ID NO:450 is the determined cDNA sequence of clone 21087.

SEQ ID NO:451 is the determined cDNA sequence of clone 21085.

SEQ ID NO:452 is the determined cDNA sequence of clone 21084.

SEQ ID NO:453 is a first partial cDNA sequence of clone 2BT1-40.

SEQ ID NO:454 is a second partial cDNA sequence of clone 2BT1-40.

SEQ ID NO:455 is the determined cDNA sequence of clone 21063.

SEQ ID NO:456 is the determined cDNA sequence of clone 21062.

SEQ ID NO:457 is the determined cDNA sequence of clone 21060.

SEQ ID NO:458 is the determined cDNA sequence of clone 21053.

SEQ ID NO:459 is the determined cDNA sequence of clone 21050.

SEQ ID NO:460 is the determined cDNA sequence of clone 21036.

SEQ ID NO:461 is the determined cDNA sequence of clone 21037.

SEQ ID NO:462 is the determined cDNA sequence of clone 21048.

SEQ ID NO:463 is a consensus DNA sequence of B726P (referred to as B726P-spliced_seq_B726P).

SEQ ID NO:464 is the determined cDNA sequence of a second splice form of B726P (referred to as 27490.seq_B726P).

SEQ ID NO:465 is the determined cDNA sequence of a third splice form of B726P (referred to as 27068.seq_B726P).

SEQ ID NO:466 is the determined cDNA sequence of a second splice form of B726P (referred to as 23113.seq_B726P).

SEQ ID NO:467 is the determined cDNA sequence of a second splice form of B726P (referred to as 23103.seq_B726P).

SEQ ID NO:468 is the determined cDNA sequence of a second splice form of B726P (referred to as 19310.seq_B726P).

SEQ ID NO:469 is the predicted amino acid sequence encoded by the upstream ORF of SEQ ID NO:463.

SEQ ID NO:470 is the predicted amino acid sequence encoded by SEQ ID NO:464.

SEQ ID NO:471 is the predicted amino acid sequence encoded by SEQ ID NO:465.

SEQ ID NO:472 is the predicted amino acid sequence encoded by SEQ ID NO:466.

SEQ ID NO:473 is the predicted amino acid sequence encoded by SEQ ID NO:467.

SEQ ID NO:474 is the determined cDNA sequence for an alternative splice form of B726P.

SEQ ID NO:475 is the amino acid sequence encoded by SEQ ID NO:474.

SEQ ID NO:476 is the isolated cDNA sequence of B720P.

SEQ ID NO:477 is the cDNA sequence of a known keratin gene.

SEQ ID NO:478 is the amino acid sequence encoded by SEQ ID NO:477.

SEQ ID NO:479 is the determined cDNA sequence for clone 19465.

SEQ ID NO:480 and 481 are PCR primers.

SEQ ID NO:482 is the cDNA sequence for the expressed downstream ORF of B726P.

SEQ ID NO:483 is the amino acid sequence for the expressed recombinant downstream ORF of B726P.

SEQ ID NO:484 is the determined full-length cDNA sequence for B720P.

SEQ ID NO:485 is the amino acid sequence encoded by SEQ ID NO:484.

SEQ ID NO:486 is the determined cDNA sequence of a truncated form of B720P, referred to as B720P-tr.

SEQ ID NO:487 is the amino acid sequence of B720P-tr.

SEQ ID NO:488 is the amino acid sequence of a naturally processed epitope of B726P recognized by B726P-specific CTL.

SEQ ID NO:489 is a DNA sequence encoding the B726P epitope set forth in SEQ ID NO:488.

SEQ ID NO:490 is a DNA sequence encoding a fusion protein wherein mammaglobin is fused to the B726P combined upstream and downstream open reading frame (ORF) (the amino acid sequence of the B726P combined ORF is disclosed herein as SEQ ID NO:475 which is encoded by the DNA sequence of SEQ ID NO:474).

SEQ ID NO:491 is a DNA sequence encoding a fusion protein wherein mammaglobin is fused to the B726P upstream ORF (the amino acid sequence of the B726P upstream ORF is disclosed herein as SEQ ID NO:469 which is encoded by the DNA sequence of SEQ ID NO:463).

SEQ ID NO:492 is a DNA sequence encoding a fusion protein wherein mammaglobin is fused to the B726P downstream ORF (the amino acid sequence of the B726P downstream ORF is disclosed herein as SEQ ID NO:176 which is encoded by the DNA sequence of SEQ ID NO:175).

SEQ ID NO:493 is the amino acid sequence encoded by the DNA sequence of SEQ ID NO:490.

SEQ ID NO:494 is the amino acid sequence encoded by the DNA sequence of SEQ ID NO:491.

SEQ ID NO:495 is the amino acid sequence encoded by the DNA sequence of SEQ ID NO:492.

SEQ ID NO:496 is amino acids 59-78 of SEQ ID NO:493.

SEQ ID NO:497 is amino acids 55-69 of SEQ ID NO:493.

SEQ ID NO:498 is amino acids 13-33 of SEQ ID NO:493.

SEQ ID NO:499 is amino acids 41-60 of SEQ ID NO:493.

SEQ ID NO:500 is amino acids 2-10 of SEQ ID NO:493.

SEQ ID NO:501 is amino acids 47-59 of SEQ ID NO:493.

SEQ ID NO:502 is amino acids 62-74 of SEQ ID NO:493.

SEQ ID NO:503 is amino acids 1-93 of SEQ ID NO:493.

SEQ ID NO:504 is the full-length cDNA sequence for B718P.

SEQ ID NO:505 is the cDNA sequence of the open reading frame of B718P including stop codon.

SEQ ID NO:506 is the cDNA sequence of the open reading frame of B718P without stop codon.

SEQ ID NO:507 is the full-length amino acid sequence of B718P.

SEQ ID NO:508 represents amino acids 1-158 of SEQ ID NO:507.

SEQ ID NO:509 represents amino acids 159-243 of SEQ ID NO:509.

SEQ ID NO:510 is the entire cDNA sequence of the open reading frame, including stop codon, of a first variant of B723P, referred to as B723P-short.

SEQ ID NO:511 is the entire cDNA sequence of the open reading frame, without stop codon, of a first variant of B723P, referred to as B723P-short.

SEQ ID NO:512 is the entire cDNA sequence of the open reading frame, including stop codon, of a second variant of B723P, referred to as B723P-long.

SEQ ID NO:513 is the entire cDNA sequence of the open reading frame, without stop codon, of a second variant of B723P, referred to as B723P-long.

SEQ ID NO:514 is the amino acid sequence of B723P-short.

SEQ ID NO:515 is the amino acid sequence of B723P-long.

SEQ ID NO:516 is amino acids 1-197 of B723P-short.

SEQ ID NO:517 is amino acids 1-232 of B723P-long.

SEQ ID NO:518 is amino acids 198-243 of B723P-short.

SEQ ID NO:519 is amino acids 218-243 of B723P-short.

SEQ ID NO:520-533 are the DNA sequences of epitopes of B726P.

SEQ ID NO:534-547 are the amino acid sequences of epitopes of B726P.

SEQ ID NO:548 is the cDNA sequence of B726P Combined ORF coding_region for expression in *E. coli.*

SEQ ID NO:549 is the cDNA sequence of B726P Upstream ORF coding_region for expression in *E. coli.*

SEQ ID NO:550 is the cDNA sequence of B726P Downstream ORF coding_region for expression in *E. coli.*

SEQ ID NO:551 is the amino acid sequence of B726P Downstream ORF encoded by the cDNA set forth in SEQ ID NO:550.

SEQ ID NO:552 is the amino acid sequence of B726P Upstream ORF with HIS, encoded by the cDNA set forth in SEQ ID NO:549.

SEQ ID NO:553 is the amino acid sequence of B726P Combined ORF correct, encoded by the cDNA set forth in SEQ ID NO:548.

SEQ ID NO:554-563 are PCR primers as described in Example 8.

SEQ ID NO:564 is the cDNA sequence for NY-BR-1, an extended sequence of B726P.

SEQ ID NO:565 is the amino acid sequence for NY-BR-1, an extended sequence of B726P, and encoded by the nucleotide sequence set forth in SEQ ID NO:564.

SEQ ID NO:566 is the cDNA sequence for B726P XC coding region with changes.

SEQ ID NO:567 is the cDNA sequence for B726P XB clone 83686 with 2 changes from the published NY-BR-1 sequence in SEQ ID NO:564.

SEQ ID NO:568 is the cDNA sequence for B726P XB clone 84330 with 4 changes from the published NY-BR-1 sequence in SEQ ID NO:564.

SEQ ID NO:569 is the cDNA sequence for B726P XB clone 84328 with 3 changes from the published NY-BR-1 sequence in SEQ ID NO:564.

SEQ ID NO:570 is the amino acid sequence for B726P XB clone 84328, encoded by the sequence set forth in SEQ ID NO:569.

SEQ ID NO:571 is the amino acid sequence for B726P XB clone 84330, encoded by the sequence set forth in SEQ ID NO:568.

SEQ ID NO:572 is the amino acid sequence for B726P XB clone 83686, encoded by the sequence set forth in SEQ ID NO:567.

SEQ ID NO:573 is the amino acid sequence for B726P XC, encoded by the sequence set forth in SEQ ID NO:566.

SEQ ID NO:574-575 are PCR primers as described in Example 12.

SEQ ID NO:576 is the full-length cDNA sequence for NY-BR-1.1.

SEQ ID NO:577 is the full-length amino acid sequence for NY-BR-1.1, encoded by the nucleotide sequence set forth in SEQ ID NO:576.

SEQ ID NO:578 is amino acids 289-308 of the B726P downstream ORF and corresponds to the peptide recognized by the 220A2.1 antibody.

SEQ ID NO:579 is amino acids 225-244 of the B726P downstream ORF and corresponds to the peptide recognized by the 220A19.1 antibody.

SEQ ID NO:580 is amino acids 232-252 of the B726P downstream ORF and corresponds to the peptide recognized by the 220A19.1 and the 220A43 antibodies.

SEQ ID NO:581 is amino acids 73-92 of the B726P downstream ORF and corresponds to the peptide recognized by the 220A94.1 antibody.

SEQ ID NO:582 is amino acids 145-164 of the B726P downstream ORF and corresponds to the peptide recognized by the 220A 151 0.1 and 220A86 antibodies.

SEQ ID NO:583 is amino acids 153-172 of the B726P downstream ORF and corresponds to the peptide recognized by the 220A 151 0.1 and 220A86 antibodies.

SEQ ID NO:584 is amino acids 1-20 of the B726P downstream ORF and corresponds to the peptide recognized by purified B726 polyclonal antibodies.

SEQ ID NO:585 is amino acids 9-28 of the B726P downstream ORF and corresponds to the peptide recognized by purified B726 polyclonal antibodies.

SEQ ID NO:586 is amino acids 17-36 of the B726P downstream ORF and corresponds to the peptide recognized by purified B726 polyclonal antibodies.

SEQ ID NO:587 is amino acids 24-44 of the B726P downstream ORF and corresponds to the peptide recognized by purified B726 polyclonal antibodies.

SEQ ID NO:588 is amino acids 97-116 of the B726P downstream ORF and corresponds to the peptide recognized by purified B726 polyclonal antibodies.

SEQ ID NO:589 is amino acids 105-124 of the B726P downstream ORF and corresponds to the peptide recognized by purified B726 polyclonal antibodies.

SEQ ID NO:590 is amino acids 113-132 of the B726P downstream ORF and corresponds to the peptide recognized by purified B726 polyclonal antibodies.

SEQ ID NO:591 is amino acids 121-140 of the B726P downstream ORF and corresponds to the peptide recognized by purified B726 polyclonal antibodies.

SEQ ID NO:592 is amino acids 129-148 of the B726P downstream ORF and corresponds to the peptide recognized by purified B726 polyclonal antibodies.

SEQ ID NO:593 is amino acids 137-156 of the B726P downstream ORF and corresponds to the peptide recognized by purified B726 polyclonal antibodies.

SEQ ID NO:594 is the amino acid sequence of peptide #2732 and corresponds to amino acids 1-20 of the B726P downstream ORF.

SEQ ID NO:595 is the amino acid sequence of peptide #2733 and corresponds to amino acids 11-30 of the B726P downstream ORF.

SEQ ID NO:596 is the amino acid sequence of peptide #2734 and corresponds to amino acids 21-40 of the B726P downstream ORF.

SEQ ID NO:597 is the amino acid sequence of peptide #2735 and corresponds to amino acids 31-50 of the B726P downstream ORF.

SEQ ID NO:598 is the amino acid sequence of peptide #2736 and corresponds to amino acids 41-60 of the B726P downstream ORF.

SEQ ID NO:599 is the amino acid sequence of peptide #2737 and corresponds to amino acids 51-70 of the B726P downstream ORF.

SEQ ID NO:600 is the amino acid sequence of peptide #2738 and corresponds to amino acids 61-80 of the B726P downstream ORF.

SEQ ID NO:601 is the amino acid sequence of peptide #2739 and corresponds to amino acids 71-90 of the B726P downstream ORF.

SEQ ID NO:602 is the amino acid sequence of peptide #2740 and corresponds to amino acids 81-100 of the B726P downstream ORF.

SEQ ID NO:603 is the amino acid sequence of peptide #2741 and corresponds to amino acids 91-110 of the B726P downstream ORF.

SEQ ID NO:604 is the amino acid sequence of peptide #2742 and corresponds to amino acids 101-120 of the B726P downstream ORF.

SEQ ID NO:605 is the amino acid sequence of peptide #2743 and corresponds to amino acids 111-130 of the B726P downstream ORF.

SEQ ID NO:606 is the amino acid sequence of peptide #2744 and corresponds to amino acids 121-140 of the B726P downstream ORF.

SEQ ID NO:607 is the amino acid sequence of peptide #2745 and corresponds to amino acids 130-151 of the B726P downstream ORF.

SEQ ID NO:608 is the amino acid sequence of peptide #2746 and corresponds to amino acids 141-160 of the B726P downstream ORF.

SEQ ID NO:609 is the amino acid sequence of peptide #2747 and corresponds to amino acids 151-170 of the B726P downstream ORF.

SEQ ID NO:610 is the amino acid sequence of peptide #2748 and corresponds to amino acids 161-180 of the B726P downstream ORF.

SEQ ID NO:611 is the amino acid sequence of peptide #2749 and corresponds to amino acids 170-190 of the B726P downstream ORF.

SEQ ID NO:612 is the amino acid sequence of peptide #2750 and corresponds to amino acids 181-200 of the B726P downstream ORF.

SEQ ID NO:613 is the amino acid sequence of peptide #2751 and corresponds to amino acids 191-210 of the B726P downstream ORF.

SEQ ID NO:614 is the amino acid sequence of peptide #2752 and corresponds to amino acids 201-220 of the B726P downstream ORF.

SEQ ID NO:615 is the amino acid sequence of peptide #2753 and corresponds to amino acids 211-230 of the B726P downstream ORF.

SEQ ID NO:616 is the amino acid sequence of peptide #2765 and corresponds to amino acids 221-240 of the B726P downstream ORF.

SEQ ID NO:617 is the amino acid sequence of peptide #2766 and corresponds to amino acids 231-250 of the B726P downstream ORF.

SEQ ID NO:618 is the amino acid sequence of peptide #2767 and corresponds to amino acids 240-260 of the B726P downstream ORF.

SEQ ID NO:619 is the amino acid sequence of peptide #2768 and corresponds to amino acids 251-270 of the B726P downstream ORF.

SEQ ID NO:620 is the amino acid sequence of peptide #2769 and corresponds to amino acids 261-280 of the B726P downstream ORF.

SEQ ID NO:621 is the amino acid sequence of peptide #2770 and corresponds to amino acids 271-290 of the B726P downstream ORF.

SEQ ID NO:622 is the amino acid sequence of peptide #2771 and corresponds to amino acids 281-300 of the B726P downstream ORF.

SEQ ID NO:623 is the amino acid sequence of peptide #2772 and corresponds to amino acids 291-310 of the B726P downstream ORF.

SEQ ID NO:624 is the amino acid sequence of peptide #2773 and corresponds to amino acids 298-317 of the B726P downstream ORF.

SEQ ID NO:625 is the amino acid sequence of peptide #3535 of B726P.

SEQ ID NO:626 is the amino acid sequence of peptide #3536 of B726P.

SEQ ID NO:627 is the amino acid sequence of peptide #3534 of B726P.

DETAILED DESCRIPTION OF THE INVENTION

The present invention is directed generally to compositions and their use in the therapy and diagnosis of cancer, particularly breast cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" "is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NO:1-61, 63-175, 178, 180, 182-468, 474, 476, 477, 479, 482, 484, 486, 489-492, 504-506, 510-513, 520-533, 548-550, 564, 566-569, and 576, or a sequence that hybridizes under moderately stringent conditions, or, alternatively, under highly stringent conditions, to a polynucleotide sequence set forth in any one of SEQ ID NO:1-61, 63-175, 178, 180, 182-468, 474, 476, 477, 479, 482, 484, 486, 489-492, 504-506, 510-513, 520-533, 548-550, 564, 566-569, and 576. Certain other illustrative polypeptides of the invention comprise amino acid sequences as set forth in any one of SEQ ID NO:62, 176, 179, 181, 469-473, 475, 478, 483, 485, 487, 488, 493-503, 507-509, 514-519, 534-547, 551-553, 565, 570-573, and 577-627.

The polypeptides of the present invention are sometimes herein referred to as breast tumor proteins or breast tumor polypeptides, as an indication that their identification has been based at least in part upon their increased levels of expression in breast tumor samples. Thus, a "breast tumor polypeptide" or "breast tumor protein," refers generally to a polypeptide sequence of the present invention, or a polynucleotide sequence encoding such a polypeptide, that is expressed in a substantial proportion of breast tumor samples, for example preferably greater than about 20%, more preferably greater than about 30%, and most preferably greater than about 50% or more of breast tumor samples tested, at a level that is at least two fold, and preferably at least five fold, greater than the level of expression in normal tissues, as determined using a representative assay provided herein. A breast tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with breast cancer. Screening for immunogenic activity can be performed using techniques well known to the skilled artisan. For example, such screens can be performed using methods such as those described in Harlow and Lane, Antibodies: A Laboratory Manual, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology,* 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NO:62, 176, 179, 181, 469-473, 475, 478, 483, 485, 487, 488, 493-503, 507-509, 514-519, 534-547, 551-553, 565, 570-573, and 577-627, or those encoded by a polynucleotide sequence set forth in a sequence of SEQ ID NO:1-61, 63-175, 178, 180, 182-468, 474, 476, 477, 479, 482, 484, 486, 489-492, 504-506, 510-513, 520-533, 548-550, 564, 566-569, and 576.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy-the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86-91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al., *Infection and Immun.* (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NO:1-61, 63-175, 178, 180, 182-468, 474, 476, 477, 479, 482, 484, 486, 489-492, 504-506, 510-513, 520-533, 548-550, 564, 566-569, and 576, complements of a polynucleotide sequence set forth in any one of SEQ ID NO:1-61, 63-175, 178, 180, 182-468, 474, 476, 477, 479, 482, 484, 486, 489-492, 504-506, 510-513, 520-533, 548-550, 564, 566-569, and 576, and degenerate variants of a polynucleotide sequence set forth in any one of SEQ ID NO:1-61, 63-175, 178, 180, 182-468, 474, 476, 477, 479, 482, 484, 486, 489-492, 504-506, 510-513, 520-533, 548-550, 564, 566-569, and 576. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NO:1-61, 63-175, 178, 180, 182-468, 474, 476, 477, 479, 482, 484, 486, 489-492, 504-506, 510-513, 520-533, 548-550, 564, 566-569, and 576, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990)

Unified Approach to Alignment and Phylogenes pp. 626-645 *Methods in Enzymology vol.* 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R.R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al, 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1(4): 225-32; Peris et al., Brain Res Mol Brain Res. 1998 Jun. 15; 57(2):310-20; U.S. Pat. No. 5,801,154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15; 25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol. Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al, Proc Natl Acad Sci USA. 1992 Aug. 15; 89(16):

7305-9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or *Neurospora* VS RNA motif. Examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; *Neurospora* VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol 11), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June; 15(6): 224-9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6; 254(5037):1497-500; Hanvey et al., Science. 1992 Nov. 27; 258(5087):1481-5; Hyrup and Nielsen, Bioorg Med. Chem. 1996 January; 4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med. Chem. 1995 April; 3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med. Chem. 1995 April; 3(4):437-45; Petersen et al., J Pept Sci. 1995 May-June; 1(3):175-83; Orum et al., Biotechniques. 1995 September; 19(3):472-80; Footer et al., Biochemistry. 1996 Aug. 20; 35(33):10673-9; Griffith et al., Nucleic Acids Res. 1995 Aug. 11; 23(15):3003-8; Pardridge et al., Proc Natl Acad Sci U S A. 1995 Jun. 6; 92(12):5592-6; Boffa et al., Proc Natl Acad Sci USA. 1995 Mar. 14; 92(6):1901-5; Gambacorti-Passerini et al., Blood. 1996 Aug. 15; 88(4):1411-7; Armitage et al., Proc Natl Acad Sci USA. 1997 Nov. 11; 94(23):12320-5; Seeger et al., Biotechniques. 1997 September; 23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15; 65(24):3545-9) and Jensen et al. (Biochemistry. 1997 Apr. 22; 36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as breast cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "$F(ab')_2$ " fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) Proc. Nat. Acad. Sci. USA 86:4220-4224; Shaw et al. (1987) J. Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml-100 μg/ml, preferably 200 ng/ml-25 μg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as *Bacillus-Calmette-Guerrin*) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., *Proc. Natl. Acad. Sci. USA* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745-1749, 1993 and reviewed by Cohen, Science 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium* quinoa saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{-A-R}, \qquad (I)$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{1-2}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antitumor immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit. Rev Ther Drug Carrier Syst 1998; 15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit. Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol. Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit. Rev Ther Drug Carrier Syst. 1988; 5(1):1-20; zur Muhlen et al., Eur J Pharm Biopharm. 1998 March; 45(2):149-55; Zambaux et al. J Controlled Release. 1998 Jan. 2; 50(1-3):31-40; and U.S. Pat. No. 5,145,684.

Cancer Therapeutic Methods

In further aspects of the present invention, the pharmaceutical compositions described herein may be used for the treatment of cancer, particularly for the immunotherapy of breast cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.11 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions Methods and Kits

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with polypeptide (e.g., 5-25 μg/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.,* 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

Example 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO:1-61, 72 and 73, respectively. Comparison of these cDNA sequences with known sequences in the gene bank using the EMBL and GenBank databases (Release 97) revealed no significant homologies to the sequences provided in SEQ ID NO:14, 21, 22, 27, 29, 30, 32, 38, 44, 45, 53, 57, 72 and 73. The sequences of SEQ ID NO:1, 3, 16, 17, 34, 48, 60 and 61 were found to represent known human genes. The sequences of SEQ ID NO:2, 4, 23, 39 and 50 were found to show some similarity to previously identified non-human genes. The remaining clones (SEQ ID NO:5-13, 15, 18-20, 24-26, 28, 31, 33, 35-37, 40-43, 46, 47, 49, 51, 52, 54-56, 58 and 59) were found to show at least some degree of homology to previously identified expressed sequence tags (ESTs).

Further studies resulted in the isolation of the full-length cDNA sequence for the clone of SEQ ID NO:57 (referred to as B718P). By computer analysis, the full-length sequence was found to contain a putative transmembrane domain at amino acids 137-158. The full-length cDNA sequence of B718P is provided in SEQ ID NO:504, with the cDNA sequence of the open reading frame including stop codon being provided in SEQ ID NO:505 and the cDNA sequence of the open reading frame without stop codon being provided in SEQ ID NO:506. The full-length amino acid sequence of B718P is provided is SEQ ID NO:507. SEQ ID NO:508 represents amino acids 1-158 of B718P, and SEQ ID NO:509 represents amino acids 159-243 of B718P.

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO:40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO:41 and 48 were found to be over-expressed in breast tumor and expressed at low levels in all other tissues tested, with the exception of bone marrow. The clone of SEQ ID NO:42 was found to be over-expressed in breast tumor and expressed at low levels in all other tissues tested except bone marrow and spinal cord. The clone of SEQ ID NO:43 was found to be over-expressed in breast tumor and expressed at low levels in all other tissues tested with the exception of spinal cord, heart and small intestine. The clone of SEQ ID NO:51 was found to be over-expressed in breast tumor and expressed at low levels in all other tissues tested with the exception of large intestine. The clone of SEQ ID NO:54 was found to be over-expressed in breast tumor and expressed at low levels in all other tissues tested with the exception of PBMC, stomach and small intestine. The clone of SEQ ID NO:56 was found to be over-expressed in breast tumor and expressed at low levels in all other tissues tested with the exception of large and small intestine, human mammary epithelia cells and SCID mouse-passaged breast tumor. The clone of SEQ ID NO:60 was found to be over-expressed in breast tumor and expressed at low levels in all other tissues tested with the exception of spinal cord and heart. The clone of SEQ ID NO:61 was found to be over-expressed in breast tumor and expressed at low levels in all other tissues tested with the exception of small intestine. The clone of SEQ ID NO:72 was found to be over-expressed in breast tumor and expressed at low levels in all other tissues tested with the exception of colon and salivary gland.

The results of a Northern blot analysis of the clone SYN18C6 (SEQ ID NO:40) are shown in FIG. 1. A predicted protein sequence encoded by SYN18C6 is provided in SEQ ID NO:62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined cDNA sequences for these clones are provided in SEQ ID NO:63-87. Comparison of the sequences of SEQ ID NO:74-87 with those in the gene bank as described above, revealed homology to previously identified human genes. No significant homologies were found to the sequences of SEQ ID NO:63-73.

Three DNA isoforms for the clone B726P (partial sequence provided in SEQ ID NO:71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P] dCTP. The sequence of the primer employed for this PCR is provided in SEQ ID NO:177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO:175, with the corresponding predicted amino acid sequence being provided in SEQ ID NO:176. The determined cDNA sequence of the isoform B726P-74 is provided in SEQ ID NO:178, with the corresponding predicted amino acid sequence being provided in SEQ ID NO:179. The determined cDNA sequence of the isoform B726P-79 is provided in SEQ ID NO:180, with the corresponding predicted amino acid sequence being provided in SEQ ID NO:181.

Efforts to obtain a full-length clone of B726P using standard techniques led to the isolation of five additional clones that represent additional 5' sequence of B726P. These clones appear to be alternative splice forms of the same gene. The determined cDNA sequences of these clones are provided in SEQ ID NO:464-468, with the predicted amino acid sequences encoded by SEQ ID NO:464-467 being provided in SEQ ID NO:470-473, respectively. Using standard computer techniques, a 3,681 bp consensus DNA sequence (SEQ ID NO:463) was created that contains two large open reading frames. The downstream ORF encodes the amino acid sequence of SEQ ID NO:176. The predicted amino acid sequence encoded by the upstream ORF is provided in SEQ ID NO:469. Subsequent studies led to the isolation of an additional splice form of B726P that has 184 bp insert relative to the other forms. This 184 bp insert causes a frameshift that brings the down stream and upstream ORFs together into a single ORF that is 1002 aa in length. The determined cDNA sequence of this alternative splice form is disclosed in SEQ ID NO:474, with the corresponding amino acid sequence being provided in SEQ ID NO:475.

Comparison of the cDNA sequence of SEQ ID NO:63 (referred to as B723P) with the sequences in the GeneSeq™ DNA database showed matches to 5 DNA sequences (Accession nos. A26456, A37144, A26424, V84525 and T22133), 4 of which appear to represent the full-length sequence of the gene. Three of these sequences encode a 243 amino acid open reading frame (ORF), while one of the DNA sequences (Accession no. A37144) contains an extra C at position 35, resulting in a 278 amino acid ORF. The open reading frame, including stop codon, of the first variant of B723P (referred to as B723P-short) is provided in SEQ ID NO:510, with the open reading frame without stop codon being provided in SEQ ID NO:511. The open reading frame, including stop codon, of the second variant of B723P (referred to as B723P-long) is provided in SEQ ID NO:512, with the open reading frame without stop codon being provided in SEQ ID NO:513. The amino acid sequences of B723P-short and B723P-long are provided in SEQ ID NO:514 and 515, respectively. Computer analysis of these sequences demonstrated the presence of putative transmembrane domains at amino acids 233-252 of the B723P-long ORF and amino acids 198-217 of the B723P-short ORF. SEQ ID NO:516, 518 and 519 represent amino acids 1-197, 198-243 and 218-243, respectively of B723P-short. SEQ ID NO:517 represents amino acids 1-232 of B723P-long.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO:182-251 and 479 were 2 or more fold over-expressed in human breast tumor tissues over normal human tissues. No significant homologies were found for nineteen of these clones, including, SEQ ID NO:185, 186, 194, 199, 205, 208, 211, 214-216, 219, 222, 226, 232, 236, 240, 241, 245, 246 and 479, with the exception of some previously identified expressed sequence tags (ESTs). The remaining clones share some homology to previously identified genes, specifically SEQ ID NO:181-184, 187-193, 195-198, 200-204, 206, 207, 209, 210, 212, 213, 217, 218, 220, 221, 223-225, 227-231, 233-235, 237-239, 242-244 and 247-251.

One of the cDNA clones isolated by PCR subtraction as described above (SEQ ID NO:476; referred to as B720P) which was shown by microarray to be over-expressed in breast tumor tissues, was found to be identical to a known keratin gene. The full-length cDNA sequence of the known keratin gene is provided in SEQ ID NO:477, with the corresponding amino acid sequence being provided in SEQ ID NO:478. Primers were generated based on the sequence of SEQ ID NO:477 and used to clone full-length cDNA from mRNA which was obtained from total RNA showing high expression of B720P in real-time PCR analysis. Products were then cloned and sequenced. The determined full-length cDNA sequence for B720P is provided in SEQ ID NO:484, with the corresponding amino acid sequence being provided in SEQ ID NO:485.

In further studies, a truncated form of B720P (referred to as B720P-tr) was identified in breast carcinomas. This antigen was cloned from mRNA derived from total breast tumor RNA that showed high expression of B720P-tr in real-time PCR analysis. mRNA was used to generate a pool of cDNA which was then used as a template to amplify the cDNA corresponding to B720P-tr by PCR. The determined cDNA sequence for B720P-tr is provided in SEQ ID NO:486. B720P-tr has an ORF of 708 base pairs which encodes a 236 amino acid protein (SEQ ID NO:487). The size of the transcript was confirmed by northern analysis.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO:185) was over-expressed in the majority of breast tumors and also in the SCID breast tumors tested (refer to Example 2); additionally, over-expression was found in a majority of normal breast tissues. Clone 19483.1 (SEQ ID NO:216) was over-expressed in a few breast tumors, with no over-expression in any normal tissues tested. Clone 19470.1 (SEQ ID NO:219) was found to be slightly over-expressed in some breast tumors. Clone 19468.1 (SEQ ID NO:222) was found to be slightly over-expressed in the majority of breast tumors tested. Clone 19505.1 (SEQ ID NO:226) was found to be slightly over-expressed in 50% of breast tumors, as well as in SCID tumor tissues, with some degree of over-expression in found in normal breast. Clone 1509.1 (SEQ ID NO:232) was found to be over-expressed in very few breast tumors, but with a certain degree of over-expression in metastatic breast tumor tissues, as well as no significant over-expression found in normal tissues. Clone 19513.1 (SEQ ID NO:236) was shown to be slightly over-expressed in few breast tumors, with no significant over-expression levels found in normal tissues. Clone 19575.1 (SEQ ID NO:240) showed low level over-expression in some breast tumors and also in normal breast. Clone 19560.1 (SEQ ID NO:241) was over-expressed in 50% of breast tumors tested, as well as in some normal breast tissues. Clone 19583.1 (SEQ ID NO:245) was slightly over-expressed in some breast tumors, with very low levels of over-expression found in normal tissues. Clone 19587.1 (SEQ ID NO:246) showed low level over-expression in some breast tumors and no significant over-expression in normal tissues.

Clone 19520.1 (SEQ ID NO:233), showing homology to clone 102D24 on chromosome 11q13.31, was found to be over-expressed in breast tumors and in SCID tumors. Clone 19517.1 (SEQ ID NO:237), showing homology to human PAC 128M19 clone, was found to be slightly over-expressed in the majority of breast tumors tested. Clone 19392.2 (SEQ ID NO:247), showing homology to human chromosome 17, was shown to be over-expressed in 50% of breast tumors tested. Clone 19399.2 (SEQ ID NO:250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO:405-415. Comparison of these sequences to those in the public database, as outlined above, revealed homologies between the sequences of SEQ ID NO:408, 411, 413 and 414 and previously isolated ESTs. The sequences of SEQ ID NO:405-407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO:316-404. Comparison of these sequences with those in the public database, as described above, revealed no significant homologies to the sequence of SEQ ID NO:366. The sequences of SEQ ID NO:321-325, 343, 354, 368, 369, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO:427-439. The determined cDNA sequences of 22 clones identified using the modified Gemtools analysis are provided in SEQ ID NO:440-462, wherein SEQ ID NO:453 and 454 represent two partial, non-overlapping, sequences of the same clone.

Comparison of the clone sequences of SEQ ID NO:436 and 437 (referred to as 263G6 and 262B2) with those in the public databases, as described above, revealed no significant homologies to previously identified sequences. The sequences of SEQ ID NO:427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-60,61, 2BT1-59, 2BT1-52 and 2BT1-40, respectively) showed some homology to previously isolated expressed sequences tags (ESTs). The sequences of SEQ ID NO:428, 430, 432, 433, 434, 439, 440, 442, 447, 448, 449, 451, 452 and 455-462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

Example 2

Isolation and Characterization of Breast Tumor Polypeptides Obtained by PCR-Based Subtraction Using SCID-Passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071-13073, 13075, 13078, 13079, 13081, 13082, 13092, 13097, 13101, 13102, 13131, 13133, 13119, 13135, 13139, 13140, 13146-13149, and 13151, with the exception of some previously identified expressed sequence tags (ESTs). The determined cDNA sequences for these clones are provided in SEQ ID NO:88-116, respectively. The isolated cDNA sequences of SEQ ID NO:117-140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414-14416, 14419, 14426, and 14427, with the exception of some previously identified expressed sequence tags (ESTs). The determined cDNA sequences for these clones are provided in SEQ ID NO:141-159, respectively. The isolated cDNA sequences of SEQ ID NO:160-174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO:252-268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO:269-314, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold overexpression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO:416-426, respectively.

Example 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 4

Elicitation of Breast Antigen-Specific CTL Responses in Human Blood

This Example illustrates the ability of the breast-specific antigen B726P to elicit a cytotoxic T lymphocyte (CTL) response in peripheral blood lymphocytes from normal humans.

Autologous dendritic cells (DC) were differentiated from monocyte cultures derived from PBMC of a normal donor by growth for five days in RPMI medium containing 10% human serum, 30 ng/ml GM-CSF and 30 ng/ml IL-4. Following five days of culture, DC were infected overnight with adenovirus expressing recombinant B726P (downstream ORF; SEQ ID NO:176) at an M.O.I. of 2.5 and matured for 8 hours by the addition of 2 micrograms/ml CD40 ligand. CD8 positive cells were enriched for by the depletion of CD4 and CD14-positive cells. Priming cultures were initiated in individual wells of several 96-well plates with the cytokines IL-6 and IL-12. These cultures were restimulated in the presence of IL-2 using autologous fibroblasts treated with IFN-gamma and transduced with B726P and CD80. Following three stimulation cycles, the presence of B726P-specific CTL activity was assessed in IFN-gamma Elispot assays (Lalvani et al., *J. Exp. Med.* 186:859-865, 1997) using IFN-gamma treated autologous fibroblasts transduced to express either B726P or an irrelevant, control, antigen as antigen presenting cells (APC). Of approximately 96 lines, one line (referred to as 6-2B) was identified that appeared to specifically recognize B726P-transduced APC but not control antigen-transduced APC. This microculture was cloned using standard protocols. B726P-specific CTL were identified by Elispot analysis and expanded for further analysis. These CTL clones were demonstrated to recognize B726P-expressing fibroblasts, but not the control antigen MART-1, using chromium-51 release assays. Furthermore, using a panel of allogeneic fibroblasts transduced with B726P in antibody blocking assays, the HLA restriction element for these B726P-specific CTL was identified as HLA-B*1501.

In order to define more accurately the location of the epitope recognized by the B726P-specific CTL clones, a deletion construct comprising only the N-terminal half (a.a. 1-129) of B726P (referred to as B726Pdelta3') was constructed in the pBIB retroviral expression plasmid. This plasmid, as well as other plasmids containing B726P, were transfected into COS-7 cells either alone or in combination with a plasmid expressing HLA-B*1501. Approximately 48 hours after transfection, a B726P-specific CTL clone (1-9B) was added at approximately $10^4$ cells per well. The cells were harvested the next day and the amount of IFN-gamma released was measured by ELISA. The CTL responded above background (EGFP) to COS-7 cells that had been transfected with both B726P and HLA-B*1501. There was no response above background to COS-7 cells that had been transfected with either B726P or HLA-B*1501 alone. Importantly, a higher response was seen with COS-7 cells that had been transfected with both HLA-B*1501 and B726Pdelta3'. This result indicated that the epitope was likely to be located in the N-terminal region (a.a. 1-129) of B726P. This region was examined and amino acid sequences that corresponded to the HLA-B*1501 peptide binding motif (*J. Immunol.* 1999, 162: 7277-84) were identified and synthesized. These peptides were pulsed at 10 ug/ml onto autologous B-LCL overnight. The next day, the cells were washed and the ability of the cells to stimulate the B726P-specific CTL clone 1-9B was assayed in a IFN-gamma ELISPOT assay. Of the eleven peptides tested, only one peptide, having the amino acid sequence SLTKRASQY (a.a. 76-84 of B726P; SEQ ID NO:488) was recognized by the CTL clone. This result identifies this peptide as being a naturally-processed epitope recognized by this B726P-specific CTL clone.

Figure 2:
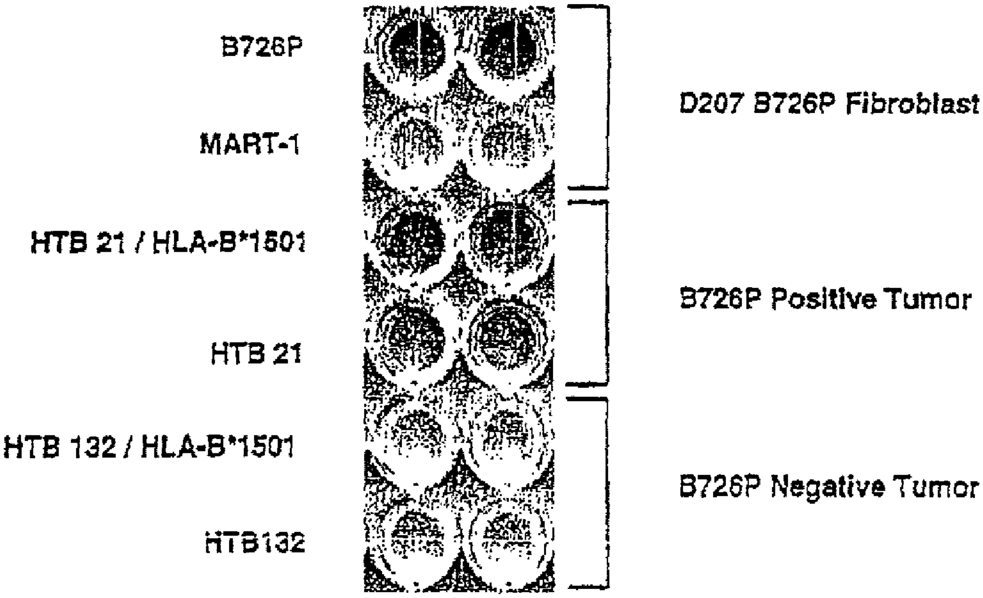
FIG. 2 shows the results of an IFN-gamma ELISPOT assay demonstrating that the B726P-specific CTL clone recognizes and lyses breast tumor cell lines expressing B726P.

In further studies, a panel of breast tumor cell lines obtained from the American Type Culture Collection (Manassas, Va.), was analyzed using real time PCR to determine their B726P message level. The cell line that expressed the highest level of B726P (referred to as HTB21) and a line that expressed no B726P (referred to as HTB132) were transduced with HLA-B*1501. These cell lines were grown up and analyzed using FACS to determine their B1501 expression. The line HTB 21 was found to endogenously express B1501. To determine if clone 1-9A would recognize the tumor cell line HTB21, an IFN-gamma ELISPOT assay was performed using 20,000 T cells, low dose IL-2 (5 ug/ml), and 20,000 of the following targets: autologous B726P or Mart-1 fibroblasts, untransduced or B1501-transduced HTB21; or untransduced or B1501-transduced HTB132. These were incubated overnight and the assay was developed the next day. The results of this assay are shown in FIG. 2. These studies demonstrate that B726P-specific CTL can recognize and lyse breast tumor cells expressing B726P.

Example 5

Identification of Immunogenic Cd4 T Cell Epitopes in Breast Antigens

Immunogenic CD4 T cell epitopes derived from the breast antigen B726P were identified as follows.

A total of thirty-five 20-mer peptides overlapping by 12 amino acids and derived from the downstream ORF of B726P (corresponding to amino acids 1-317 of SEQ ID NO:176) were generated by standard procedure. Dendritic cells (DC) were derived from PBMC of a normal male donor using GMCSF and IL-4 by standard protocol. Purified CD4 T cells were generated from the same donor as the DC using MACS beads and negative selection of PBMCs. DC were pulsed overnight with pools of the 20-mer peptides, with each peptide at an individual concentration of 0.5 micrograms/mL. Pulsed DC were washed and plated at 10,000 cells/well of 96-well U bottom plates, and purified CD4 T cells were added at 100,000 cells/well. Cultures were supplemented with 10 ng/mL IL-6 and 5 ng/mL IL-12 and incubated at 37° C. Cultures were restimulated as above on a weekly basis using DC made and pulsed as above as the antigen presenting cell, supplemented with 10 u/mL IL-2 and 5 ng/mL IL-7. Following three in vitro stimulation cycles (the initial priming+two restimulations), cell lines (each corresponding to one well) were tested for specific proliferation and cytokine production in response to the stimulating pool versus an irrelevant pool of peptides derived from unrelated antigens. A number of individual CD4 T cell lines (36/672 by IFN-gamma and 64/672 by proliferation) demonstrated significant cytokine release (IFN-gamma) and proliferation in response to the B726P peptide pools but not to the control peptide pool. Twenty-five of these T cell lines were restimulated on the appropriate pool of B726P peptides and reassayed on autologous DC pulsed with either the individual peptides or recombinant B726P protein made in *E. coli*. Approximately 14 immunogenic peptides were recognized by the T cells from the entire set of peptide antigens tested. The amino acid sequences of these 14 peptides are provided in SEQ ID NO:534-547, with the corresponding DNA sequences being provided in SEQ ID NO:520-533, respectively. In some cases the peptide reactivity of the T cell line could be mapped to a single peptide but some could be mapped to more than one peptide in each pool. Thirteen of the fifteen T cell lines recognized the recombinant B726P protein. These results demonstrate that 13 of the 14 peptide sequences (SEQ ID NO:534-542 and 544-547) may be naturally processed CD4 epitopes of the B726P protein.

Example 6

Preparation and Characterization of Antibodies Against Breast Tumor Antigen B726P Polyclonal antibodies against both the downstream (SEQ ID NO:176) and upstream (SEQ ID NO:469) ORF of the breast tumor antigen B726P were prepared as follows.

The downstream or upstream ORF of B726P expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2L-baffled Erlenmeyer flask. When the Optical Density (at 560 nm) of the culture reached 0.4-0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10-20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, such as HiPrepQ (Biorad), was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of the B726P antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12-24 hours followed by centrifugation.

Ninety-six well plates were coated with B726P antigen by incubating with 50 microliters (typically 1 microgram) of recombinant protein at 4° C. for 20 hours. 250 Microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the calorimetric reaction was stopped with 100 microliters of 1N $H_2SO_4$ and read immediately at 450 nm. All the polyclonal antibodies showed immunoreactivity to the appropriate B726P antigen.

B) Preparation of Polyclonal Antibodies Against B709P and B720P

The breast antigens B709P (SEQ ID NO:62) and B720P (SEQ ID NO:485) expressed in an *E. coli* recombinant expression system were grown overnight in LB Broth with the appropriate antibiotics at 37° C. in a shaking incubator. Ten ml of the overnight culture was added to 500 ml of 2×YT plus appropriate antibiotics in a 2L-baffled Erlenmeyer flask. When the optical density (at 560 nanometers) of the culture reached 0.4-0.6, the cells were induced with IPTG (1 mM). Four hours after induction with IPTG, the cells were harvested by centrifugation. The cells were washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, the mixture was run through a French Press at a pressure of 16,000 psi. The cells were centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature (RT) with continuous agitation. After incubation, the resin and protein mixture were poured through a disposable column and the flow through was collected. The column was then washed with 10-20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. The proteins were then vialed after filtration through a 0.22-micron filter and frozen until needed for immunization.

Four hundred micrograms of antigen was combined with 100 micrograms of muramyldipeptide (MDP). An equal volume of Incomplete Freund's Adjuvant (IFA) was added and mixed, and the mixture was injected into a rabbit. The rabbit was boosted with 100 micrograms of antigen mixed with an equal volume of IFA every four weeks. The animal was bled seven days following each boost. Sera was generated by incubating the blood at 4° C. for 12-24 hours followed by centrifugation.

The reactivity of the polyclonal antibodies to recombinant antigen (B709P or B720P) was determined by ELISA as follows. Ninety-six well plates were coated with antigen by incubating with 50 microliters (typically 1 microgram) at 4° C. for 20 hrs. 250 microliters of BSA blocking buffer was added to the wells and incubated at RT for 2 hrs. Plates were washed 6 times with PBS/0.01% Tween. Rabbit sera were diluted in PBS. Fifty microliters of diluted sera was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB Microwell Peroxidase Substrate was added to each well. Following a 15-minute incubation in the dark at RT, the calorimetric reaction was stopped with 100 microliters of 1N $H_2SO_4$ and read immediately at 450 nm. The polyclonal antibodies showed immunoreactivity to the appropriate antigen.

Example 7

Protein Expression of Breast Tumor Antigens

The downstream ORF of B726P (SEQ ID NO:176), together with a C-terminal 6×His Tag, was expressed in insect cells using the baculovirus expression system as follows.

The cDNA for the full-length downstream ORF of B726P was PCR amplified using the primers of SEQ ID NO:480 and 481. The PCR product with the expected size was recovered from agarose gel, restriction digested with EcoRI and Hind III, and ligated into the transfer plasmid pFastBac1, which was digested with the same restriction enzymes. The sequence of the insert was confirmed by DNA sequencing.

The recombinant transfer plasmid pFBB726P was used to make recombinant bacmid DNA and virus using the Bac-To-Bac Baculovirus expression system (BRL Life Technologies, Gaithersburg, Md.). High Five cells were infected with the recombinant virus BVB726P to produce protein. The cDNA and amino acid sequences of the expressed B726P recombinant protein are provided in SEQ ID NO:482 and 483, respectively.

Example 8

Generation of Constructs for Protein Expression of B726P in *E. coli*

Three different open reading frames (ORFs) of B726P were subcloned into pPDM, a modified pET28 vector for expression in *E. coli.*

Construct for the expression of B726P Upstream ORF in *E. coli* (cDNA: SEQ ID NO:549; amino acid: SEQ ID NO:552):

The partial B726P upstream ORF (A) from clone 23113 was PCR amplified with the following primers:

```
PDM-416
                                          (SEQ ID NO: 554)
5' gtcggctccatgagtcccgcaaaag 3' Tm 63° C.

PDM-431
                                          (SEQ ID NO: 555)
5' cgagaattcaatacttaagaagaccatctttaccag 3'
Tm 61° C.
```

The amplification conditions were as follows 10 μl 10× Pfu buffer, 1 μl 10 μM dNTPs, 2 μl 10 μM each oligo, 83 μl sterile water, 1.5 μl Pfu DNA polymerase (Stratagene, La Jolla, Calif.), 1 μl PCR 23113. The reaction was first denatured for 2 minutes at 96° C., followed by 40 cylces of 96° C. for 20 seconds, 62° C. for 15 seconds, and extension at 72° C. for 2 minutes. This was followed by a final extension of 72° C. for 4 minutes.

The second partial B726P upstream ORF (B) from clone 19310 was PCR amplified with the following primers:

```
PDM-432
                                          (SEQ ID NO: 556)
5' cataagcttaaggctaactgcggaatgaaag 3' Tm 63° C.

PDM-427
                                          (SEQ ID NO: 557)
5' cccgcagaattcaacatgcaattttcatgtaagag 3'
Tm 62° C.
```

The amplification and cycling conditions were as described above. The first PCR product was digested with EcoRI and cloned into pPDM His (a modified pET28 vector) that had been digested with EcoRI and Eco72I. The second PCR product was digested with BfrI and EcoRI and cloned into the resulting construct: pPDM B726P UP-A-5 at the EcoRI and BfrI sites. The construct (PPDM B726P Up-4) was confirmed to be correct through sequence analysis and transformed into BL21 (DE3) pLys S and BL21 CodonPlus RIL (DE3) cells. Protein expression was confirmed by Coomassie stained SDS-PAGE and N-terminal protein sequence analysis.

Construct for B726P D-ORF expression in *E. coli* (cDNA: SEQ ID NO:550; amino acid: SEQ ID NO:551):

The B726P D-ORF was PCR amplified with the following primers:

```
PDM-290
                                          (SEQ ID NO: 558)
5' ctaaatgccggcacaagagctctgc 3' Tm 61° C.

PDM-291
                                          (SEQ ID NO: 559)
5' cgcgcagaattctattatataacttctgtttctgc 3'
Tm 61° C.
```

The reaction conditions were as described. The cycling conditions were altered slightly in that the annealing temperature was lowered to 61° C. from 62° C. and was held for 15 seconds. The extension time was also increased to 2 minutes and 15 seconds. The PCR product was digested with NaeI and EcoRI and cloned into pPDM His which has been digested with Eco72I and EcoRI. Construct was confirmed by sequencing and then transformed into BL21 (DE3) pLys S cells (Novagen, Madison, Wis.). Protein expression was confirmed by Coomassie stained SDS-PAGE and N-terminal protein sequence analysis.

Construct for B726P Combined ORF expression in *E. coli* (cDNA: SEQ ID NO:548; amino acid: SEQ ID NO:553):

The B726P C-1 coding region was PCR amplified including the 183 bp insert, with the following primers:

```
PDM-750
                                          (SEQ ID NO: 560)
5' ggggaattgtgagcggataacaattc 3' Tm 58° C.

PDM-752
                                          (SEQ ID NO: 561)
5' cgtagaattcaacctgatttaaattactttctacac 3'
Tm 59° C.
```

The B726P Downstream ORF was PCR amplified with the following primers:

```
PDM-753
                                          (SEQ ID NO: 562)
5' gaaagtaatttaaatcaggtttctcacactc 3' Tm 59° C.

PDM-751
                                          (SEQ ID NO: 563)
5' gaggccccaaggggttatgctag 3' Tm 61° C.
```

The reaction conditions for these PCR reactions were the same as described above. The cycling conditions were as follows: 1st PCR: The reaction was first denatured for 2 minutes at 96° C., followed by 40 cylces of 96° C. for 20 seconds, 58° C. for 15 seconds, and extension at 72° C. for 4 minutes. This was followed by a final extension of 72° C. for 4 minutes; 2 PCR: The reaction was first denatured for 2 minutes at 96° C., followed by 40 cylces of 96° C. for 20 seconds, 59° C. for 15 seconds, and extension at 72° C. for 2 minutes. This was followed by a final extension of 72° C. for 4 minutes. The first PCR product was digested with EcoRI and cloned into pPDM His (a modified pET28 vector) at the Eco 721 and EcoRI sites. The construct was confirmed to be correct through sequence analysis. The second PCR product was digested with EcoRI and cloned into pPDM His at the same sites. The resulting constructs pPDM B726P UA-8 and pPDM B726P DA-7 respectively were digested with SwaI and EcoRI. The pPDM B726P UA-8 construct was used as vector and the insert from the pPDM B726P DA-7 was cloned into this construct successfully. The construct was confirmed to be correct through sequence analysis and then transformed into BLR (DE3) pLys S and HMS 174 (DE3) pLys S cells (Novagen, Madison, Wis.). Protein expression was confirmed by Coomassie stained SDS-PAGE and N-terminal protein sequence analysis.

Example 9

Additional Sequence Identified for Breast Tumor Antigen B726P by Bioinformatic Analysis The combined ORF of the breast tumor antigen, B726P (amino acid sequence set forth in SEQ ID NO:475), was used to search public databases. A sequence essentially identical to the combined ORF with additional N-terminal sequence was identified in the GenBank nonredundant protein database and the cDNA and predicted amino acid sequences are set forth in SEQ ID NO:564 and 565, respectively. The gene is also referred to as NY-BR-1 and was described in described in Cancer Research 61(5):2055-2061, Mar. 1, 2001.

Example 10

Analysis of B726P Expression Using Immunohistochemistry

Affinity purified polyclonal antibodies anti-B726Pup (generated against the B726P upstream ORF protein) and anti-B726Pdown (generated against the B726P downstream ORF) were used to assess B726P protein expression in breast cancer and in a variety of normal tissue sections.

In order to determine which tissues express the breast cancer antigen protein B726P immunohistochemistry (IHC) analysis was performed on a diverse range of tissue sections. Tissue samples were fixed in formalin solution for 12-24 hrs and embedded in paraffin before being sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (either rabbit affinity purified anti-B726Pdown or anti-B726Pup) was added to each section for 25 minutes followed by 25 minute incubation with anti-rabbit biotinylated antibody. Endogenous peroxidase activity was blocked by three 1.5 minute incubations with hydrogen peroxidase. The avidin biotin complex/horse radish peroxidase (ABC/HRP) system was used along with DAB chromogen to visualize antigen expression. Slides were counterstainied with hematoxylin to visualize cell nuclei. Anti-B726Pup and anti-B726Pdown immunoreactivity was observed in about 30-40% of breast cancer samples analyzed but not observed in a majority of various normal tissues. Anti-B726Pdown and anti-b726Pup also stained roughly the same breast cancer samples. Thus, these data confirm earlier microarray analysis (see Example 1) showing that B726P is overexpressed in breast tumor tissue as compared to normal tissue. Therefore, this antigen may be used in diagnostic and immunotherapeutic applications for breast cancer.

Example 11

Generation of Monoclonal Antibodies to B726P Downstream and Upstream ORFs

Production and purification of protein used for antibody generation. B726 upstream ORF and B726 downstream ORF proteins were expressed in an *E. coli* recombinant expression system (see Example 8). Cells were grown overnight in LB Broth with the appropriate antibiotics at 37° C. in a shaking incubator. The next morning, 10 ml of the overnight culture was added to 500 ml of 2×YT plus appropriate antibiotics in a 2L-baffled Erlenmeyer flask. When the optical density (at 560 nanometers) of the culture reached 0.4-0.6 the cells were induced with IPTG (1 mM). Four hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole.

The solubilized protein was added to 5 ml of nickel-chelate resin (Qiagen, Valencia, Calif.) and incubated for 45 min to 1 hour at room temperature with continuous agitation. After incubation, the resin and protein mixture were poured through a disposable column and the flow through was collected. The column was then washed with 10-20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then submitted to Quality Control for final release. The release criteria were purity as determined by SDS-PAGE or HPLC, concentration as determined by Lowry assay or Amino Acid Analysis, identity as determined by amino terminal protein sequence, and endotoxin level as determined by the *Limulus* (LAL) assay. The proteins were then vialed after filtration through a 0.22-micron filter and the antigens were frozen until needed for immunization.

To generate anti-B726P mouse monoclonal antibodies, mice were immunized IP with 50 micrograms of recombinant B726P upstream ORF and B726P downstream ORF proteins that had been mixed to form an emulsion with an equal volume of Complete Freund's Adjuvant (CFA). Every three weeks animals were injected IP with 50 micrograms of recombinant B726P upstream ORF and B726P downstream ORF that had been mixed with an equal volume of IFA to form an emulsion. After the fourth injection, spleens were isolated and standard hybridoma fusion procedures were used to generate anti-B726P mouse monoclonal antibody hybridomas. Anti-B726P monoclonal antibodies were screened using the ELISA analysis using the bacterially expressed recombinant B726P upstream ORF and B726P downstream ORF proteins.

A list of the mouse anti-B726P monoclonal antibodies that were generated, as well as their anti-B726P reactivity in an ELISA assay and Western blot are shown in Table 2. The hybridomas were then subcloned and the subclones further tested for reactivity with B726P upstream ORF and B726P downstream ORF proteins. Several monoclonal antibodies showed particularly favorable reactivity: 220A2-21, 220A19-25, 220A94-29, 220A151-33.

For Western blot analysis, recombinant B726P upstream ORF and B726P downstream ORF protein was diluted with SDS-PAGE loading buffer containing beta-mercaptoethanol, then boiled for 10 minutes prior to loading the SDS-PAGE gel. Protein was transferred to nitrocellulose and probed with each of the anti-B726P hybridoma supernatants. Protein A-HRP was used to visualize the anti-B726P reactive bands by incubation in ECL substrate.

TABLE 2

B726PUP AND B726PDOWN MONOCLONAL ANTIBODY REACTIVITY

| Anti-B726P | ELISA | | | Western Blots | |
|---|---|---|---|---|---|
| mAbs | B726PDown | B726PUp | L523S | B726Pdown | B726Pup |
| 220A2 | +++ | + | − | +++ | ++ |
| 220A10 | − | − | − | N/A | N/A |
| 220A14 | +++ | +++ | +++ | +++ | ++ |
| 220A19 | ++ | − | − | ++ | + |
| 220A43 | +++ | + | − | +++ | ++ |
| 220A86 | +++ | + | − | +++ | ++ |
| 220A94 | +++ | − | − | ++ | +/− |
| 220A123 | ++ | − | − | + | − |
| 220A139 | +/− | − | − | + | − |
| 220A140 | − | − | − | N/A | N/A |
| 220A141 | − | − | − | N/A | N/A |
| 220A143 | − | − | − | N/A | N/A |
| 220A151 | ++ | − | − | ++ | − |
| 220A176 | +/− | − | − | + | − |

Example 12

Identification of Additional Sequences for B726P

Additional 5' sequence was obtained for B726P—this sequence was obtained by PCR from 1st strand cDNA prepared from three separate mRNA sources (metastatic breast tumor, breast tumor, normal testis). Disclosed herein are clones that were isolated, each with differences from the expected published sequence of NY-BR-1.

A 1300 bp fragment of B726P otherwise known as NY-BR-1 was PCR amplified from 1st strand cDNA and cloned into pPDM, a modified pET28 vector as follows:

The B726P XB coding region (NY-BR-1) was PCR amplified with the following primers

```
PDM-784
5' cacacaaagaggaagaagaccatc 3' Tm 56° C.

PDM-814
5' gattcttttgtaggacatgcaatcatc 3' Tm 55° C.
```

The following PCR conditions were used: 10 μl 10× Herculase buffer, 1 μl 10 mM dNTPs, 2 μl 10.μM each oligo, 83 μl sterile water, 1.5 μl Herculase DNA polymerase (Stratagene, La Jolla, Calif.), 50 ng DNA. The thermalcycling conditions were as follows:

98° C. 3 minutes

98° C. 40 seconds, 51° C. 15 seconds, 72° C. 4 minutes, X 10 cycles

98° C. 40 seconds, 51° C. 15 seconds, 72° C. 5 minutes, X 10 cycles

98° C. 40 seconds, 51° C. 15 seconds, 72° C. 6 minutes, X 10 cycles

98° C. 40 seconds, 51° C. 15 seconds, 72° C. 7 minutes, X 10 cycles

72° C. 10 minutes

The PCR product was ligated into the pPDM vector (a modified pET28) that had been digested with Eco72I and de-phosphorylated. PCR amplification of this gene proved very difficult and required the use of a polymerase lacking proofreading capabilities. However, use of such an enzyme, in this case, Herculase from Stratagene (La Jolla, Calif.), led to what is likely PCR errors in the resulting clones. The cDNA sequence of three of the isolated clones containing mutations are disclosed in SEQ ID NO:567-569 with the corresponding amino acid sequences disclosed in SEQ ID NO:572, 571, and 570, respectively.

The resulting construct, pPDM B726P XB (clone 83686), was then digested with BglII and the insert which dropped out from the 5' vector BglII site and the internal BglII site at amino acids 390-391 was cloned into the pPDM B726P C—ORF (SEQ ID NO:548) that had been digested with BglII and was de-phosphorylated. This construct, pPDM B726P XC, was then DNA sequenced and showed two nucleotide changes, which result in two amino acid changes. The cDNA of the full-length clone containing these 2 mutations is disclosed in SEQ ID NO:566 with the corresponding amino acid sequence in SEQ ID NO:573. The full-length expected, published NY-BR-1 is disclosed in SEQ ID NO:564 (cDNA); amino acid SEQ ID NO:565.

Example 13

Isolation of Additional 3' Sequence and Real-Time PCR Analysis of B726P Homolog NY-BR1.1

A sequence homolog to the breast candidate B726P, called NY-BR-1.1, was identified and published in Cancer Research 61(5):2055-2061; Mar. 1, 2001. The NY-BR-1.1 gene, thought to be located on chomosome 9 based on 100% sequence identity to genomic sequence from chromosome 9, was shown to be expressed as mRNA in breast tumors as well as in normal brain. However, the published sequence was lacking 3' sequence. Published incomplete sequence for NY-BR-1.1 is represented by GenBank accession number AF269088. A recent BlastN search of the GenBank High Throughput Genomic Sequence database using Ny-Br-1.1 as a query sequence showed a 100% match to the working draft sequence of chromosome 9 (GenBank accession number AL359312), yielding further 3' DNA sequence for Ny-Br-111. The compilation of the Ny-Br-1.1 sequence with the additional 3' sequence from chromosome 9 yielded a 3720 bp ORF sequence (SEQ ID NO:576) which encodes a 1240 amino acid protein sequence (SEQ ID NO:577).

Real time PCR primers were designed to a unique region of NY-BR-1.1 to distinguish its mRNA expression profile from B726P. This experiment represents relative values, as it was done without template. The first-strand cDNA used in the quantitative real-time PCR was synthesized from 20 μg of total RNA that was treated with DNase I (Amplification Grade, Gibco BRL Life Technology, Gaithersburg, Md.), using Superscript Reverse Transcriptase (RT) (Gibco BRL Life Technology, Gaithersburg, Md.). Real-time PCR was performed with a GeneAmp™ 5700 sequence detection system (PE Biosystems, Foster City, Calif.). The 5700 system uses SYBR™ green, a fluorescent dye that only intercalates into double stranded DNA, and a set of gene-specific forward and reverse primers. The increase in fluorescence was monitored during the whole amplification process. The optimal concentration of primers was determined using a checkerboard approach and a pool of cDNAs from tumors was used in this process. The PCR reaction was performed in 25 µl volumes that included 2.5 µl of SYBR green buffer, 2 µl of cDNA template and 2.5 µl each of the forward and reverse primers for the gene of interest. The cDNAs used for quantitative real time PCR reactions were diluted 1:10 for each gene of interest and 1:100 for the β-actin control. Levels of mRNA were expressed relative to ureter where NY-BR-1.1 expression was not observed when compared to the β-actin control.

The real time PCR results show that mRNA expression for NY-BR-1.1 is present in breast tumors as well as in normal adrenal gland, brain, retina and testis.

Example 14

Characterization of B726P Monoclonal and Purified Polyclonal Antibody Epitopes Mouse monoclonal antibodies and rabbit polyclonal sera were raised against *E. coli* derived B726P recombinant protein and tested by ELISA as described in further detail below, for antibody epitope recognition against overlapping 20 mer peptides that correspond to the amino acid sequence of the downstream ORF of B726P (B726P dORF, set forth in SEQ ID NO:176, encoded by SEQ ID NO:175). Numerous peptides were recognized by the monoclonal and polyclonal antibodies. The corresponding amino acid sequences of these peptide antibody epitopes are summarized in Table 3 and are set forth in SEQ ID NO:578-593.

ELISA ANALYSIS: B726P recombinant protein and peptides were coated onto 96 well ELISA plate: 50 ul/well at 2 ug/ml for 20 hrs at 4 C. Plates were then washed 5 times with PBS+0.1% Tween 20 and blocked with PBS+1% BSA for 2 hr. Affinity purified B726P polyclonal antibodies were then added to the wells at 1 ug/ml and B726P monoclonal supernatants were added neat (220A43 and 220A86 were diluted 1/60 and 1/20 respectively). Plates were incubated at room temperature for 30 minutes and then washed again as above, followed by the addition of 50 ul/well donkey anti-mouse-Ig-HRP antibody for 30 minutes at room temperature. Plates were washed, then developed by the addition of 100 ul/well of TMB substrate. The reaction was incubated 15 minutes in the dark at room temperature and then stopped by the addition of 100 ul/well of 1N H2SO4. Plates were read at OD450 in an automated plate reader. Peptides with OD450 readings three times background or above were considered to be positively recognized by the corresponding antibody.

Example 15

Analysis of Autoantibodies to B726P in Breast Cancer Sera and Epitope Mapping of the Antigenic Sites Specific B726P peptide epitopes were identified that react with autoantibodies in the serum of breast cancer patients. Thirty-three overlapping peptides were synthesized spanning the entire B726P protein. These 33 peptides were tested in ELISAs to evaluate which epitopes reacted with breast cancer sera. Reactive epitopes were identified throughout the molecule and a total of 16/74 sera samples from breast cancer patients had reactivity with one or more peptides.

Thirty-one overlapping synthetic peptides spanning the entire B726P downstream ORF sequence (amino acid sequence set forth in SEQ ID NO:176) were synthesized and 30 of these were tested in ELISA with sera from breast cancer patients as well as control sera. The amino acid sequences of the 31 overlapping peptides of the B726P downstream ORF are set forth in SEQ ID NO:594-624. Three additional peptides of B726P, set forth in SEQ ID NO:625-627 were also tested. Several peptides throughout the molecule showed reactivity, in particular peptide #2735 (amino acids 31-50; SEQ ID NO:597), peptide #2747 (amino acids 151-170; SEQ ID NO:609), peptide #2750 (amino acids 181-200; SEQ ID NO:612), peptide #2753 (amino acids 211-230; SEQ ID NO:615), and peptide #2766 (amino acids 231-250; SEQ ID NO:617). A total of 16/74 breast cancer sera were reactive with at least one peptide.

B726P antibody epitopes were also mapped using rabbit antisera generated against the B726P downstream ORF (SEQ ID NO:176). The epitopes identified using the rabbit antisera were as follows: peptide #2732 (amino acids 1-20; SEQ ID NO:594), peptide # 2733 (amino acids 11-30; SEQ ID NO:595), peptide #2742 (amino acids 101-120; SEQ ID NO:604), peptide #2743 (amino acids 111-130; SEQ ID NO:605), peptide #2744 (amino acids 121-140; SEQ ID NO:606), peptide #2745 (amino acids 130-151; SEQ ID NO:607), peptide #2751 (amino acids 191-210; SEQ ID NO:613), and peptide #2753 (amino acid 211-230; SEQ ID NO:615). Some low level reactivity was observed for peptide #2772 (amino acids 291-310; SEQ ID NO:623) and peptide #2773 (amino acids 298-317; SEQ ID NO:624).

The above results confirm that B726P can be used alone or in combination with other breast tumor antigens as a vaccine target. Additionally, these results show that detection of antibodies to B726P can be used as a diagnostic indicator of breast cancer either alone or in combination with detection of

TABLE 3

Peptides recognized by B726P Antibodies

| | B726P Monoclonal Supernatant | | | | | | B726P Purified Polyclonal |
|---|---|---|---|---|---|---|---|
| | 220A2.1 | 220A19.1 | 220A94.1 | 220A151.1 | 220A43 | 220A86 | (1 ug/ml) |
| B726P peptides (amino acids) | 289-308 | 225-244, 232-252 | 73-252 | 145-164, 153-172 | 232-252 | 145-164, 153-172 | 1-20, 9-28, 17-36, 24-44, 97-116, 105-124, 113-132, 121-140, 129-148, 137-156 |

antibodies to other antigens (e.g. Her-2/Neu or other antigens known to be expressed in breast cancer tissue).

Example 16

Immunohistochemical Analysis of B726P Expression 1N Metastatic Breast Cancer

Affinity purified polyclonal antibodies anti-B726Pdown (generated against the B726P downstream ORF) were used to assess B726P protein expression in metastatic breast cancer samples.

In order to determine which tissues express the breast cancer antigen protein B726P immunohistochemistry (IHC) analysis was performed on a diverse range of tissue sections. Tissue samples were fixed in formalin solution for 12-24 hrs and embedded in paraffin before being sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (rabbit affinity purified anti-B726Pdown) was added to each section for 25 minutes followed by 25 minute incubation with anti-rabbit biotinylated antibody. Endogenous peroxidase activity was blocked by three 1.5 minute incubations with hydrogen peroxidase. The avidin biotin complex/horse radish peroxidase (ABC/HRP) system was used along with DAB chromogen to visualize antigen expression. Slides were counterstainied with hematoxylin to visualize cell nuclei.

Anti-B726Pdown immunoreactivity was observed in 7 of 10 metastatic breast cancer samples analyzed but not observed in various normal tissues including normal breast. Thus, these data confirm earlier microarray analysis (see Example 1) showing that B726P is overexpressed in breast tumor tissue as compared to normal tissue. Therefore, this antigen may be used in diagnostic and immunotherapeutic applications for breast cancer.

Example 17

Analysis of B726P Expression Using Immunoprecipitation and Western Blot Analysis Affinity purified polyclonal antibodies generated against the B726P downstream ORF protein set forth in SEQ ID NO:176 (anti-B726Pdown) were used to assess the protein expression of the combined ORF of B726P in breast cancer cell lines as compared to normal cells as described below. Since the combined ORF includes both the upstream and downstream ORFs, the antibodies generated against the downstream ORF crossreact with the combined ORF polypeptide as set forth in SEQ ID NO:475.

Cells were lysed in 1% Triton lysis buffer on ice for 10 minutes. Lysates were centrifuge at 15000 rpm and supernatant was saved for immunoprecipitation (IP)/Western analysis. 2 μg of anti-B726down polyclonal antibody was added to the supernatant and rocked overnight at 4° C. 20 μl of protein G bead slurry was added and incubated for 1 hour. Beads were then washed 3 times with 1 ml of lysis buffer. LDS sample buffer and β-mercaptoethanol were added and the samples were heated for 5 min at 95° C. Samples were size fractionated by gel electrophoresis, transferred to nitrocellulose and Western blotted with the mouse anti-B726down monoclonal antibody A2.1.

$^{35}S$ methionine labeling/IP analysis was carried out as follows: Cells were grown in 10% Fetal Bovine Serum (FBS) media to desired density. Cells were then starved with DMEM lacking methionine containing 0.1% FBS mediafor 10-15 minutes. FBS was added to a final concentration of 10% along with $^{35}S$-Methionine translabel (300 μCi-1 mCi). After incubating for 3-4 hours the cells were harvested, washed, and lysed. B726P was immunoprecipitated as described above and samples were size fractionated by gel electrophoresis before being exposed to autoradiography film.

The results from the above described experiments showed that the full length 148 kDa form (also called NYBR1), the 110 kDa combined ORF form, and the 35 kDa downstream ORF form are all expressed in breast tumor cell lines HTB21 and BT474 but not in the SKBR3 normal breast cell line. Therefore, these results confirm that these forms of the B726P protein are expressed in breast tumor cell lines and not in normal cells.

U.S. patents, U.S. patent application publications, U.S. patent applications, foreign patents, foreign patent applications and non-patent publications referred to in this specification and/or listed in the Application Data Sheet, are incorporated herein by reference in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated polypeptide comprising a variant of the polypeptide of SEQ ID NO:475 wherein said variant comprises an amino acid sequence that is at least 95% identical to the polypeptide of SEQ ID NO:475 along its length.

2. A fusion protein comprising at least one polypeptide according to claim 1.

3. A composition comprising a first component selected from the group consisting of physiologically acceptable carriers and immunostimulants, and a second component selected from the group consisting of:

(a) a polypeptide according to claim 1; and (b) a fusion protein according to claim 2.

4. The fusion protein of claim 2 wherein the fusion protein comprises a fusion partner selected from the group consisting of: a protein D or a derivative thereof comprising the first N-terminal 100-110 amino acids of protein D, a C-terminal domain of the LYTA protein, Ra12, the non-structural protein from influenza virus (NS1), and an endosomal/lysosomal compartment targeting signal.

5. The composition of claim 3, wherein said immunostimulant is an adjuvant that induces a predominantly Th1 type immune response.

6. The composition of claim 5, wherein said adjuvant is selected from the group consisting of: 3D-MPL, QS21, a mixture of QS21 and cholesterol, and a CpG oligonucleotide.

* * * * *

SEQUENCE LISTING

```
<160> NUMBER OF SEQ ID NOS: 627

<210> SEQ ID NO 1
<211> LENGTH: 281
<212> TYPE: DNA
<213> ORGANISM: Homo sapien

<400> SEQUENCE: 1

caatgacagt caatctctat cgacagcctg cttcatattt agctattgtt cgtattgcct      60

tctgtcctag gaacagtcat atctcaagtt caaatgccac aacctgagaa gcggtgggct     120

aagataggtc ctactgcaaa ccacccctcc atatttccgt acgcaattac aattcagttt     180
```

-continued

```
ctgtgacatc tctttacacc actggaggaa aaatgagata ttctctgatt tattctacta    240

taacactcta catagagcta tggtgagtgc taaccacatc g                        281


<210> SEQ ID NO 2
<211> LENGTH: 300
<212> TYPE: DNA
<213> ORGANISM: Homo sapien

<400> SEQUENCE: 2

gaggtcctgg gctaacctaa tggtttatta ttggtggaga gaaagatctg gaaatacttg     60

aggttattac atactagatt agcttctaat gtgaaccatt tttcttttaa cagtgataaa    120

ttattatttc cgaagttaac tgttcccttg gtcgtgatac acactcgatt aacaaacata    180

ctgttgtatt ttttccagtt ttgtttggct atgccaccac agtcatcccc agggtctata    240

catactatgt ctcaactgta ttatttgcca tttttggcat tagaatgctt cgggaaggct    300


<210> SEQ ID NO 3
<211> LENGTH: 302
<212> TYPE: DNA
<213> ORGANISM: Homo sapien

<400> SEQUENCE: 3

ggccgaggta attggttaag tctaaagaga ttattattcc ttgatgtttg ctttgtattg     60

gctacaaatg tgcagaggta atacatatgt gatgtcgatg tctctgtctt tttttttgtc    120

tttaaaaaat aattggcagc aactgtattt gaataaaatg atttcttagt atgattgtac    180

agtaatgaat gaaagtggaa catgtttctt tttgaaaggg agagaattga ccatttattg    240

ttgtgatgtt taagttataa cttatcgagc acttttagta gtgataactg tttttaaact    300

tg                                                                   302


<210> SEQ ID NO 4
<211> LENGTH: 293
<212> TYPE: DNA
<213> ORGANISM: Homo sapien

<400> SEQUENCE: 4

tgtaccaatc ctttggcaca agaatatgta agaactatag ttgtttttat tggtttttgt     60

tcttgagatt gttttcattc tgtttttgac tgtatctctt taggaggctg aggatggcat    120

tattgcttat gatgactgtg gggtgaaact gactattgct tttcaagcca aggatgtgga    180

aggatctact tctcctcaaa tacgagataa ggcaagataa ttctgctcat tcgagagagg    240

gttaagagtt gtcatcttaa tcataaatcc tgcaggatgg gttcttcaaa ttt          293


<210> SEQ ID NO 5
<211> LENGTH: 275
<212> TYPE: DNA
<213> ORGANISM: Homo sapien

<400> SEQUENCE: 5

cgaggtttgg aatcagactt ctgtgtccag taaaaaactc ctgcactgaa gtcattgtga     60

cttgagtagt tacagactga ttccagtgaa cttgatctaa tttcttttga tctaatgaat    120

gtgtctgctt accttgtctc cttttaattg ataagctcca agtagttgct aatttttga     180

caactttaaa tgagtttcat tcacttcttt tacttaatgt tttaagtata gtaccaataa    240

tttcattaac ctgttctcaa gtggtttagc tacca                              275
```

-continued

<210> SEQ ID NO 6
<211> LENGTH: 301
<212> TYPE: DNA
<213> ORGANISM: Homo sapien

<400> SEQUENCE: 6

```
gaggtctggt ttcctgggta tgcctggact gttgcccagt gtaagatctg tgcaagccat     60

attggatgga agtttacggc caccaaaaaa gacatgtcac ctcaaaaatt ttggggctta    120

acgcgatctg ctctgttgcc cacgatccca gacactgaag atgaaataag tccagacaaa    180

gtaatacttt gcttgtaaac agatgtgata gagataaagt tatctaacaa attggttata    240

ttctaagatc tgctttggaa attattgcct ctgatacata cctaagtaaa cataacatta    300

a                                                                    301
```

<210> SEQ ID NO 7
<211> LENGTH: 301
<212> TYPE: DNA
<213> ORGANISM: Homo sapien

<400> SEQUENCE: 7

```
gtccagtttg tacacagtga ttccttatgc acgccgaaag ggtttccgta aaaatgacat     60

tatatacaaa tctgtacacc catccaccag agcgattctc cagctcccag agggagttat    120

caacttaaag caggatacct gaggtttcat gtctttagtt gccttatcat aatcccaaat    180

atacatttca gggtttgttt ttgtttttaa agacactttc ctggaatatg tgcactatgg    240

ttaaaattaa aaacaaaagt aataaaataa aatgatcgct ggaaggactg acctccccac    300

c                                                                    301
```

<210> SEQ ID NO 8
<211> LENGTH: 301
<212> TYPE: DNA
<213> ORGANISM: Homo sapien

<400> SEQUENCE: 8

```
ctgtcctcat ctctgcaaag ttcagcttcc ttccccaggt ctctgtgcac tctgtcttgg     60

atgctctggg gagctcatgg gtggaggagt ctccaccaga gggaggctca ggggactggt    120

tgggccaggg atgaatattt gagggataaa aattgtgtaa gagccaaaga attggtagta    180

gggggagaac agagaggagc tgggctatgg gaaatgattt gaataatgga gctgggaata    240

tggctggata tctggtacta aaaaagggtc tttaagaacc tacttcctaa tctcttcccc    300

a                                                                    301
```

<210> SEQ ID NO 9
<211> LENGTH: 301
<212> TYPE: DNA
<213> ORGANISM: Homo sapien

<400> SEQUENCE: 9

```
gaggtctgcc taagtagagg acaaagactt cctcctttca aaggagaact gagcccagga     60

ttggtaagtt taaggcactt aaccttgacc agctctgtag gtctggagca ttctggtccc    120

tggccgcttt caccaccagg cccttctcac ttatccacct cacatactgc cccagcattc    180

ctttggcatt gcgagctgtg acttgacaca ttttaatgac aagattgaag tagctacctt    240

gcaggataga ttttctgggg tataggggac aaaccaacag tgccatcagg tgtcttaaca    300

c                                                                    301
```

-continued

<210> SEQ ID NO 10
<211> LENGTH: 301
<212> TYPE: DNA
<213> ORGANISM: Homo sapien

<400> SEQUENCE: 10
ggcaggtcca acagttcttc cagttctggt cgagctttga atcgtccctt gaagtcttct 60
tcagtgtgct ccttcactga cagtctgact ccttcaggaa gactgctttg gattatttcc 120
aagaaaattt ctgcaaacgt agcactcaaa ccgctgatct gaaccactcg ctcatgggtg 180
gtaagcactg agtccaggag cattttgctg ccttggtcct gcaactgcaa cacttctatg 240
gttttggttg gcattgcata actttcctcg actttaatgg agagagattg cagaggttgt 300
g 301

<210> SEQ ID NO 11
<211> LENGTH: 301
<212> TYPE: DNA
<213> ORGANISM: Homo sapien

<400> SEQUENCE: 11
aggtctgtga ctttcaccca ggacccagga cgcagccctc cgtgggcact gccggcgcct 60
tgtctgcaca ctggaggtcc tccattacag aggcccagcg cacatcgctg gccccacaaa 120
cgttcagggg tacagccatg gcagctcctt cctctgccgt gagaaaagtg cttggagtac 180
ggtttgccac acacgtgact ggacagtgtc caattcaaat ctttcagggc agagtccgag 240
cagcgcttgg tgacagcctg tcctctcctg ctctccaaag gccctgctcc ctgtcctctc 300
t 301

<210> SEQ ID NO 12
<211> LENGTH: 301
<212> TYPE: DNA
<213> ORGANISM: Homo sapien

<400> SEQUENCE: 12
gaggtctggg attacaggca cgtgccacca cacctagcta atttttgagc atggggctca 60
aaggaactgc tctctggggc atgtcagatt tcggatttgg ggctgcacac tgatactctc 120
taagtggtgg aggaacttca tcccactgaa attcctttgg catttggggt tttgtttttc 180
tttttttcct tcttcatcct cctccttttt taaaagtcaa cgagagcctt cgctgactcc 240
accgaagaag tgcaccactg ggagccaccc cagtgccagg cgcccgtcca gggacacaca 300
c 301

<210> SEQ ID NO 13
<211> LENGTH: 256
<212> TYPE: DNA
<213> ORGANISM: Homo sapien

<400> SEQUENCE: 13
ttttttggca taaaaaacac aatgatttaa tttctaaagc acttatatta ttatggcatg 60
gtttgggaaa caggttatta tattccacat aggtaattat gcagtgcttc tcatggaaaa 120
aatgcttagg tattggcctt ttctctggaa accatatttt tcctttttta ataatcaact 180
aaaatgtata tgttaaaaag cctcatcttt tgattttcaa tatacaaaat gctttcttta 240
aaagaacaag attcaa 256

-continued

<210> SEQ ID NO 14
<211> LENGTH: 301
<212> TYPE: DNA
<213> ORGANISM: Homo sapien

<400> SEQUENCE: 14
ggtccttgat agaggaagag gaatatccaa ggcaaagcca ccaccacgtc caacctcctc 60
atcctctacc tttcctgtcc ccagaggtat gagatagacc ccctggcctg gttcctgcac 120
tgtgctaggc ccacagtgga cacttccacc ttaatggaga ataggcccca tggagtggag 180
gtccctcctc catggcctgc aacccaatga ctatgggggt gacacaagtg acctctgccc 240
tgtgatggct caacaccatc acacgcaact gtccagacaa gccccctcaa cgggctgctg 300
t 301

<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct 60
ctctttctgc ttttctgatc atcctaaagg ctgaatacat cctcctcctg tgtggaggac 120
acgaagcaat actaaaatca atacactcga tcaggtcttc atcagatacc acgtcactgt 180
gggtagagtg ctaattttca acaaatgtgg tgttcttagg gccccacaag gtagtccttt 240
ctcaaggtcg ctgggccac 259

<210> SEQ ID NO 16
<211> LENGTH: 301
<212> TYPE: DNA
<213> ORGANISM: Homo sapien

<400> SEQUENCE: 16
cgaggttgtt cacattttca aataaataat actccccgta agtaataact gcaaccaatc 60
agtgttattc agtgctatgc ctccttgtaa tgggtagtta ttaattattt tcagagcttt 120
ctggaaatac tgtcctaact ggctatgttt aggatctttg ttatctctga agacaaagaa 180
agaactagga ctcttaattt tggggtgctt cttgactctt agttgggaaa ctgaaaatat 240
ttccaacctt ttacccacgt caatggcata ttctgggaat caccaccacc accaccacta 300
c 301

<210> SEQ ID NO 17
<211> LENGTH: 301
<212> TYPE: DNA
<213> ORGANISM: Homo sapien

<400> SEQUENCE: 17
gcccgggcag gtctggggcc tagggtggct ctttgcaaag ctgaggggca agctaaggaa 60
gccaggcagg tcaggggccc tttcggcctt ctcaagcctc cacctgagtt ctcgtcaatg 120
ccagtctccc tggtatgatt ggggacatta tcagagaaac atctaatagc gcacatctgg 180
gcacccacac tctgcttcag ttgcatccat cctcccaccc caaattcaac tcctgaccca 240
atacaaaaga ctttttttaac caggatttct tcttgcagga aagctgactt ggaaacacgg 300
g 301

<210> SEQ ID NO 18

-continued

<211> LENGTH: 301
<212> TYPE: DNA
<213> ORGANISM: Homo sapien

<400> SEQUENCE: 18
attacaggca cgtgccacca cacctagcta atttttgagc atggggctca aaggaactgc 60
tctctggggc atgtcagatt tcggatttgg ggctgcacac tgatactctc taagtggtgg 120
aggaacttca tcccactgaa attcctttgg catttggggt tttgtttttc tttttttcct 180
tcttcatcct cctccttttt taaaagtcaa cgagagcctt cgctgactcc accgaagaag 240
tgcaccactg ggaccaccc agtgccaggc gcccgtccag ggacacacac agtcttcact 300
g 301

<210> SEQ ID NO 19
<211> LENGTH: 301
<212> TYPE: DNA
<213> ORGANISM: Homo sapien

<400> SEQUENCE: 19
agaatctctg cactgtcatc aggtacaaca aaagatcaaa cccctgtccc gatgttaact 60
ttttaactta aaagaatgcc agaaaaccca gatcaacact ttccagctac gagccgtcca 120
caaaggccac ccaaaggcca gtcagactcg tgcagatctt attttttaat agtagtaacc 180
acaatacaca gctctttaaa gctgttcata ttcttccccc attaaacacc tgccccgggc 240
ggccaagggc gaattctgca gatatccatc acactggcgg ccgctcgagc atgcatctag 300
a 301

<210> SEQ ID NO 20
<211> LENGTH: 290
<212> TYPE: DNA
<213> ORGANISM: Homo sapien

<400> SEQUENCE: 20
aggttttttt tttttttttt tttttttttt tttttccctt tcaattcatt taatttcaac 60
aatctgtcaa aaaacagcca ataaacaaat actgaattac attctgctgg gtttttttaaa 120 ggctctaaac tataaaaaca tcttgtgtct cccaccctga ccaccctgct acttttccat 180
ataccacagg ccacccataa acacaaagcc agggggtgaa gctgacatgg tctatttgga 240
gccagtaaac aggagggcga taagtcctga taagcactta tggacaatat 290

<210> SEQ ID NO 21
<211> LENGTH: 301
<212> TYPE: DNA
<213> ORGANISM: Homo sapien

<400> SEQUENCE: 21
agaaaggtaa ctgccagcca ggcttgcatt gtttagccag aaattgctgc ttggttctag 60
actctttaaa aaaaaaaaat acccagggtt tgtcatcatt ttcagaggca gagtgccaaa 120
tatcacccaa agctcttgtg tctttttttt accccttat tttattttta tttattaatt 180
ttttgtgcaa acatcaaatg tcactggtgt tcacagaagg cttttttgac tagccttaaa 240
ttcctgagtc aaaagattaa tcagattttc aggcagtgtt taatcaggtg ctttgtcctg 300
t 301

<210> SEQ ID NO 22
<211> LENGTH: 301

-continued

<212> TYPE: DNA
<213> ORGANISM: Homo sapien

<400> SEQUENCE: 22
gacgccatgc accctccggt aaccagcagc cgcctgtcca tcccccaaga ccggaaaggc 60
agcagcagcc cccgggagcc cagggctgtc ctcggtgcat ctggctgcag agggaaattg 120
atgaccttac acagcaacta gcggccatgc agtccttcac tgacaagttc caggaccttt 180
gaagttggag ccagcgtccg gagctgcagc caagcgagtt tcctccttat cctccttagc 240
cagggctttt tctcttccgc tgcatttgcc cccttcccaa cgcaattcaa agcagttgtg 300
a 301

<210> SEQ ID NO 23
<211> LENGTH: 381
<212> TYPE: DNA
<213> ORGANISM: Homo sapien

<400> SEQUENCE: 23
cgaggtccag acagtggacc aagagatacg ctacataaat tggggtttca caattcttac 60
attatttgtc tgtcacagaa gagagctgct tatgattttg aaggggtcag ggagggtggg 120
agttggtaaa gagtagggta tttctataac agatattatt cagtcttatt tcctaagatt 180
ttgttgtaac ttaaggtatc ttgctacagt agacagaatt ggtaatagca acttttaaaa 240
ttgtcattag ttctgcaata ttagctgaaa tgtagtacag aaaagaatgt acatttagac 300
atttgggttc agttgcttgt agtctgtaaa tttaaaacag cttaatttgg tacaggttac 360
acatatggac ctcccgggcg g 381

<210> SEQ ID NO 24
<211> LENGTH: 214
<212> TYPE: DNA
<213> ORGANISM: Homo sapien

<400> SEQUENCE: 24
aatgatgtaa aaattaatca acagggctgc cacttgcgaa tcccctccaa ggatgctgtg 60
caaagggtct cattggtcct gatgaataat cttgtgactg tacatattcc tgggtgcatg 120
tccacaaata ctgaggtata gcctgcatgc cactaaaaat aacaaaggtt tcaggggtgg 180
aaacattgtc caccacactg tcatgaccat cttt 214

<210> SEQ ID NO 25
<211> LENGTH: 302
<212> TYPE: DNA
<213> ORGANISM: Homo sapien

<400> SEQUENCE: 25
gggggcactg agaactccct ctggaattct tggggggtgt tggggagaga ctgtgggcct 60
ggagataaaa cttgtctcct ctaccaccac cctgtaccct agcctgcacc tgtcctcatc 120
tctgcaaagt tcagcttcct tccccaggtc tctgtgcact ctgtcttgga tgctctgggg 180
agctcatggg tggaggagtc tccaccagag ggaggctcag gggactggtt gggccaggga 240
tgaatatttg agggataaaa attgtgtaag aagccaaaga aattggtagt agggggggaga 300 ac 302

<210> SEQ ID NO 26
<211> LENGTH: 301
<212> TYPE: DNA

<213> ORGANISM: Homo sapien

<400> SEQUENCE: 26

```
ttggagaacg cgctgacata ctgctcggcc acagtcagtg aagctgctgc atctccatta     60

tgttgtgtca gagctgcagc caggattcga atagcttcag ctttagcctt ggccttcgcc    120

agaactgcac tggcctctcc tgctgcctga tttatctgtg cagccttttc tgcttcggag    180

gccaggatct gggcctgttt cttcccttct gccacattga tggccgactc tcgggtcccc    240

tcagactcta gaactgtggc ccgtttccgc cgctctgcct ccacctgcat ctgcatagac    300

t                                                                    301
```

<210> SEQ ID NO 27
<211> LENGTH: 301
<212> TYPE: DNA
<213> ORGANISM: Homo sapien

<400> SEQUENCE: 27

```
aaatcagtca tcacatctgt gaaaagagtg ctagttataa caaatgagat cacaaatttg     60

accattttat tagacaccct ctattagtgt taacagacaa agatgaaggt taagttgaaa    120

tcaaattgaa atcatcttcc ctctgtacag attgcaatat ctgataatac cctcaacttt    180

cttggtgcaa attaattgcc tggtactcac agtccagtgt taacaggcaa taatggtgtg    240

attccagagg agaggactag gtggcaggaa aataaatgag attagcagta tttgacttgg    300

a                                                                    301
```

<210> SEQ ID NO 28
<211> LENGTH: 286
<212> TYPE: DNA
<213> ORGANISM: Homo sapien

<400> SEQUENCE: 28

```
tttttttttg cacaggatgc acttattcta ttcattctcc cccacccttc ccatatttac     60

atccttagag gaagagaggg gtaaggtgat aaagtaactg aaggaccgca agacgggtat    120

gtcccttgtt caccaaatgg tcaaagggtc aaagatcgga ggaggtcagg gggtaacgca    180

ggaacaggtg agggcgtttc gccctctctc cctctcccct tttcaacctc ttaatcactg    240

gctaactcgc gacctcatgg gttaattcgt aagcttacac gcgttg                   286
```

<210> SEQ ID NO 29
<211> LENGTH: 301
<212> TYPE: DNA
<213> ORGANISM: Homo sapien

<400> SEQUENCE: 29

```
gtcatgttct tgctcttcct tctttacaca tttgagttgt gccttctgtt cttaaagaga     60

ttttcctttg ttcaaaggat ttattcctac catttcacaa atccgaaaat aattgaggaa    120

acaggttaca tcattccaat tttgccttgg gtttgaagag tctctcatgg tggcacagtc    180

ctccagggta gctatgttgt tgggctcccc tacatcccag aagctcagag actttgtcaa    240

aggtgtgccg tccacccatt gccactgacc ctcgacaacc tggtctgaca gtccaataaa    300

a                                                                    301
```

<210> SEQ ID NO 30
<211> LENGTH: 332
<212> TYPE: DNA
<213> ORGANISM: Homo sapien -continued

<400> SEQUENCE: 30
gagcagaatt gatgcctatg gctccaagtc aaatactgct aatctcattt attttcctgc 60
cacctagtcc tctcctctgg aatcacacca ttattgcctg ttaacactgg actgtgagta 120
ccaggcaatt aatttgcacc aagaaagttg agggtattat cagatattgc aatctgtaca 180
gagggaagat gatttcaatt tgatttcaac ttaaccttca tctttgtctg ttaacactaa 240
tagagggtgt ctaataaaat ggtcaaattt gtgatctcat ttgttataac tagcactctt 300
ttcacagatg tgatgactga tttccagcag ac 332

<210> SEQ ID NO 31
<211> LENGTH: 141
<212> TYPE: DNA
<213> ORGANISM: Homo sapien

<400> SEQUENCE: 31
aaaggctatc aagtactttg aaggacagga aggaatgaac acacccaggt ggacgtttgg 60
tttcatttgc aggggttcag ggagggttgc aggggttcag ggagggctct tgtcccacaa 120
ccgggggaag ggagagggca c 141

<210> SEQ ID NO 32
<211> LENGTH: 201
<212> TYPE: DNA
<213> ORGANISM: Homo sapien

<400> SEQUENCE: 32
gagctgatct cacagcacat acagaatgat gctactatgt agaccctcac tcccttggga 60
aatctgtcat ctaccttaaa gagagaaaaa agatggaaca taggcccacc tagtttcatc 120
catccaccta cataaccaac atagatgtga ggtccactgc actgatagcc agactgcctg 180
gggtaaacct tttcagggag g 201

<210> SEQ ID NO 33
<211> LENGTH: 181
<212> TYPE: DNA
<213> ORGANISM: Homo sapien

<400> SEQUENCE: 33
tttcaaaaca ctcatatgtt gcaaaaaaca catagaaaaa taaagtttgg tgggggtgct 60
gactaaactt caagtcacag acttttatgt gacagattgg agcagggttt gttatgcatg 120
tagagaaccc aaactaattt attaaacagg atagaaacag gctgtctggg tgaaatggtt 180
c 181

<210> SEQ ID NO 34
<211> LENGTH: 151
<212> TYPE: DNA
<213> ORGANISM: Homo sapien

<400> SEQUENCE: 34
atgtcctgca cagtatagct tggacctctg ggcctgaacc agggtgagca tcaaggcccc 60
catttctcct caccacgggg tcgcttgtca gctccaagaa ccagtctggc cccactgaga 120
acttttcagt cgagggcctg atgaatcttg g 151

<210> SEQ ID NO 35
<211> LENGTH: 291
<212> TYPE: DNA

-continued

<213> ORGANISM: Homo sapien

<400> SEQUENCE: 35
tctttagggc aaaatcatgt ttctgtgtac ctagcaatgt gttcccattt tattaagaaa 60
agctttaaca cgtgtaatct gcagtcctta acagtggcgt aattgtacgt acctgttgtg 120
tttcagtttg tttttcacct ataatgaatt gtaaaaacaa acatacttgt ggggtctgat 180
agcaaacata gaaatgatgt atattgtttt ttgttatcta tttattttca tcaatacagt 240
attttgatgt attgcaaaaa tagataataa tttatataac aggttttctg t 291

<210> SEQ ID NO 36
<211> LENGTH: 201
<212> TYPE: DNA
<213> ORGANISM: Homo sapien

<400> SEQUENCE: 36
ctgatacaat tataataacg gttccctgaa ccttttagag tgcaattaag aacaaaaact 60
aaattttgtt tacatgaata tggaataaat acaataatca aaatatgact ctccctaaaa 120
gtgaaacaca caagccaatc cggaactgct gtgcgaaaga taaaatcgag aaaggcaagg 180
tttcggtagg aggacgcgat g 201

<210> SEQ ID NO 37
<211> LENGTH: 121
<212> TYPE: DNA
<213> ORGANISM: Homo sapien

<400> SEQUENCE: 37
catcacactg gcggccgctc gagcatgcat ctagagggcc caattcgccc tataatgagt 60
cgtattacaa ttcactggcc gtcgttttac aacgtcgtga ctgggaaaac cctggcgtta 120
c 121

<210> SEQ ID NO 38
<211> LENGTH: 200
<212> TYPE: DNA
<213> ORGANISM: Homo sapien

<400> SEQUENCE: 38
aaacatgtat tactctatat ccccaagtcc tagagcatga cctgcatgtt ggagatgttg 60
tacagcaatg tatttatcca gacatacata tatgatattt agagacacag tgattctttt 120
gataacacca cacatagaac attataatta cacacaaatt tatggtaaaa gaattaatat 180
gctgtctggt gctgctgtta 200

<210> SEQ ID NO 39
<211> LENGTH: 760
<212> TYPE: DNA
<213> ORGANISM: Homo sapien

<400> SEQUENCE: 39
gcgtggtcgt cggccgaggt cctgggctag acctaatggt ttattattgg tggagagaaa 60
gatctggaaa tacttgaggt tattacatac tagattagct tctaatgtga accatttttc 120
ttttaacagt gatcaaatta ttatttcgaa gttaatcgtt cccttggtgg ctgcatacac 180
atcgcattaa caaacatact gttgtatttt ttcccagttt tgtttggcta tgccaccaca 240
gtcatcccca gggtctatac atactatgtt tcaactgtat tatttgccat ttttggcatt 300
agaatgcttc gggaaggctt aaagatgagc cctgatgagg gtcaagagga actggaagaa 360

-continued

```
gttcaagctg aattaaagaa gaaagatgaa gaagtaagcc atggcactgt tgatctggac    420

caaaaaggca ctcaactagg aataaacact ctacagaggt ttctcagtgg ccccatctgt    480

gtgatatgcg gggctacaca aaaatagctt cttttgcttt gttctgttct tatacctgtc    540

tgtgatctga cttggggttg gtgtgaatgt agtagagaaa ggaagctgac agatgaatac    600

tgaacacagg taatcagttt ccttaattag gttgattata agctcctgaa aagcaggaac    660

tgtattttat aattttacct gtttctcccg tggtgtctag gatagtaagt gagcagagca    720

gtaaatactg tttggtttgt tcagacctgc ccgggcggcc                          760
```

<210> SEQ ID NO 40
<211> LENGTH: 452
<212> TYPE: DNA
<213> ORGANISM: Homo sapien

<400> SEQUENCE: 40

```
aatcactaaa gatattgact agagaatgct gtgtgctatt tcaattacat ttgtttttct     60

tttattaaca ggaattttga ttcttcaagg aagtggctca atttcaattt caggtgacca    120

ggtttatcgt gacttttcct tcttgtttac ttttcgctag gaaggggagt tgtaggggca    180

gattcaggta ttggaatagg aaaattacgt ctaaaccatg gaaatcttgg aaatggaatt    240

ggtggaagtg ggcgaaatgg atatgggtaa gggaacacaa aaaaccctga agctaattca    300

tcgctgtcac tgatacttct tttttctcgt tcctggtctt gagagactgg gaaaccaaca    360

gccactgcca agatggctgt gatcaggagg agaactttct tcatctcaaa cgtttcagtc    420

agttctttct ctcacctcgg ccgcgaccac gc                                  452
```

<210> SEQ ID NO 41
<211> LENGTH: 676
<212> TYPE: DNA
<213> ORGANISM: Homo sapien

<400> SEQUENCE: 41

```
aatctttgaa tgccaagtct cttctgtact ttcttttatt aacatcatag tctttgcatc     60

aagatacata gcaatgatag caggtttctt tttaaagctt agtattaata ttaaatattt    120

ttccccattt aaattttaca ttacttgcca agaaaaaaaa aaaattaaaa ctcaagttac    180

ttgaagcctg gacacacttc catgattagc cgggctaggt aaaagttggt ggctttattc    240

ttcctgctct ataagcagat ccaggcccta gaaagatggg accagggtat ataattgttt    300

ttgaaaagtg tgctacaaaa atggatggcc tgttataagc caggatacaa agttaaggat    360

gggggtaagg gagggacatt ttcttccaga agaaaagaca gaatttctga agagtcccag    420

tccataattt tcccaaaatg gttggaggag agggtaaaat ctcaacatga gtttcaaagt    480

actgtctctg tgaggggccg gtagatgcct tgctgaggag ggatggctaa tttggaccat    540

gccccatccc cagctaggag aatggaaatg gaaactttaa ttgcccagtg ggtgtgaaag    600

tgggctgaag cttggttggt actgaattct ctaagaggtt tcttctagaa acagacaact    660

cagacctgcc cgggcg                                                    676
```

<210> SEQ ID NO 42
<211> LENGTH: 468
<212> TYPE: DNA
<213> ORGANISM: Homo sapien

<400> SEQUENCE: 42

-continued

```
agcgtggtcg cggccgaggt ttggccggga gcctgatcac ctgccctgct gagtcccagg      60

ctgagcctca gtctccctcc cttggggcct atgcagaggt ccacaacaca cagatttgag     120

ctcagccctg gtgggcagag aggtagggat ggggctgtgg ggatagtgag gcatcgcaat     180

gtaagactcg ggattagtac acacttgttg attaatggaa atgtttacag atccccaagc     240

ctggcaaggg aatttcttca actccctgcc ccccagccct ccttatcaaa ggacaccatt     300

ttggcaagct ctatgaccaa ggagccaaac atcctacaag acacagtgac catactaatt     360

aaaacccccct gcaaagccca gcttgaaacc ttcacttagg aacgtaatcg tgtcccctat    420

cctacttccc cttcctaatt ccacagacct gcccgggcgg ccgctcga                  468
```

<210> SEQ ID NO 43
<211> LENGTH: 408
<212> TYPE: DNA
<213> ORGANISM: Homo sapien

<400> SEQUENCE: 43

```
atcatatcaa aacactatct tcccatctgt ttctcaatgc ctgctacttc ttgtagatat      60

ttcatttcag gagagcagca gttaaacccg tggattttgt agttaggaac ctgggttcaa     120

acctctttcc actaattggc tatgtctctg gacagttttt tttttttttt tttttttaa      180

accctttctg aactttcact ttctatggct acctcaaaga attgttgtga ggcttgagat     240

aatgcatttg taaagggtct gccagatagg aagatgctag ttatggattt acaaggttgt     300

taaggctgta agagtctaaa acctacagtg aatcacaatg catttacccc cactgacttg     360

gacataagtg aaaactagcc cgaagtctct ttttcaaatt acttacag                  408
```

<210> SEQ ID NO 44
<211> LENGTH: 160
<212> TYPE: DNA
<213> ORGANISM: Homo sapien

<400> SEQUENCE: 44

```
tggtcgcggc cgaggtcttg tgtgccctgt ggtccagggg accaagaaca acaagatcca      60

ctctctgtgc tacaatgatt gcaccttctc acgcaacact ccaaccagga ctttcaacta     120

caacttctcc gctttggcaa acaccgtcac tcttgctgga                          160
```

<210> SEQ ID NO 45
<211> LENGTH: 231
<212> TYPE: DNA
<213> ORGANISM: Homo sapien

<400> SEQUENCE: 45

```
cgagcggccg cccgggcagg tctggggagg tgattccatc cagagtcata tctgttgtca      60

ccccaataag tcgatcagca aggctgacag gctgtgagga aaccccggcc ttgtagcctg     120

tcacctctgg ggggatgatg actgcctggc agacgtaggc tgtgatagat ttgggagaaa     180

acctgactca ccctcaggaa tccggaggtc ggtgacattg tcggtgcaca c              231
```

<210> SEQ ID NO 46
<211> LENGTH: 371
<212> TYPE: DNA
<213> ORGANISM: Homo sapien

<400> SEQUENCE: 46

```
cccgggcagg tctgtgtaac atgccaaggc tttgcacttt ctgcagagca gttttttatt      60

ttccttatca ggtacaggtt ttggtttttc ttgactatct ctgatgaatt tttcatgagt     120
```

-continued

```
ctgtatatgc agaatctttt ccctaaatac tgcttcgtcc catgtctgaa ggcgtaaaat    180

aaagtcattc atcatttttt ctttgtacat gtttatttgt tctttttcaa ttacaccaag    240

cattactagt cagaaggaag cacttgctac ctcttgctct tcctctgcct ctggtttgga    300

tcattttgat gacattgccc acattactca tgaaggatga caagattgca ctgtgcaatg    360

tcaattgcct t                                                         371
```

<210> SEQ ID NO 47
<211> LENGTH: 261
<212> TYPE: DNA
<213> ORGANISM: Homo sapien

<400> SEQUENCE: 47

```
gccctgtttt tatacacttc acatttgcag aaatataatg atgccctcat tatcagtgag     60

catgcacgaa tgaaagatgc tctggattac ttgaaagact tcttcagcaa tgtccgagca    120

gcaggattcg atgagattga gcaagatctt actcagagat ttgaagaaaa gctgcaggaa    180

ctagaaagtg tttccaggga tcccagcaat gagaatccta aacttgaaga cctctgcttc    240

atcttacaag aagagtacca c                                              261
```

<210> SEQ ID NO 48
<211> LENGTH: 701
<212> TYPE: DNA
<213> ORGANISM: Homo sapien

<400> SEQUENCE: 48

```
cgagcggccc ccgggcaggt ccaattagta caagtctcat gatataatca ctgcctgcat     60

acatatgcac agatccagtt agtgagtttg tcaagcttaa tctaattggt taagtctcaa    120

agagattatt attcttgatg tttgctttgt attggctaac aaatgtgcag aggtaataca    180

tatgtgatgt ccgatgtctc tgtctttttt tttgtcttta aaaaataatt ggcagcaact    240

gtatttgaat aaaatgattt cttagtatga ttgtaccgta atgaatgaaa gtggaacatg    300

tttctttttg aaagggagag aattgaccat ttattattgt gatgtttaag ttataactta    360

ttgagcactt ttagtagtga taactgtttt taaacttgcc taatatcctt cttgggtatt    420

gtttgtaatg tgacttattt aacccccttt tttgtttgtt taagttgctg ctttaggtta    480

acagcgtgtt ttagaagatt taaatttttt tcctgtctgc acaattagtt attcagagca    540

agagggcctg attttataga agccccttga aaagaggtcc agatgagagc agagatacag    600

tgagaaatta tgtgatctgt gtgttgtggg aagagaattt tcaatatgta actacggagc    660

tgtagtgcca ttagaaactg tgaatttcca aataaatttg a                        701
```

<210> SEQ ID NO 49
<211> LENGTH: 270
<212> TYPE: DNA
<213> ORGANISM: Homo sapien

<400> SEQUENCE: 49

```
agcggccgcc cgggcaggtc tgatattagt agctttgcaa ccctgataga gtaaataaat     60

tttatgggcg ggtgccaaat actgctgtga atctatttgt atagtatcca tgaatgaatt    120

tatggaaata gatatttgtg cagctcaatt tatgcagaga ttaaatgaca tcataatact    180

ggatgaaaac ttgcatagaa ttctgattaa atagtgggtc tgtttcacat gtgcagtttg    240

aagtatttaa attaaccact cctttcacag                                     270
```

-continued

<210> SEQ ID NO 50
<211> LENGTH: 271
<212> TYPE: DNA
<213> ORGANISM: Homo sapien

<400> SEQUENCE: 50
atgcatttat ccatatgaac ttgattattc tgaattactg actataaaaa ggctattgtg 60
aaagatatca cactttgaaa cagcaaatga attttcaatt ttacatttaa ttataagacc 120
acaataaaaa gttgaacatg cgcatatcta tgcatttcac agaagattag taaaactgat 180
ggcaacttca gaattatttc atgaagggta caaacagtct ttaccacaat tttcccatgg 240
tcttatcctt caaaataaaa ttccacacac t 271

<210> SEQ ID NO 51
<211> LENGTH: 241
<212> TYPE: DNA
<213> ORGANISM: Homo sapien

<400> SEQUENCE: 51
tggtcgcggc cgaggtgtga ggagatgaac tttgtgttaa tggggggcac tttaaatcga 60
aatggcttat ccccaccgcc atgtaagtta ccatgcctgt ctcctccctc ctacacattt 120
ccagctcctg ctgcagttat tcctacagaa gctgccattt accagccctc tgtgattttg 180
aatccacgag cactgcaggc cctccacagc gttactaccc agcaggcact cagctcttca 240
t 241

<210> SEQ ID NO 52
<211> LENGTH: 271
<212> TYPE: DNA
<213> ORGANISM: Homo sapien

<400> SEQUENCE: 52
tccaagactt aaaacttagg aaacacctat gatgccactt taactggaag taatggagac 60
atctgattcc aaattcacat tttaaatgcc tatttgcaat cagcaaagag ccaggtatgc 120
tgcatgctgc ttgctgtaag ttacgatttg gcttcactag ctcaaatttt ttcactccac 180
caaaagataa ggcacaggcc cgtttgtcca atcaagtttg ctgaaaatac tgcagcctga 240
gtgtagacaa acttcccctg aatttgctag a 271

<210> SEQ ID NO 53
<211> LENGTH: 493
<212> TYPE: DNA
<213> ORGANISM: Homo sapien

<400> SEQUENCE: 53
ttagcgtggt cgcggtccga ggtctggcct gactagctca ctctgaagag tgtctttcac 60
atggattaac caaaaaatgc attactgcct ttggcacact gtcttgaata ttctttctga 120
caatgagaaa atatgattta atggagtcgt tcaataacct cacaatctcg ctgttccgag 180
cagatagttt tcgtgccaac aggaactggc acatctagca ggttcacggc atgacctttt 240
tgtggactgg ctggcataat tggaatgggt tttgattttt cttctgctaa taactcttca 300
agcttttgaa gttttcaagc attcctctcc agttgcctgt ggttggttct tgaacaccat 360
ctccaacccc accacctcca gatgcaacct tgtctcgtga tacagacctg cccgggcggc 420
cctcaagggc gaattctgca gatatccatc acactggcgg ccgctcgagc atgcatctag 480
agggcccaat tcg 493

-continued

<210> SEQ ID NO 54
<211> LENGTH: 321
<212> TYPE: DNA
<213> ORGANISM: Homo sapien

<400> SEQUENCE: 54
cgtggtcgcg gccgaggtct gtttgcttgt tggtgtgagt ttttcttctg gagactttgt 60
actgaatgtc aataaactct gtgattttgt taggaagtaa aactgggatc tatttagcca 120
ctggtaagct tctgaggtga aggattcagg gacatctcgt ggaacaaaca ctccccactg 180
gactttctct ctggagatac ccttttgaat atacaatggc cttggctcac taggtttaaa 240
tacaaacaag tctgaaaccc actgaagact gagagattgc agcaatattc tctgaattag 300
gatcgggttc cataactcta a 321

<210> SEQ ID NO 55
<211> LENGTH: 281
<212> TYPE: DNA
<213> ORGANISM: Homo sapien

<400> SEQUENCE: 55
ttgcaaatga aactgtggat gtataataag aaaacacaag ggtttattct taacactaaa 60
attaacatgc cacacgaaga ctgcattaca gctctctgtt tctgtaatgc agaaaaatct 120
gaacagccca ccttggttac agctagcaaa gatggttact tcaaagtatg gatattaaca 180
gatgactctg acatatacaa aaaagctgtt ggctggacct gtgactttgt tggtagttat 240
cacaagtatc aagcaactaa ctgttgtttc tccgaagatg g 281

<210> SEQ ID NO 56
<211> LENGTH: 612
<212> TYPE: DNA
<213> ORGANISM: Homo sapien

<400> SEQUENCE: 56
gcgtggtcgc ggccgaggtc ctgtccgggg gcactgagaa ctccctctgg aattcttggg 60
gggtgttggg gagagactgt gggcctggag ataaaacttg tctcctctac caccaccctg 120
taccctagcc tgcacctgtc ctcatctctg caaagttcag cttccttccc caggtctctg 180
tgccactctg tcttggatgc tctggggagc tcatgggtgg aggagtctcc accagaggga 240
ggctcagggg actggttggg ccagggatga atatttgagg gataaaaatt gtgtaagagc 300
caaagaattg gtagtagggg gagaacagag aggagctggg ctatgggaaa tgatttgaat 360
aatggagctg ggaatatggc tggatatctg gtactaaaaa agggtcttta agaacctact 420
tcctaatctc ttccccaatc caaaccatag ctgtctgtcc agtgctctct tcctgcctcc 480
agctctgccc caggctcctc ctagactctg tccctgggct agggcagggg aggagggaga 540
gcagggttgg gggagaggct gaggagagtg tgacatgtgg ggagaggacc agacctgccc 600
gggcggccgt cg 612

<210> SEQ ID NO 57
<211> LENGTH: 363
<212> TYPE: DNA
<213> ORGANISM: Homo sapien

<400> SEQUENCE: 57
gtcgcggccg aggtcctgag cgtcacccta gttctgcccc tttttagctg tgtagacttg 60

-continued

```
gacaagacat ttgacttccc tttctccttg tctataaaat gtggacagtg gacgtctgtc    120

acccaagaga gttgtgggag acaagatcac agctatgagc acctcgcacg gtgtccagga    180

tgcacagcac aatccatgat gcgttttctc cccttacgca ctttgaaacc catgctagaa    240

aagtgaatac atctgactgt gctccactcc aacctccagc gtggatgtcc ctgtctgggc    300

cctttttctg tttttattc tatgttcagc accactggca ccaaatacat tttaattcac    360

cga                                                                  363
```

<210> SEQ ID NO 58
<211> LENGTH: 750
<212> TYPE: DNA
<213> ORGANISM: Homo sapien

<400> SEQUENCE: 58

```
cgtggtcgcg gccgaggtct aattccacct gactggcaga acctgcgccc ctcgcctaac     60

ctgcgccctt ctcccaactc gcgtgcctca cagaacccag gtgctgcaca gccccgagat    120

gtggcccttc ttcaggaaag agcaaataag ttggtccaag tacttgatgc ttaaggaata    180

cacaaaggtg cccatcaagc gctcagaaat gctgagagat atcatccgtg aatacactga    240

tgtttatcca gaaatcattg aacgtgcatg ctttgtccta gagaagaaat ttgggattca    300

actgaaagaa attgacaaag aagaacacct gtatattctc atcagtaccc ccgagtccct    360

ggctggcata ctgggaacga ccaaagacac acccaagctc ggtctcttct tggtgattct    420

gggtgtcatc ttcatgaatg gcaaccgtgc cagtgaggct gtcttttggg aggcactacg    480

caagatggga ctgcgtcctg ggtgagaca tcccctccct tggagatcta aggaaacttc    540

tcacctatga gtttgtaaag cagaaatacc tggactacag acgagtgccc aacagcaacc    600

ccccggagta tgagttcctc tggggcctcc gtccctacca tgagactagc aagatgaaaa    660

tgctgagatt cattgcagag gttcagaaaa gagaccctcg tgactggact gcacagttca    720

tggaggctgc agatgaggac ctgcccgggc                                     750
```

<210> SEQ ID NO 59
<211> LENGTH: 505
<212> TYPE: DNA
<213> ORGANISM: Homo sapien

<400> SEQUENCE: 59

```
tggccgcccg ggcaggtcca gtctacaagc agagcactct catggggagc accagatgag     60

ttccagccgc agttctttta taagctttaa gtgcctcatg aagacgcgag gatctcttcc    120

aagtgcaacc tggtcacatc agggcacatt cagcagcaga agtctgtttc cagtatagtc    180

cttggtatgg ctaaattcca ctgtcccttt ctcagcagtc aataatccat gataaattct    240

gtacaacact gtagtcaata acagcagcac cagacagcat attaattctt ttaccataaa    300

tttgtgtgta attataatgt tctatgtgtg gtgttatcaa aagaatcact gtgtctctaa    360

atatcatata tgtatgtctg gataaataca ttgctgtaca acatctccaa catgcaggtc    420

atgctctaag acttggggat atagagtaat acatgtttcg tggacctcgg ccgcgaccac    480

gctaagggcg aattctgcag atatc                                          505
```

<210> SEQ ID NO 60
<211> LENGTH: 520
<212> TYPE: DNA
<213> ORGANISM: Homo sapien

<400> SEQUENCE: 60

-continued

```
cgtggtcgcg gccgaggtcc tcaggacaag gaaacaggta tcagcatgat ggtagcagaa     60

accttatcac caaggtgcag gagctgactt cttccaaaga gttgtggttc cgggcagcgg    120

tcattgcctg cccttgctgg agggctgatt ttagtgttgc ttattatgtt ggccctgagg    180

atgcttcgaa gtgaaaataa gaggctgcag gatcagcggc aacagatgct ctcccgtttg    240

cactacagct ttcacggaca ccattccaaa aaggggcagg ttgcaaagtt agacttggaa    300

tgcatggtgc cggtcagtgg gcacgagaac tgctgtctga cctgtgataa aatgagacaa    360

gcagacctca gcaacgataa gatcctctcg cttgttcact ggggcatgta cagtgggcac    420

gggaagctgg aattcgtatg acggagtctt atctgaacta cacttactga acagcttgaa    480

ggacctgccc gggcggccgc tcgaaagggg cgaattctgc                          520
```

<210> SEQ ID NO 61
<211> LENGTH: 447
<212> TYPE: DNA
<213> ORGANISM: Homo sapien

<400> SEQUENCE: 61

```
agagaggtgt ttttattctt tggggacaaa gccgggttct gtgggtgtag gattctccag     60

gttctccagg ctgtagggcc cagaggctta atcagaattt tcagacaaaa ctggaacctt    120

tctttttttcc cgttggttta tttgtagtcc ttgggcaaac caatgtcttt gttcgaaaga    180

gggaaaataa tccaaacgtt tttcttttaa cttttttttt aggttcaggg gcacatgtgt    240

aggcttgcta tataggtaaa ttgcatgtca ccagggtttg ttgtacagat tatttcatca    300

tccagataaa aagcatagta ccagataggt agttttttga tcctcaccct ccttccatgc    360

tccgacctca ggtaggcccc agtgtctgac ctgcccggcg gcccgctcga aagggccaat    420

tctgcagata tccatcacac tggccgg                                        447
```

<210> SEQ ID NO 62
<211> LENGTH: 83
<212> TYPE: PRT
<213> ORGANISM: Homo sapien

<400> SEQUENCE: 62

```
Lys Lys Val Leu Leu Leu Ile Thr Ala Ile Leu Ala Val Ala Val Gly
 1               5                  10                  15

Phe Pro Val Ser Gln Asp Gln Glu Arg Glu Lys Arg Ser Ile Ser Asp
            20                  25                  30

Ser Asp Glu Leu Ala Ser Gly Phe Phe Val Phe Pro Tyr Pro Tyr Pro
        35                  40                  45

Phe Arg Pro Leu Pro Pro Ile Pro Phe Pro Arg Phe Pro Trp Phe Arg
    50                  55                  60

Arg Asn Phe Pro Ile Pro Ile Pro Ser Ala Pro Thr Thr Pro Leu Pro
65                  70                  75                  80

Ser Glu Lys
```

<210> SEQ ID NO 63
<211> LENGTH: 683
<212> TYPE: DNA
<213> ORGANISM: Homo sapien

<400> SEQUENCE: 63

```
acaaagattg gtagctttta tattttttta aaaatgctat actaagagaa aaaacaaaag     60

accacaacaa tattccaaat tataggttga gagaatgtga ctatgaagaa agtattctaa    120
```

-continued

```
ccaactaaaa aaaatattga aaccactttt gattgaagca aaatgaataa tgctagattt    180

aaaaacagtg tgaaatcaca ctttggtctg taaacatatt tagctttgct tttcattcag    240

atgtatacat aaacttattt aaaatgtcat ttaagtgaac cattccaagg cataataaaa    300

aaagwggtag caaatgaaaa ttaaagcatt tattttggta gttcttcaat aatgatrcga    360

gaaactgaat tccatccagt agaagcatct ccttttgggt aatctgaaca agtrccaacc    420

cagatagcaa catccactaa tccagcacca attccttcac aaagtccttc cacagaagaa    480

gtgcgatgaa tattaattgt tgaattcatt tcagggcttc cttggtccaa ataaattata    540

gcttcaatgg gaagaggtcc tgaacattca gctccattga atgtgaaata ccaacgctga    600

cagcatgcat ttctgcattt tagccgaagt gagccactga acaaaactct tagagcacta    660

tttgaacgca tctttgtaaa tgt                                            683
```

<210> SEQ ID NO 64
<211> LENGTH: 749
<212> TYPE: DNA
<213> ORGANISM: Homo sapiens
<220> FEATURE:
<221> NAME/KEY: misc_feature
<222> LOCATION: 534
<223> OTHER INFORMATION: n = A,T,C or G

<400> SEQUENCE: 64

```
ctgttcattt gtccgccagc tcctggactg gatgtgtgaa aggcatcaca tttccatttt     60

cctccgtgta aatgttttat gtgttcgcct actgatccca ttcgttgctt ctattgtaaa    120

tatttgtcat ttgtatttat tatctctgtg ttttccccct aaggcataaa atggtttact    180

gtgttcattt gaacccattt actgatctct gttgtatatt tttcatgcca ctgctttgtt    240

ttctcctcag aagtcgggta gatagcattt ctatcccatc cctcacgtta ttggaagcat    300

gcaacagtat ttattgctca gggtcttctg cttaaaactg aggaaggtcc acattcctgc    360

aagcattgat tgagacattt gcacaatcta aaatgtaagc aaagtaagtc attaaaaata    420

caccctctac ttgggcttta tactgcatac aaatttactc atgagccttc ctttgaggaa    480

ggatgtggat ctccaaataa agatttagtg tttattttga gctctgcatc ttancaagat    540

gatctgaaca cctctccttt gtatcaataa atagccctgt tattctgaag tgagaggacc    600

aagtatagta aaatgctgac atctaaaact aaataaatag aaaacaccag gccagaacta    660

tagtcatact cacacaaagg gagaaattta aactcgaacc aagcaaaagg cttcacggaa    720

atagcatgga aaaacaatgc ttccagtgg                                      749
```

<210> SEQ ID NO 65
<211> LENGTH: 612
<212> TYPE: DNA
<213> ORGANISM: Homo sapiens

<400> SEQUENCE: 65

```
acagcagcag tagatggctg caacaacctt cctcctaccc cagcccagaa aatatttctg     60

ccccacccca ggatccggga ccaaaataaa gagcaagcag gccccccttca ctgaggtgct   120

gggtagggct cagtgccaca ttactgtgct ttgagaaaga ggaaggggat ttgtttggca    180

ctttaaaaat agaggagtaa gcaggactgg agaggccaga gaagatacca aaattggcag    240

ggagagacca tttggcgcca gtcccctagg agatgggagg agggagatag gtatgagggt    300

aggcgctaag aagagtagga ggggtccact ccaagtggca gggtgctgaa atgggctagg    360
```

-continued accaacagga cactgactct aggtttatga cctgtccata cccgttccac agcagctggg 420
tgggagaaat caccattttg tgacttctaa taaaataatg ggtctaggca acagttttca 480
atggatgcta aaacgattag gtgaaaagtt gatggagaat tttaattcag gggaattagg 540
ctgataccat ctgaaaccat ttggcatcat taaaaatgtg acaacctggt ggctgccagg 600
gaggaagggg ag 612

<210> SEQ ID NO 66
<211> LENGTH: 703
<212> TYPE: DNA
<213> ORGANISM: Homo sapiens

<400> SEQUENCE: 66
tagcgtggtc gcggccgagg tacattgatg ggctggagag cagggttggc agcctgttct 60
gcacagaacc aagaattaca gaaaaaagtc caggagctgg agaggcacaa catctccttg 120
gtagctcagc tccgccagct gcagacgcta attgctcaaa cttccaacaa agctgcccag 180
accagcactt gtgttttgat tcttcttttt tccctggctc tcatcatcct gcccagcttc 240
agtccattcc agagtcgacc agaagctggg tctgaggatt accagcctca cggagtgact 300
tccagaaata tcctgaccca caaggacgta acagaaaatc tggagaccca agtggtagag 360
tccagactga gggagccacc tggagccaag gatgcaaatg gctcaacaag gacactgctt 420
gagaagatgg gagggaagcc aagacccagt gggcgcatcc ggtccgtgct gcatgcagat 480
gagatgtgag ctggaacaga ccttcctggc ccacttcctg atcacaagga atcctgggct 540
tccttatggc tttgcttccc actgggattc ctacttaggt gtctgccctc aggggtccaa 600
atcacttcag gacaccccaa gagatgtcct ttagtctctg cctgaggcct agtctgcatt 660
tgtttgcata tatgagaggg tacctgcccg ggcggccgct cga 703

<210> SEQ ID NO 67
<211> LENGTH: 1022
<212> TYPE: DNA
<213> ORGANISM: Homo sapiens

<400> SEQUENCE: 67
cttgagaaag caggattgtt ttaagttcca agatttaaca aacttactgt tcagcatcat 60
attcaagcct aaaaggaaga taggattttc aagatatatt tccaacttct ttaacatggc 120
accatggatg aactgtttct cagcactgtg ctgcttcact tggaattaag gatgaattgg 180
gaggagacag tatgacatag gtgggtaggt tgggtggtga ggggaaccag ttctaatagt 240
cctcaactcc actccagctg ttcctgttcc acacggtcca ctgagctggc ccagtccctt 300
tcactcagtg tgtcaccaaa ggcagcttca aggctcaatg gcaagagacc acctataacc 360
tcttcacctt ctgctgcctc tttctgctgc cactgactgc catggccatc tgctatagcc 420
gcattgtcct cagtgtgtcc aggccccaga caaggaaggg gagccatggt gagactccaa 480
ttcccaggcc ttaatcctta accctagacc tgttgcctct agcatcattt atttatctac 540
ctacctaata gctatctacc agtcattaaa ccatggtgag attctaacca tgtctagcac 600
ctgatgctag agataatttt gttgaatccc ttcaattata aacagctgag ttagctggac 660
aaggactagg gaggcaatca gtattattta ttcttgaaca ccatcaagtc tagacttggt 720
ggcttcatat ttctatcata atccctgggg gtaagaaatc atatagcccc aggttgggaa 780
ggggaaaacg gtttgcaaca ttctcctcct tgtaggaggc gagctctgtc tcactagcta 840
tgcccctcca tcaattcacc ctatactcag atcagaagct gagtgtctga attacagtat 900

-continued

```
attttctaaa ttcctagccc ctgctggtga atttgccctc ccccgctcct ttgacaattg    960

tccccgtgtt cgtctccggg ccctgagact ggccctgctt atcttgctga ccttcatcct   1020

ct                                                                  1022
```

<210> SEQ ID NO 68
<211> LENGTH: 449
<212> TYPE: DNA
<213> ORGANISM: Homo sapiens

<400> SEQUENCE: 68

```
ccagatccat tttcagtggt ctggatttct ttttattttc ttttcaactt gaaagaaact     60

ggacattagg ccactatgtg ttgttactgc cactagtgtt caagtgcctc ttgttttccc    120

agagatttcc tgggtctgcc agaggcccag acaggctcac tcaagctctt taactgaaaa    180

gcaacaagcc actccaggac aaggttcaaa atggttacaa cagcctctac ctgtcgcccc    240

agggagaaag gggtagtgat acaagtctca tagccagaga tggttttcca ctccttctag    300

atattcccaa aaagaggctg agacaggagg ttattttcaa ttttattttg gaattaaata    360

ctttttttccc tttattactg ttgtagtccc tcacttggat atacctctgt tttcacgata    420

gaaataaggg aggtctagag cttctattc                                      449
```

<210> SEQ ID NO 69
<211> LENGTH: 387
<212> TYPE: DNA
<213> ORGANISM: Homo sapiens
<220> FEATURE:
<221> NAME/KEY: misc_feature
<222> LOCATION: 22, 26, 36, 45, 54, 56, 62, 63, 73, 92, 98, 105, 155,
174, 194, 302, 312, 358, 375, 378, 381
<223> OTHER INFORMATION: n = A,T,C or G

<400> SEQUENCE: 69

```
gcccttagcg tgggtcgcgg cncgangtct ggagcntatg tgatncctat ggtncncagg     60

cnnatactgc tantctcatt tattctcctg cnacctantc ctctnctctg gaatcacacc    120

attattgcct gttaacactg gactgtgagt accangcaat taatttgcac caanaaagtt    180

gagggtatta tcanatattg caatctgtac agagggaaga tgatttcaat ttgatttcaa    240

cttaaccttc atctttgtct gttaacacta atagagggtg tctaataaaa tggcaaattt    300

gngatctcat tnggtataac tacactcttt ttcacagatg tgatgactga atttccanca    360

acctgcccgg gcggncgntc naagggc                                        387
```

<210> SEQ ID NO 70
<211> LENGTH: 836
<212> TYPE: DNA
<213> ORGANISM: Homo sapiens

<400> SEQUENCE: 70

```
tattccattt acaaaataaa ttcagccctg cactttcttt agatgccttg atttccagaa     60

tggagcttag tgctactgaa taccctggcc acagagccac ctcaggatat tcttttctcc    120

accctagttt atttatttat agatatctgt ttacaaagtc tgtagtaaat cctgatgctg    180

accatctgaa atgtactttt tttctgaatg ctgtttcaat ctaaaatagc agcttttgag    240

aaaacaatga tgtaaattcc ttatgataaa aggatgattc tatatattct ttaatgatat    300

taaatatgcc gaagccaagc acacagtctt tctaaagtgt gtgtatgttt gtgtgaatgt    360

gaatgatact gatcttatat ctgttaaaag ttgttttaaa aagctgtggc atcccattgt    420
```

-continued

```
tcatatttgc caagtcttct gtaaagatgt ctaggacgaa atattttatg tgctaatgca    480

tgtatttgta aaccagattt gtttaccact caaaattaac ttgttttctt catccaaaaa    540

agtttatttc ttccacgtac ttaaattttc tgtgtgggta taatatagct ttctaatttt    600

tttctttcac aaaggcaggt tcaaaattct gttgaaagaa aaatgctttc tgaaactgag    660

gtataacacc agagcttgct gtttaaagga ttatatgatg tacatcagtt ctataaatgt    720

gctcagcagt ttaacatgtg aatcctgttt taaagtgctc agatttcaac tgtgtaagcc    780

attgatataa cgctgtaatt aaaaatgttt atatgaaaaa aaaaaaaaaa aaaaaa        836
```

<210> SEQ ID NO 71
<211> LENGTH: 618
<212> TYPE: DNA
<213> ORGANISM: Homo sapiens

<400> SEQUENCE: 71

```
gttgcagtga gctcaagtgt tgggtgtatc agctcaaaac accatgtgat gccaatcatc     60

tccacaggag caatttgttt accttttttt tctgatgctt tactaacttc atcttttaga    120

tttaaatcat tagtagatcc tagaggagcc agtttcagaa aatatagatt ctagttcagc    180

accacccgta gttgtgcatt gaaataatta tcattatgat tatgtatcag agcttctggt    240

tttctcattc tttattcatt tattcaacaa ccacgtgaca aacactggaa ttacaggatg    300

aagatgagat aatccgctcc ttggcagtgt tatactatta tataacctga aaaaacaaac    360

aggtaatttt cacacaaagt aatagatatc atgacacatt taaaataggg cactactgga    420

acacacagat aggacatcca ggttttgggt caatattgta gactttttgg tggatgagat    480

atgcaggttg atrccagaag gacaacaaaa acatatgtca gatagaaggg aggagcaaat    540

gccaagagct ggagctgagg aagatcactg tgaaattcta tgtagtctag ttggctggat    600

gctagagcaa agaggtgg                                                  618
```

<210> SEQ ID NO 72
<211> LENGTH: 806
<212> TYPE: DNA
<213> ORGANISM: Homo sapiens

<400> SEQUENCE: 72

```
tctacgatgg ccatttgctc attgtctttc ctctgtgtgt agtgagtgac cctggcagtg     60

tttgcctgct cagagtggcc cctcagaaca acagggctgg ccttggaaaa accccaaaac    120

aggactgtgg tgacaactct ggtcaggtgt gatttgacat gagggccgga ggcggttgct    180

gacggcagga ctggagaggc tgcgtgcccg gcactggcag cgaggctcgt gtgtccccca    240

ggcagatctg ggcactttcc caacccaggt ttatgccgtc tccagggaag cctcggtgcc    300

agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctccccccgcc ctgtggttgg    540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780
```

-continued tttagatgtt gaaaaaaaaa aaaaaa 806

<210> SEQ ID NO 73
<211> LENGTH: 301
<212> TYPE: DNA
<213> ORGANISM: Homo sapiens
<220> FEATURE:
<221> NAME/KEY: misc_feature
<222> LOCATION: 59
<223> OTHER INFORMATION: n = A,T,C or G

<400> SEQUENCE: 73
actctggtaa gcttgttgtt gtccaagtga agctccctca gatgaggcgt gttggccana 60
gagccattgt caacagcaga gatgctgttg aaactcaatc ccaacttagc caaattattc 120
agtcctttca ggctagctgc atcaactctg ctgattttgt tgccatcaag atgtaattcc 180
gtaagggaag gaggaagacc ttgaggaatg ctggygatat tggyatcagc aatgcggatg 240
tasgaagagc ttcttcmttc cctggaaagc cccattttca atyccttgag ctcttcakcg 300
g 301

<210> SEQ ID NO 74
<211> LENGTH: 401
<212> TYPE: DNA
<213> ORGANISM: Homo sapiens

<400> SEQUENCE: 74
agtttacatg atccctgtaa cagccatggt ctcaaactca gatgcttcct ccatctgcca 60
agtgtgttct ggatacagag cacatcgtgg cttctggggt cacactcagc ttaggctgtg 120
ggtccacaga gcactcatct ggctgggcta tggtggtggt ggctctactc aagaagcaaa 180
gcagttacca gcacattcaa acagtgtatt gaacatcttt taaatatcaa agtgagaaac 240
aagaaggcaa cataataatg ttatcagaaa gatgttagga agtaaggaca gctgtgtaaa 300
gcttgaggct gaaaagtagc ttgccagctt catttctttg gtttcttggg tagtgggccg 360
ccggaacagc aagatgtgag gttctggttc atggatcata t 401

<210> SEQ ID NO 75
<211> LENGTH: 612
<212> TYPE: DNA
<213> ORGANISM: Homo sapiens

<400> SEQUENCE: 75
ttatttttca atttttattt tggttttctt acaaaggttg acattttcca taacaggtgt 60
aagagtgttg aaaaaaaaat tcaaattttt ggggagcgag ggaaggagtt aatgaaactg 120
tattgcacaa tgctctgatc aatccttctt tttctctttt gcccacaatt taagcaagta 180
gatgtgcaga agaaatggaa ggattcagct ttcagttaaa aaagaagaag aagaaatggc 240
aaagagaaag ttttttcaaa tttctttctt ttttaattta gattgagttc atttatttga 300
aacagactgg gccaatgtcc acaaagaatt cctggtcagc accaccgatg tccaaaggtg 360
caatatcaag gaagggcagg cgtgatggct tatttgtttt gtattcaatg attgtctttc 420
cccattcatt tgtcttttta gagcagccat ctacaagaac agtgtaagtg aacctgctgt 480
tgccctcagc aacaagttca acatcattag agccctgtag aatgacagcc tttttcaggt 540
tgccagtctc ctcatccatg tatgcaatgc tgttcttgca gtggtaggtg atgttctgag 600
aggcatagtt gg 612

-continued

<210> SEQ ID NO 76
<211> LENGTH: 844
<212> TYPE: DNA
<213> ORGANISM: Homo sapiens

<400> SEQUENCE: 76

```
ggctttcgag cggccgcccg ggcaggtctg atggttctcg taaaaacccc gctagaaact     60
gcagagacct gaaattctgc catcctgaac tcaagagtgg agaatactgg gttgacccta    120
accaaggatg caaattggat gctatcaagg tattctgtaa tatggaaact ggggaaacat    180
gcataagtgc caatcctttg aatgttccac ggaaacactg gtggacagat tctagtgctg    240
agaagaaaca cgtttggttt ggagagtcca tggatggtgg ttttcagttt agctacggca    300
atcctgaact tcctgaagat gtccttgatg tgcagcykgc attccttcga cttctctcca    360
gccgagcttc ccagaacatc acatatcact gcaaaaatag cattgcatac atggatcagg    420
ccagtggaaa tgtaaagaag gccctgaagc tgatggggtc aaatgaaggt gaattcaagg    480
ctgaaggaaa tagcaaattc acctacacag ttctggagga tggttgcacg aaacacactg    540
gggaatggag caaaacagtc tttgaatatc gaacacgcaa tgctgttcct tgacattgca    600
ccaccaatgt ccagaggtgc aatgtcaagg aacggcaggc gagatggctt atttgttttg    660
tattcaatga ttgtcttgcc ccattcattt gtctttttgg agcagccatc gactaggaca    720
gagtaggtga acctgctgtt gccctcagca acaagttcca catcgttgga accctgcaga    780
agcacagcct tgttcaarct gcccgtctcc tcatccagat acctcggccg cgaccacgct    840
aatc                                                                 844
```

<210> SEQ ID NO 77
<211> LENGTH: 314
<212> TYPE: DNA
<213> ORGANISM: Homo sapiens

<400> SEQUENCE: 77

```
ccagtcctcc acttggcctg atgagagtgg ggagtggcaa gggacgtttc tcctgcaata     60
gacacttaga tttctctctt gtgggaagaa accacctgtc catccactga ctcttctaca    120
ttgatgtgga aattgctgct gctaccacca cctcctgaag aggcttccct gatgccaatg    180
ccagccatcc tggcatcctg gccctcgagc aggctgcggt aagtagcgat ctcctgctcc    240
agccgtgtct ttatgtcaag cagcatcttg tactcctggt tctgagcctc catctcgcat    300
cggagctcac tcag                                                      314
```

<210> SEQ ID NO 78
<211> LENGTH: 548
<212> TYPE: DNA
<213> ORGANISM: Homo sapiens

<400> SEQUENCE: 78

```
accaagagcc aagtgttaca caggatattt taaaaataaa atgtttttgg aatcctcacc     60
tcccatgcta tcttctaaga taactacaaa tattcttcaa agatttaact gagttctgcc    120
aaggacctcc caggactcta tccagaatga ttattgtaaa gctttacaaa tcccaccttg    180
gccctagcga taattaggaa atcacaggca aacctcctct ctcggagacc aatgaccagg    240
ccaatcagtc tgcacattgg ttttgttaga tactttgtgg agaaaaacaa aggctcgtga    300
tagtgcagct ctgtgcctac agagagcctc ccttttggtt ctgaaattgc tgatgtgaca    360
gagacaaagc tgctatgggt ctaaaacctt caataaagta actaatgaca ctcaaggtcc    420
```

-continued

```
tgggactctg agacagacgg tggtaaaacc cacagctgcg attcacattt ccaatttatt    480

ttgagctctt tctgaagctg ttgcttccta cctgagaatt cccatttaga gagctgcaca    540

gcacagtc                                                             548
```

<210> SEQ ID NO 79
<211> LENGTH: 646
<212> TYPE: DNA
<213> ORGANISM: Homo sapiens

<400> SEQUENCE: 79

```
accccgtcac tatgtgaata aaggcagcta gaaaatggac tcaattctgc aagccttcat     60

ggcaacagcc catattaaga cttctagaac aagttaaaaa aaatcttcca tttccatcca    120

tgcatgggaa aagggcttta gtatagttta ggatggatgt gtgtataata ataaaatgat    180

aagatatgca tagtggggga ataaagcctc agagtccttc cagtatgggg aatccattgt    240

atcttagaac cgagggattt gtttagattg ttgatctact aattttttc ttcacttata     300

tttgaatttt caatgatagg acttattgga aattggggat aattctgttg tggtattaaa    360

taatattcat tttttaaaaa ctcatcttgg tattgagtta gtgcattgac ttccaatgaa    420

ttgacataag cccatatttc attttaacca gaaacaaaaa ctagaaaatg ttactcccta    480

aataggcaac aatgtatttt ataagcactg cagagattta gtaaaaaaca tgtatagtta    540

ctttagaaac aacttctgac acttgagggt tacccaatgg tctccttccc attctttata    600

tgaggtaaat gcaaaccagg gagccaccga ataaacagcc ctgagt                   646
```

<210> SEQ ID NO 80
<211> LENGTH: 276
<212> TYPE: DNA
<213> ORGANISM: Homo sapiens
<220> FEATURE:
<221> NAME/KEY: misc_feature
<222> LOCATION: 16, 29, 32, 45, 53, 55, 58, 59, 65, 66, 75, 77, 85, 90,
97, 109, 112, 163, 170
<223> OTHER INFORMATION: n = A,T,C or G

<400> SEQUENCE: 80

```
gtctgaatga gcttcnctgc gagatggganc ancataaccc agaantccaa aancntanng     60

aacgnnaaaa cccgntngaa caagnaaacn gcaactnacg gccgcctgnt gnagggcgag    120

gacgcccacc tctcctcctc ccagttctcc tctggatcgc agncatccan agatgtgacc    180

tcttccagcc gccaaatccg caccaaggtc atggatgtgc acgatggcaa ggtgggtgtc    240

cacccacgaa caggtccttc gcaccaagaa ctgagg                             276
```

<210> SEQ ID NO 81
<211> LENGTH: 647
<212> TYPE: DNA
<213> ORGANISM: Homo sapiens

<400> SEQUENCE: 81

```
gtcctgcctt tcatcttttc tttaaaaaaa ataaatgttt acaaaacatt tccctcagat     60

tttaaaattc atggaagtaa taaacagtaa taaaatatgg atactatgaa aactgacaca    120

cagaaaaaca taaccataaa atattgttcc aggatacaga tattaattaa gagtgacttc    180

gttagcaaca cgtagacatt catacatatc cggtggaaga ctggtttctg agatgcgatt    240

gccatccaaa cgcaaatgct tgatcttgga gtaggrtaat ggccccagga tcttgcagaa    300

gctctttatg tcaaacttct caagttgatt gacctccagg taatagtttt caaggttttc    360
```

-continued attgacagtt ggtatgtttt taagcttgtt ataggacaga tccagctcaa ccagggatga 420
cacattgaaa gaatttccag gtattccact atcagccagt tcgttgtgag ataaacgcag 480
atactgcaat gcattaaaac gcttgaaata ctcatcaggg atgttgctga tcttattgtt 540
gtctaagtag agagttagaa gagagacagg gagaccagaa ggcagtctgg ctatctgatt 600
gaagctcaag tcaaggtatt cgagtgattt aagaccttta aaagcag 647

<210> SEQ ID NO 82
<211> LENGTH: 878
<212> TYPE: DNA
<213> ORGANISM: Homo sapiens

<400> SEQUENCE: 82
ccttctttcc ccactcaatt cttcctgccc tgttattaat taagatatct tcagcttgta 60
gtcagacaca atcagaatya cagaaaaatc ctgcctaagg caaagaaata taagacaaga 120
ctatgatatc aatgaatgtg ggttaagtaa tagatttcca gctaaattgg tctaaaaaag 180
aatattaagt gtggacagac ctatttcaaa ggagcttaat tgatctcact tgttttagtt 240
ctgatccagg gagatcaccc ctctaattat ttctgaactt ggttaataaa agtttataag 300
atttttatga agcagccact gtatgatatt ttaagcaaat atgttattta aaatattgat 360
ccttcccttg gaccaccttc atgttagttg ggtattataa ataagagata caaccatgaa 420
tatattatgt ttatacaaaa tcaatctgaa cacaattcat aaagatttct cttttatacc 480
ttcctcactg gccccctcca cctgcccata gtcaccaaat tctgttttaa atcaatgacc 540
taagatcaac aatgaagtat tttataaatg tatttatgct gctagactgt gggtcaaatg 600
tttccatttt caaattattt agaattctta tgagtttaaa atttgtaaat ttctaaatcc 660
aatcatgtaa aatgaaactg ttgctccatt ggagtagtct cccacctaaa tatcaagatg 720
gctatatgct aaaaagagaa aatatggtca agtctaaaat ggctaattgt cctatgatgc 780
tattatcata gactaatgac atttatcttc aaaacaccaa attgtcttta gaaaaattaa 840
tgtgattaca ggtagagaac ctcggccgcg accacgct 878

<210> SEQ ID NO 83
<211> LENGTH: 645
<212> TYPE: DNA
<213> ORGANISM: Homo sapiens

<400> SEQUENCE: 83
acaaacattt tacaaaaaag aacattacca atatcagtgg cagtaagggc aagctgaaga 60
ataaatagac tgagtttccg ggcaatgtct gtcctcaaag acatccaaac tgcgttcagg 120
cagctgaaac aggcttcttt cccagtgaca agcatatgtg gtcagtaata caaacgatgg 180
taaatgaggc tactacatag gcccagttaa caaactcctc ttctcctcgg gtaggccatg 240
atacaagtgg aactcatcaa ataatttaaa cccaaggcga taacaacgct atttcccatc 300
taaactcatt taagccttca caatgtcgca atggattcag ttacttgcaa acgatcccgg 360
gttgtcatac agatacttgt ttttacacat aacgctgtgc catcccttcc ttcactgccc 420
cagtcaggtt tcctgttgtt ggaccgaaag gggatacatt ttagaaatgc ttccctcaag 480
acagaagtga gaaagaaagg agaccctgag gccaggatct attaaacctg gtgtgtgcgc 540
aaaagggagg gggaaggcag gaatttgaaa ggataaacgt ctcctttgcg ccgaggaatc 600
aggaagcgtg actcacttgg gtctgggacg ataccgaaat ccggt 645

-continued

<210> SEQ ID NO 84
<211> LENGTH: 301
<212> TYPE: DNA
<213> ORGANISM: Homo sapiens
<220> FEATURE:
<221> NAME/KEY: misc_feature
<222> LOCATION: 270, 284
<223> OTHER INFORMATION: n = A,T,C or G

<400> SEQUENCE: 84
tctgatgtca atcacaactt gaaggatgcc aatgatgtac caatccaatg tgaaatctct 60
cctcttatct cctatgctgg agaaggatta gaaggttatg tggcagataa agaattccat 120
gcacctctaa tcatcgatga gaatggagtt catgggctgg tgaaaaatgg tatttgaacc 180
agataccaag ttttgtttgc cacgatagga atagctttta tttttgatag accaactgtg 240
aacctacaag acgtcttgga caactgaagn ttaaatatcc acangggttt attttgcttg 300
g 301

<210> SEQ ID NO 85
<211> LENGTH: 296
<212> TYPE: DNA
<213> ORGANISM: Homo sapiens
<220> FEATURE:
<221> NAME/KEY: misc_feature
<222> LOCATION: 16, 20, 240
<223> OTHER INFORMATION: n = A,T,C or G

<400> SEQUENCE: 85
agcgtgggtc gcggcncgan gtagagaacc gactgaaacg tttgagatga agaaagttct 60
cctcctgatc acagccatct tggcagtggc tgttggtttc ccagtctctc aagaccagga 120
acgagaaaaa agaagtatca gtgacagcga tgaattagct tcagggtttt ttgtgttccc 180
ttacccatat ccatttcgcc cacttccacc aattccattt ccaagatttc catggtttan 240
acgtaatttt cctattccaa tacctgaatc tgcccctaca actccccttc ctagcg 296

<210> SEQ ID NO 86
<211> LENGTH: 806
<212> TYPE: DNA
<213> ORGANISM: Homo sapiens

<400> SEQUENCE: 86
tctacgatgg ccatttgctc attgtctttc ctctgtgtgt agtgagtgac cctggcagtg 60
tttgcctgct cagagtggcc cctcagaaca acagggctgg ccttggaaaa accccaaaac 120
aggactgtgg tgacaactct ggtcaggtgt gatttgacat gagggccgga ggcggttgct 180
gacggcagga ctggagaggc tgcgtgcccg gcactggcag cgaggctcgt gtgtccccca 240
ggcagatctg ggcactttcc caacccaggt ttatgccgtc tccagggaag cctcggtgcc 300
agagtggtgg gcagatctga ccatccccac agaccagaaa caaggaattt ctgggattac 360
ccagtccccc ttcaacccag ttgatgtaac cacctcattt tttacaaata cagaatctat 420
tctactcagg ctatgggcct cgtcctcact cagttattgc gagtgttgct gtccgcatgc 480
tccgggcccc acgtggctcc tgtgctctag atcatggtga ctcccccgcc ctgtggttgg 540
aatcgatgcc acggattgca ggccaaattt cagatcgtgt ttccaaacac ccttgctgtg 600
ccctttaatg ggattgaaag cacttttacc acatggagaa atatattttt aatttgtgat 660
gcttttctac aaggtccact atttctgagt ttaatgtgtt tccaacactt aaggagactc 720
taatgaaagc tgatgaattt tcttttctgt ccaaacaagt aaaataaaaa taaaagtcta 780

-continued

```
tttagatgtt gaaaaaaaaa aaaaaa                                          806


<210> SEQ ID NO 87
<211> LENGTH: 620
<212> TYPE: DNA
<213> ORGANISM: Homo sapiens

<400> SEQUENCE: 87

tttttgcatc agatctgaaa tgtctgagag taatagtttc tgttgaattt ttttttgttc      60

atttttctgc acagtccatt ctgtttttat tactatctag gcttgaaata tatagtttga     120

aattatgaca tccttcctct ttgttatttt cctcatgatt gctttggcta ttcaaagttt     180

attttagttt catgtaaatt tttgaattgt attttccatt attgtgaaaa tagtaccact     240

gcaattttaa taggaagttt attgaatcta tagattactt tggataatat ggcacttcaa     300

taatattcat gttttcaatt catagacaaa atattttaaa atttatttgt atcttttcta     360

atttttcctt tttttattgt aaagatttac ctccttggtt aatattttcc tcagaaattt     420

attatttaag gtatagtcaa taaaattttc ttcctctatt ttgtcagata gtttaagtgt     480

atgaaaccat agatatactt gtatgttaat tttatatttt gctaatttac tgagtgtatt     540

tattagttta gagaggtttt aatgtactgt ttatggtttt ttaaatataa gattacttat     600

tttttaaaaa aaaaaaaaaa                                                 620


<210> SEQ ID NO 88
<211> LENGTH: 308
<212> TYPE: DNA
<213> ORGANISM: Homo sapiens
<220> FEATURE:
<221> NAME/KEY: misc_feature
<222> LOCATION: 9, 189, 194, 206, 238, 296
<223> OTHER INFORMATION: n = A,T,C or G

<400> SEQUENCE: 88

tagctgtgnt cagcaggccg aggttttttt tttttttgag atggagtctc gccctgtcac      60

ccaggctgga gtgcagtggc ctgatctcag ctcactgcaa gctccacctc ctggattcac     120

gctattctcc tgcctcagcc tcccaagtag ctgggactac aggcgcccgc caccacgccc     180

agctaattnt ttgnattttt agtacnagat gcggtttcat cgtgttagcc agcatggnct     240

cgatctcctg acctcgtgaa ctgcccgcct cggcctccca aagacctgcc cgggcnggcc     300

gctcgaaa                                                              308


<210> SEQ ID NO 89
<211> LENGTH: 492
<212> TYPE: DNA
<213> ORGANISM: Homo sapiens
<220> FEATURE:
<221> NAME/KEY: misc_feature
<222> LOCATION: 448
<223> OTHER INFORMATION: n = A,T,C or G

<400> SEQUENCE: 89

agcggccgcc cgggcaggtc tgttaagtaa catacatatc accttaataa aaatcaagat      60

gaaatgtttt agaaactatt ttatcaaaag tggctctgat acaaagactt gtacatgatt     120

gttcacagca gcactattaa tgccaaaaag tagacaaaac ctaaatgtcc attaactgat     180

aagcaaaatg tggtatatcc atacaatgga atattatgta gcccacaaca tggcatggag     240

tactacaaca tggatgagcc tcaaaaacgt tatgctaaat gaaaaaagtc agatatagga     300

aaccacatgt catatgatcc catttatatg aaatagccag aaaaggcaag tcatagaaac     360
```

-continued

```
aagatagatc ggaaaatggg ttggaggact acaaatggca ccagggatct ttgaagttga    420

tggaaatggt ctaaaatcag actgtggntg tggttgaaca agtctgtaaa tttaccaaaa    480

tgcgttaata ca                                                        492


<210> SEQ ID NO 90
<211> LENGTH: 390
<212> TYPE: DNA
<213> ORGANISM: Homo sapiens
<220> FEATURE:
<221> NAME/KEY: misc_feature
<222> LOCATION: 106, 184, 206, 209, 234, 314
<223> OTHER INFORMATION: n = A,T,C or G

<400> SEQUENCE: 90

tcgagcggcc gcccgggcag gtacaagctt tttttttttt tttttttttt ttttctaaca     60

gttctctgtt ttattgcaat acagcaaagt ctggttaata ttaagngata tcaacataaa    120

gtattggtga ggagtctttt gtgacatttt ttaccatccc accttaaata tttctgtgca    180

aaanaatcca catcattgtt tggtancana ggatctctta aaaagttccc taanacactg    240

agggcataaa accaaacaaa ataaaataag gagtgatagg ctaaagcagt atcttcccct    300

ccatccacat ttgncaagca ttatattcta accaaaaaat gatcacacca ggccatgcaa    360

aactgtccaa tattaccgag aaaaaaccct                                     390


<210> SEQ ID NO 91
<211> LENGTH: 192
<212> TYPE: DNA
<213> ORGANISM: Homo sapiens

<400> SEQUENCE: 91

agcgtggtcg cggccgaggt ctgtcaatta atgctagtcc tcaggattta aaaaataatc     60

ttaactcaaa gtccaatgca aaaacattaa gttggtaatt actcttgatc ttgaattact    120

tccgttacga aagtccttca catttttcaa actaagctac tatatttaag gcctgcccgg    180

gcggccgctc ga                                                        192


<210> SEQ ID NO 92
<211> LENGTH: 570
<212> TYPE: DNA
<213> ORGANISM: Homo sapiens
<220> FEATURE:
<221> NAME/KEY: misc_feature
<222> LOCATION: 519, 559
<223> OTHER INFORMATION: n = A,T,C or G

<400> SEQUENCE: 92

agcgtggtcg cggccgaggt ctgacaacta acaaagaagc aaaaactggc atcttggaca     60

tcctagtatt acacttgcaa gcaattagaa cacaaggagg gccaaggaaa aagtttagct    120

ttgaatcact tccaaatcta ctgattttga ggttccgcag tagttctaac aaaacttttc    180

agacaatgtt aactttcgat taagaaagaa aaaaaacccca aacatcttca ggaattccat    240

gccaggttca gtctcttcca gtgagcccgc ttgctaaaag tccacgtgca ccattaatta    300

gctgggctgg cagcaccatg taaaaagaag cctattcacc accaaccaca cagactagac    360

atgtaaagta ggatcaagta atggatgaca accatggtcg tggaatatgg tcaatgagag    420

tcagaaaagt acaggcacca gtacaagcag cagataacag aattgacggg ccaaaggata    480

aaaataggct tatttaaata ggatgctaca gaacacatnc acttctaatt ggaagctgct    540
```

-continued

```
ttacactggg tggcattgna ccatatgcat                                      570


<210> SEQ ID NO 93
<211> LENGTH: 446
<212> TYPE: DNA
<213> ORGANISM: Homo sapiens
<220> FEATURE:
<221> NAME/KEY: misc_feature
<222> LOCATION: 328, 389
<223> OTHER INFORMATION: n = A,T,C or G

<400> SEQUENCE: 93

tcgagcggcc gcccgggcag gtccaggttt ttatttagtt gtgtaatctt ggacaagtta      60

cctaactttt ttgagtctga atatatttaa tctgcaaaat gagaatcatg ataatacgtc     120

ataggcttaa ttaggaggat taaatgaaat aatttatagg tggtgccatg gttacataca     180

agtattagta gttaattctt ttcctttgtt tacttttata gtataggttg gatgaaggtt     240

ccagtatagg caaaaatact acttgggggt aaagtagagt gtgatacttt atttgaaatg     300

ttccctgaat ctgatcttta ctttttgnta ctgctgcact acccaaatcc aaattttcat     360

cccaacattc ttggatttgt gggacagcng tagcagcttt tccaatataa tctatactac     420

atcttttctt actttggtgc tttttg                                          446


<210> SEQ ID NO 94
<211> LENGTH: 409
<212> TYPE: DNA
<213> ORGANISM: Homo sapiens

<400> SEQUENCE: 94

cgagcggccg cccgggcagg tccatcagct cttctgctta gaatacgagg cagacagtgg      60

agaggtcaca tcagttatcg tctatcaggg tgatgaccca agaaaggtga gtgagaaggt     120

gtcggcacac acgcctctgg atccacccat gcgagaagcc ctcaagttgc gtatccagga     180

ggagattgca aagcgccaga gccaacactg accatgttga aggcgttctc tccaggctgg     240

attcactgca ctcggaagaa ttctgcccag ggaatttagt gtgggggtac caggaccagt     300

ttgtcttgat cttgagaccc ccagagctgc tgcatccata gggtgttgca ggactacacc     360

tggcctgcct tgcagtcatt ctttcttata tgttgaccca tttgcccaa                 409


<210> SEQ ID NO 95
<211> LENGTH: 490
<212> TYPE: DNA
<213> ORGANISM: Homo sapiens
<220> FEATURE:
<221> NAME/KEY: misc_feature
<222> LOCATION: 486
<223> OTHER INFORMATION: n = A,T,C or G

<400> SEQUENCE: 95

tcgagcggcc gcccgggcag gtcctacttg tttgcagctt ccacacactg cacctaccta      60

ctacctctct tccatgctta actgggttta gaaaggtgag ctatgcgtag aagaactact     120

tgggatattc aagtgctgta tttgaacgat aagcctatag ataacagtct gaagctgcaa     180

gggagacttt gttagtacac tactataaac aggtaaacta cctgtttgta cttgatatag     240

tgcatatgaa atgactgatt taatacaaaa ctacagaaca tgcaaaattt tttctgagat     300

gttaagtatt acttcagtgg agaacaaaac ttacttaacc tttcgctaat gcatgtagta     360

ccagaaagca aacatggttt tagcttcctt tactcaaaat atgaacatta agtggttgtg     420

aattttgtct gccaagtggt tcagaaaata cattataaat aacctaagtt aaaaaaaaga     480
```

-continued aactgngaac 490

<210> SEQ ID NO 96
<211> LENGTH: 223
<212> TYPE: DNA
<213> ORGANISM: Homo sapiens

<400> SEQUENCE: 96
agcgtggtcg cggccgaggt ctggaagccc accctaggac ttgaatggca ccttgtcctt 60
tctctgccag taatgcaatc caacacaata tgctacaggg aaaacagaat ttccacggtg 120
ccgccctctg gtacaaggga aacagcacgc aaagcaaaag gccacagagg gctccctgag 180
aatccagtac aactaagcga ggacctgccc gggcggccgc tcg 223

<210> SEQ ID NO 97
<211> LENGTH: 527
<212> TYPE: DNA
<213> ORGANISM: Homo sapiens
<220> FEATURE:
<221> NAME/KEY: misc_feature
<222> LOCATION: 404, 436, 451, 476
<223> OTHER INFORMATION: n = A,T,C or G

<400> SEQUENCE: 97
tcgagcggcc gcccgggcag gtctgtgcag gagacactga agtgggtagt gtccataatc 60
tttttagcct gttgctgaaa ttccagttgt actccttcaa accaaaatgc ttacaggatc 120
atgggaaagc ctcggttgca gaaatcaaga caggcaagtg ggaagataac tcggctttga 180
ggttaaacag atctgggttc aaagcatagt ttcactctct gtcttgtgaa gtgtcctggg 240
tgaagtcatt tcctctcttg aatttcagag aggatgaaaa tataaaaagt ataataacta 300
tcttcataat ctttgtgagg attaaagaag acgaagtgtg tgaaaagcta agcacagagc 360
aggcattcta caataagtag ttattatttt tggaaccatc ccgnccctag ccccagccca 420
attaccttct cttagnctct tcatatcgaa ngccgtaatc ttgaccttct cttgcnactg 480
gattggtgct ggttgatgcc caaacttccc gagatgctgt ctgggaa 527

<210> SEQ ID NO 98
<211> LENGTH: 514
<212> TYPE: DNA
<213> ORGANISM: Homo sapiens
<220> FEATURE:
<221> NAME/KEY: misc_feature
<222> LOCATION: 455
<223> OTHER INFORMATION: n = A,T,C or G

<400> SEQUENCE: 98
tcgagcggcc gcccgggcag gtctggctcc catggccctt ggggtggcct gactctgtca 60
ctattcctaa aaccttctag gacatctgct ccaggaagaa ctttcaacac caaaattcat 120
ctcaatttta cagatgggaa aagtgattct gagaccagac cagggtcagg ccaaggtcat 180
ccagcatcag tggctgggct gagactgggc ccagggaacc ctgtctgctc ctctttttcc 240
cagagctgtg agttctctag ccaaggctgc actcttgagg gagagccagg aagcatagct 300
gaggccatga caacctcact cttcacctga aaatttaacc cgtggcagag gatccaggca 360
catataggct tcggagccaa acaggacctc ggccgcgacc acgctaagcc gaattccagc 420
acactggcgg ccgttactag tggatcccga gcttnggtac caagcttggc gtaatcatgg 480
gcatagctgg ttcctggggt gaaaatggta tccg 514

-continued

<210> SEQ ID NO 99
<211> LENGTH: 530
<212> TYPE: DNA
<213> ORGANISM: Homo sapiens
<220> FEATURE:
<221> NAME/KEY: misc_feature
<222> LOCATION: 430, 522
<223> OTHER INFORMATION: n = A,T,C or G

<400> SEQUENCE: 99
tcgagcggcc gcccgggcag gtctgaagaa acaggtataa atttggcagc cagtaatttt 60
gacagggaag ttacagcttg catgacttta aatatgtaaa tttgaaaata ctgaatttcg 120
agtaatcatt gtgctttgtg ttgatctgaa aaatataaca ctggctgtcg aagaagcatg 180
ttcaaaaata tttaattcac ttcaaaatgt catacaaatt atggtggttt ctatgcaccc 240
ctaaagcttc aagtcattta gctcaggtac atactaaagt aatatattaa ttcttccagt 300
acagtggtgt ttcataccat tgacatttgc ataccctaga ataatttaag aaagacatgt 360
gtaatattca caatgttcag aaaagcaagc aaaaggtcaa ggaacctgct ttggttcttc 420
tggagatggn ctcatatcag cttcataaac attcattcta caaaatagta agctaaccat 480
ttgaacccca atttccagat taagcatatt ttctcataaa tnatgaagcc 530

<210> SEQ ID NO 100
<211> LENGTH: 529
<212> TYPE: DNA
<213> ORGANISM: Homo sapiens

<400> SEQUENCE: 100
agcgtggtcg cggccgaggt ccaggcacgg tggcttatgt gtgtaatccc agcacttggg 60
gaggctgagg gaggtggatc acttgagtcc aggagtttga gaccagtctg ggcaacatgg 120
cgaaacttca tcactaccaa agaagaaaaa aattagccag gtgtggtggt gtatgcctgt 180
agtcccagat actctggtgg ctgaggtgag aggatagctt gagcccagga aattgaggct 240
gcagtgaact atgattgcac tactgtgctc cagcttgggc aacagagtga gatcttgtct 300
ccaaaagtcc ttgaaggatt ttaggaagtt gttaaaagtc ttgaaacgat gtttgggggc 360
atgttagggt tcttgaatgt ttaattcctc taataactgc ttattcaaga gaagcatttc 420
tgactgggtg cggggcagtg gcttcatgcc ccataatccc agtactttgg gaggctgaag 480
caggaacatt gcttgagccc aggacttcaa gaacagcctg ggtaacata 529

<210> SEQ ID NO 101
<211> LENGTH: 277
<212> TYPE: DNA
<213> ORGANISM: Homo sapiens

<400> SEQUENCE: 101
tcgagcggcc gcccgggcag gtcgcaggaa gaggatggaa actgaggagt ccaggaagaa 60
gagggaacga gatcttgagc tggaaatggg agatgattat attttggatc ttcagaagta 120
ctgggattta atgaatttgt ctgaaaaaca tgataagata ccagaaatct gggaaggcca 180
taatatagct gattatattg atccagccat catgaagaaa ttggaagaat tagaaaaaga 240
agaagagctg agaacagacc tcggccgcga ccacgct 277

<210> SEQ ID NO 102
<211> LENGTH: 490
<212> TYPE: DNA
<213> ORGANISM: Homo sapiens -continued

<400> SEQUENCE: 102
gcgtggtcgc ggccgaggtc tgacggcttt gctgtcccag agccgcctaa acgcaagaaa 60
agtcgatggg acagttagag gggatgtgct aaagcgtgaa atcagttgtc cttaattttt 120
agaaagattt tggtaactag gtgtctcagg gctgggttgg ggtccaaagt gtaaggaccc 180
cctgccctta gtggagagct ggagcttgga gacattaccc cttcatcaga aggaattttc 240
ggatgttttc ttgggaagct gttttggtcc ttggaagcag tgagagctgg gaagcttctt 300
ttggctctag gtgagttgtc atgtgggtaa gttgaggtta tcttgggata aagggtcttc 360
tagggcacaa aactcactct aggtttatat tgtatgtagc ttatattttt tactaaggtg 420
tcaccttata agcatctata aattgacttc tttttcttag ttgtatgacc tgccccgggc 480
ggccgctcga 490

<210> SEQ ID NO 103
<211> LENGTH: 490
<212> TYPE: DNA
<213> ORGANISM: Homo sapiens

<400> SEQUENCE: 103
gagcggccgc ccgggcaggt ccaaaccagc ttgctcataa gtcattaacc aaatccatta 60
taggtaattt gttcagttca atgtttacaa ttcttatgga aaaaattagc aacacacaca 120
tttaaaacgt gtgcatttac ctttgcgtga gtgcttaaaa tacatatttc tatttcaaga 180
tgacatttaa aaattattct aatatatcag cagcaaaaat ataatttgca attacaaaaa 240
actaaactag aatccttaag ttattctcat gtttacagtt gtgattcttt aataaatact 300
attatgcagc tctattgttt aagctttctg gatttggttt aaacacatgc atatatattg 360
tcaattgtgg gaagctttac aagttatatt ccatgcactt tttggacaga gttctaacag 420
agccagccag tccacaaaac aggcaagaca aaagttgaat taactggggc aaaataggac 480
tcttatgcaa 490

<210> SEQ ID NO 104
<211> LENGTH: 489
<212> TYPE: DNA
<213> ORGANISM: Homo sapiens

<400> SEQUENCE: 104
cgtggtcgcg gccgaggtcc aggctggtct cgaactcctg accttgtgat ctgcccgcct 60
cggcctccca aagtgttggg attacaggca tgagccactg cgcccgaccg agttgaacat 120
ttaatgtcag actaggccag agtttctcaa tctttttatt ctcacttccc aaaggagccg 180
ttggagattt tcccctcaat ctctctcctt catgaaattt cataccacaa atatagtatg 240
ttttatttat gtactgtgac cctttgaagg atcacaaacc aatataatag tttttctttt 300
taacccgtca aggaccaagt ttttgcccct gttggaaatg cataaactgg actgatgaat 360
tggtatagat ggcttttatc atgaggatca gaaaaacttg aaattccttg gctacgacac 420
tccatattta tcaccgtata gggaggacct tggtatgggg aagtagaaac acttctacac 480
tttacagca 489

<210> SEQ ID NO 105
<211> LENGTH: 479
<212> TYPE: DNA
<213> ORGANISM: Homo sapiens
<220> FEATURE:

-continued

<221> NAME/KEY: misc_feature
<222> LOCATION: 142, 453
<223> OTHER INFORMATION: n = A,T,C or G

<400> SEQUENCE: 105
gcgtggtcgc ggccgaggtc tgactggctt cagccccaga agttgagctg gcctttagac 60
aaaataattg cacctccctc tgctgcttat tcccttccgt ttttcatttg agtgtgaaca 120
gttagataaa atctgtggct gnctcttcca ccttgctcta gtttccattg ctgtgagcag 180
gccctcctat gccccgcatt tagctacaat gctgtggact cacttgattc tttttctccg 240
agctttgtct agaaatatgt gaaggtgagg ttaagtgctt ctctgtgtag atccacttag 300
ccctgtctgc tgtctcgatg ggcgttgctt cgtctctcct ctcttccatc ctttccattt 360
gcttctcacc accttctggc ttctttttctt aatgcaataa aggcagtttc taacaaagaa 420
agaatgtggg ctttggagtt agacagacct ggntttaaat tctgcttctg gctctccaa 479

<210> SEQ ID NO 106
<211> LENGTH: 511
<212> TYPE: DNA
<213> ORGANISM: Homo sapiens

<400> SEQUENCE: 106
tcgcggccga ggtccaaaac gtggattcca atgacctgcc ttgagcccgc ggttgccagg 60
agttggacct gcagtagtat gggaagctca cggcctaaat accgactgcc ctctgacccc 120
accgtccagc gattctagaa catttctagt aggaaagaca tagcaaggga ttttcatgat 180
tgggaaatac tgggagacaa gctgaagatt tgttaagggc tatgcttctg tcatctttta 240
ggtatttaag gctactcctt tagctagcta ctttgagctg tttaaagtga ctatctccct 300
acacagagtt acacaatgag catctctgaa agagaatatt accctggatt tccaaagatg 360
tactctaaca ggatgaccag gcaaaaggtg acccgggggga ggagtctgtt ataacactcg 420
gacccacatg ttctcaaggc acttcagaac tttgggaaat cattttgtac cggatcctca 480
gaaagcattt atggaaatac acatccttta g 511

<210> SEQ ID NO 107
<211> LENGTH: 451
<212> TYPE: DNA
<213> ORGANISM: Homo sapiens

<400> SEQUENCE: 107
ggccgcccgg gcaggtccag aatatcaaat caaaaggtca caaatgttca cttcctcctc 60
caccctctta catattggat cttcaattgc aatagggagt gtaagatggg cattttagag 120
acgtagttgc atcagcagaa gcaaacccat cttatacaaa tgggttttgg ggataggaaa 180
aggctgctaa aaattcacaa gtcaccattc cccagaagca atgaatagcc gtagaagacc 240
aaggaagatc aacaagtttc caaagtgcta aagccagaga tttggccctt ccaaaatacc 300
accaggacgc ctggacccgt gggctctccg catgtcacca ctgactgcca ggatgctgct 360
gcacctccct tccttgagac acaacagaga gacagtgaag tcacccaaga ctgggatcat 420
cagaggctcc tcatgcttgc tacagagaag c 451

<210> SEQ ID NO 108
<211> LENGTH: 461
<212> TYPE: DNA
<213> ORGANISM: Homo sapiens

<400> SEQUENCE: 108

-continued

```
ccgcccgggc aggtcctgaa aacattcaga ctaatcaaaa tggtactact gtaacttctt     60

ataatacata atataaaagt ttttgaaaga tatagacaca attaacccct aaacaacaca    120

ctatctgatt ctcaaaagca atggctattt aacaagatgt aaaaggacaa taacatatca    180

aagaactttc acacacctaa agatagcatt tagcagcaag ttagtcagac aaaacaaaca    240

caaatatttt cacatttcct atgtttgttt ttaactttac ttcataaagc cactgataat    300

tgaggtttct ttcaagtata agatttctaa aattaaaaac tgtttttgac atatttttat    360

aaagaaataa aaagcaaaac gcaatccaac tatttatatg agtccctctt ctccaacagc    420

tttagatggt tttctgagta ctttttttaca cagaatattt t                       461
```

<210> SEQ ID NO 109
<211> LENGTH: 441
<212> TYPE: DNA
<213> ORGANISM: Homo sapiens

<400> SEQUENCE: 109

```
ggccgcccgg gcaggtctga ttataagaga aagaaatcca gtgacacgag ggcaggcagg     60

ccccgctctg ctctgatcga gaaaagcttc ctgatgtcag ggagatggaa ctgccaccat    120

cagaaccatg gcactttggg tgaaggtgtg tcagcgacca agggggcagg aaatgggcag    180

tgactaaggg ggcaggaaac aggcaggcac atggcaaggt tctcccagcc catcagccca    240

gtgatggcct cgattttgaa gctgcactac tgtctgaaaa gcacaattac tggtgactct    300

taacaaactt cagcatactg gggaaggaga ctgtcaagta actgaattgg aaagatgaaa    360

aagaaccatc tctaaaagtt gatgcttgtc agaagaataa cctcctttgt gcaagtcttg    420

caacatcttc attcaaccac a                                               441
```

<210> SEQ ID NO 110
<211> LENGTH: 451
<212> TYPE: DNA
<213> ORGANISM: Homo sapiens
<220> FEATURE:
<221> NAME/KEY: misc_feature
<222> LOCATION: 260, 361
<223> OTHER INFORMATION: n = A,T,C or G

<400> SEQUENCE: 110

```
ggtcgcggcc gaggtctggg gaaggggtga gaatccctgg gccttgccca gtcctgagct     60

ctgggtgtct gcagggaagc acagtggtga gttagtgtta aagaaagcat ccagagaggt    120

aagaggggct tgggtagcac cctttgcctc tgtcacttcc gcaaaaactt cttgttgagg    180

aggaagatga gaaggttgac attgactttg gccttgttga agagtttcat gacagccaca    240

ccctcatact ggagctgcan gagatcctga tagtgaagct tgaaatcgct ccatgtccac    300

acccaggaac ttggcattta cttcaaactt tcctgcctca tctcccggcg tgatgtcaaa    360

natgacgttt cttgaagtga gaggcgggaa agatcttcaa tttccaccaa agacaccctt    420

tttccaggaa gcttgagcaa caagtgtaat g                                    451
```

<210> SEQ ID NO 111
<211> LENGTH: 407
<212> TYPE: DNA
<213> ORGANISM: Homo sapiens
<220> FEATURE:
<221> NAME/KEY: misc_feature
<222> LOCATION: 26, 33, 36, 79, 105, 111, 133, 149, 186, 206, 220, 239,
245, 259, 336, 375, 383, 393
<223> OTHER INFORMATION: n = A,T,C or G -continued

<400> SEQUENCE: 111
ggccgacgtt cgacctgact tctttngagc agntgncact acccgtcttg aggaatgccg 60
actgcagaca gtggcccang gcaaagagtg tgcgtcatcg atganattgg naagatggag 120
ctcttcagtc agnttttcat tcaagctgnt cgtcagacgc tgtctacccc agggactata 180
atcctnggca caatcccagt tcctanagga aagccactgn ctcttgtaga agaaatcana 240
cacanaaagg atgtgaacng tgtttaatgt caccaaggga aaacatgaaa ccaccttctg 300
ccagatatcg ggacgttgcg tgcagatcaa gcacgnaagt gaagacgcgt gcattccttg 360
ccttccgtga acgantgccc agntcaagaa gancctgatg gaaccct 407

<210> SEQ ID NO 112
<211> LENGTH: 401
<212> TYPE: DNA
<213> ORGANISM: Homo sapiens
<220> FEATURE:
<221> NAME/KEY: misc_feature
<222> LOCATION: 363
<223> OTHER INFORMATION: n = A,T,C or G

<400> SEQUENCE: 112
tcgcggccga ggtcggccga ggtctgacat ctgttgtctg tgataaccac ttctgtattg 60
cgtcttaacc acttctgtat tgtgtggttt taactgccta aggcggcaat gggcagtggg 120 ccccttttccc ttaggatggg tatcaattca acaatattta taaggcattt actgtgtgct 180
aagcatttgg aagacccagg ctacaaaata agacatagtt cctgccctcc aggccagcag 240
agggaggcac aaatacccag gaatctctga tgggtgtgaa gtgcggtcgt gggccacaga 300
aaatgaccgt catggagacc ctgctaaagg tcggaccctg agcccaaagg ggtattcaga 360
agnggagatg attttggccc cactcataga tgggtggcaa a 401

<210> SEQ ID NO 113
<211> LENGTH: 451
<212> TYPE: DNA
<213> ORGANISM: Homo sapiens

<400> SEQUENCE: 113
gtcgcggccg aggtccatat taaaaagtcc atcataaaca aagactcctc ctcatggtat 60
gaatatgctc catatgccca taatggtgca taacggactt agaaattcca atgagtctta 120
gggttgaaat ttccaatgac ctgagcaagg cagctcccta tagcttctgg ataacatttt 180
acacccagag ttcaggctta aacagaccta tcaacacaat tattttcgga ttgtctgtct 240
agaaaacggc aatgctcaaa ggaatataaa taagggtggg gggacatatg cttccagcct 300
ggcctttctc catgtggtaa aaaacaatgg aatggctgtg ttaatttttt tttaatcttt 360
tctgaccttt actatgtttg gtaatggaaa taagtcaggg aaaacaaaat gaacaggtct 420
catcacttaa ttaatactgg gttttcttct t 451

<210> SEQ ID NO 114
<211> LENGTH: 441
<212> TYPE: DNA
<213> ORGANISM: Homo sapiens

<400> SEQUENCE: 114
ggccgcccgg gcaggtccat cctgtcagag atgggagaag tcacagacgg aatgatggat 60
acaaagatgg ttcactttct tacacactat gctgacaaga ttgaatctgt tcatttttca 120

-continued

```
gaccagttct ctggtccaaa aattatgcaa gaggaaggtc agcctttaaa gctacctgac    180

actaagagga cactgttgtt tacatttaat gtgcctggct caggtaacac ttacccaaag    240

gatatggagg cactgctacc cctgatgaac atggtgattt attctattga taaagccaaa    300

aagttccgac tcaacagaga aggcaaacaa aaagcagata agaaccgtgc ccgagtagaa    360

gagaacttct tgaaacttga cacatgtgca aagacaggaa gcagcacagt ctcggcggga    420

ggaagaaaaa aagaacagag a                                               441


<210> SEQ ID NO 115
<211> LENGTH: 431
<212> TYPE: DNA
<213> ORGANISM: Homo sapiens
<220> FEATURE:
<221> NAME/KEY: misc_feature
<222> LOCATION: 317
<223> OTHER INFORMATION: n = A,T,C or G

<400> SEQUENCE: 115

gccgcccggg caggtccatt ggcggtgaca aaaggaaaag aagcaaagag actcagtcca     60

taatgctgat tagttagaag aaagggctag gattgagaaa gtaccaggaa cttttaatta    120

tttaaaagag aatgctgact gttaatgttt taaatcttac tgttcaaatg tactaatatg    180

aatttttacc ctttgtgcat gaatattcta aacaactaga agacctccac aatttagcag    240

ttatgaaagt taaacttttt attataaaaa ttctaaacct tactgctcct ttaccaggaa    300

catgacacac tatttancat cagttgcata cctcgccaat agtataattc aactgtcttg    360

cccgaacaat catctccatc tggaagacgt aagcctttag aaacacattt ttctattaat    420

ttctctagaa c                                                          431


<210> SEQ ID NO 116
<211> LENGTH: 421
<212> TYPE: DNA
<213> ORGANISM: Homo sapiens

<400> SEQUENCE: 116

gtcgcggccg aggtccagaa atgaagaaga agtttgcaga tgtatttgca aagaagacga     60

aggcagagtg gtgtcaaatc tttgacggca cagatgcctg tgtgactccg gttctgactt    120

ttgaggaggt tgttcatcat gatcacaaca aggaaccggg gctcgtttat caccagtgag    180

gagcaggacg tgagccccccg ccctgcacct ctgctgttaa acaccccagc catcccttct    240

ttcaaaaggg atcctttcat aggagaacac actgaggaga tacttgaaga atttggattc    300

agcccgcgaa gagatttatc aagcttaact cagataaaat cattgaaagt aataaggtaa    360

aagctaagtc tctaacttcc aggcccacgg ctcaagtgaa tttcgaatac tgcatttaca    420

g                                                                     421


<210> SEQ ID NO 117
<211> LENGTH: 489
<212> TYPE: DNA
<213> ORGANISM: Homo sapiens

<400> SEQUENCE: 117

agcgtggtcg cggccgaggt aaggctgcga ggttgtggtg tctgggaaac tccgaggaca     60

gagggctaaa tccatgaagt ttgtggatgg cctgatgatc cacagcggag accctgttaa    120

ctactacgtt gacactgctg tgcgccacgt gttgctcaga cagggtgtgc tgggcatcaa    180

ggtgaagatc atgctgccct gggacccaac tggtaagatt ggccctaaga agcccctgcc    240
```

-continued

```
tgaccacgtg agcattgtgg aacccaaaga tgagatactg cccaccaccc ccatctcaga    300

acagaagggt gggaagccag agccgcctgc catgccccag ccagtcccca cagcataaca    360

gggtctcctt ggcagacctg cccgggcggc cgctcgaaag cccgaattcc agcacactgg    420

cggccgttac tagtggatcc cagctcggta ccaagcttgg cgtaatcatg gtcatagctg    480

gtttcctgt                                                            489
```

<210> SEQ ID NO 118
<211> LENGTH: 489
<212> TYPE: DNA
<213> ORGANISM: Homo sapiens

<400> SEQUENCE: 118

```
tcgagcggcc gcccgggcag gtattgaata cagcaaaatt ctatatacaa agtgacctgg     60

acctgctgct tcaaaacatg atcctttctt actaatatct tgatagtcgg tccatagagc    120

attagaaagc aattgactct taaataaaca gaaaagtgcc taatgcacat taaatgaatg    180

gcctaactac tggaacttta gtagttctat aaggtgatta acataggtag gatccagttc    240

ctatgacagg ctgctgaaga acagatatga gcatcaagag gccattttgt gcactgccac    300

cgtgatgcca tcgtgtttct ggatcataat gttcccatta tctgattcta gacacaccac    360

aggaatatca gtggggtcag aggttagctt agctgcttgc tgggctagaa cagatatcac    420

tccagcatgc tcatctgaca gggtcccgcg gcaacccaga ttaagtcctt gtgaatctgt    480

gcacaggga                                                            489
```

<210> SEQ ID NO 119
<211> LENGTH: 181
<212> TYPE: DNA
<213> ORGANISM: Homo sapiens

<400> SEQUENCE: 119

```
taggttccag agacttttgg cccaggagga atatttactt ttagctctgg acatcattac     60

aaaaaggaat atttcccaaa cctcttcaga ccgagaatac atgggtaaaa ttattaaata    120

gttgtataat aaaaataatt ttttccttaa aaaaaaaaaa aacctcggcc gcgaccacgc    180

t                                                                    181
```

<210> SEQ ID NO 120
<211> LENGTH: 489
<212> TYPE: DNA
<213> ORGANISM: Homo sapiens
<220> FEATURE:
<221> NAME/KEY: misc_feature
<222> LOCATION: 422, 487
<223> OTHER INFORMATION: n = A,T,C or G

<400> SEQUENCE: 120

```
gcgtggtcgc ggccgaggtc catttaaaac aaagaaaaat actaaagcca ctagtaaaca     60

tctgatgtgc aaaatacaac atcctctagt tggctttatg ccattattac ataagctcca    120

aatagctcat cttaaattaa aaagaaaaag tggctgtccc atctctgctg cataaatcag    180

attttttttt aaaggtttag agtactttaa ggaagggaag ttcaaaactg ccagtgaaat    240

tcacagagaa tacaaattta gcaatttaat ttcccaaagc tctttgaaga agcaagagag    300

tctctcttct taatgcagtg ttctcccaag aggaactgta attttgcttg gtacttatgc    360

tgggagatat gcaaaatgtg tttttcaatg tttgctagaa tataatggtt cctcttcagt    420
```

-continued

```
gnctggttca tcctggaact catgggttaa gaaggacttc ttggagccga actgcccggg    480

cgggccntt                                                            489


<210> SEQ ID NO 121
<211> LENGTH: 531
<212> TYPE: DNA
<213> ORGANISM: Homo sapiens

<400> SEQUENCE: 121

cgagcggccg cccgggcagg tggccagcgc tggtcccgca gacgccgaga tggaggaaat     60

atttgatgat gcgtcacctg gaaagcaaaa ggaaatccaa gaaccagatc ctacctatga    120

agaaaaaatg caaactgacc gggcaaatag attcgagtat ttattaaagc agacagaact    180

ttttgcacat ttcattcaac ctgctgctca gaagactcca acttcacctt tgaagatgaa    240

accagggcgc ccacgaataa aaaaagatga gaagcagaac ttactatccg ttggcgatta    300

ccgacaccgt agaacagagc aagaggagga tgaagagcta ttaacagaaa gctccaaagc    360

aaccaatgtt tgcactcgat ttgaagactc tccatcgtat gtaaaatggg gtaaactgag    420

agattatcag gtcccgagga ttaaactggc tcatttcttt gtatgagaat ggcatcaatg    480

gtatccttgc agatgaaatg ggcctaggaa agactcttca acaatttctc t             531


<210> SEQ ID NO 122
<211> LENGTH: 174
<212> TYPE: DNA
<213> ORGANISM: Homo sapiens

<400> SEQUENCE: 122

tcgagcggcc gcccgggcag gtctgccaac agcagaggcg gggcctccgg catcttcaaa     60

gcacctctga gcaggctcca gccctctggc tgcgggaggg gtctggggtc tcctctgagc    120

tcggcagcaa agcagatgtt atttctctcc cgcgacctcg gccgcgacca cgct          174


<210> SEQ ID NO 123
<211> LENGTH: 531
<212> TYPE: DNA
<213> ORGANISM: Homo sapiens
<220> FEATURE:
<221> NAME/KEY: misc_feature
<222> LOCATION: 152, 373, 482, 494, 496, 502
<223> OTHER INFORMATION: n = A,T,C or G

<400> SEQUENCE: 123

agcgtggtcg cggccgaggt cctcaaccaa gagggttgat ggcctccagt caagaaactg     60

tggctcatgc cagcagagct ctctcctcgt ccagcaggcg ccatgcaagg gcaggctaaa    120

agacctccag tgcatcaaca tccatctagc anagagaaaa ggggcactga agcagctatg    180

tctgccaggg gctaggggct cccttgcaga cagcaatgct acaataaagg acacagaaat    240

gggggaggtg ggggaagccc tatttttata acaaagtcaa acagatctgt gccgttcatt    300

cccccagaca cacaagtaga aaaaaaccaa tgcttgtggt ttctgccaag atggaatatt    360

cctccttcct aanttccaca catggccgtt tgcaatgctc gacagcattg cactgggctg    420

cttgtctctg tggtctgggc accagtagct tgggccccat atacacttct cagttcccac    480

anggcttatg gccnangggc angctccaat tttcaagcac cacgaaggaa g             531


<210> SEQ ID NO 124
<211> LENGTH: 416
<212> TYPE: DNA
<213> ORGANISM: Homo sapiens
```

-continued

<400> SEQUENCE: 124
tcgagcggcc gcccgggcag gtccatctat actttctaga gcagtaaatc tcataaattc 60
acttaccaag cccaggaata atgactttta aagccttgaa tatcaactaa gacaaattat 120
gccaattctg atttctcaca tatacttaga ttacacaaag ataaagcttt agatgtgatc 180
attgtttaat gtagacttat ctttaaagtt tttaattaaa aactacagaa gggagtaaac 240
agcaagccaa atgatttaac caaatgattt aagagtaaaa ctcactcaga aagcattata 300
cgtaactaaa tatacatgag catgattata tacatacatg aaactgcaat tttatggcat 360
tctaagtaac tcatttaagt acatttttgg catttaaaca aagatcaaat caagct 416

<210> SEQ ID NO 125
<211> LENGTH: 199
<212> TYPE: DNA
<213> ORGANISM: Homo sapiens
<220> FEATURE:
<221> NAME/KEY: misc_feature
<222> LOCATION: 112, 160, 195
<223> OTHER INFORMATION: n = A,T,C or G

<400> SEQUENCE: 125
agcgtggtcg cggccgaggt gctttttttt tttttttttt tttttttttt gctattctaa 60
aggggaaggc cccttttttat taaacttgta cattttactt tccttctttc anaatgctaa 120
taaaaaactt ttgtttatac ttaaaaaaac cataaatcan acaaacaaaa gaaacgattc 180
caacatcact tctgngatg 199

<210> SEQ ID NO 126
<211> LENGTH: 490
<212> TYPE: DNA
<213> ORGANISM: Homo sapiens

<400> SEQUENCE: 126
cgtggtcgcg gccgaggtcc agttgctcta agtggattgg atatggttgg agtggcacag 60
actggatctg ggaaaacatt gtcttatttg cttcctgcca ttgtccacat caatcatcag 120
ccattcctag agagaggcga tgggcctatt tgtttggtgc tggcaccaac tcgggaactg 180
gcccaacagg tgcagcaagt agctgctgaa tattgtagag catgtcgctt gaagtctact 240
tgtatctacg gtggtgctcc taagggacca caaatacgtg atttggagag aggtgtggaa 300
atctgtattg caacacctgg aagactgatt gactttttag agtgtggaaa aaccaatctg 360
agaagaacaa cctaccttgt ccttgatgaa gcagatagaa tgcttgatat gggctttgaa 420
ccccaaataa ggaagattgt ggatcaaata agacctgata ggcaaactct aatgtggagt 480
gcgacttggc 490

<210> SEQ ID NO 127
<211> LENGTH: 490
<212> TYPE: DNA
<213> ORGANISM: Homo sapiens

<400> SEQUENCE: 127
cgtggtcgcg gccgaggtcg gccgaggtct ggagatctga gaacgggcag actgcctcct 60
caagtgggtc cctgacccct gacccccgag cagcctaact gggaggcacc ccccagcagg 120
ggcacactga cacctcacac ggcagggtat tccaacagac ctgaagctga gggtcctgtc 180
tgttagaagg aaaactaaca agcagaaagg acagccacat caaaaaccca tctgtacatc 240

-continued

```
accatcatca aagaccaaaa gtaaataaaa ccacaaagat gggaaaaaaa cagaacagaa    300

aaactggaaa ctctaaaaag cagagcacct ctcctcttcc aaaggaacgc agttcctcac    360

cagcaatgga acaaagctgg atggagaatg actttgacga gctgagaaaa gaacgcttca    420

gacgatcaaa ttactctgag ctacgggagg acattcaaac caaaggcaaa gaagttgaaa    480

actttgaaaa                                                           490
```

<210> SEQ ID NO 128
<211> LENGTH: 469
<212> TYPE: DNA
<213> ORGANISM: Homo sapiens
<220> FEATURE:
<221> NAME/KEY: misc_feature
<222> LOCATION: 69, 106, 140, 152, 165, 196, 224, 233, 241, 258, 260, 267, 291, 347, 395
<223> OTHER INFORMATION: n = A,T,C or G

<400> SEQUENCE: 128

```
cgtggtcgcg gccgaggtgc tttttttttt tttttttttt tttttttttt tgctgattta     60

ttttttctnt ttattgttac atacaatgta taaacacata aaacanaaaa cagtagggat    120

cctctaggat ctctagggan acagtaaagt anaaagaggt ctcanaaaca tttttttaaa    180

gtacaagaca ttcagngctc ggcccaaagg cgtaaaaggt ttanagccag canatagctg    240

nactaaaggc tccgtctntn tccccanagc caggacaacc ccagggagct ntccattagc    300

agccagtcca cgcaggcagg atgctgcgga aaaagctcta tgctganaac attccccttg    360

atggaaagaa gggcaacaca aaaggggtaa ctaanagctc cttcctctcg tgagggcgac    420

aactgaggaa cagaaaagga gtgtcccatg tcacttttga ccccctccc                469
```

<210> SEQ ID NO 129
<211> LENGTH: 419
<212> TYPE: DNA
<213> ORGANISM: Homo sapiens

<400> SEQUENCE: 129

```
gcgtggtcgc ggccgaggtc tgattttcat ttaaatattt cagagctata gcatttgcct     60

ccatgctcaa atccacacca ttggggctta agccgctcat gccaacatta gcaaatgaca    120

tgcagtttaa tccagagatc actgcttctg ggctgatgca tgccaacaca ctggcgtgat    180

ccacgttatg tgcatttttc ttcactttag tgggagaatc aatttttact ccaaggcttc    240

ttagttgctt aagagttgca ttaaggacac aatctttgtc caccagtctt gaatgatgtg    300

tttttttctt tgtatggtaa acgttttggg ttctggtgca ttcatgactg ataattactg    360

ctttggtaga cggctgctca agtttccttg gaggaactat ttaataggtg ggttacttg     419
```

<210> SEQ ID NO 130
<211> LENGTH: 354
<212> TYPE: DNA
<213> ORGANISM: Homo sapiens

<400> SEQUENCE: 130

```
agcgtggtcg cggccgaggt ccatctgagg agataaccac atcactaaca aagtgggagt     60

gaccccgcag agcacgctgt ggaattccat agttggtctc atccctggtc agtttccaca    120

tgatgatggt cttatctcga gaggcggaga ggatcatgtc cgggaactgc ggggtagtag    180

cgatctgggt tacccagccg ttgtggccct tgagggtgcc acgaagggtc atctgctcag    240

tcatggcggc ggcgagagcg tgtgtcgctg cagcgacgag gatggcactg gatggcttag    300
```

-continued

```
agaaactagc accacaacct ctcctgccgc acctgcccgg gcggcccgct cgaa          354


<210> SEQ ID NO 131
<211> LENGTH: 474
<212> TYPE: DNA
<213> ORGANISM: Homo sapiens
<220> FEATURE:
<221> NAME/KEY: misc_feature
<222> LOCATION: 421
<223> OTHER INFORMATION: n = A,T,C or G

<400> SEQUENCE: 131

cgagcggccg cccgggcagg tctggcagca gcttcctctg gaataattga cagctttgtg     60

ctgcctgact aaaatttgaa atgacaaccg ctgaatgtaa aatgatgtac ctacaatgag    120

agagatttag gaatactatc tgtcaatcca tagatgtaga aacaaaacaa actacagaat    180

gaaaacaaac ttattttaaa ccaaagaaac aaatgtatcc aaaatatagt ccatgatata    240

tttgattact agtataacca cagttgaaaa cttaaaaaaa aaaattgaca ttttttgtaa    300

tgggtactaa tggatttata aaaggtttct gtttccaaag atgttattgg ggtccacata    360

ttccttgaag acttcagcat cccaaagccc gacatcagag atactttcct ttagccattg    420

nttcccgtaa cttgcccact ccatggtgat gtgacaggct tcccttcatt agca          474


<210> SEQ ID NO 132
<211> LENGTH: 474
<212> TYPE: DNA
<213> ORGANISM: Homo sapiens
<220> FEATURE:
<221> NAME/KEY: misc_feature
<222> LOCATION: 403
<223> OTHER INFORMATION: n = A,T,C or G

<400> SEQUENCE: 132

ggccgaggtg gggaattcat gtggaggtca gagtggaagc aggtgtgaga gggtccagca     60

gaaggaaaca tggctgccaa agtgtttgag tccattggca agtttggcct ggccttagct    120

gttgcaggag gcgtggtgaa ctctgcctta tataatgtgg atgctgggca cagagctgtc    180

atctttgacc gattccgtgg agtgcaggac attgtggtag gggaagggac tcattttctc    240

atcccgtggg tacagaaacc aattatcttt gactgccgtt ctcgaccacg taatgtgcca    300

gtcatcactg gtagcaaaga tttacagaat gtcaacatca cactgcgcat cctcttccgg    360

cctgtcgcca gccagcttcc tcgcatcttc accagcatcg ganaggacta tgatgaaccg    420

tgtgctgccg tccatcacaa ctgagatcct caagtcagtg gtggctcgct ttga          474


<210> SEQ ID NO 133
<211> LENGTH: 387
<212> TYPE: DNA
<213> ORGANISM: Homo sapiens

<400> SEQUENCE: 133

tgctcgagcg gccgccagtg tgatggatat ctgcagaatt cggcttagcg tggtcgcggc     60

cgaggtctgc gggcccctta gcctgccctg cttccaagcg acggccatcc cagtagggga    120

ctttcccaca ctgtgccttt acgatcagcg tgacagagta gaagctggag tgcctcacca    180

cacggcccgg aaacagcggg aagtaactgg aaagagcttt aggacagctt agatgccgag    240

tgggcgaatg ccagaccaat gatacccaga gctacctgcc gccaacttgt tgagatgtgt    300

gtttgactgt gagagagtgt gtgtttgtgt gtgtgttttg ccatgaactg tggccccagt    360

gtatagtgtt tcagtggggg agaactg                                        387
```

<210> SEQ ID NO 134
<211> LENGTH: 401
<212> TYPE: DNA
<213> ORGANISM: Homo sapiens

<400> SEQUENCE: 134
ggccgcccgg gcaggtctga tgaagaacac gggtgtgatc cttgccaatg acgccaatgc 60
tgagcggctc aagagtgttg tgggcaactt gcatcggctg ggagtcacca acaccattat 120
cagccactat gatgggcgcc agttccccaa ggtggtgggg ggctttgacc gagtactgct 180
ggatgctccc tgcagtggca ctggggtcat ctccaaggat ccagccgtga agactaacaa 240
ggatgagaag gacatcctgc gcttgtgctc acctccagaa ggaagttgct cctgagtgct 300
attgactctt gtcaatgcga ccttcaagac aggaggctac ctggtttact gcacctgttc 360
tatcacagtg agacctctgc catggcagaa caggggaagc t 401

<210> SEQ ID NO 135
<211> LENGTH: 451
<212> TYPE: DNA
<213> ORGANISM: Homo sapiens

<400> SEQUENCE: 135
ggtcgcggcc gaggtctgtt cctgagaaca gcctgcattg gaatctacag agaggacaac 60
taatgtgagt gaggaagtga ctgtatgtgg actgtggaga aagtaagtca cgtgggccct 120
tgaggacctg gactgggtta ggaacagttg tactttcaga ggtgaggtgt cgagaaggga 180
aagtgaatgt ggtctggagt gtgtccttgg ccttggctcc acagggtgtg ctttcctctg 240
gggccgtcag ggagctcatc ccttgtgttc tgccagggtg gggtaccggg gtttgacact 300
gaggagggta acctgctggc tggagcggca gaacagtggc cttgatttgt cttttggaag 360
attttaaaaa ccaaaaagca taaacattct ggtccttcac aatgctttct ctgaagaaat 420
acttaacgga aggacttctc cattcaccat t 451

<210> SEQ ID NO 136
<211> LENGTH: 411
<212> TYPE: DNA
<213> ORGANISM: Homo sapiens

<400> SEQUENCE: 136
ggccgcccgg gcaggtctga atcacgtaga atttgaagat caagatgatg aagccagagt 60
tcagtatgag ggttttcgac ctgggatgta tgtccgcgtt gagattgaaa atgttccctg 120
tgaatttgtg cagaactttg accccccttta ccccattatc ctgggtggct tgggcaacag 180
tgagggaaat gttggacatg tgcaggtggg tccctttgct gcgtatttgg tgcctgaggc 240
tctgtggatt tcccctccat caatcatctt accctctcat ccccctcaga tgcgtctgaa 300
gaaacatctc tggtataaga aaatcctcaa gtcccaagat ccaatcatat tttctgtagg 360
gtggaggaag tttcagacca tcctgctcta ttatatccga agaccacaat g 411

<210> SEQ ID NO 137
<211> LENGTH: 211
<212> TYPE: DNA
<213> ORGANISM: Homo sapiens
<220> FEATURE:
<221> NAME/KEY: misc_feature
<222> LOCATION: 186
<223> OTHER INFORMATION: n = A,T,C or G -continued

<400> SEQUENCE: 137
cggccgcccg ggcaggtcgg ttggtgcggc ctccattgtt cgtgttttaa ggcgccatga 60
ggggtgacag aggccgtggt cgtggtgggc gctttggttc cagaggaggc ccaggaggag 120
ggttcaggcc ctttgcacca catatcccat ttgacttcta tttgtgtgaa atggcctttc 180
cccggntcaa gccagcacct cgatgaaact t 211

<210> SEQ ID NO 138
<211> LENGTH: 471
<212> TYPE: DNA
<213> ORGANISM: Homo sapiens

<400> SEQUENCE: 138
gccgcccggg caggtctggg ctggcgactg gcatccaggc cgtaactgca aatctatgct 60
aggcggggtc tcccttctgt gtgttcaagt gttctcgact tggattctta actattttaa 120
aaaatgcact gagtttgggt taaaaaccaa ccaccaaaat ggatttcaac acagctctaa 180
agccaagggc gtggccggct ctcccaacac agcgactcct ggaggccagg tgcccatggg 240
cctacatccc ctctcagcac tgaacagtga gttgattttt ctttttacaa taaaaaaagc 300
tgagtaatat tgcataggag taccaagaaa ctgcctcatt ggaaacaaaa actatttaca 360
ttaaataaaa agcctggccg caggctgcgt ctgccacatt tacagcacgg tgcgatgcac 420
acggtgacca aaccacggag gcaagcttct ggcactcaca ccacgacccg c 471

<210> SEQ ID NO 139
<211> LENGTH: 481
<212> TYPE: DNA
<213> ORGANISM: Homo sapiens
<220> FEATURE:
<221> NAME/KEY: misc_feature
<222> LOCATION: 384
<223> OTHER INFORMATION: n = A,T,C or G

<400> SEQUENCE: 139
gtcgcggccg aggtctgttc tttagctcag atttaaacct gctgtctctt ctttatttgc 60
agaatgaatt cccagttcct gagcagttca agaccctatg gaacgggcag aagttggtca 120
ccacagtgac agaaattgct ggataagcga agtgccactg ggttctttgc cctcccttca 180
caccatggga taaatctgta tcaagacggt tcttttctag atttcctcta cctttttgct 240
cttaaaactg cttctctgct ctgagaagca cagctacctg ccttcactga aatatacctc 300
aggctgaaat ttggggtggg atagcaggtc agttgatctt ctgcaggaag gtgcagcttt 360
tccatatcag ctcaaccacg ccgncagtcc attcttaagg aactgccgac taggactgat 420
gatgcatttt agcttttgag cttttggggg gtattctacc aaccaacagt ccatttggaa 480
a 481

<210> SEQ ID NO 140
<211> LENGTH: 421
<212> TYPE: DNA
<213> ORGANISM: Homo sapiens
<220> FEATURE:
<221> NAME/KEY: misc_feature
<222> LOCATION: 372
<223> OTHER INFORMATION: n = A,T,C or G

<400> SEQUENCE: 140
gtcgcggccg aggtttccca tttaagaaaa atagatcttg agattctgat tcttttccaa 60
acagtcccct gctttcatgt acagcttttt ctttacctta cccaaaattc tggccttgaa 120

-continued

```
gcagttttcc tctatggctt tgcctttctg attttctcag aggctcgagt ctttaatata    180

accccaaatg aaagaaccaa ggggaggggt gggatggcac tttttttttgt tggtcttgtt   240

ttgttttgtt ttttggttgg ttgggttccg ttattttttta agattagcca ttctctgctg   300

ctatttccct acataatgtc aatttttaac cataattttg acatgattga gatgtacttg    360

aggctttttt gntttaattg agaaaagact ttgcaatttt ttttttagga tgagcctctc    420

c                                                                    421
```

<210> SEQ ID NO 141
<211> LENGTH: 242
<212> TYPE: DNA
<213> ORGANISM: Homo sapiens
<220> FEATURE:
<221> NAME/KEY: misc_feature
<222> LOCATION: 4, 6, 20, 31, 35, 39, 72, 94, 141, 142, 211, 222
<223> OTHER INFORMATION: n = A,T,C or G

<400> SEQUENCE: 141

```
cgantngccc gcccgggcan gtctgtctaa ntttntcang gaccacgaac agaaactcgt     60

gcttcaccga anaacaatat cttaaacatc gaanaattta aatattatga aaaaaaacat    120

tgcaaaatat aaaataaata nnaaaaggaa aggaaacttt gaaccttatg taccgagcaa    180

atccaggtct agcaaacagt gctagtccta nattacttga tntacaacaa cacatgaata    240

ca                                                                   242
```

<210> SEQ ID NO 142
<211> LENGTH: 551
<212> TYPE: DNA
<213> ORGANISM: Homo sapiens
<220> FEATURE:
<221> NAME/KEY: misc_feature
<222> LOCATION: 15, 19, 32, 73, 110, 278, 405, 436, 473, 510
<223> OTHER INFORMATION: n = A,T,C or G

<400> SEQUENCE: 142

```
agcgtggtcg cggcncgang tccacagggc anatattctt ttagtgtctg gaattaaaat     60

gtttgaggtt tangtttgcc attgtctttc caaaaggcca aataattcan atgtaaccac    120

accaagtgca aacctgtgct ttctatttca cgtactgttg tccatacagt tctaaataca    180

tgtgcagggg attgtagcta atgcattaca cagtcgttca gtcttctctg cagacacact    240

aagtgatcat accaacgtgt tatacactca actagaanat aataagcttt aatctgaggg    300

caagtacagt cctgacaaaa gggcaagttt gcataataga tcttcgatca attctctctc    360

caaggggccc gcaactaggc tattattcat aaaacacaac tgaanagggg attggtttta    420

ctggtaaatc atgtgntgct aaatcatttt ctgaacagtg gggtctaaat cantcattga    480

tttagtggca gccacctgcc cggcggccgn tcgaagccca attctgcaga tatccatcac    540

actggcggcc g                                                         551
```

<210> SEQ ID NO 143
<211> LENGTH: 515
<212> TYPE: DNA
<213> ORGANISM: Homo sapiens
<220> FEATURE:
<221> NAME/KEY: misc_feature
<222> LOCATION: 5, 286, 498
<223> OTHER INFORMATION: n = A,T,C or G

<400> SEQUENCE: 143

-continued

```
cgagnggccc gcccgggcag gtatcttcac aaactcaaca aaggcactac atgagacttc     60

acattcccct agtccaatag ctgacaaatt tttgcaacgt tctgcaatgc gaattaactc    120

ttcatcaagt ggccgtaatc catttgcaca cactactagt tcaaccagtc tagggcatgt    180

cattcccaca cggccaagca catctttgct tactgatctc ccaaagtaca gatgggtggc    240

aggtatttca tagcgaaaga aggggtcaaa ttcttcttca tataanaaaa aatacatcac    300

taagttcact ttgggtgaat gtctgatgaa agcatcccag ctactcttct gaatagtatg    360

gaagtgtgtc tgtccaggat tctcactgac tacatcaatg cgcaaatgtt ctaatcgaac    420

atgtttttca gaagacaatg caagtaacaa ctcatcactc aataagtggt aagttcaggg    480

ctagttctct taagccgnga cactgatcag cacac                               515
```

<210> SEQ ID NO 144
<211> LENGTH: 247
<212> TYPE: DNA
<213> ORGANISM: Homo sapiens
<220> FEATURE:
<221> NAME/KEY: misc_feature
<222> LOCATION: 11, 20, 42, 115, 152, 165, 181, 195, 208, 221
<223> OTHER INFORMATION: n = A,T,C or G

<400> SEQUENCE: 144

```
tgcattctct ntggatgcan acctgcccgt tggtagggac tntgctcaca cggaacatgg     60

acggttacac ctgtgccgtg ggtgacgtcc accagcttct ggatcatctc ggcgngggtg    120

ttgtggaagg gcagactatc cacctccatg cncacgatgc ccganacgcc actccggact    180

ntgtgctgca ccaanatgcc cagcattnta tcttcaagca nagcacttat cagggtcctt    240

ggcacac                                                              247
```

<210> SEQ ID NO 145
<211> LENGTH: 309
<212> TYPE: DNA
<213> ORGANISM: Homo sapiens
<220> FEATURE:
<221> NAME/KEY: misc_feature
<222> LOCATION: 18, 155, 247
<223> OTHER INFORMATION: n = A,T,C or G

<400> SEQUENCE: 145

```
cgtgggtcgc ggcccgangt ctgctgtaac aaaacaccat agtctgggca gctcatagac     60

aatggaattt tatttctcac gcttctggag gctggattcc aagatcaagg ttccaggaga    120

ctcagtgtct ggcaaggtct cggtttctgc ctcanagatg gtgccatctg gctgtgtcct    180

cacaagtagg aaggtgcaag aagctcccct caggctctgt ctgtaagaca ctgatcccat    240

tcatganggg gaaacgtaat gacctaatca gcccccagag accccacttc taacaccatc    300

accttgggg                                                            309
```

<210> SEQ ID NO 146
<211> LENGTH: 486
<212> TYPE: DNA
<213> ORGANISM: Homo sapiens
<220> FEATURE:
<221> NAME/KEY: misc_feature
<222> LOCATION: 16, 97, 154, 244, 275, 322, 347, 349, 352, 357, 449,
460, 472
<223> OTHER INFORMATION: n = A,T,C or G

<400> SEQUENCE: 146

```
agcgtgggtc gcggcncgac gtcctgtcca tatttcacag cccgagaact aatacaagat     60
```

-continued

```
gctgacatca tattttgtcc ctacaactat cttctanatg cacaaataag ggaaagtatg    120

gatttaaatc tgaaagaaca ggttgtcatt ttanatgaag ctcataacat cgaggactgt    180

gctcgggaat cagcaagtta cagtgtaaca gaagttcagc ttcggtttgc tcgggatgaa    240

ctanatagta tggtcaacaa taatataagg aaganagatc atgaacccct acgagctgtg    300

tgctgtagcc tcattaattg gntagaagca aacgctgaat atcttgnana angagantat    360

gaatcagctt gtaaaatatg gagtggaaat gaaatgctct taactttaca caaaatgggt    420

atcaccactg ctacttttcc cattttgcng gtaagatatn ttttctacct gngaaacgta    480

tttaag                                                               486
```

<210> SEQ ID NO 147
<211> LENGTH: 430
<212> TYPE: DNA
<213> ORGANISM: Homo sapiens
<220> FEATURE:
<221> NAME/KEY: misc_feature
<222> LOCATION: 13, 26, 28, 289, 299, 352, 390, 399
<223> OTHER INFORMATION: n = A,T,C or G

<400> SEQUENCE: 147

```
gccgcccggg cangttcgac attacntnga gttccatgat gtacaattct ttcacgaaaa     60

acaatgaatg caagaatttg aggatctcct tactcctccc ttttacagat ggtctctcaa    120

tcccttcttc ttcctcttca tcttcatctt cttctgaacg cgctgccggg taccacggct    180

ttctttgtct ttatcgtgag atgaaggtga tgcttctgtt tcttctacca taactgaaga    240

aatttcgctg caagtctctt gactggctgt ttctccgact tcgcctttnt gtcaaacgng    300

agtcttttta cctcatgccc ctcagcttca cagcatcttc atctggatgt tnatttctca    360

aagggctcac tgaggaaact tctgattcan atgtcgaana gcactgtgaa gttttctctt    420

cattttgctg                                                           430
```

<210> SEQ ID NO 148
<211> LENGTH: 483
<212> TYPE: DNA
<213> ORGANISM: Homo sapiens
<220> FEATURE:
<221> NAME/KEY: misc_feature
<222> LOCATION: 20, 24, 53, 55, 374, 381, 423, 431, 459
<223> OTHER INFORMATION: n = A,T,C or G

<400> SEQUENCE: 148

```
cccgggcagg tctgtgttgn tttncaaccg gtgtcctccc cagcgtccag aananggaaa     60

tgtggagcgg gtgatgatga cccctcgctg tcctgtcacc tcctgcacag cttcgtatgt    120

gggtctggtc tgggaccacc cgtacaggtt gtgcacgttg tagtgctcca cgggggagct    180

gtccggcagg atctgctgac tctccatgca cagagtcttg ctgctcaggc ccttgtccct    240

agattccaaa tatggcatat agggtggggt tatttagcat ttcattgctg cagcccctga    300

cagatccatc cacaaaattt gatggctcat tcatatcaat ccacaatcca tcaaacttca    360

agctcttctc tggntctcga nggtttgcat agaactcttc tatctctttc ttccaccacg    420

canacctcgg ncgcgaccac gctaagccga attctgcana tatccatcac actggcggcc    480

gct                                                                  483
```

<210> SEQ ID NO 149
<211> LENGTH: 439
<212> TYPE: DNA
<213> ORGANISM: Homo sapiens -continued
<220> FEATURE:
<221> NAME/KEY: misc_feature
<222> LOCATION: 11, 359, 384, 402
<223> OTHER INFORMATION: n = A,T,C or G

<400> SEQUENCE: 149
ctttcacgaa nacaatgaat gcaagaattt gaggatctcc ttactcctcc cttttacaga 60
tggtctctca atcccttctt cttcctcttc atcttcatct tcttctgaac gcgctgccgg 120
gtaccacggc tttctttgtc tttatcgtga gatgaaggtg atgcttctgt ttcttctacc 180
ataactgaag aaatttcgct gcaagtctct tgactggctg tttctccgac ttcgcctttt 240
tgcaaacgtg agtcttttta cctcatgccc ctcagcttcc acagcatctt catctggatg 300
ttcatttctc aaagggctca ctgaggaaac ttctgactca catgtcgaag aagcactgng 360
agtttctctt catttgctgc aaanttgctc tttgctggct gngctctcag accacccatt 420
tggctgcatg gggctgac 439

<210> SEQ ID NO 150
<211> LENGTH: 578
<212> TYPE: DNA
<213> ORGANISM: Homo sapiens
<220> FEATURE:
<221> NAME/KEY: misc_feature
<222> LOCATION: 4, 15, 260, 336, 371, 430, 461, 535, 572
<223> OTHER INFORMATION: n = A,T,C or G

<400> SEQUENCE: 150
ggcncgcccg ggcangtcca ctccactttt gagctctgag ggaatacctt caggagggac 60
agggtcaggg agtcctggca gctccgcagc agagattcac attcattcag agacttgttg 120
tccagtgcaa tgccattgat cgcaacgatc ctgtctccca cagcaaggga cccttcttta 180
gcggcagggc ttccaggcag cacagcggca gcatacactc cattctccag actgatgcca 240
ctgtctttct gtccactgan gttgatgtgc agcggcgtga ccaccttccc acccagggac 300
ttcctccgcc gcacgaccat gttgatgggc cccctnccca ttgaggagcg ccttgatggc 360
ctgcttcttg nccttggtga tgaagtccac atcggtgatt ctcacagcca gtcattgacc 420
cttaagcggn catcagcaat gcttcctttg gccactttag ngacaaatat gccacagtcc 480
ccgggaaaca agggtcattc acaccttctg gcatatcaaa cacctcggcc gggancacta 540
agccgaattc tgcagatatc catcacactg gngggccg 578

<210> SEQ ID NO 151
<211> LENGTH: 503
<212> TYPE: DNA
<213> ORGANISM: Homo sapiens
<220> FEATURE:
<221> NAME/KEY: misc_feature
<222> LOCATION: 392, 464
<223> OTHER INFORMATION: n = A,T,C or G

<400> SEQUENCE: 151
cgagcggccc gcccgggcag gtctgggaga tcagcgactg ctgccacgtg cccagaaatg 60
gctcgtcctt tcactacagc ggaatgcaat gagggtgggt gagaagatga tgggtcggtt 120
atttcattcc ttttcttttt acaacttcac tttcagagac ttcagcgttc catgtctgct 180
gtgctgtgga acccagagtg ctcttgcctg gatggctgag aatcccttgg accctggaag 240
cacctactcc atgatggccc ggtatagtgc aggctcaata taatcttccc ggtatcttga 300
gttgataact cgttgccgtt tcttttcttg cttaacctct ttctctgtga aaatctcatt 360

-continued

```
gaagcgcatg tctgaagcta ctgacagtct anatttgact ctcttgggaa gctcttcatc    420

cagtgtgtat acatcatctc tcttaaccac aagttggagc catncttaaa cttcacctgg    480

tacatttgga tagggtggga ggc                                            503
```

<210> SEQ ID NO 152
<211> LENGTH: 553
<212> TYPE: DNA
<213> ORGANISM: Homo sapiens
<220> FEATURE:
<221> NAME/KEY: misc_feature
<222> LOCATION: 293, 432, 459, 481, 536
<223> OTHER INFORMATION: n = A,T,C or G

<400> SEQUENCE: 152

```
agcgtggtcg cggcccgagg tccactgagc tccgccttcc ccgggctccc tgaggaagca     60

gagtcctgac ttccaggaag gacaggacac agaggcaaga actcagcctg tgaggctctg    120

ggtggctcct gaggccagag gacgccttcc gcgatccatg gctcagcatc gtccttctgg    180

cttcccagcc ccgggccgaa cgttcgggtt aataagcaga gcagttattc ggctcctggc    240

aggagctccc ccgttagttt ccacgttgtg agcacattca tacttaagac tgnttctctt    300

tgtgttttaa gcgtctgtct ctgtagtaaa ctgaaatgtt aacagaaatg cagacctgcc    360

cgggcggccg ctcgaaagcc gaattctgca gatatccatc acactggcgg ccgctcgagc    420

atgcatctag anggcccaat tcgccctata gtgagtcgna ttacaattca ctgggccgcg    480

ntttacaacg tcgtgactgg gaaaaccctg cggtacccac ttaatcgcct tgcagnacat    540

ccccctttcg cca                                                       553
```

<210> SEQ ID NO 153
<211> LENGTH: 454
<212> TYPE: DNA
<213> ORGANISM: Homo sapiens
<220> FEATURE:
<221> NAME/KEY: misc_feature
<222> LOCATION: 198, 307, 325, 347, 386, 389, 392, 415, 425
<223> OTHER INFORMATION: n = A,T,C or G

<400> SEQUENCE: 153

```
tcgagcggct cgcccgggca ggtccaccta gcatggctcc tctaaacacg caactcagcg     60

aggggacccc cttcacctct ggcaagagag ctgggtagat cagaaacttg gtgacacctg    120

gctagcacag agcaggctca cttgtcttgg tcccactacc cagattcctg cagacattgc    180

aaaccaaatg aaggttgntg aatgacccct gtccccagcc acttgttttg gtatcatctg    240

ctctgcagtg gaatgcctgt gtgtttgagt tcactctgca tctgtatatt tgagtataga    300

aaccgantca agtgatctgt gcatncagac acactggggc acctganacac agaacaaatc    360

accttaacga tctggaatga aactgnganc antgcccgcc tgggtgggtc tgganaaact    420

gccgncttct tgttggacct tggccgcacc acct                                454
```

<210> SEQ ID NO 154
<211> LENGTH: 596
<212> TYPE: DNA
<213> ORGANISM: Homo sapiens
<220> FEATURE:
<221> NAME/KEY: misc_feature
<222> LOCATION: 19, 33, 37, 131, 377, 425, 439, 505
<223> OTHER INFORMATION: n = A,T,C or G

<400> SEQUENCE: 154

```
agcgtggtcg cggcccgang gcggcctcct gantganggg aagggacgtg ggggcggcca     60
```

-continued

```
cggcaggatt aacctccatt tcagctaatc atgggagaga ttaaagtctc tcctgattat    120

aactggttta naggtacagt tccccttaaa aagattattg tggatgatga tgacagtaag    180

atatggtcgc tctatgacgc gggcccccga agtatcaggt gtcctctcat attcctgccc    240

cctgtcagtg gaactgcaga tgtctttttc cggcagattt tggctctgac tggatggggt    300

taccgggtta tcgctttgca gtatccagtt tattgggacc atctcgagtt cttgtgatgg    360

attcacaaaa cttttanacc atttacaatt ggataaagtt catctttttg gcgcttcttt    420

gggangcttt ttggcccana aatttgctga atacactcac aaatctccta gaagccattc    480

cctaatcctc tgcaattcct tcagngacac ctctatcttc aaccaacttg gactggaaac    540

agctttggct gatgcctgca tttatgctca aaaaatagtt cttggaaatt ttcatc        596
```

<210> SEQ ID NO 155
<211> LENGTH: 343
<212> TYPE: DNA
<213> ORGANISM: Homo sapiens
<220> FEATURE:
<221> NAME/KEY: misc_feature
<222> LOCATION: 6, 12, 23, 44, 58, 86, 99, 279, 310, 319
<223> OTHER INFORMATION: n = A,T,C or G

<400> SEQUENCE: 155

```
ctcganttgg cncgcccggg cangtctgcc tggtttttga ccgngcgagc tatttagnct     60

ctggctctgt ttccggagct caaggnaaaa atcttgaana actcgagcag cttctgtgga    120

tagccttggg tacacatact gccgagcata gccaatgtac tttctcaata gctggtgggg    180

aatgggatct attgtttctc caggaaccac ctttagtctt tctgataatg gcttctcaga    240

aactacttca agtacggaag tatttgaatc ttgactatnc atacgagcta ctgtggcact    300

gctaatgggn tctctgctnt ccagctctta ttgcaatcac atg                      343
```

<210> SEQ ID NO 156
<211> LENGTH: 556
<212> TYPE: DNA
<213> ORGANISM: Homo sapiens
<220> FEATURE:
<221> NAME/KEY: misc_feature
<222> LOCATION: 34, 375, 530
<223> OTHER INFORMATION: n = A,T,C or G

<400> SEQUENCE: 156

```
tcgagcggcc cgcccgggca ggtctggcac cacncagatc gattaactgg ctcatctgat     60

ctcgtggccc ccaccctgga actgacttag cacaaaagga cacctcaatt ccttatgatt    120

tcatctccga cccaaccaat caacaccctt gactcactgg ccttcccccct cccaccaaat    180

tatccttaaa aactctgatc cccgaatgct cagggagatc gatttgagta ctaataagac    240

tccagtctcc tgcacaagca gctctgtgta ctcttcctct attgcaattc ctgtcttgat    300

aaatcggctc tgtgtaggcg gcggaagaag tgaacctgtt gggcggttac cacctctgtc    360

gtgtgtgaca gttgntttga atctctaatt gctcagtaca gatccacatg caggttaagt    420

aagaagcttt tgaagaaaat ggaaagtctt aagtgatggc ttccaagaaa tcaaacctac    480

attaattagg gaacaacgga ctttacgtat cacaaatgaa gagactgacn aagtaaatca    540

acttggcctt ttctta                                                    556
```

<210> SEQ ID NO 157
<211> LENGTH: 333
<212> TYPE: DNA

-continued

<213> ORGANISM: Homo sapiens
<220> FEATURE:
<221> NAME/KEY: misc_feature
<222> LOCATION: 18, 40, 55, 57, 60, 91, 97, 103, 110, 161, 173, 193,
195, 196, 214, 231, 233, 238, 263, 264, 266, 283, 284, 287, 297,
298, 323, 331
<223> OTHER INFORMATION: n = A,T,C or G

<400> SEQUENCE: 157
ggtccacaaa aatatatnaa ataagctgga tatataaaan caaacactta acatngncan 60
cattccttca gttattcaaa ctcactgata nctaacnggg agnagttggn attctggaag 120
acttcctaag ctaaaagtat atttacatat ttacaacaca ngtaaatata acngaagaac 180
tacttcaaat aangnngaaa ttccagaatt ctanagattt atagctatag ntnacaanta 240
tcaccaattg gtttgcaatc aannngnccag cactacttat gannaangtt taactannaa 300
accaaaaggg gagaaaacct ggnagggaaa nat 333

<210> SEQ ID NO 158
<211> LENGTH: 629
<212> TYPE: DNA
<213> ORGANISM: Homo sapiens
<220> FEATURE:
<221> NAME/KEY: misc_feature
<222> LOCATION: 345, 565
<223> OTHER INFORMATION: n = A,T,C or G

<400> SEQUENCE: 158
tcgagcggcc gcccgggcag gtctggtaca tttgtgcgag gtccggcact ctgttctcat 60
ccagtaagtg gtcgagccct ttctgcagaa ttgctgttaa atgttctcct aatagctgtt 120
tctccacaca agcaatcagt ggtttctgtg tgctgtggtc caagtaagtg attactctgt 180
ctccctcttc ttctaagcgt ttacttacat ggttaagata ttctggaacc tctctttcct 240
gcattaacct ttggccttcg gcagcatata agcaattagt ctcttccaaa aatttcagtt 300
caaatgaatc tttatacacc tgcaggtcag acagcatgcc caggnaggct ccgcaacagg 360
ctccggtcca cggcctcgcc gctcctctcg cgctcgatca gcagtaggat tccatcaatg 420
gttttactct gaaccatttt atcactaata atatgggttc taaacagttc taatcccata 480
tcccagatgg agggcagcgt ggagttctgc agcacatagg tgcggtccaa gaacaggaag 540
atgcttctga tcatgaatca tttgnctggc aatggtcctg ccagcacgtg gtaatctttc 600
ttttaaaaat aaacccttat ctaaacgtc 629

<210> SEQ ID NO 159
<211> LENGTH: 629
<212> TYPE: DNA
<213> ORGANISM: Homo sapiens
<220> FEATURE:
<221> NAME/KEY: misc_feature
<222> LOCATION: 33, 546, 576
<223> OTHER INFORMATION: n = A,T,C or G

<400> SEQUENCE: 159
tcgagcggcc gcccgggcag gttctagagg ganaatctgg ctgatttggg aataaaatat 60
aatcgaatat tcaacaccat gaagataaat cttattttgg aaatctactg accttaatac 120
cccaagcttg ccctgaatac tttgattgga attggaatat atcaaaaaag gttagtattt 180
ttgttgtagt taggatacta aaaggatatt agttacccaa gagatccaat ttgtttttct 240
gatgaatagt gttcagtaaa atgaagcagt cttaagagtg actaataatt tcaaagtgat 300
ttttcgtcta ttcttaatat tttttaatta tttattttta agagttttat accttgagca 360

-continued

```
gatacaatga tccgctttag tgagaggaca atttctgatt gattgttttc tcttcaggcc    420

atctcacctc ttcattctct tgttacattt gaagcagttg atataatggg tttatacttt    480

aaaagataga catggtgcca tgaagtttgg ggaagttggg tgaattatcc cattctagtt    540

acagangagc tttccttaaa tgccctttac ttctangttt ggtcaagaag tcattttctg    600

agtaaaagtt attttcatat atgttgggg                                     629
```

```
<210> SEQ ID NO 160
<211> LENGTH: 519
<212> TYPE: DNA
<213> ORGANISM: Homo sapiens
<220> FEATURE:
<221> NAME/KEY: misc_feature
<222> LOCATION: 46, 309, 397, 430, 434, 471, 497
<223> OTHER INFORMATION: n = A,T,C or G

<400> SEQUENCE: 160

tcgagcggcg cgcccgggca ggtctgctgg gattaatgcc aagttnttca gccataaggt     60

agcgaaatct agcagaatcc agattacatc cacttccaat cacgcggtgt ttgggtaatc    120

cacttagttt ccagataaca tacgtaagaa tgtccactgg gttggaaacc acaattatga    180

tgcaatcagg actgtacttg acgatctgag gaataatgaa tttgaagaca ttaacatttc    240

tctgcaccag attgagccga ctctcccctt cttgctgacg gactcctgca gttaccacta    300

caatcttana attgggcggg tcacagaata atctttatct gccacaattt taggtgctga    360

agaaataagc tcccatgctg cagatccatc atttctnctt taagcttatc ttccaaaaca    420

tccacaagan caangttcat cagccagaga ctttcccaga atgctgatag nacacgccat    480

accaacttgt ccaacancca ctacagcgat cttattggt                           519
```

```
<210> SEQ ID NO 161
<211> LENGTH: 446
<212> TYPE: DNA
<213> ORGANISM: Homo sapiens
<220> FEATURE:
<221> NAME/KEY: misc_feature
<222> LOCATION: 5, 32, 36, 269, 354, 381
<223> OTHER INFORMATION: n = A,T,C or G

<400> SEQUENCE: 161

cgagnggccc gcccgggcag gtccagtaag cntttnacga tgatgggaaa ggttatgcaa     60

ggtcccagcg gtacaacgag ctgtttctac atcatttgta ttctgcatgg tacgtacaat    120

agcagacacc atctgaggag aacgcatgat agcgtgtctg gaagcttcct ttttagaaag    180

ctgatggacc ataactgcag ccttattaac caccacctgg tcctcgtcat ttagcagttt    240

tgtcagttca gggattgcac gtgtggcang ttctgcatca tcttgatagt taatcaagtt    300

tacaactggc atgtttcagc atctgcgatg ggctcagcaa acgctggaca ttantgggat    360

gagcagcatc aaactgtgta natgggatct gcatgccctc atctaatgtc tcagggaaca    420

tagcagctcg taccctctga gctcga                                         446
```

```
<210> SEQ ID NO 162
<211> LENGTH: 354
<212> TYPE: DNA
<213> ORGANISM: Homo sapiens
<220> FEATURE:
<221> NAME/KEY: misc_feature
<222> LOCATION: 6, 19, 36, 116, 152, 174, 186, 196, 223, 249
<223> OTHER INFORMATION: n = A,T,C or G
```

-continued

<400> SEQUENCE: 162
agcgtngtcg cggcccgang tcctgggaag cctttnttgc tgagcctcac agcctctgtc 60
aggcggctgc ggatccagcg gtccaccagg ctctcatggc ctccgggctg ggaggngggt 120
gagggcacaa aacccttccc aaggccacga anggcaaact tggtggcatt ccanagcttg 180
ttgcanaagt ggcggnaacc cagtatccgg ttcacatcca ggntgatgtc acgaccctgg 240
gacatgtang cacataatcc aaaccggaga gcatcggtgc cacattcacg aatccccgct 300
gggaagtcag ctttctgccc ttctttggcc ttctccacct cgctgggatc cagg 354

<210> SEQ ID NO 163
<211> LENGTH: 258
<212> TYPE: DNA
<213> ORGANISM: Homo sapiens
<220> FEATURE:
<221> NAME/KEY: misc_feature
<222> LOCATION: 7, 24, 32, 153, 198, 205
<223> OTHER INFORMATION: n = A,T,C or G

<400> SEQUENCE: 163
tttttcncca agtcctcttg ccgngggatc tngactgcaa tttaagacac ttctaattag 60
ttatacccag gccctgcaaa attgctgggt ttatataata tattcttgct gcacgaagat 120
ttattattct gttggatgat tctattttaa ttntatttat tctggccaaa aaagaacctt 180
ctccgctcgt caagagangc caatntgtct tgaaggacaa gagaaagatg ctaacacaca 240
ctttcttctt cttgagga 258

<210> SEQ ID NO 164
<211> LENGTH: 282
<212> TYPE: DNA
<213> ORGANISM: Homo sapiens
<220> FEATURE:
<221> NAME/KEY: misc_feature
<222> LOCATION: 97, 130, 163, 178, 203, 204
<223> OTHER INFORMATION: n = A,T,C or G

<400> SEQUENCE: 164
ggaacatatt acttttaaat tacttgggtc aatgaaacat ttaataaaaa catttgcttc 60
tctatataat acgtatgtat aaaataagcc ttttcanaaa ctctggttct cataatcctc 120
tataaatcan atgatctgac ttctaagagg aacaaattac agnaaggggt atacattnat 180
gaatactggt agtactagag ganngacgct aaaccactct actaccactt gcggaactct 240
cacagggtaa atgacaaagc caatgactga ctctaaaaac aa 282

<210> SEQ ID NO 165
<211> LENGTH: 462
<212> TYPE: DNA
<213> ORGANISM: Homo sapiens
<220> FEATURE:
<221> NAME/KEY: misc_feature
<222> LOCATION: 10, 33, 36, 49, 198, 222, 243, 278, 357, 385, 399, 405, 437
<223> OTHER INFORMATION: n = A,T,C or G

<400> SEQUENCE: 165
gcccgggcan gtcctgtaat cccagctact cangangctg agtcatgana atcgcctgaa 60
tccgggaggt agaggccgca gcgagcaaag attaagccac tgcactccag tctgggtgac 120
agagtgagaa tctgtctgtt gctcctctgg cattggtctg aaatgggttt gtagaacatg 180
ccacagaagg accagcanca gcaacaaatg gatttgtgga angcgtagct ccaaatggag 240

-continued

```
cangcacact tgatgaagca cgctgtgtct gtgcagangc aaccactggc actgttccaa    300

aaacattgct gctagcatta cttgtggaag tatacgcatt actggaggtg gctgcanaac    360

tgaaaacgct gtctagttct gccanagctg catacttgnc tgaanatgca cttgactgac    420

tgggaactga accacanaac caacaggacc tttacctgtg ga                       462


<210> SEQ ID NO 166
<211> LENGTH: 365
<212> TYPE: DNA
<213> ORGANISM: Homo sapiens
<220> FEATURE:
<221> NAME/KEY: misc_feature
<222> LOCATION: 14, 18
<223> OTHER INFORMATION: n = A,T,C or G

<400> SEQUENCE: 166

cgtgggtcgc ggcncgangt ctgaaaccaa tccagaacta aacatcagca cacaaaaaat     60

accaggatag atggaatcaa aagactctga agccaaaagg aggctaggga gagcaactga    120

acttagcaag ctgaggactt cagtgtccat catccgatcc tgccctgtaa caacaggtct    180

atatgataga gatattccat ctgagctgga ggccattatc cttagcaaac taacacagaa    240

cagaaaacca aatacatgtt ctcatttaga agtaggagct aaatgatgag aactcaagga    300

cacaaagaaa ggaacaacag acactggggc ctacttgagg gtggagggtg ggaggaggga    360

gaaga                                                                365


<210> SEQ ID NO 167
<211> LENGTH: 364
<212> TYPE: DNA
<213> ORGANISM: Homo sapiens
<220> FEATURE:
<221> NAME/KEY: misc_feature
<222> LOCATION: 19, 342, 361
<223> OTHER INFORMATION: n = A,T,C or G

<400> SEQUENCE: 167

agcgtggtcg cggcgcgang tccagcccta gcttgcctgt gactccgcct tcactgggtg     60

ctctctctaa aagttgctga ctctttactg tatctcccaa ttcccactcc attggttcca    120

taaggggagg ggtgtctcac tcaacatggt gttcctggta ccaagaactg gctgacgaag    180

ctgggtgccg tggctcatgc ctgtaatccc agcacttttg ggaggccaag aagggcggat    240

cacctgaggt ctggagttca agatcagcct gaccaacatg atgaaaccaa gtctccacta    300

aaaatataaa acaattagcc aggcatggtg gtgggtgcct gnaatcccag ctactgggga    360

ngct                                                                 364


<210> SEQ ID NO 168
<211> LENGTH: 447
<212> TYPE: DNA
<213> ORGANISM: Homo sapiens
<220> FEATURE:
<221> NAME/KEY: misc_feature
<222> LOCATION: 407, 414, 437
<223> OTHER INFORMATION: n = A,T,C or G

<400> SEQUENCE: 168

cccgggcagg tcaaaaccca aaacctttca ttttagccca aaccagctca tgattaggta     60

tacaaggata acagaaccag ttgtcaggac gagcatttga caagtaaaag caattcttgc    120

aaagctgcag ttcatccagc tcatggcatg tgtctttata tagcatcctc gcaatgtcag    180

cttgctcact gtctgctcca tagaaaatca cggtattgtg gagaagcaat tgggcatcag    240
```

-continued

```
ctttgaactc ttcataactt cggtatttcc cttcattcac tttctcttga atggtgggaa    300

cgtccacaga cctcggccgc gaccacgcta agcccgaatt ctgcagatat ccatcacact    360

ggcggccgtt cgagcatggc atctagaagg cccaattcgc ctatagngag tcgnattacc    420

aattcactgg ccgtcgnttt acaacgc                                        447


<210> SEQ ID NO 169
<211> LENGTH: 524
<212> TYPE: DNA
<213> ORGANISM: Homo sapiens
<220> FEATURE:
<221> NAME/KEY: misc_feature
<222> LOCATION: 4, 6, 39, 40, 235, 248, 313, 340, 359, 382, 389, 420,
      434, 442, 453, 496
<223> OTHER INFORMATION: n = A,T,C or G

<400> SEQUENCE: 169

cgantngcgc gcccgggcag gtctgagcag cctttctgnn tgctggacta ttgggattgg     60

gttcatccaa cagagactgt atggatgtta gaatggaaga cacatcatag gttggactcc    120

aacggttctg aagtatgtcc agacatatac taccatctgc atagactaag aacaaagaag    180

taggtacatt aaacgtaaca agaccactaa ggttttaaca ttatagacaa aacanaaata    240

gtcaaganta ctttgctttt gaagtttaaa gattcctatg ttgcttccca gttaactgcc    300

taaaaagata agncataacc accactagtg aaataatcan gatgatcaga gaatgtcana    360

tgtgatcagt ataaaactgg angatattna gtgtcatcct ttggaaaagg ctgccctatn    420

atccaggaaa tcanaaacat tnttgaacag ggnccctagc tatccacaga catgtgggaa    480

attcattccc caaatngtag gctggatccc ctatctgaaa taac                     524


<210> SEQ ID NO 170
<211> LENGTH: 332
<212> TYPE: DNA
<213> ORGANISM: Homo sapiens
<220> FEATURE:
<221> NAME/KEY: misc_feature
<222> LOCATION: 5, 10, 63, 66, 90, 93, 96, 186, 207, 261, 290, 324, 326
<223> OTHER INFORMATION: n = A,T,C or G

<400> SEQUENCE: 170

tcgancggcn cgcccgggca ggtgacaaac ctgttattga agatgttggt tctgatgagg     60

aanaanatca gaagggatgg tgacaagaan aanaanaaga agattaagga aaagtacatc    120

gatcaagaag agctcaacaa aacaaagccc atctggacca gaaatcccga cgatattact    180

aatgangagt acggagaatt ctataanagc ttgaccaatg actgggaaga tcacttggca    240

gtgaagcatt tttcagttga nggacagttg gaattcagag cccttctatn tgtcccacga    300

cgtgctcctt ttgatctgtt tganancaga aa                                  332


<210> SEQ ID NO 171
<211> LENGTH: 334
<212> TYPE: DNA
<213> ORGANISM: Homo sapiens
<220> FEATURE:
<221> NAME/KEY: misc_feature
<222> LOCATION: 5, 9, 200, 228, 232
<223> OTHER INFORMATION: n = A,T,C or G

<400> SEQUENCE: 171

cgagnggcnc gcccgggcag gtctgttgat agcgacttaa cagaaaagtc tagacaaaca     60

taagcataaa aaattacagt ctttctaccc ttgggaatgg ggagaaaaag gaatctctac    120
```

-continued cccaagacca gaaataataa gtcctgtttc tggtcctgaa catccagaat tatggaggct 180
ttggcctgac accacattan aatttggtct ggaaatcaaa ctttaganac angagatcgt 240
aagccatttt atactatcga cctaaattcc agtctaacgg ttcctttaca aagttgcgga 300
aagccctctt atatgctagc tgtaggaaat atag 334

<210> SEQ ID NO 172
<211> LENGTH: 439
<212> TYPE: DNA
<213> ORGANISM: Homo sapiens
<220> FEATURE:
<221> NAME/KEY: misc_feature
<222> LOCATION: 19, 375, 388, 390, 395, 409, 426, 434
<223> OTHER INFORMATION: n = A,T,C or G

<400> SEQUENCE: 172
agcgtggtcg cggcccgang tctgcctata aaactagact tctgacgctg ggctccagct 60
tcattctcac aggtcatcat cctcatccgg gagagcagtt gtctgagcaa cctctaagtc 120
gtgctcatac tgtgctgcca aagctgggtc catgacaact tctggtgggg cgagagcagg 180
catggcaaca aattccaagt tagggtctcc aatgagcttc ctagcaagcc agaggaaggg 240
cttttcaaag ttgtagttac ttttggcaga aatgtcgtag tactgaagat tcttctttcg 300
gtggaagaca atggatttcg ccttcacttt ctgccttaat atccactttg gtgccacaca 360
acacaatggg gatgntttca cacacttngn accanatctc tatgccagnt aggccatttt 420
ggaagnactt cganggtac 439

<210> SEQ ID NO 173
<211> LENGTH: 599
<212> TYPE: DNA
<213> ORGANISM: Homo sapiens
<220> FEATURE:
<221> NAME/KEY: misc_feature
<222> LOCATION: 5, 31
<223> OTHER INFORMATION: n = A,T,C or G

<400> SEQUENCE: 173
cgatnggccg cccgggcagg tcctgtaaaa naggaaattc agacatcgta cgactcgtaa 60
ttgaatgtgg agctgactgc aatattttgt caaagcacca gaatagtgcc ctgcactttg 120
cgaagcagtc taacaatgtg cttgtgtacg acttgctgaa gaaccattta gagacacttt 180
caagagtagc agaagagaca ataaaggatt actttgaagc tcgccttgct ctgctagaac 240
cagtttttcc aatcgcatgt catcgactct gtgagggtcc agatttttca acagatttca 300
attaccaacc cccacagaac ataccagaag gctctggcat cctgctgttt atcttccatg 360
caaacttttt gggtaaagaa gttattgctc ggctctgtgg accgtgtagt gtacaagctg 420
tagttctgaa tgataaattt cagcttcctg tttttctggg tctcgctctg ttgtccaggc 480
tggagtgcag tggcgcggat tacagctcac tggagtcttg acttcccagg cacaagcaat 540
cctcccacct cagcctccta actacctggg actaaaaatg caccgccacc acattccgg 599

<210> SEQ ID NO 174
<211> LENGTH: 458
<212> TYPE: DNA
<213> ORGANISM: Homo sapiens
<220> FEATURE:
<221> NAME/KEY: misc_feature
<222> LOCATION: 30, 32, 35, 51, 61, 213, 261, 327, 347, 359, 377, 418
<223> OTHER INFORMATION: n = A,T,C or G -continued

<400> SEQUENCE: 174

```
tcgatttggc cgcccgggca ggtccatgcn gnttntgccc attcccatgg ngcccgacaa     60
ncccatcccc gaggccgaca tccccatgtt catgttcatg cccaccatgc cctggctcat    120
ccctgcgctg ttccccagag gggccattcc catggtgccc gtcattacac cgggcatgtt    180
cataggcatg ggtcccccca ggagagggtt agnttgaggc cggacaggaa gcatgtttga    240
tggagaactg aggttcacag nctccaaaac tttgagtcat cacattcata ggctgctgca    300
tattctgtct gctgaatcca ttgtatncag tgatggcctg ctggggnttt ggaaggctng    360
cataccaggt agtaagntcg tctaggctga tgtttacacc tggggtcaga ccaagtanga    420
gggcaaggtt ttgctgactg attttctgga cccatatc                            458
```

<210> SEQ ID NO 175
<211> LENGTH: 1206
<212> TYPE: DNA
<213> ORGANISM: Homo sapiens

<400> SEQUENCE: 175

```
ggcacgagga agttttgtgt actgaaaaag aaactgtcag aagcaaaaga aataaaatca     60
cagttagaga accaaaaagt taaatgggaa caagagctct gcagtgtgag gtttctcaca    120
ctcatgaaaa tgaaaattat ctcttacatg aaaattgcat gttgaaaaag gaaattgcca    180
tgctaaaact ggaaatagcc acactgaaac accaatacca ggaaaaggaa aataaatact    240
ttgaggacat taagatttta aaagaaaaga atgctgaact tcagatgacc ctaaaactga    300
aagaggaatc attaactaaa agggcatctc aatatagtgg gcagcttaaa gttctgatag    360
ctgagaacac aatgctcact tctaaattga aggaaaaaca agacaaagaa atactagagg    420
cagaaattga atcacaccat cctagactgg cttctgctgt acaagaccat gatcaaattg    480
tgacatcaag aaaaagtcaa gaacctgctt tccacattgc aggagatgct tgtttgcaaa    540
gaaaaatgaa tgttgatgtg agtagtacga tatataacaa tgaggtgctc catcaaccac    600
tttctgaagc tcaaaggaaa tccaaaagcc taaaaattaa tctcaattat gccggagatg    660
ctctaagaga aaatacattg gtttcagaac atgcacaaag agaccaacgt gaaacacagt    720
gtcaaatgaa ggaagctgaa cacatgtatc aaaacgaaca agataatgtg aacaaacaca    780
ctgaacagca ggagtctcta gatcagaaat tatttcaact acaaagcaaa aatatgtggc    840
ttcaacagca attagttcat gcacataaga aagctgacaa caaaagcaag ataacaattg    900
atattcattt tcttgagagg aaaatgcaac atcatctcct aaaagagaaa aatgaggaga    960
tatttaatta caataaccat ttaaaaaacc gtatatatca atatgaaaaa gagaaagcag   1020
aaacagaagt tatataatag tataacactg ccaaggagcg gattatctca tcttcatcct   1080
gtaattccag tgtttgtcac gtggttgttg aataaatgaa taaagaatga gaaaaccaga   1140
agctctgata cataatcata atgataatta tttcaatgca caactacggg tggtgctgct   1200
cgtgcc                                                              1206
```

<210> SEQ ID NO 176
<211> LENGTH: 317
<212> TYPE: PRT
<213> ORGANISM: Homo sapiens

<400> SEQUENCE: 176

```
Met Gly Thr Arg Ala Leu Gln Cys Glu Val Ser His Thr His Glu Asn
 1               5                   10                  15
```

-continued

```
Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Glu Ser Leu Thr Lys Arg
65                  70                  75                  80

Ala Ser Gln Tyr Ser Gly Gln Leu Lys Val Leu Ile Ala Glu Asn Thr
                85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300

Tyr Gln Tyr Glu Lys Glu Lys Ala Glu Thr Glu Val Ile
305                 310                 315
```

<210> SEQ ID NO 177
<211> LENGTH: 20
<212> TYPE: DNA
<213> ORGANISM: Artificial Sequence
<220> FEATURE:
<223> OTHER INFORMATION: Made in the lab

<400> SEQUENCE: 177

```
ccaatcatct ccacaggagc                                                20
```

<210> SEQ ID NO 178
<211> LENGTH: 1665
<212> TYPE: DNA
<213> ORGANISM: Homo sapiens

<400> SEQUENCE: 178

```
gcaaactttc aagcagagcc tcccgagaag ccatctgcct tcgagcctgc cattgaaatg     60
```

-continued

```
caaaagtctg ttccaaataa agccttggaa ttgaagaatg aacaaacatt gagagcagat    120

cagatgttcc cttcagaatc aaaacaaaag aaggttgaag aaaattcttg ggattctgag    180

agtctccgtg agactgtttc acagaaggat gtgtgtgtac ccaaggctac acatcaaaaa    240

gaaatggata aaataagtgg aaaattagaa gattcaacta gcctatcaaa aatcttggat    300

acagttcatt cttgtgaaag agcaagggaa cttcaaaaag atcactgtga acaacgtaca    360

ggaaaaatgg aacaaatgaa aaagaagttt tgtgtactga aaaagaaact gtcagaagca    420

aaagaaataa aatcacagtt agagaaccaa aaagttaaat gggaacaaga gctctgcagt    480

gtgaggtttc tcacactcat gaaaatgaaa attatctctt acatgaaaat tgcatgttga    540

aaaaggaaat tgccatgcta aaactggaaa tagccacact gaaacaccaa taccaggaaa    600

aggaaaataa atactttgag gacattaaga ttttaaaaga aaagaatgct gaacttcaga    660

tgaccctaaa actgaaagag gaatcattaa ctaaaagggc atctcaatat agtgggcagc    720

ttaaagttct gatagctgag aacacaatgc tcacttctaa attgaaggaa aaacaagaca    780

aagaaatact agaggcagaa attgaatcac accatcctag actggcttct gctgtacaag    840

accatgatca aattgtgaca tcaagaaaaa gtcaagaacc tgctttccac attgcaggag    900

atgcttgttt gcaaagaaaa atgaatgttg atgtgagtag tacgatatat aacaatgagg    960

tgctccatca accactttct gaagctcaaa ggaaatccaa aagcctaaaa attaatctca   1020

attatgccgg agatgctcta agagaaaata cattggtttc agaacatgca caaagagacc   1080

aacgtgaaac acagtgtcaa atgaaggaag ctgaacacat gtatcaaaac gaacaagata   1140

atgtgaacaa acacactgaa cagcaggagt ctctagatca gaaattattt caactacaaa   1200

gcaaaaatat gtggcttcaa cagcaattag ttcatgcaca taagaaagct gacaacaaaa   1260

gcaagataac aattgatatt cattttcttg agaggaaaat gcaacatcat ctcctaaaag   1320

agaaaaatga ggagatattt aattacaata accatttaaa aaaccgtata tatcaatatg   1380

aaaaagagaa agcagaaaca gaaaactcat gagagacaag cagtaagaaa cttcttttgg   1440

agaaacaaca gaccagatct ttactcacaa ctcatgctag gaggccagtc ctagcattac   1500

cttatgttga aaatcttacc aatagtctgt gtcaacagaa tacttatttt agaagaaaaa   1560

ttcatgattt cttcctgaag cctgggcgac agagcgagac tctgtctcaa aaaaaaaaaa   1620

aaaaaaagaa agaaagaaat gcctgtgctt acttcgcttc ccagg                   1665
```

<210> SEQ ID NO 179
<211> LENGTH: 179
<212> TYPE: PRT
<213> ORGANISM: Homo sapiens

<400> SEQUENCE: 179

```
Ala Asn Phe Gln Ala Glu Pro Pro Glu Lys Pro Ser Ala Phe Glu Pro
 1               5                  10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
                85                  90                  95
```

-continued

```
Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Lys Leu Ser Glu Ala Lys Glu Ile Lys
    130                 135                 140

Ser Gln Leu Glu Asn Gln Lys Val Lys Trp Glu Gln Glu Leu Cys Ser
145                 150                 155                 160

Val Arg Phe Leu Thr Leu Met Lys Met Lys Ile Ile Ser Tyr Met Lys
                165                 170                 175

Ile Ala Cys
```

<210> SEQ ID NO 180
<211> LENGTH: 1681
<212> TYPE: DNA
<213> ORGANISM: Homo sapiens

<400> SEQUENCE: 180

```
gatacagtca ttcttgtgaa agagcaaggg aacttcaaaa agatcactgt gaacaacgta     60

caggaaaaat ggaacaaatg aaaaagaagt tttgtgtact gaaaaagaaa ctgtcagaag    120

caaaagaaat aaaatcacag ttagagaacc aaaaagttaa atgggaacaa gagctctgca    180

gtgtgagatt gactttaaac caagaagaag agaagagaag aaatgccgat atattaaatg    240

aaaaaattag ggaagaatta ggaagaatcg aagagcagca taggaaagag ttagaagtga    300

aacaacaact tgaacaggct ctcagaatac aagatataga attgaagagt gtagaaagta    360

atttgaatca ggtttctcac actcatgaaa atgaaaatta tctcttacat gaaaattgca    420

tgttgaaaaa ggaaattgcc atgctaaaac tggaaatagc cacactgaaa caccaatacc    480

aggaaaagga aaataaatac tttgaggaca ttaagatttt aaaagaaaag aatgctgaac    540

ttcagatgac cctaaaactg aaagaggaat cattaactaa aagggcatct caatatagtg    600

ggcagcttaa agttctgata gctgagaaca caatgctcac ttctaaattg aaggaaaaac    660

aagacaaaga aatactagag gcagaaattg aatcacacca tcctagactg gcttctgctg    720

tacaagacca tgatcaaatt gtgacatcaa gaaaaagtca agaacctgct ttccacattg    780

caggagatgc ttgtttgcaa agaaaaatga atgttgatgt gagtagtacg atatataaca    840

atgaggtgct ccatcaacca ctttctgaag ctcaaaggaa atccaaaagc ctaaaaatta    900

atctcaatta tgccggagat gctctaagag aaaatacatt ggtttcagaa catgcacaaa    960

gagaccaacg tgaaacacag tgtcaaatga aggaagctga acacatgtat caaaacgaac   1020

aagataatgt gaacaaacac actgaacagc aggagtctct agatcagaaa ttatttcaac   1080

tacaaagcaa aaatatgtgg cttcaacagc aattagttca tgcacataag aaagctgaca   1140

acaaaagcaa gataacaatt gatattcatt ttcttgagag gaaaatgcaa catcatctcc   1200

taaaagagaa aaatgaggag atatttaatt acaataacca tttaaaaaac cgtatatatc   1260

aatatgaaaa agagaaagca gaaacagaaa actcatgaga gacaagcagt aagaaacttc   1320

ttttggagaa acaacagacc agatctttac tcacaactca tgctaggagg ccagtcctag   1380

cattacctta tgttgaaaaa tcttaccaat agtctgtgtc aacagaatac ttattttaga   1440

agaaaaattc atgatttctt cctgaagcct acagacataa aataacagtg tgaagaatta   1500

cttgttcacg aattgcataa aagctgccca ggatttccat ctaccctgga tgatgccgga   1560

gacatcattc aatccaacca gaatctcgct ctgtcactca ggctggagtg cagtgggcgc   1620
```

-continued

```
aatctcggct cactgcaact ctgcctccca ggttcacgcc attctctggc acagcctccc   1680

g                                                                   1681


<210> SEQ ID NO 181
<211> LENGTH: 432
<212> TYPE: PRT
<213> ORGANISM: Homo sapiens

<400> SEQUENCE: 181

Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Lys Phe Cys
            20                  25                  30

Val Leu Lys Lys Lys Leu Ser Glu Ala Lys Glu Ile Lys Ser Gln Leu
        35                  40                  45

Glu Asn Gln Lys Val Lys Trp Glu Gln Glu Leu Cys Ser Val Arg Leu
    50                  55                  60

Thr Leu Asn Gln Glu Glu Glu Lys Arg Arg Asn Ala Asp Ile Leu Asn
65                  70                  75                  80

Glu Lys Ile Arg Glu Glu Leu Gly Arg Ile Glu Glu Gln His Arg Lys
                85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
        115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300

Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350
```

-continued

```
Ser Leu Asp Gln Lys Leu Phe Gln Leu Gln Ser Lys Asn Met Trp Leu
        355                 360                 365

Gln Gln Gln Leu Val His Ala His Lys Lys Ala Asp Asn Lys Ser Lys
    370                 375                 380

Ile Thr Ile Asp Ile His Phe Leu Glu Arg Lys Met Gln His His Leu
385                 390                 395                 400

Leu Lys Glu Lys Asn Glu Glu Ile Phe Asn Tyr Asn Asn His Leu Lys
                405                 410                 415

Asn Arg Ile Tyr Gln Tyr Glu Lys Glu Lys Ala Glu Thr Glu Asn Ser
            420                 425                 430
```

<210> SEQ ID NO 182
<211> LENGTH: 511
<212> TYPE: DNA
<213> ORGANISM: Homo sapiens

<400> SEQUENCE: 182

```
gaagtttcat gaggtttagc ttttctgggc tggggagtgg agagaaagaa gttgcagggc     60

ttacaggaaa tcccagagcc tgaggttttc tcccagattt gagaactcta gattctgcat    120

cattatcttt gagtctatat tctcttgggc tgtaagaaga tgaggaatgt aataggtctg    180

ccccaagcct ttcatgcctt ctgtaccaag cttgtttcct tgtgcatcct tcccaggctc    240

tggctgcccc ttattggaga atgtgatttc caagacaatc aatccacaag tgtctaagac    300

tgaatacaaa gaacttcttc aagagttcat agacgacaat gccactacaa atgccataga    360

tgaattgaag gaatgttttc ttaaccaaac ggatgaaact ctgagcaatg ttgaggtgtt    420

tatgcaatta atatatgaca gcagtctttg tgatttattt taactttctg caagaccttt    480

ggctcacaga actgcagggt atggtgagaa a                                   511
```

<210> SEQ ID NO 183
<211> LENGTH: 260
<212> TYPE: DNA
<213> ORGANISM: Homo sapiens

<400> SEQUENCE: 183

```
cacctcgcgg ttcagctcct ctgtcttggt gaagaaccat tcctcggcat ccttgcggtt     60

cttctctgcc atcttctcat actggtcacg catctcgttc agaatgcggc tcaggtccac    120

gccaggtgca gcgtccatct ccacattgac atctccaccc acctggcctc tcagggcatt    180

catctcctcc tcgtggttct tcttcaggta ggccagctcc tccttcaggc tctcaatctg    240

catctccagg tcagctctgg                                                260
```

<210> SEQ ID NO 184
<211> LENGTH: 461
<212> TYPE: DNA
<213> ORGANISM: Homo sapiens

<400> SEQUENCE: 184

```
gtctgatggg agaccaaaga atttgcaagt ggatggtttg gtatcactgt aaataaaaag     60

agggcctttt ctagctgtat gactgttact tgaccttctt tgaaaagcat tcccaaaatg    120

ctctatttta gatagattaa cattaaccaa cataattttt tttagatcga gtcagcataa    180

atttctaagt cagcctctag tcgtggttca tctctttcac ctgcatttta tttggtgttt    240

gtctgaagaa aggaaagagg aaagcaaata cgaattgtac tatttgtacc aaatctttgg    300

gattcattgg caaataattt cagtgtggtg tattattaaa tagaaaaaaa aaattttgtt    360
```

-continued

```
tcctaggttg aaggtctaat tgataccgtt tgacttatga tgaccattta tgcactttca    420

aatgaatttg ctttcaaaat aaatgaagag cagacctcgg c                        461
```

<210> SEQ ID NO 185
<211> LENGTH: 531
<212> TYPE: DNA
<213> ORGANISM: Homo sapiens

<400> SEQUENCE: 185

```
tctgatttta tttccttctc aaaaaaagtt atttacagaa ggtatatatc aacaatctga     60

caggcagtga acttgacatg attagctggc atgatttttt cttttttttc cccaaaacat    120

tgtttttgtg gccttgaatt ttaagacaaa tattctacac ggcatattgc acaggatgga    180

tggcaaaaaa aagtttaaaa acaaaaaccc ttaacggaac tgccttaaaa aggcagacgt    240

cctagtgcct gtcatgttat attaaacata catacacaca atctttttgc ttattataat    300

acagacttaa atgtacaaag atgttttcca ctttttttcaa tttttaaaca caacagctat    360

aaacctgaac acatatgcta tcatcatgcc ataagactaa aacaattata tttagcgaca    420

agtagaaagg attaaatagt caaatacaag aatgaaaaac gcagtacata gtgtcgcgaa    480

ctcaaatcgg catttagata gatccagtgg tttaaacggc acgtttttgc t             531
```

<210> SEQ ID NO 186
<211> LENGTH: 441
<212> TYPE: DNA
<213> ORGANISM: Homo sapiens

<400> SEQUENCE: 186

```
cattcctttc ctcgcgttgg ggtttctctg tgtcagcgag cctcggtaca ctgatttccg     60

atcaaaagaa tcatcatctt taccttgact tttcagggaa ttactgaact ttcttctcag    120

aagatagggc acagccattg ccttggcctc acttgaaggg tctgcatttg ggtcctctgg    180

tctcttgcca agtttcccaa ccactcgagg gagaaatatc gggaggtttg acttcctccg    240

gggctttccc gagggcttca ccgtgagccc tgcggccctc agggctgcaa tcctggattc    300

aatgtctgaa acctcgctct ctgcctgctg gacttctgag gccgtcactg ccactctgtc    360

ctccagctct gacagctcct catctgtggt cctgttgtac tggacggggt ccccagggtc    420

ctgggggctt ttttcctgtc t                                              441
```

<210> SEQ ID NO 187
<211> LENGTH: 371
<212> TYPE: DNA
<213> ORGANISM: Homo sapiens

<400> SEQUENCE: 187

```
aaaagtgaat gagtaactat tatattgttg gcaataataa gttgcaaaat catcaggctg     60

caggctgctg atggtgagag tgaactctgt cccagatcca ctgccgctga accttgatgg    120

gaccccagat tctaaactag acgccttatg gatcaggagc tttggggctt tccctggttt    180

ctgttgatac caggccaacc aactactaac actctgactg gcccggcaag tgatggtgac    240

tctgtctcct acagttgcag acagggtgga aggagactgg gtcatctgga tgtcacattt    300

ggcacctggg agccagagca gcaggagccc caggagctga gcggggaccc tcatgtccat    360

gctgagtcct g                                                         371
```

<210> SEQ ID NO 188
<211> LENGTH: 226

-continued

<212> TYPE: DNA
<213> ORGANISM: Homo sapiens

<400> SEQUENCE: 188
ggtatataaa ttgagatgcc cccccaggcc agcaaatgtt cctttttgtt caaagtctat 60
ttttattcct tgatattttt cttttttttt tttttgtgga tggggacttg tgaatttttc 120
taaaggtgct atttaacatg ggaggagagc gtgtgcggct ccagcccagc ccgctgctca 180
ctttccaccc tctctccacc tgcctctggc ttctcaggac ctgccc 226

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: 43, 112, 131, 156, 195, 208, 221, 317, 333, 367
<223> OTHER INFORMATION: n = A,T,C or G

<400> SEQUENCE: 189
tgggtgaagt ttattctgtt ttcacatcta ggttgttggg ganagtgata gacaaagttc 60
tggattctgg gcatcgtcgg cgcatgcttg taatcctact tgggaggttg anacaggaga 120
cctcggccgc naccacgcta agggcgaatt ctgcanatat ccatcacact ggcggccgct 180
cgagcatgca tctanagggc ccaattcncc ctatagtgag ncgtattaca attcactggc 240
cgtcgtttta caacgtcgtg actgggaaaa ccctggcgtt acccaactta atcgccttgc 300
agcacatccc cctttcncca gctggcttaa tancgaagag gcccgcaccg atcgcccttc 360
ccaacanttg cgcagcctga atggcgaatg g 391

<210> SEQ ID NO 190
<211> LENGTH: 501
<212> TYPE: DNA
<213> ORGANISM: Homo sapiens

<400> SEQUENCE: 190
catcttggcc tttttgagct gtttccgctt cttctcatcc cggtcactgt caccctcatt 60
actggaggag ctggcagagg cgttgctgtc aaactcctct gccacatctt cctcctcttc 120
acctgggttg aatgactcat cggtttcttc tcctgagtca tcgctgctgt cattggcatt 180
ctcctcccgg atcttgcctt cctccttcat cctctccaag taggcatcat gctggtcctc 240
atcagagtca gcatattcat cgtagcttgg gttcatgccc tctttcaatc ctcggttttt 300
gatgttgagc tttttcgcgt tgacaaaatc aaacagtttc ccgtactcct ccctctcaat 360
gctgctgaag gtatactgag tgccctgctt ggtctcaatt tcaaagtcaa aggaacgagt 420
agtagtggta ccacgagcaa agttgacaaa ggagatctca tcgaagcgga tgtgcacagg 480
tggcttgtgg acgtagatga a 501

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: 49
<223> OTHER INFORMATION: n = A,T,C or G

<400> SEQUENCE: 191
ggaaaaactg tgaaaaatat atctgaattt attaagtaca gtataaaana gggttgtggc 60

-continued

```
aacagaaagt aaaaactaac atggattgct ataaatatgc tgaagcctag ttgttcaaat    120

gatacaattc tctcatgcta ctctaaagtt tataaagaaa aaggatttac actttacaca    180

ctgtacacaa aaggaatacc ttctgagagc cagggagtgg ggaaagggga aggagacttg    240

a                                                                    241


<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: 6, 17, 23, 26, 70, 227, 245
<223> OTHER INFORMATION: n = A,T,C or G

<400> SEQUENCE: 192

tggtcntgga ttcacanata aantanatcg actaaaactg gcagaaattg tgaagcaggt     60

gatagaagan caaaccacgt cccacgaatc ccaataatga cagcttcaga ctttgctttt    120

ttaacaattt gaaaaattat tctttaatgt ataaagtaat tttatgtaaa ttaataaatc    180

ataatttcat ttccacattg attaaagctg ctgtatagat ttagggngca ggacttaata    240

atagnggaaa tgaaattatg atttattaat c                                   271


<210> SEQ ID NO 193
<211> LENGTH: 351
<212> TYPE: DNA
<213> ORGANISM: Homo sapiens

<400> SEQUENCE: 193

agtcgaggcg ctgatcccta aaatggcgaa catgtgtttt catcatttca gccaaagtcc     60

taacttcctg tgcctttcct atcacctcga gaagtaatta tcagttggtt tggatttttg    120

gaccaccgtt cagtcatttt gggttgccgt gctcccaaaa cattttaaat gaaagtattg    180

gcattcaaaa agacagcaga caaaatgaaa gaaaatgaga gcagaaagta agcatttcca    240

gcctatctaa tttctttagt tttctatttg cctccagtgc agtccatttc ctaatgtata    300

ccagcctact gtactattta aaatgctcaa tttcagcacc gatggacctg c             351


<210> SEQ ID NO 194
<211> LENGTH: 311
<212> TYPE: DNA
<213> ORGANISM: Homo sapiens

<400> SEQUENCE: 194

ctgagacaca gaggcccact gcgaggggga cagtggcggt gggactgacc tgctgacagt     60

caccctccct ctgctgggat gaggtccagg agccaactaa aacaatggca gaggagacat    120

ctctggtgtt cccaccaccc tagatgaaaa tccacagcac agacctctac cgtgtttctc    180

ttccatccct aaaccacttc cttaaaatgt ttggatttgc aaagccaatt tggggcctgt    240

ggagcctggg gttggatagg gccatggctg gtcccccacc atacctcccc tccacatcac    300

tgacacagac c                                                         311


<210> SEQ ID NO 195
<211> LENGTH: 381
<212> TYPE: DNA
<213> ORGANISM: Homo sapiens

<400> SEQUENCE: 195

tgtcagagtg gcactggtag aagttccagg aaccctgaac tgtaagggtt cttcatcagt     60
```

-continued

```
gccaacagga tgacatgaaa tgatgtactc agaagtgtcc tggaatgggg cccatgagat    120

ggttgtctga gagagagctt cttgtcctgt ctttttcctt ccaatcaggg gctcgctctt    180

ctgattattc ttcagggcaa tgacataaat tgtatattcg gttcccggtt ccaggccagt    240

aatagtagcc tctgtgacac cagggcgggg ccgagggacc acttctctgg gaggagaccc    300

aggcttctca tacttgatga tgtagccggt aatcctggca cgtggcggct gccatgatac    360

cagcagggaa ttgggtgtgg t                                              381


<210> SEQ ID NO 196
<211> LENGTH: 401
<212> TYPE: DNA
<213> ORGANISM: Homo sapiens

<400> SEQUENCE: 196

cacaaacaag aggagcacca gacctcctct tggcttcgag atggcttcgc cacaccaaga     60

gcccaaacct ggagacctga ttgagatttt ccgccttggc tatgagcact gggccctgta    120

tataggagat ggctacgtga tccatctggc tcctccaagt gagtaccccg gggctggctc    180

ctccagtgtc ttctcagtcc tgagcaacag tgcagaggtg aaacgggagc gcctggaaga    240

tgtggtggga ggctgttgct atcgggtcaa caacagcttg gaccatgagt accaaccacg    300

gcccgtggag gtgatcacca gttctgcgaa ggagatggtt ggtcagaaga tgaagtacag    360

tattgtgagc aggaactgtg agcactttgt cacccagacc t                        401


<210> SEQ ID NO 197
<211> LENGTH: 471
<212> TYPE: DNA
<213> ORGANISM: Homo sapiens

<400> SEQUENCE: 197

ctgtaatgat gtgagcaggg agccttcctc cctgggccac ctgcagagag ctttcccacc     60

aactttgtac cttgattgcc ttacaaagtt atttgtttac aaacagcgac catataaaag    120

cctcctgccc caaagcttgt gggcacatgg gcacatacag actcacatac agacacacac    180

atatatgtac agacatgtac tctcacacac acaggcacca gcatacacac gtttttctag    240

gtacagctcc caggaacagc taggtgggaa agtcccatca ctgagggagc ctaaccatgt    300

ccctgaacaa aaattgggca ctcatctatt ccttttctct tgtgtcccta ctcattgaaa    360

ccaaactctg gaaaggaccc aatgtaccag tatttatacc tctagtgaag cacagagaga    420

ggaagagagc tgcttaaact cacacaacaa tgaactgcag acacagacct g             471


<210> SEQ ID NO 198
<211> LENGTH: 201
<212> TYPE: DNA
<213> ORGANISM: Homo sapiens

<400> SEQUENCE: 198

ggtccattga ggctctgtcg gccatgccca cagttcgaag ctttgccaac gaggagggcg     60

aagcccagaa gtttagggaa aagctgcaag aaataaagac actcaaccag aaggaggctg    120

tggcctatgc agtcaactcc tggaccacta gtatttcagg tatgctgctg aaagtgggaa    180

tcctctacat tggtgggcag a                                              201


<210> SEQ ID NO 199
<211> LENGTH: 551
<212> TYPE: DNA
```

-continued

<213> ORGANISM: Homo sapiens

<400> SEQUENCE: 199
tctggcacag atcttcaccc acacggcggt ccacgtgctg atcatcttcc gggtctcacc 60
gggcctggaa cacaccatct tccccatgag cccggtgccc agtctggtga cttccatctt 120
ggcccctggc cttatgtccc agttatgacc cctgacttca actctggctc ttaccctgta 180
actccagtcc atctctgaca tttttaacac ccggccttgt gaccgtggac atagctcctg 240
acctcgattc ccatcttgag cccagtgtta gtccatgaga tcatgacctg actcctggtc 300
tccaaccttg tgatcctaat tctgggacct caatcctagc ctctgaactt gggaccctgg 360
agctcctgac cttagtcctg accgctaccc ttgattctga cctttgatcc tgtaacttag 420
gggtggcccc tgaccttatt actgtcattt agctccttga ccttgccact tcaatcctgg 480
ctttatgacc tcctactctc aattttaact ttaaccaaat gaccaaattt gtgacactaa 540
atgaccacaa t 551

<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: 8, 36, 40, 78, 165, 170, 171, 173, 203, 207, 208
<223> OTHER INFORMATION: n = A,T,C or G

<400> SEQUENCE: 200
cagctcancg ggcgacatgc ccctacaagt tggcanaagn ggctgccact gctgggtttg 60
tgtaagagag gctgctgnca ccattacctg cagaaacctt ctcatagggg ctacgatcgg 120
tactgctagg gggcacatag cgcccatggg tgtggtaggt ggggnactcn ntnataggat 180
ggtaggtatc ccgggctgga aanatgnnca g 211

<210> SEQ ID NO 201
<211> LENGTH: 111
<212> TYPE: DNA
<213> ORGANISM: Homo sapiens

<400> SEQUENCE: 201
ccagtgaaag gaaacaaaac tggcagtttg tccatttgaa tatcagacct agtttcttct 60
taatttccac actatttctc ccatattcct taaacttctt ggcatccacc t 111

<210> SEQ ID NO 202
<211> LENGTH: 331
<212> TYPE: DNA
<213> ORGANISM: Homo sapiens

<400> SEQUENCE: 202
tgaaaataca gaataccagg tggtcccaaa tgtttgaagt tctttgaaca gaaagagaga 60
ggagagagag agagaggaaa attccctaac ccttggttta aagacaatat tcatttattg 120
ctcaaatgat gcttttaagg gaggacagtg gaataaaata aacttttttt ttctccctac 180
aatacataga agggttatca aaccactcaa gtttcaaaat ctttccaggg tccaatatca 240 cttttttttct ttcggttcaa tgaaaagcta aatgtaataa tactaattat agataaaatt 300
ttattttact ttttaaaaat ttgtccagac c 331

<210> SEQ ID NO 203
<211> LENGTH: 491

-continued

<212> TYPE: DNA
<213> ORGANISM: Homo sapiens

<400> SEQUENCE: 203
agtcacccag tctacttagt acctggttgc tgcctctgac cttttcagct tgataccctg 60
ggctttagtg taaccaataa atctgtagtg accttacctg tattccctgt gctatcctgt 120
gggaaggtag gaatgggcta agtatgatga atgtataggt tagggatctt ttggttttaa 180
atcacagaaa acctaattca aactggctta aaataaaaag gatttattgg ttcatgtaac 240
tagaaagtcc ataggtagtg ctggctccag gtgaagactt gacccagtag ttcagtatgt 300
ctctaaatac cggactgact tttttctcac tgttgcatct tctgtaggac catttaagtc 360
tgggccactt aatggctgcc agcattccta agattacact tttccccatt tatgtccaat 420
cagaaaaaga aggcatcttt gtaccagaaa tctcagcaaa agccctaata ttcacactga 480
ttaggacctg c 491

<210> SEQ ID NO 204
<211> LENGTH: 361
<212> TYPE: DNA
<213> ORGANISM: Homo sapiens

<400> SEQUENCE: 204
tcccttcctc ccccatgtga taaatgggtc cagggctgat caaagaactc tgactgcaga 60
actgccgctc tcagtggaca gggcatctgt tatcctgaga cctgtggcag acacgtcttg 120
ttttcatttg atttttgtta agagtgcagt attgcagagt ctagaggaat ttttgtttcc 180
ttgattaaca tgattttcct ggttgttaca tccagggcat ggcagtggcc tcagccttaa 240
acttttgttc ctactcccac cctcagcgaa ctgggcagca cggggagggt ttggctaccc 300
ctgcccatcc ctgagccagg taccaccatt gtaaggaaac actttcagaa attcagacct 360
c 361

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: 2, 3
<223> OTHER INFORMATION: n = A,T,C or G

<400> SEQUENCE: 205
cnngtacagt tcttcctgga tggccgacac agatcctggg gaaaggcaat cctggcactg 60
ctctgaaacc agagctcctc ctccctcccc gggcagggtg gagctgagaa gggctgctct 120
agcgttggga ctccacctcc atacacctga tattttgata gggcaggtcc ctgctatggg 180
ccactgttct gggcagtata gtatgcttga cagcatcctt ggcatctatc caccagatcc 240
cagagcaccc gctactagct gtgacaacat cctccaaaca ttgcaaaatt tcccctggga 300
ggcaagattg cctcagatgg gagaatcacg ctctagggaa atctgctggt atgagaaccc 360
caactcccca ctccactgag cctccagatg gcgagcaggc tgcagctcca gcacagacac 420
gaagctccct ccagccactg acggtccatg gctggggtta cccaggacct c 471

<210> SEQ ID NO 206
<211> LENGTH: 261
<212> TYPE: DNA
<213> ORGANISM: Homo sapiens -continued

<400> SEQUENCE: 206
tagagtattt agagtcctga gataacaagg aatccaggca tcctttagac agtcttctgt 60
tgtcctttct tcccaatcag agatttgtgg atgtgtggaa tgacaccacc accagcaatt 120
gtagccttga tgagagaatc caattcttca tctccacgaa tagcaagttg caagtgacga 180
ggggtaatac gctttacctt taagtctttt gatgcatttc ctgccagttc aagtacctct 240
gcggtgaggt actccaggat g 261

<210> SEQ ID NO 207
<211> LENGTH: 361
<212> TYPE: DNA
<213> ORGANISM: Homo sapiens

<400> SEQUENCE: 207
gctctccggg agcttgaaga agaaactggc tacaaagggg acattgccga atgttctcca 60
gcggtctgta tggacccagg cttgtcaaac tgtactatac acatcgtgac agtcaccatt 120
aacggagatg atgccgaaaa cgcaaggccg aagccaaagc caggggatgg agagtttgtg 180
gaagtcattt ctttacccaa gaatgacctg ctgcagagac ttgatgctct ggtagctgaa 240
gaacatctca cagtggacgc cagggtctat tcctacgctc tagcactgaa acatgcaaat 300
gcaaagccat ttgaagtgcc cttcttgaaa ttttaagccc aaatatgaca ctggacctgc 360
c 361

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: 10, 27, 37, 46, 75, 95, 102, 137, 143, 202, 234, 278, 310, 351
<223> OTHER INFORMATION: n = A,T,C or G

<400> SEQUENCE: 208
agaggagatn tttgccatgc ctgaatnctt tcctatncca ccctancact taacatatta 60
cttagtctgc tttgntaaaa gcaagtatta ccttnaactt gnctcttact ctttgccctt 120
tagctaacta ataaagnttg atntaggcat tattatataa ttctgagtca ttcatggtat 180
ctctcatgtt tgatgtattt tncaaactaa gatctatgat agttttttt ccanagttcc 240 attaaatcat ttatttcctt tactttctca cctctgtnga aacatttaga aactggattt 300
gggaacccan ttttggaaaa ccagattcat agtcatgaaa atggaaactt ncatattctg 360
tttttgaaaa gatgtggacc t 381

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: 83
<223> OTHER INFORMATION: n = A,T,C or G

<400> SEQUENCE: 209
gtggagagca agtgatttat taaagcaaga cgttgaaacc tttacattct gcagtgaaga 60
tcagggtgtc attgaaagac agnggaaacc aggatgaaag tttttacatg tcacacacta 120
catttcttca atattttcac caggacttcc gcaatgaggc ttcgtttctg aagggacatc 180

-continued

```
tgatccgtgc atctcttcac tcctaacttg gctgcaacag cttccacctg c            231


<210> SEQ ID NO 210
<211> LENGTH: 371
<212> TYPE: DNA
<213> ORGANISM: Homo sapiens

<400> SEQUENCE: 210

tccatcctgg ttttgcagag atcaggttgt tgacagttcc tggttgaccc acagctaccc     60

atgtcagtta tctccactaa catatccaag aatctttgta ggacaatttc tccacctgca    120

aggtttttta ggtagaactc ttcttttaag gcaattagcc cattgccaaa aggttttact    180

gtcttaaagc tgtctttctg agatctaatt ccaaggactt ctccacagct aagtgagatg    240

cctcacacca ttaggtgatg ctttggacag aacagagtat tttcatcttg tgtttaaagc    300

aattccttgg cttcggctcc tcaccacttt ctatgccagt ctcccattta tgtccctagt    360

aatgcctatg c                                                         371


<210> SEQ ID NO 211
<211> LENGTH: 471
<212> TYPE: DNA
<213> ORGANISM: Homo sapiens

<400> SEQUENCE: 211

tttattttaa aagaaaaaaa ttaaaataga gccaacaaat gcaattaaga aaaaaaaagt     60

attgagacac aaggggacct acatgttctg gtctaagaag catgcaagta ttacaaagca    120

ttccagatac agtatgacag aggaacagtg aacaagcatt ggaacgatgc tctttctttc    180

agaaacggga agtctaacag ttatgttttc acaatggtag tgattaaacc atctttattt    240

ttaaggaatt ttataggaag aattttagca ccatcattaa aggaaaaata ataatacctt    300

tttagccctg cctatctcca gtcttggaat aataacagaa gcatagcacc tttcagtatc    360

taaaatataa acaagaatag taagtccatc ccagcttcta gagatgaggt agctcatgct    420

aagaaatgtt gggtcatttt tcctatgaaa gttcaaaggc caaatggtca c            471


<210> SEQ ID NO 212
<211> LENGTH: 401
<212> TYPE: DNA
<213> ORGANISM: Homo sapiens

<400> SEQUENCE: 212

tggcctgtct ccttcacata gtccatatca ccacaaatca cacaacaaaa gggagaggat     60

atattttggg ttcaaaaaaa gtaaaaagat aatgtagctg catttctttg gttattttgg    120

gccccaaata tttcctcatc tttttgttgt tgtcatggat ggtggtgaca tggacttgtt    180

tatagaggac aggtcagctc tctggctcgg tgatctacat tctgaagttg tctgaaaatg    240

tcttcatgat taaattcagc ctaaacgttt tgccgggaac actgcagaga caatgctgtg    300

agtttccaac ctcagcccat ctgcgggcag agaaggtcta gtttgtccat caccattatg    360

atatcaggac tggttacttg gttaaggagg ggtctacctc g                        401


<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: 239, 290, 358, 359, 391, 393
<223> OTHER INFORMATION: n = A,T,C or G
```

-continued

<400> SEQUENCE: 213
tgtgaagcat acataaataa atgaagtaag ccatactgat ttaatttatt ggatgttatt 60
ttccctaaga cctgaaaatg aacatagtat gctagttatt tttcagtgtt agccttttac 120
tttcctcaca caatttggaa tcatataata taggtacttt gtccctgatt aaataatgtg 180
acggatagaa tgcatcaagt gtttattatg aaaagagtgg aaaagtatat agcttttanc 240
aaaaggtgtt tgcccattct aagaaatgag cgaatatata gaaatagtgn gggcatttct 300
tcctgttagg tggagtgtat gtgttgacat ttctccccat ctcttcccac tctgtttnnt 360
ccccattatt tgaataaagt gactgctgaa nangactttg aatccttatc cacttaattt 420
aatgtttaaa gaaaaaccta taatggaaag tgagactcct t 461

<210> SEQ ID NO 214
<211> LENGTH: 181
<212> TYPE: DNA
<213> ORGANISM: Homo sapiens

<400> SEQUENCE: 214
cctgagcttc tactcctttc ccttaagatt cctccaaagc accagctcca taaaatcctt 60
cagctcccca gacccacacc aagaacccca catgttaatt ggatcagcca aatctacaag 120
cagataagtc ctaaggagaa tgccgaagcg tttttcttct tcctcaagcc tagcatgaga 180
c 181

<210> SEQ ID NO 215
<211> LENGTH: 581
<212> TYPE: DNA
<213> ORGANISM: Homo sapiens

<400> SEQUENCE: 215
ctgctttaag aatggtttc cacctttcc ccctaatctc taccaatcag acacatttta 60
ttatttaaat ctgcacctct ctctatttta tttgccaggg gcacgatgtg acatatctgc 120
agtcccagca cagtgggaca aaaagaattt agaccccaaa agtgtcctcg gcatggatct 180
tgaacagaac cagtatctgt catggaactg aacattcatc gatggtctcc atgtattcat 240
ttattcactt gttcattcaa gtatttattg aatacctgcc tcaagctaga gagaaaagag 300
agtgcgcttt ggaaatttat tccagttttc agcctacagc agattatcag ctcggtgact 360
tttctttctg ccaccattta ggtgatggtg tttgattcag agatggctga atttctattc 420
ttagcttatt gtgactgttt cagatctagt ttgggaacag attagaggcc attgtcctct 480
gtcctgatca ggtggcctgg ctgtttcttt ggatccctct gtcccagagc cacccagaac 540
cctgactctt gagaatcaag aaaacaccca gaaaggacct c 581

<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: 37, 38, 164, 176, 254
<223> OTHER INFORMATION: n = A,T,C or G

<400> SEQUENCE: 216
ccgatgtcct gcttctgtgg accaggggct cctctgnngg tggcctcaac cacggctgag 60
atccctagaa gtccaggagc tgtggggaag agaagcactt agggccagcc agccgggcac 120

-continued

```
ccccacttgc gccccgaccc acgctcacgc accagacctg cccnggcggt cgctcnaaag    180

ggcgaattct gcagatatcc atcacactgg cggacgctcg agcatgcatc tagagggccc    240

aattcaccct atantgagtc gtattacaat tcactggccg t                        281
```

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: 33, 322
<223> OTHER INFORMATION: n = A,T,C or G

<400> SEQUENCE: 217

```
atagcaggtt tcaacaattg tcttgtagtt tgnagtaaaa agacataaga aagagaaggt     60

gtggtttgca gcaatccgta gttggtttct caccataccc tgcagttctg tgagccaaag    120

gtcttgcaga aagttaaaat aaatcacaaa gactgctgtc atatattaat tgcataaaca    180

cctcaacatt gctcagagtt tcatccgttt ggttaagaaa acattccttc aattcatcta    240

tggcatttgt agtggcattg tcgtctatga actcttgaag aagttctttg tattcagtct    300

tagacacttg tggattgatt gncttggaaa tcacattctc caataaggga cctcgg        356
```

<210> SEQ ID NO 218
<211> LENGTH: 321
<212> TYPE: DNA
<213> ORGANISM: Homo sapiens

<400> SEQUENCE: 218

```
ttgtccatcg ggagaaaggt gtttgtcagt tgtttcataa accagattga ggaggacaaa     60

ctgctctgcc aatttctgga tttctttatt ttcagcaaac actttcttta aagcttgact    120

gtgtgggcac tcatccaagt gatgaataat catcaagggt ttgttgcttg tcttggattt    180

atatagagct tcttcatatg tctgagtcca gatgagttgg tcaccccaac ctctggagag    240

ggtctggggc agtttgggtc gagagtcctt tgtgtccttt ttggctccag gtttgactgt    300

ggtatctctg gacctgcctg g                                              321
```

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: 41
<223> OTHER INFORMATION: n = A,T,C or G

<400> SEQUENCE: 219

```
ccggttaggt ccacgcgggg gcagtggagg cacaggctca nggtggccgg gctacctggc     60

accctatggc ttacaaagta gagttggccc agtttccttc cacctgaggg gagcactctg    120

actcctaaca gtcttccttg ccctgccatc atctggggtg gctggctgtc aagaaaggcc    180

gggcatgctt tctaaacaca gccacaggag gcttgtaggg catcttccag gtggggaaac    240

agtcttagat aagtaaggtg acttgtctaa g                                   271
```

<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: 32, 43
<223> OTHER INFORMATION: n = A,T,C or G

<400> SEQUENCE: 220
gtcctacgac gaggaccagc ttttcttctt cnacttttcc canaacactc gggtgcctcg 60
cctgcccgaa tttgctgact gggctcagga acagggagat gctcctgcca ttttatttga 120
caaagagttc tgcgagtgga tgatccagca aatagggcca aaacttgatg ggaaaatccc 180
ggtgtccaga gggtttccta tcgctgaagt gttcacgctg aagcccctgg agtttggcaa 240
gcccaacact ttggtctgtt ttgtcagtaa tctcttccca cccatgctga cagtgaactg 300
gtagcatcat tccgtccctg tggaaggatt tgggcctact tttgtctcag a 351

<210> SEQ ID NO 221
<211> LENGTH: 371
<212> TYPE: DNA
<213> ORGANISM: Homo sapiens

<400> SEQUENCE: 221
gtctgcagaa gcgtgtctga ggtgtccggt ggaggtggca gccgagctct gggactaatc 60
accgtgctgg ggacggcacc gcgtcaggat gcaggcagat ccctgcagaa gtgtctaaaa 120
ttcacactcc tcttctggag ggacgtcgat ggtattagga tagaagcacc aggggacccc 180
acgaacggtg tcgtcgaaac agcagccctt atttgcacac tgggagggcg tgacaccagg 240
aaaaccacaa ttctgtcttt cacgggggc cactgtacac gtctctgtct gggcctcggc 300
cagggtgccg agggccagca tggacaccag gaccagggcg cagatcacct tgttctccat 360
ggtggacctc g 371

<210> SEQ ID NO 222
<211> LENGTH: 471
<212> TYPE: DNA
<213> ORGANISM: Homo sapiens

<400> SEQUENCE: 222
gtccatgttc catcattaat gttccaacat caccagggac acaaagctgc aaaaatgaga 60
agggaaataa ggttagagaa aggatccggg caatcttaag gactgaggaa gacatgttcc 120
ccaacccttg aactcacaaa ccctgaagct caaggattgc atccttcctc caaatctcac 180
tcaacataat aagtgcagaa caacatgcca aagcactgta tgaagcacta gggacaaaga 240
caaggtcaaa atccttgtaa ccaaatttaa tggtattgta atgcagtgtt aacacaggac 300
agtaacagaa cacccaagaa ccaaacagaa gagggtaggg ataagcataa atgaagtaac 360
atgaaataaa cttccaaatg gaaaacttgt ccataccccc agggcaagtc aactacagtc 420
tcccaaagga cataaattcc acttagggca cactagacag aaaacaatat t 471

<210> SEQ ID NO 223
<211> LENGTH: 411
<212> TYPE: DNA
<213> ORGANISM: Homo sapiens

<400> SEQUENCE: 223
agttgctcta caatgacaca caaatcccgt taaataaatt ataaacaagg gtcaattcaa 60
atttgaagta atgttttagt aaggagagat tagaagacaa caggcatagc aaatgacata 120
agctaccgat taactaatcg gaacatgtaa aacagttaca aaaataaacg aactctcctc 180
ttgtcctaca atgaaagccc tcatgtgcag tagagatgca gtttcatcaa agaacaaaca 240

-continued

```
tccttgcaaa tgggtgtgac gcggttccag atgtggattt ggcaaaacct catttaagta    300

aaaggttagc agagcaaagt gcggtgcttt agctgctgct tgtgccgctg tggcgtcggg    360

gaggctcctg cctgagcttc cttccccagc tttgctgcct gagaggaacc a             411
```

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: 31
<223> OTHER INFORMATION: n = A,T,C or G

<400> SEQUENCE: 224

```
ggtctgaagt ttgataacaa agaaatatat ntaagacaaa aatagacaag agttaacaat     60

aaaaacacaa ctatctgttg acataacata tggaaacttt ttgtcagaaa gctacatctt    120

cttaatctga ttgtccaaat cattaaaata tggatgattc agtgccattt tgccagaaat    180

tcgtttggct ggatcataga ttaacatttt cgagagcaaa tccaagccat tttcatccaa    240

gtttttgaca tgggatgcta ggcttcctgg tttccatttg ggaaatgtat tcttatagtc    300

ctgtaaagat tccacttctg g                                              321
```

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: 34
<223> OTHER INFORMATION: n = A,T,C or G

<400> SEQUENCE: 225

```
atgtctgggg aaagagttca ttggcaaaag tgtnctccca agaatggttt acaccaagca     60

gagaggacat gtcactgaat ggggaaaggg aacccccgta tccacagtca ctgtaagcat    120

ccagtaggca ggaagatggc tttgggcagt ggctggatga aagcagattt gagataccca    180

gctccggaac gaggtcatct tctacaggtt cttccttcac tgagacaatg aattcagggt    240

gatcattctc t                                                         251
```

<210> SEQ ID NO 226
<211> LENGTH: 331
<212> TYPE: DNA
<213> ORGANISM: Homo sapiens
<220> FEATURE:
<221> NAME/KEY: misc_feature
<222> LOCATION: 26, 34, 35, 36, 37, 39
<223> OTHER INFORMATION: n = A,T,C or G

<400> SEQUENCE: 226

```
gttaggtccc aggccccccg ccaagnggtt accnnnntna ccactcctga cccaaaaatc     60

aggcatggca ttaaaacgtt gcaaattcct ttactgttat cccccccacc accaggacca    120

tgtagggtgc agtctttact ccctaacccg tttcccgaaa aaggtgctac ctcctttcca    180

gacagatgag agagggcagg acttcaggct ggatccacca ctgggctctc cctcccccag    240

cctggagcac gggaggggag gtgacggctg gtgactgatg gatgggtagt gggctgagaa    300

gaggggacta ggaagggcta ttccaggctc a                                   331
```

<210> SEQ ID NO 227
<211> LENGTH: 391

-continued

<212> TYPE: DNA
<213> ORGANISM: Homo sapiens

<400> SEQUENCE: 227
aggtctgccc ttgaagtata ggaaggaatc atagttggag gacttctgca ttatttgttg 60
gctgaagcta gaagtgcaac cccctcctga tttctgcagc aagatgaact gccttatccc 120
cagcccgcag gaatgttcat atctgagcaa tcaatgggca ctgtgttcaa ccacgccatt 180
ttcaagattg gctccttaaa ccacccacaa ggcaccagct ctgggagaag ctgcagggag 240
aagagaacaa agccctcgct gtgatcagga tgggtgtctc atacctttc tctggggtca 300 ttccaggtat gagacagagt tgaacctgcg catgagcgtg gaggccgaca tcaacggcct 360
gcgcagggtg ctggatgagc tgaccctgga c 391

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 228
gttgtccata gccacctcct gggatagaag ctttntagtt catagttcga ttagtgtgtc 60
cttaggacat aggtccagcc ctacagatta gctgggtgaa gaaggcaagt gtctcgacag 120
ggcttagtct ccaccctcag gcatggaacc attcagggtg aagcctggga tgtgggcaca 180
ggagactcag gctgatataa aaataacaaa atcagtaata aaaaaattat aaaacctgtt 240
gcttgtctga atagatttga gcaacagtct tgcttttgtt aaaatcctgg agccgttaag 300
tcctgaatat tcttctggac atcattgctg gctggagaaa ggagccccag gcccggctcg 360
gctgacatct gtcaggtttg gaagtctcat c 391

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: 202
<223> OTHER INFORMATION: n = A,T,C or G

<400> SEQUENCE: 229
gtccatggct tctcacccag acagtctttc tgggcaactt ggggaagccc ctgttctgct 60
caagtctcac cccatggaag aggtggggga agggggcctt ggtttttcag gaagacgggt 120
tggagagcac gagtcactac aaagcagtaa aagtgaatgg tgtctccagg ggctgggtcc 180
agaacaccgc ggagagcccc anccataaag gtgtgttccg cctctggcct gcaggaatct 240
ctttgaatct ctttgattgg tggctccaag agcaatggga agtcaacagc caggaggctg 300
gactgggttc cctgggaccc cgaggtccca gaggctgctg g 341

<210> SEQ ID NO 230
<211> LENGTH: 511
<212> TYPE: DNA
<213> ORGANISM: Homo sapiens

<400> SEQUENCE: 230
gtccaagcca aggaaaccat tcccttacag gagacctccc tgtacacaca ggaccgcctg 60

-continued gggctaaagg aaatggacaa tgcaggacag ctagtgtttc tggctacaga aggggaccat 120
cttcagttgt ctgaagaatg gttttatgcc cacatcatac cattccttgg atgaaacccg 180
tatagttcac aatagagctc agggagcccc taactcttcc aaaccacatg ggagacagtt 240
tccttcatgc ccaagcctga gctcagatcc agcttgcaac taatccttct atcatctaac 300
atgccctact tggaaagatc taagatctga atcttatcct ttgccatctt ctgttaccat 360
atggtgttga atgcaagttt aattaccatg gagattgttt tacaaacttt tgatgtggtc 420
aagttcagtt ttagaaaagg gagtctgttc cagatcagtg ccagaactgt gcccaggccc 480
aaaggagaca actaactaaa gtagtgagat a 511

<210> SEQ ID NO 231
<211> LENGTH: 311
<212> TYPE: DNA
<213> ORGANISM: Homo sapiens

<400> SEQUENCE: 231
ggtccaagta agctgtgggc aggcaagccc ttcggtcacc tgttggctac acagacccct 60
cccctcgtgt cagctcaggc agctcgaggc ccccgaccaa cacttgcagg ggtccctgct 120
agttagcgcc ccaccgccgt ggagttcgta ccgcttcctt agaacttcta cagaagccaa 180
gctccctgga gccctgttgg cagctctagc tttgcagtcg tgtaattggc ccaagtcatt 240
gtttttctcg cctcactttc caccaagtgt ctagagtcat gtgagcctcg tgtcatctcc 300
ggggtggacc t 311

<210> SEQ ID NO 232
<211> LENGTH: 351
<212> TYPE: DNA
<213> ORGANISM: Homo sapiens

<400> SEQUENCE: 232
tcgtttagct aataatccct tccttgatga tacactccaa cttcttgttt ttctttattt 60
ctaaaaagcg gttctgtaac tctcaatcca gagatgttaa aaatgtttct aggcacggta 120
ttagtaaatc aagtaaattt catgtcctct taaaggacaa acttccagag atttgaatat 180
aaatttttat atgtgttatt gattgtcgtg taacaaatgg cccccacaaa ttagtagctt 240
aaaatagcat ttatgatgtc actgttttct ttgccttttc attaatgttc tgtacagacc 300
tatgtaaaca acttttgtat atgcatatag gatagctttt ttgagggtat a 351

<210> SEQ ID NO 233
<211> LENGTH: 511
<212> TYPE: DNA
<213> ORGANISM: Homo sapiens

<400> SEQUENCE: 233
aggtctggat gtaaggatgg atgctctcta tacatgctgg gttggggatg ctgggactgc 60
acagccaccc ccagtatgcc gctccaggac tctgggacta gggcgccaaa gtgtgcaaat 120
gaaaatacag gatacccagg gaactttgaa tttcagattg tgaaaagaaa acaaatcttg 180
agactccaca atcaccaagc taaaggaaaa agtcaagctg ggaactgctt agggcaaagc 240
tgcctcccat tctattcaca gtcatccccc tgaggctcac ctgcatagct gattgcttcc 300
tttcccctat cgcttctgta aaaatgcaga ctcactgagc cagactaaat tgtgtgttca 360
gtggaaggct gatcaagaac tcaaaagaat gcaacctttt gtctcttatc tactacaacc 420
aggaagcccc cacttaaggg ttgtcccacc ttactggact gaaccaaggt acatcttaca 480

-continued

```
cctactgatt gatgtctcat gtccccctaa g                              511


<210> SEQ ID NO 234
<211> LENGTH: 221
<212> TYPE: DNA
<213> ORGANISM: Homo sapiens

<400> SEQUENCE: 234

caggtccagc gaaggggctt cataggctac accaagcatg tccacataac cgaggaagct    60

ctctccatca gcatagcctc cgatgaccat ggtgttccac aaagggttca tcttcgagcg   120

ccggctgtac atggccctgg tcagccatga atgaatagct ctaggactat agctgtgtcc   180

atctcccaga agctcctcat caatcaccat ctggccgaga c                       221


<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: 33
<223> OTHER INFORMATION: n = A,T,C or G

<400> SEQUENCE: 235

ggtccaagaa agggacatct atgtgaaagt ganactgaga cagtgctggt cacaggtcat    60

gctgcagaat aatacattcc caggcactgt cacgtggggg acccaagagg ccccaggagt   120

gacctataac ctctccagaa agaccactct gtgtggcatc acagtccaca cagtttaagg   180

aaatatttag acttaacaat cagacaccag ctcttactca cacttacact cacagcccac   240

acacaagtgt gcaaacatac acacacatat atatttcctg atacattcat ggaatatcag   300

agccctgccc tgaagtcgtt agtgtctctg ctccccaaac cgctgctccc acattggcta   360

agctccctca agagacctca g                                             381


<210> SEQ ID NO 236
<211> LENGTH: 441
<212> TYPE: DNA
<213> ORGANISM: Homo sapiens

<400> SEQUENCE: 236

aggtcctgtt gccccttctt tttgcccaac ttcgccattt gggaattgga atatttaccc    60

aacacctgta ctgcattgaa tattggaagc aaataacttg gctttgatct tataggctca   120

cagatggagg aacgtacctt gaagttcaga tgagatttcg gacttttgag ttgatgctga   180

aacagcttga gatttttggg gactactgag agatgataat tgtattgtgc aatatgagaa   240

ggacatgaga tttggtgggc ataggtgtga aatgacattg tttggatgtg tttaccctcc   300

aaatctcttg ttgaatgtga tcttaaacgt tggtggtggg cctagtggaa ggtgttgaat   360

catgggggtg gactcttcat aatttgctta gctccatccc cttggtgatg agcaagtcct   420

tgctctgttg tgtcacatga g                                             441


<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: 81, 90, 194, 209, 210, 211, 219, 233
<223> OTHER INFORMATION: n = A,T,C or G
```

-continued

<400> SEQUENCE: 237

```
tcctaaaaaa ttagctgacc ttgttaaaaa tgttggcgtg agcagtatat tattacctat     60
cttttttat tgtgtgtgtg ngtgtgtgtn ttaaactaat tggctgaaat atctgcctgt    120
ttccctcttt acatttttct tgtttctttc cttatttatc tttgtccatc ttgagatcta    180
ctgtaaagtg aatnttttaa tgaaaacann nccaagttnt actctcactg ggnttgggac    240
atcagatgta attgagaggc caacaggtaa gtcttcatgt c                        281
```

<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: 30, 85
<223> OTHER INFORMATION: n = A,T,C or G

<400> SEQUENCE: 238

```
gtctgcctcc tcctactgtt tccctctatn aaaaagcctc cttggcgcag gttccctgag     60
ctgtgggatt ctgcactggt gcttnggatt ccctgatatg ttccttcaaa tccactgaga    120
attaaataaa catcgctaaa g                                              141
```

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: 29, 30, 65, 86, 471, 489
<223> OTHER INFORMATION: n = A,T,C or G

<400> SEQUENCE: 239

```
aacaatctaa acaaatccct cggttctann atacaatgga ttccccatat tggaaggact     60
ctgangcttt attcccccac tatgcntatc ttatcatttt attattatac acacatccat    120
cctaaactat actaaagccc ttttcccatg catggatgga aatggaagat ttttttttaa    180
cttgttctag aagtcttaat atgggctgtt gccatgaagg cttgcagaat tgagtccatt    240
ttctagctgc ctttattcac atagtgatgg ggtactaaaa gtactgggtt gactcagaga    300
gtcgctgtca ttctgtcatt gctgctactc taacactgag caacactctc ccagtggcag    360
atcccctgta tcattccaag aggagcattc atccctttgc tctaatgatc aggaatgatg    420
cttattagaa aacaaactgc ttgacccagg aacaagtggc ttagcttaag naaacttggc    480
tttgctcana tccctgatcc t                                              501
```

<210> SEQ ID NO 240
<211> LENGTH: 451
<212> TYPE: DNA
<213> ORGANISM: Homo sapiens

<400> SEQUENCE: 240

```
tgtcctgaaa ggccattact aatagaaaca cagcctttcc aatcctctgg aacatattct     60
gtctgggttt ttaatgtctg tggaaaaaaa ctaaacaagt ctctgtctca gttaagagaa    120
atctattggt ctgaaggttt ctgaacctct ttctggttct cagcagaagt aactgaagta    180
gatcaggaag gggctgcctc aggaaaattc ctagatccta ggaattcagt gagaccctgg    240
gaaggaccag catgctaatc agtgtcagtg aatccacagt ctttacttcc tgcctcataa    300
agggccaggt ctccccagta ccaagtcctt tcctcatgaa gttgtgttgc ctcaggctgt    360
```

-continued

```
ttagggacca ttgcctgtct tggtcacatg agtctgtctc cttactttag tccctgggca    420

atccttgctt aatgcttttg ttgactcaac g                                    451
```

```
<210> SEQ ID NO 241
<211> LENGTH: 411
<212> TYPE: DNA
<213> ORGANISM: Homo sapiens
<220> FEATURE:
<221> NAME/KEY: misc_feature
<222> LOCATION: 62, 82, 364, 370, 385
<223> OTHER INFORMATION: n = A,T,C or G

<400> SEQUENCE: 241

aatctccagt gtgatggtat cggggttaga gcttcaatct ccagtgtgat ggtactgcag     60

cnagagcttc aatctccagt gngatggtat tagggttaga tcttcaatct ccagtgtgat    120

ggtatcaggg ttagagcttc agcctccagt gtgatggtat cagggttaga gcttcagcct    180

ccagtgtgat ggtatcgggg ttagatcttc aatccccagt ggtggtggtt agagcttcaa    240

tctccagtgt gatggtattg gggttagagc ttcaatctcc agtctgatgg tgtttcggga    300

tggggctttt aagatgtaat tagggtttaa gatcataagg gacctggtct gatggggatt    360

agtncgcttn tatgaagaga cacangaggg cttgctctat ctctgactct c             411
```

```
<210> SEQ ID NO 242
<211> LENGTH: 351
<212> TYPE: DNA
<213> ORGANISM: Homo sapiens

<400> SEQUENCE: 242

ttccccttca caacagtaga gacctacaca gtgaactttg gggacttctg agatcagcgt     60

cctaccaaga ccccagccca actcaagcta cagcagcagc acttcccaag cctgctgacc    120

acagtcacat cacccatcag cacatggaag gcccctggta tggacactga aaggaagggc    180

tggtcctgcc cctttgaggg ggtgcaaaca tgactgggac ctaagagcca gaggctgtgt    240

agaggctcct gctccacctg ccagtctcgt aagaaatggg gttgctgcag tgttggagta    300

ggggcagagg gagggagcca aggtcactcc aataaaacaa gctcatggca c             351
```

```
<210> SEQ ID NO 243
<211> LENGTH: 241
<212> TYPE: DNA
<213> ORGANISM: Homo sapiens

<400> SEQUENCE: 243

gtctgtgctt tatcaggaaa agcacaagaa tatgtttttc tacctaaaac cctcttctac     60

tttaaaaatg gtttgctgaa tttttctatg tttttaaaat gtttttatgc tttttttaa    120

acacgtaaag gatggaacct aatcctctcc cgagacgcct cctttgtgtt aatgcctatt    180

cttacaacag agaaacaagt acattaatat aaaaacgagt tgattattgg ggtataaaat    240

a                                                                    241
```

```
<210> SEQ ID NO 244
<211> LENGTH: 301
<212> TYPE: DNA
<213> ORGANISM: Homo sapiens

<400> SEQUENCE: 244

ggtccagagc aatagcgtct gtggtgaagc gcctgcactc ctcgggagac atgcctggct     60
```

-continued

```
tatatgctgc atccacataa ccatagataa aggtgctgcc ggagccacca atggcaaaag    120

gctgtcgagt cagcattcct cccagggttc catatacctg acctccttca cgttggtccc    180

agccagctac catgagatgt gcagacaagt cctctcgata tttatagctg atatttctca    240

ccacatttgc agcagccaaa acaagtggag gttcctccag ttctatccca tggagctcca    300

g                                                                    301
```

<210> SEQ ID NO 245
<211> LENGTH: 391
<212> TYPE: DNA
<213> ORGANISM: Homo sapiens

<400> SEQUENCE: 245

```
ctgacactgc tgatgtgggc cggggggcgc cgaggcacaa ctggtggccg gaccattgag     60

gcacctggag ggtaggcagc ttgtggtgca gacaccacag agagagaaaa gttggatgga    120

gtggtgggaa taatcagggt ggcacactgt gcctagaagc ttccagggcc accaagagaa    180

tgggaaggga aactacaaca ttcacaacag aaataggagt caattcactt agacccagaa    240

ctccagaaag ggggagtgta ggaatctaca atttcaaagc cagctcgtgt ctacctagag    300

ccccaaactg cataagcacc aggattgtac accttagtcc ctcaagatag tttcaagtga    360

gcgtgcaatt cactcttaca gaggagggcc t                                   391
```

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: 26, 80, 82, 185, 255, 259
<223> OTHER INFORMATION: n = A,T,C or G

<400> SEQUENCE: 246

```
tcctccacag gggaagcagg aagttngacc agcttcaggc tggaacgtgc ccagggcaca     60

gagctggcaa ggtgcaaagn cntctgcaga atattcacca ggttgacaca gacctccaca    120

ttcagacata ttccaagctt ctggggtctt cagggcccca gaatttcctg gtcttgggca    180

tggtncacaa gtcatttgtc cttcctcatt ttggaaggtt ccatttggac ataaaatgca    240

agcgttctcg tgctncatna taataggtcc cagcctgcac tgacacattt g             291
```

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: 80, 110, 125, 245, 249, 279, 318, 336, 339, 455, 471
<223> OTHER INFORMATION: n = A,T,C or G

<400> SEQUENCE: 247

```
cactgagtga atgagtatat aatttatgaa aacagaaaag tgctttggaa aaaaaaaaag     60

acaacaggag tacatacagn gaaccaaaaa gagtgtacca ggaggagcan accctgaaca    120

gttanaacta tggaaatcgc tatgctttgt gttgtcacag gagttaaaat aggaataccc    180

tgcatacaat aaatatttat tggataaata actaagcctg atacccttt caatgcgtta    240

tacanactnt atcatcacac cactaatcta agttctcana agttaaacat tacaagactt    300

cagaacaaca taggcgtntt tggctccatt taacanaana aggaccatag tgatcattta    360

atctctatga gtctgtctta tcttctggaa aaggggccta acaccatttc cttttgcaaa    420
```

-continued aaggtagctg ccttgcttcc agttctacca tcctntagca acccatcttt n 471

<210> SEQ ID NO 248
<211> LENGTH: 551
<212> TYPE: DNA
<213> ORGANISM: Homo sapiens

<400> SEQUENCE: 248
ccatgggatc aggaatgggg tcaggtcagt tgacctgagc atacccatta aacatgttca 60
aatgtcccca tcccacccac tcacatgaca tggctcccga gccctgagat ctgtatccca 120
agaacctcag ttgagaaata tttatggcag cttcactgtt gctcaagagc ctgggtattg 180
tagcagcctg ggggcaggtt gtccctaatg ttctccaagt tcttcacatc agccagaatc 240
ccatctatgc ttgtctccag caaatggagg tggcccctct gctgacgtgc cctctcttcc 300
agctctgaca tcatgggccg cagttggctg ttgatctggg tcttggctcg ggaaagcttc 360
tgctccagta agaccagccc ctcttcatct acactgagag gctggtccat cagatgcagg 420
aggccgtcta atgtgttgag tgtgtcttgg attgtaaccc cagcgttctt ggctctggta 480
tcaaccttct gggcttctgt aatcaccatc tgtactgcat ccatattcgt gtcgaactcc 540
agctccttcc t 551

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: 3, 96
<223> OTHER INFORMATION: n = A,T,C or G

<400> SEQUENCE: 249
atntccagag ggaccgtaag actggtacaa gtttacacca taagaggcga cgtggtcagc 60
cacaatgtct tcacctccac aggggctcat cacggnggtc agggcaaggg cccccagcat 120
cagagctttg tttaggatca tcctcttccc aaggcagcct tagcagttgc tgacctgccc 180
g 181

<210> SEQ ID NO 250
<211> LENGTH: 551
<212> TYPE: DNA
<213> ORGANISM: Homo sapiens

<400> SEQUENCE: 250
tctgtagcta ggatgagctg gctctcaagc aaaagtttgt cttcctgggt ccatttgtgg 60
ttatcacttg ttattgaatg tacatcacaa attaaagtct gcattgttgg acgtaagaga 120
atgtgccgac tttggtaacc aggagatttc atgttactgg actgcctgta gtcacgtatt 180
tctgctatga cacatccgca atgaaaaata ttaacctgag atttttctag gagatcaacc 240
aaaataggag gtaattcttc tgcatccaaa tattcaagca actctccttc ttcatagggc 300
agtcgaatgg tctcggaatc tgatccgttt tttcccctga gcatcagaga atatccctca 360
tttcctgggt atagattgac cactaaacat gacaaagtct cttgcataac aagcttctct 420
aacaagttca catttcttct taatttctta acttcaggtt ctttttcaca ttcttcaata 480
tacaagtcat aaagtttttg aaatacagat tttcttccac ttgataggta tttcctttta 540
ggaggtctct g 551

-continued

<210> SEQ ID NO 251
<211> LENGTH: 441
<212> TYPE: DNA
<213> ORGANISM: Homo sapiens

<400> SEQUENCE: 251
tgtctgctct cccatcctgg ttactatgag tcgctcttgg cagaaaggac cacagatgga 60
gagcttggca ctcgctccaa ctttgccgaa aagaggacaa ccaccaaagt agtaggtaaa 120
aacacaattt tagcagcagt gaaataaaaa gaggaagtga ggatggggcc aggccgcaac 180
tataattaaa ctgtctgttt aggagaagct gaatccagaa gaaacacaag ctgtaaagtg 240
agagaggaca gggagcaggg cctttggaga gcaggagagg acaggctgtc accaagcgct 300
gctcggactc tgccctgaaa gatttgaatt ggacactgtc cagtcacgtg tgtggcaaac 360
cgtactccaa gcacttttct cacggcagag gaaggagctg ccatggctgt acccctgaac 420
gtttgtgggg ccagcgatgt g 441

<210> SEQ ID NO 252
<211> LENGTH: 406
<212> TYPE: DNA
<213> ORGANISM: Homo sapiens

<400> SEQUENCE: 252
tttttttttg aacaagtaaa aatttcttta tttgctgaca ataagataac ctacagggaa 60
aacctgatga aatctattaa aaagttacta aaactaataa aagaatttag gaaggttata 120
gaatgtaaga ccaagacaca aaaatcaatt acatttctat ataatagcaa tgaacagata 180
ctgaaatttt aaaaactaaa tcattttaca aaagtatcac aatatgaaac actccgggat 240
aaattggata aaagatgtgc aagactgtac aaaagctaca aaacatttat gaaggaaatt 300
ggaagataga aacaagatag aaaatgaaaa tattgtcaag agtttcagat agaaaatgaa 360
aaacaagcta agacaagtat tggagaagta tagaagatag aaaaat 406

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: 224
<223> OTHER INFORMATION: n = A,T,C or G

<400> SEQUENCE: 253
gaaggagttc agtagcaaag tcacacctgt ccaattccct gagctttgct cactcagcta 60
atgggatggc aaaggtggtg gtgctttcat cttcaggcag aagcctctgc ccatccccct 120
caagggctgc aggcccagtt ctcatgctgc ccttgggtgg gcatctgtta acagaggaga 180
acgtctgggt ggcggcagca gctttgctct gagtgcctac aaanctaatg cttggtgcta 240
gaaacatcat cattattaaa cttcagaaaa gcagcagcca tgttcagtca ggctcatgct 300
gcctcactgc ttaagtgcct gcaggagccg cctgccaagc tccccttcct acacctggca 360
cactggggtc tgcacaaggc tttgtcaacc aaagacagct tccccctttt gattgcctgt 420
agactttgga gccaagaaac actctgtgtg actctacaca cacttcaggt ggtttgtgct 480
tcaaagtcat tgatgcaact tgaaaggaaa cagtttaatg gtggaaatga actaccattt 540
ataa 544

-continued

<210> SEQ ID NO 254
<211> LENGTH: 339
<212> TYPE: DNA
<213> ORGANISM: Homo sapiens

<400> SEQUENCE: 254
tggcattcag ggcagtgtct tctgcatctc ctaggaacct cgggagcggc agctccggcg 60
cctggtagcg agaggcgggt tccggagatc ccggcctcac ttcgtcccac tgtggttagg 120
ggtgagtcct gcaaatgtta agtgatttgc tcaaggtgcc catttcgcag gaattggagc 180
ccaggccagt tctctgagcc tatcattagg gctaaaggag tgcgtgatca gaatggtgtc 240
tggacggttc tacttgtcct gcctgctgct ggggtccctg ggctctatgt gcatcctctt 300
cactatctac tggatgcagt actggcgtgg tggctttgc 339

<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: 11, 39, 70, 87, 103, 120, 177, 181, 220, 229, 233, 341, 345, 366, 380, 402
<223> OTHER INFORMATION: n = A,T,C or G

<400> SEQUENCE: 255
gaggtttttt nttttttttt tttttttttt caattaaana tttgatttat tcaagtatgt 60
gaaaacattn tacaatggaa acttttntta aatgctgcat gtnctgtgct atggaccacn 120
cacatacagc catgctgttt caaaaaaactt gaaatgccat tgatagttta aaaactntac 180
ncccgatgga aaatcgagga aaacaattta atgtttcatn tgaatccana ggngcatcaa 240
attaaatgac agctccactt ggcaaataat agctgttact tgatggtatc caaaaaaaaa 300
tggttgggga tggataaatt caaaaatgct tccccaaagg ngggnggttt ttaaaaagtt 360
tcaggncaca acccttgcan aaaacactga tgcccaacac antga 405

<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: 6
<223> OTHER INFORMATION: n = A,T,C or G

<400> SEQUENCE: 256
gggcangtct ggtcctctcc ccacatgtca cactctcctc agcctctccc ccaaccctgc 60
tctccctcct cccctgccct agcccaggga cagagtctag gaggagcctg gggcagagct 120
ggaggcagga agagagcact ggacagacag ctatggtttg gattggggaa gaggttagga 180
agtaggttct taaagaccct tttttagta 209

<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: 306, 311, 343
<223> OTHER INFORMATION: n = A,T,C or G

<400> SEQUENCE: 257
tctggacacc ataatccctt ttaagtggct ggatggtcac acctctccca ttgacaagct 60

-continued

```
gggttaagtc aataggttga ctaggatcaa cacgacccaa atcaataaga tactgcagtc    120
tattgagact caaaggctta tactggcgtc tgaaactatg tccttcgtta aacccgtatt    180
ttgggattcg gatgtaaaat ggagtctggc ctccctcaaa gcccaagcgg ggccgggttc    240
ctctttgcct ttctccttta tggcctctgc cacattttct acctcttctc cgacctcttg    300
gtcttntctc nggtttcttg gagccgggat tcggctttaa gtn                      343
```

<210> SEQ ID NO 258
<211> LENGTH: 519
<212> TYPE: DNA
<213> ORGANISM: Homo sapiens

<400> SEQUENCE: 258

```
gcggcttctg acttctagaa gactaaggct ggtctgtgtt tgcttgtttg cccacctttg     60
gctgataccc agagaacctg ggcacttgct gcctgatgcc cacccctgcc agtcattcct    120
ccattcaccc agcgggaggt gggatgtgag acagcccaca ttggaaaatc cagaaaaccg    180
ggaacaggga tttgcccttc acaattctac tccccagatc ctctcccctg gacacaggag    240
acccacaggg caggacccta agatctgggg aaaggaggtc ctgagaacct tgaggtaccc    300
ttagatcctt ttctacccac tttcctatgg aggattccaa gtcaccactt ctctcaccgg    360
cttctaccag ggtccaggac taaggcgttt tctccatagc ctcaacattt tgggaatctt    420
cccttaatca cccttgctcc tcctgggtgc ctggaagatg gactggcaga gacctctttg    480
ttgcgttttg tgctttgatg ccaggaatgc cgcctagtt                           519
```

<210> SEQ ID NO 259
<211> LENGTH: 371
<212> TYPE: DNA
<213> ORGANISM: Homo sapiens

<400> SEQUENCE: 259

```
attgtcaact atatacacag tagtgaggaa taaaatgcac acaaaacaat ggatagaata     60
tgaaaatgtc ttctaaatat gaccagtcta gcatagaacc ttcttctctt ccttctcagg    120
tcttccagct ccatgtcatc taacccactt aacaaacgtg gacgtatcgc ttccagaggc    180
cgtcttaaca actccatttc caaaagtcat ctccagaaga catgtatttt ctatgatttc    240
ttttaaacaa atgagaattt acaagatgtg taactttcta actctatttt atcatacgtc    300
ggcaacctct ttccatctag aagggctaga tgtgacaaat gttttctatt aaaaggttgg    360
ggtggagttg a                                                         371
```

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: 57, 189, 208, 256, 426
<223> OTHER INFORMATION: n = A,T,C or G

<400> SEQUENCE: 260

```
ttggattttt tgacttgcga tttcagtttt tttacttttt tttttttttt ttttganaaa     60
tactatattt attgtcaaag agtggtacat aggtgagtgt tcatcttccc tctcatgccg    120
gtatactctg cttcgctgtt tcagtaaaag ttttccgtag ttctgaacgt cccttgacca    180
caccataana caagcgcaag tcactcanaa ttgccactgg aaaactggct caactatcat    240
```

-continued ttgaggaaag actganaaag cctatcccaa agtaatggac atgcaccaac atcgcggtac 300
ctacatgttc ccgtttttct gccaatctac ctgtgtttcc aagataaatt accacccagg 360
gagtcacttc ctgctatgtg aacaaaaacc cggtttcttt ctggaggtgc ttgactactc 420 tctcgngagc 430

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: 178
<223> OTHER INFORMATION: n = A,T,C or G

<400> SEQUENCE: 261
tcctgacgat agccatggct gtaccactta actatgattc tattccaact gttcagaatc 60
atatcacaaa atgacttgta cacagtagtt tacaacgact cccaagagag gaaaaaaaaa 120
aaaaaagacg cctcaaaatt cactcaactt ttgagacagc aatggcaata ggcagcanag 180
aagctatgct gcaactgagg gcacatatca ttgaagatgt cacaggagtt taagagacag 240
gctggaaaaa atctcatact aagcaaacag tagtatctca taccaagcaa aaccaagtag 300
tatctgctca gcctgccgct aacagatctc acaatcacca actgtgcttt aggactgtca 360
ccaaa 365

<210> SEQ ID NO 262
<211> LENGTH: 500
<212> TYPE: DNA
<213> ORGANISM: Homo sapiens

<400> SEQUENCE: 262
cctagatgtc atttgggacc cttcacaacc attttgaagc cctgtttgag tccctgggat 60
atgtgagctg tttctatgca taatggatat tcggggttaa caacagtccc ctgcttggct 120
tctattctga atccttttct ttcaccatgg ggtgcctgaa gggtggctga tgcatatggt 180
acaatggcac ccagtgtaaa gcagctacaa ttaggagtgg atgtgttctg tagcatccta 240
tttaaataag cctattttat cctttggccc gtcaactctg ttatctgctg cttgtactgg 300
tgcctgtact tttctgactc tcattgacca tattccacga ccatggttgt catccattac 360
ttgatcctac tttacatgtc tagtctgtgt ggttggtggt gaataggctt ctttttacat 420
ggtgctgcca gcccagctaa ttaatggtgc acgtggactt ttagcaagcg ggctcactgg 480
aagagactga acctggcatg 500

<210> SEQ ID NO 263
<211> LENGTH: 413
<212> TYPE: DNA
<213> ORGANISM: Homo sapiens

<400> SEQUENCE: 263
ctcagagagg ttgaaagatt tgcctacgaa agggacagtg atgaagctaa gctctagatc 60
caggatgtct gacttcaaat tgaaactccc aaagtaatga gtttggaagg gtggggtgtg 120
gcctttccag gatgggggtc ttttctgctc ccagcggata gtgaaacccc tgtctgcacc 180
tggttgggcg tgttgctttc ccaaaggttt tttttttagg tccgtcgctg tcttgtggat 240
taggcattat tatctttact ttgtctccaa ataacctgga gaatggagag agtagtgacc 300
agctcagggc cacagtgcga tgaggaccat cttctcacct ctctaaatgc aggaagaaac 360

-continued

```
gcagagtaac gtggaagtgg tccacaccta ccgccagcac attgtgaatg aca          413


<210> SEQ ID NO 264
<211> LENGTH: 524
<212> TYPE: DNA
<213> ORGANISM: Homo sapiens

<400> SEQUENCE: 264

tccaatgggg ccctgagagc tgtgacagga actcacactc tggcactggc agcaaaacac     60

cattccaccc cactcatcgt ctgtgcacct atgttcaaac tttctccaca gttccccaat    120

gaagaagact catttcataa gtttgtggct cctgaagaag tcctgccatt cacagaaggg    180

gacattctgg agaaggtcag cgtgcattgc cctgtgtttg actacgttcc cccagagctc    240

attaccctct ttatctccaa cattggtggg aatgcacctt cctacatcta ccgcctgatg    300

agtgaactct accatcctga tgatcatgtt ttatgaccga ccacacgtgt cctaagcaga    360

ttgcttaggc agatacagaa tgaagaggag acttgagtgt tgctgctgaa gcacatcctt    420

gcaatgtggg agtgcacagg agtccaccta aaaaaaaaaa tccttgatac tgttgcctgc    480

ctttttagtc accccgtaac aagggcacac atccaggact gtgt                     524


<210> SEQ ID NO 265
<211> LENGTH: 344
<212> TYPE: DNA
<213> ORGANISM: Homo sapiens

<400> SEQUENCE: 265

tcctttcttc tacttcagga gatgattcaa agttacttgt ggacatttct ttaagttctg     60

aagacaaatg agacaggatt tggcctgcgg gttcttcaga cttctctacc acctccatta    120

actcttcatc ttggcttgac gtaggcaatg cactattttg ctcttttgtt tctggagatg    180

acccagcacc acttctttct cttggcgggg ttctaagtgt gtctttgaat accagtgaag    240

actcaggcct atcctgtact ggaaagggac taaatttgtc tttctgtcta ggaggtgatg    300

cagtagcatc ctcctgaggg ggtaaggcca ttttctcttt ttga                     344


<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: 78
<223> OTHER INFORMATION: n = A,T,C or G

<400> SEQUENCE: 266

ccacaatgtc cataacttga gcaggctttg gcatcccacc acccccttca gaccaataca     60

cactatgttg gaggaacnac tttaaaatgt aaaatgagaa atgggcactg aacactccat    120

cctcactccc aacagcccac ccacacacct cttcaactgc tatccaaaca tggaggagct    180

cttgtggaag agaggctcaa caccaaataa                                     210


<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: 5, 19, 31
<223> OTHER INFORMATION: n = A,T,C or G
```

-continued

<400> SEQUENCE: 267
tcggncctcc caccctctna ctgaaattct ntgaaattct cccctttggg atgaggatgg 60
caaccccagg catgtaccct cccaacctgg gacccgacct aataccctaa catcctgctg 120
acagtggctg ttctcgctgg gcaggcgtcc caaagcacat cgagccagat tcaggcagag 180
tggaactggc ccctcagcca tcagtggagg tggcctggga ggctctaccc tgaacggg 238

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: 459
<223> OTHER INFORMATION: n = A,T,C or G

<400> SEQUENCE: 268
tcctcaagga catgcccctt gatagaaact cagttcctgt ctccagttcc ctcctggacc 60 tgatcccccca aatgcagggc ctgggactat atccagttcc ttattttcag aggcccatgc 120
acaagatgca cagcaaataa gtgctgaata aagacccagc tactgctagc ttaccctgct 180
ccaaacattc accaagtcct cagcaaagag ggccatccat tcacctcttc taaaaacaca 240
ctgagctccc cagtctatac cccaagatat gcttggctcc caactatccc tcctctctca 300
tctccaagcc agtttcccct ttctaagtat actgatatta ccaaagacac tgacaatctt 360
cttttcctac ctctccccag tgactaggtt tgcagcagga gctctataag tcctagtata 420
cagcagaagc tccataaatg tgtgctgacc taacattang c 461

<210> SEQ ID NO 269
<211> LENGTH: 434
<212> TYPE: DNA
<213> ORGANISM: Homo sapiens

<400> SEQUENCE: 269
ctgtgttggt gagcaccgat tcccactcaa tatggcgtgg cttacagtct tcattaggtt 60
cccgctccca accagaatga ggaatgatca cttcatctgt caaggcatgc agtgcatggt 120
ccacaatctc cattttgatt gagtcatggg atgaaagatt ccacagggtt ccggtaataa 180
cttcagtaag gtccatatca cgagcctttc gaagcaatcg cacaagggca ggcacaccat 240
cacagttttt tatggcaatc ttgttatcct ggtcacgtcc aaaagagata ttcttgagag 300
ctccacaggc tccaaggtgc acttcctttt tgggatggtc taacaatccc accagtactg 360
ggatgccctt gagcttccgc acgtcagtct tcaccttgtc attgcggtag cataagtgtt 420
gcaggtatgc aaga 434

<210> SEQ ID NO 270
<211> LENGTH: 156
<212> TYPE: DNA
<213> ORGANISM: Homo sapiens

<400> SEQUENCE: 270
ctgcaccagc gattaccagt ggcattcaaa tactgtgtga ctaaggattt tgtatgctcc 60
ccagtagaac cagaatcaga caggtatgag ctagtcaaca gcaagtcttt gttggattcg 120
agtaggctca ggatctgctg aaggtcggag gagtta 156

<210> SEQ ID NO 271
<211> LENGTH: 533

-continued

<212> TYPE: DNA
<213> ORGANISM: Homo sapiens
<220> FEATURE:
<221> NAME/KEY: misc_feature
<222> LOCATION: 100, 137, 383, 385, 411
<223> OTHER INFORMATION: n = A,T,C or G

<400> SEQUENCE: 271
ccactgtcac ggtctgtctg acacttactg ccaaacgcat ggcaaggaaa aactgcttag 60
tgaagaactt agaagctgtg gagaccttgg ggtccacgtn caccatctgc tctgataaaa 120
ctggaactct gactcanaac cggatgacag tggcccacat gtggtttgac aatcaaatcc 180
atgaagctga tacgacagag aatcagagtg gtgtctcttt tgacaagact tcagctacct 240
ggcttgctct gtccagaatt gcaggtcttt gtaacagggc agtgtttcag gctaaccagg 300
aaaacctacc tattcttaag cgggcagttg caggagatgc ctctgagtca gcactcttaa 360
agtgcataga gctgtgctgt ggntncgtga aggagatgag agaaagatac nccaaaatcg 420
tcgagatacc cttcaactcc accaacaagt accagttgtc tattcataag aaccccaaca 480
catcggagcc ccaacacctg ttggtgatga agggcgcccc agaaaggatc cta 533

<210> SEQ ID NO 272
<211> LENGTH: 630
<212> TYPE: DNA
<213> ORGANISM: Homo sapiens

<400> SEQUENCE: 272
tggtattttt ctttttcttt tggatgtttt atactttttt ttcttttttc ttctctattc 60
ttttcttcgc cttcccgtac ttctgtcttc cagttttcca cttcaaactt ctatcttctc 120
caaattgttt catcctacca ctcccaatta atctttccat tttcgtctgc gtttagtaaa 180
tgcgttaact aggctttaaa tgacgcaatt ctccctgcgt catggatttc aaggtctttt 240
aatcaccttc ggtttaatct ctttttaaaa gatcgccttc aaattatttt aatcacctac 300
aacttttaaa ctaaacttta agctgtttaa gtcaccttca ttttaatcta aaagcattgc 360
ccttctattg gtattaattc ggggctctgt agtcctttct ctcaattttc ttttaaatac 420
attttttact ccatgaagaa gcttcatctc aacctccgtc atgttttaga aaccttttat 480
cttttccttc ctcatgctac tcttctaagt cttcatattt tctcttaaaa tcttaagcta 540
ttaaaattac gttaaaaact taacgctaag caatatctta gtaacctatt gactatattt 600
tttaagtagt tgtattaatc tctatctttc 630

<210> SEQ ID NO 273
<211> LENGTH: 400
<212> TYPE: DNA
<213> ORGANISM: Homo sapiens

<400> SEQUENCE: 273
tctggtttgc cctccagttc attctgaatc tagacttgct cagcctaatc aagttcctgt 60
acaaccagaa gcgacacagg ttcctttggt atcatccaca agtgaggggt acacagcatc 120
tcaacccttg taccagcctt ctcatgctac agagcaacga ccacagaagg aaccaattga 180
tcagattcag gcaacaatct ctttaaatac agaccagact acagcatcat catcccttcc 240
tgctgcgtct cagcctcaag tatttcaggc tgggacaagc aaacctttac atagcagtgg 300
aatcaatgta aatgcagctc cattccaatc catgcaaacg gtgttcaata tgaatgcccc 360
agttcctcct gttaatgaac cagaaacttt aaaacagcaa 400

-continued

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: 2
<223> OTHER INFORMATION: n = A,T,C or G

<400> SEQUENCE: 274
tntgagtatg tcccagagaa ggtgaagaaa gcggaaaaga aattagaaga gaatccatat 60
gaccttgatg cttggagcat tctcattcga gaggcacaga atcaacctat agacaaagca 120
cggaagactt atgaacgcct tgttgcccag ttccccagtt ctggcagatt ctggaaactg 180
tacattgaag cagaggttac tattttattt tattttttct tatatcagta ttgcagcatt 240
cactgtagtg atagaaaaca agttaggaac atagccaatt aggacaagga ggatttaaat 300
gtgtcttacc tttattttgt aaaataggta taaaggagta attaaaatga a 351

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: 4, 11, 12, 13
<223> OTHER INFORMATION: n = A,T,C or G

<400> SEQUENCE: 275
gcgnggtcgc nnncgaggtc tgagaagccc ataccactat ttgttgagaa atgtgtggaa 60
tttattgaag atacagggtt atgtaccgaa ggactctacc gtgtcagcgg gaataaaact 120
gaccaagaca atattcaaaa gcagtttgat caagatcata atatcaatct agtgtcaatg 180
gaagtaacag taaatgctgt agctggagcc cttaaagctt tctttgcaga tctgccagat 240
cctttaattc catattctct tcatccagaa ctattggaag cagcaaaaat cccggataaa 300
acagaacgtc ttcatgcctt gaaagaaatt gttaagaaat ttcatcctgt aaactatgat 360
gtattcagat acgtgataac a 381

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: 5
<223> OTHER INFORMATION: n = A,T,C or G

<400> SEQUENCE: 276
gctcngactc cggcgggacc tgctcggagg aatggcgccg ccgggttcaa gcactgtctt 60
cctgttggcc ctgacaatca tagccagcac ctgggctctg acgcccactc actacctcac 120
caagcatgac gtggagagac taaaagcctc gctggatcgc cctttcacaa atttggaatc 180
tgccttctac tccatcgtgg gactcagcag ccttggtgct caggtgccag atgcaaagaa 240
agcatgtacc tacatcagat ctaaccttga tcccagcaat gtggattccc tcttctacgc 300
tgcccaggcc agccaggccc tctcaggatg tgagatctct atttcaaatg agaccaaaga 360
tctgcttctg gcagacctcg gccgcgacca 390

<210> SEQ ID NO 277
<211> LENGTH: 378

-continued

<212> TYPE: DNA
<213> ORGANISM: Homo sapiens

<400> SEQUENCE: 277
tgggaacttc tggggtagga cgttgtctgc tatctccagt tccacagacc caaccagtta 60
cgatggtttt ggaccattta tgccgggatt cgacatcatt ccctataatg atctgcccgc 120
actggagcgt gctcttcagg atccaaatgt ggctgcgttc atggtagaac caattcaggg 180
tgaagcaggc gttgttgttc cggatccagg ttacctaatg ggagtgcgag agctctgcac 240
caggcaccag gttctcttta ttgctgatga aatacagaca ggattggcca gaactggtag 300
atggctggct gttgattatg aaaatgtcag acctgatata gtcctccttg gaaaggccct 360
ttctgggggc ttataccc 378

<210> SEQ ID NO 278
<211> LENGTH: 366
<212> TYPE: DNA
<213> ORGANISM: Homo sapiens

<400> SEQUENCE: 278
ggagggcaca ttccttttca cctcagagtc ggtcggggaa ggccacccag ataagatttg 60
tgaccaaacc agtgatgctg tccttgatgc ccaccttcag caggatcctg atgccaaagt 120
agcttgtgaa actgttgcta aaactggaat gatccttctt gctggggaaa ttacatccag 180
agctgctgtt gactaccaga aagtggttcg tgaagctgtt aaacacattg gatatgatga 240
ttcttccaaa ggttttgact acaagacttg taacgtgctg gtagccttgg agcaacagtc 300
accagatatt gctcaaggtg ttcatcttga cagaaatgaa gaagacattg gtgctggaga 360
ccaggg 366

<210> SEQ ID NO 279
<211> LENGTH: 435
<212> TYPE: DNA
<213> ORGANISM: Homo sapiens

<400> SEQUENCE: 279
cctaagaact gagacttgtg acacaaggcc aacgacctaa gattagccca gggttgtagc 60
tggaagacct acaacccaag gatggaaggc ccctgtcaca aagcctacct agatggatag 120
aggacccaag cgaaaaagat atctcaagac taacggccgg aatctggagg cccatgaccc 180
agaacccagg aaggatagaa gcttgaagac ctggggaaat cccaagatga gaaccctaaa 240
ccctacctct tttctattgt ttacacttct tactcttaga tatttccagt tctcctgttt 300
atctttaagc ctgattcttt tgagatgtac tttttgatgt tgccggttac ctttagattg 360
acaagtatta tgcctggcca gtcttgagcc agctttaaat cacagctttt acctatttgt 420
taggctatag tgttt 435

<210> SEQ ID NO 280
<211> LENGTH: 435
<212> TYPE: DNA
<213> ORGANISM: Homo sapiens

<400> SEQUENCE: 280
tctggatgag ctgctaactg agcacaggat gacctgggac ccagcccagc caccccgaga 60
cctgactgag gccttcctgg caaagaagga gaaggccaag gggagccctg agagcagctt 120
caatgatgag aacctgcgca tagtggtggg taacctgttc cttgccggga tggtgaccac 180

-continued

```
ctcgaccacg ctggcctggg gcctcctgct catgatccta cacctggatg tgcagcgtga    240

gcccagacct gtccgggcgg ccgctcgaaa ttccagcaca ctggcggccg ttactagtgg    300

atccgagctc ggtaccaagc ttggcgtaat catggtcata gctgtttcct gtgtgaaatt    360

gttatccgct cacaattcca cacaacatac gagccggaag cataaagtgt aaagcctggg    420

gtgcctaatg agtga                                                     435
```

<210> SEQ ID NO 281
<211> LENGTH: 440
<212> TYPE: DNA
<213> ORGANISM: Homo sapiens

<400> SEQUENCE: 281

```
catctgatct ataaatgcgg tggcatcgac aaaagaacca ttgaaaaatt tgagaaggag     60

gctgctgaga tgggaaaggg ctccttcaag tatgcctggg tcttggataa actgaaagct    120

gagcgtgaac gtggtatcac cattgatatc tccttgtgga aatttgagac cagcaagtac    180

tatgtgacta tcattgatgc cccaggacac agagacttta tcaaaaacat gattacaggg    240

acatctcagg ctgactgtgc tgtcctgatt gttgctgctg gtgttggtga atttgaagct    300

ggtatctcca agaatgggca gacccgagag catgcccttc tggcttacac actgggtgtg    360

aaacaactaa ttgtcggtgt taacaaaatg gattccactg agccccctac agccagaaga    420

gatatgagga aattgttaag                                                440
```

<210> SEQ ID NO 282
<211> LENGTH: 502
<212> TYPE: DNA
<213> ORGANISM: Homo sapiens

<400> SEQUENCE: 282

```
tctgtggcgc aggagccccc tcccccggca gctctgacgt ctccaccgca gggactggtg     60

cttctcggag ctcccactcc tcagactccg gtggaagtga cgtggacctg gatcccactg    120

atggcaagct cttccccagc gatggttttc gtgactgcaa gaagggggat cccaagcacg    180

ggaagcggaa acgaggccgg ccccgaaagc tgagcaaaga gtactgggac tgtctcgagg    240

gcaagaagag caagcacgcg cccagaggca cccacctgtg ggagttcatc cgggacatcc    300

tcatccaccc ggagctcaac gagggcctca tgaagtggga gaatcggcat gaaggcgtct    360

tcaagttcct gcgctccgag gctgtggccc aactatgggg ccaaaagaaa aagaacagca    420

acatgaccta cgagaagctg agccgggcca tgaggtacta ctacaaacgg gagatcctgg    480

aacgggtgga tggccggcga ct                                             502
```

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: 130, 147, 221, 225, 242, 246, 261, 279, 292, 294, 298,
314, 323, 332, 339, 342, 343, 350, 351, 356, 361, 362, 368, 372,
375, 379, 380, 382, 387, 390, 392, 394, 401, 404, 406, 409,
413, 423, 431, 433
<223> OTHER INFORMATION: n = A,T,C or G

<400> SEQUENCE: 283

```
ccatattaga ttactggaac atctaagcat cagtgtgtga ccatgcgaac aaaagacttc     60

ggggagtgtc tatttttaaa aaggtttatg tgtgtcgagg cagttgtaaa agatttactg    120
```

-continued

```
cagaatcaan cccactttta ggcttangac caggttctaa ctatctaaaa atattgactg    180

ataacaaaaa gtgttctaaa tgtggctatt ctgatccata nttgnttttt aaagaaaaaa    240

antgtntata cagaaagagt ntaaaagttc tgtgaattna atgcaaatta gncnccantc    300

ttgacttccc aaanacttga ttnatacctt tnactcctnt cnnttcctgn ncttcnttaa    360

nntcaatnat tnggnagtnn anggccntcn gnanaacacc nttncncgnt ccncgcaatc    420

canccgcctt nan                                                       433
```

<210> SEQ ID NO 284
<211> LENGTH: 479
<212> TYPE: DNA
<213> ORGANISM: Homo sapiens

<400> SEQUENCE: 284

```
tctggaagga tcagggatct gagcaaagcc aagtttactt aagctaagcc acttgttcct     60

gggtcaagca gtttgttttc taataagcat cattcctgat cattagagca aagggatgaa    120

tgctcctctt ggaatgatac aggggatctg ccactgggag agtgttgctc agtgttagag    180

tagcagcaat gacagaatga cagcgactct ctgagtcaac ccagtacttt tagtaccccg    240

tcactatgtg aataaaggca gctagaaaat ggactcaatt ctgcaagcct tcatggcaac    300

agcccatatt aagacttcta gaacaagtta aaaaaaaatc ttccatttcc atccatgcat    360

gggaaaaggg ctttagtata gtttaggatg gatgtgtgta taataataaa atgataagat    420

atgcatagtg ggggaataaa gcctcagagt ccttccagta tggggaatcc attgtatct     479
```

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: 27, 83, 90, 93, 96, 184, 207, 227, 232, 293, 306, 307, 328, 331, 339, 343, 347, 349, 350, 370, 371, 382, 383, 414, 418, 434
<223> OTHER INFORMATION: n = A,T,C or G

<400> SEQUENCE: 285

```
ttttttttt ttttttttt tcaatanaaa tgccataatt tattccattg tataaaaaag     60

tcatccttat gtaacaaaat gtnttcttan aanaanaaat atattatttc aggtcataaa    120

taatcagcaa acatacaact gttggcaact aaaaaaaaac ccaacactgg tattttccat    180

cagngctgaa aacaaacctg cttaaanata tatttacagg gatagtncag tnctcaaaaa    240

caaaaattga ggtattttgg ttcttctagg agtagacaat gacattttgg gangggcaga    300

cccctnnccc aaaaaataaa ataagggnat nttcttcant atngaanann gggggcgccc    360

cggggaaaan naaaccttgg gnngggggtt tggcccaagc ccttgaaaaa aaantttntt    420

tcccaaaaaa aacng                                                     435
```

<210> SEQ ID NO 286
<211> LENGTH: 301
<212> TYPE: DNA
<213> ORGANISM: Homo sapiens

<400> SEQUENCE: 286

```
cctggtttct ggtggcctct atgaatccca tgtagggtgc agaccgtact ccatccctcc     60

ctgtgagcac cacgtcaacg gctcccggcc cccatgcacg ggggagggag ataccccaa    120

gtgtagcaag atctgtgagc ctggctacag cccgacctac aaacaggaca agcactacgg    180
```

-continued

```
atacaattcc tacagcgtct ccaatagcga gaaggacatc atggccgaga tctacaaaaa    240

cggccccgtg gagggagctt tctctgtgta ttcggacttc ctgctctaca agtcaggagt    300

g                                                                    301
```

```
<210> SEQ ID NO 287
<211> LENGTH: 432
<212> TYPE: DNA
<213> ORGANISM: Homo sapiens

<400> SEQUENCE: 287

tccagcttgt tgccagcatg agaaccgcca ttgatgacat tgaacgccgg gactggcagg     60

atgacttcag agttgccagc caagtcagcg atgtggcggt acagggggac cccccttctca   120

acggcaccag ctttgcagac ggcaagggac acccccagaa tggcgttcgc accaaactta    180

gatttatttt ctgttccatc catctcgatc atcagtttgt caatcttctc ttgttctgtg    240

acgttcagtt tcttgctaac cagggcaggc gcaatagttt tattgatgtg ctcaacagcc    300

tttgagacac ccttccccat atagcgagtc ttatcattgt cccggagctc tagggcctca    360

tagataccag ttgaagcacc actgggcaca gcagctctga agagaccttt tgaggtgaag    420

agatcaacct ca                                                        432
```

```
<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: 254
<223> OTHER INFORMATION: n = A,T,C or G

<400> SEQUENCE: 288

tctggctcaa gtcaaagtcc tggtcctctt ctccgcctcc ttcttcatca tagtaataaa     60

cgttgtcccg ggtgtcatcc tctgggggca gtaagggctc tttgaccacc gctctcctcc    120

gaagaaacag caagagcagc agaatcagaa ttagcaaagc aagaattcct ccaagaatcc    180

ccagaatggc aggaatttgc aatcctgctt cgacaggctg tgccttccta cagacgccgg    240

cggccccttc acantcacac acgctgacct ctaaggtggt cacttggtct ttattctggt    300

tatccatgag cttgagattg attttg                                         326
```

```
<210> SEQ ID NO 289
<211> LENGTH: 451
<212> TYPE: DNA
<213> ORGANISM: Homo sapiens

<400> SEQUENCE: 289

gtcccggtgt ggctgtgccg ttggtcctgt gcggtcactt agccaagatg cctgaggaaa     60

cccagaccca agaccaaccg atggaggagg aggaggttga gacgttcgcc tttcaggcag    120

aaattgccca gttgatgtca ttgatcatca atactttcta ctcgaacaaa gagatctttc    180

tgagagagct catttcaaat tcatcagatg cattggacaa aatccggtat gaaagcttga    240

cagatcccag taaattagac tctgggaaag agctgcatat taaccttata ccgaacaaac    300

aagatcgaac tctcactatt gtggatactg gaattggaat gaccaaggct gacttgatca    360

ataaccttgg tactatcgcc aagtctggga ccaaagcgtt catggaagct ttgcaggctg    420

gtgcagatat ctctatgatt ggacctcggc c                                   451
```

-continued

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: 421
<223> OTHER INFORMATION: n = A,T,C or G

<400> SEQUENCE: 290
tttttttttt tcaaaacagt atattttatt ttacaatagc aaccaactcc ccagtttgtt 60
tcaattgtga catctagatg gcttaagatt actttctggt ggtcacccat gctgaacaat 120
atttttcaat cttccaaaca gcaaagactc aaaagagatt ctgcatttca catcagttca 180
caagttcaag agtcttccat ttatcttagc ttttggaata aattatcttt gaggtagaag 240
gacaatgacg aagccactta attccttgtg tctgcataaa agcagattta ttcatcacaa 300
cttcatttat gtgaataaag cagatgatga taaaatgttc tcttattctt gtttaatcag 360
tagtggtagt gatgccagaa acttgtaaat gcacttcaaa ccaattgtgg ctcaagtgta 420
ngtggttccc caaggctggt accaatgaga ctggggtttg ggaattagtt ggtcatcatc 480
cctcctgctg ccca 494

<210> SEQ ID NO 291
<211> LENGTH: 535
<212> TYPE: DNA
<213> ORGANISM: Homo sapiens

<400> SEQUENCE: 291
tcgcgtgctt aacatgaaaa caaactttgt gctgtttggt tcattgtatg cattgatgga 60
gtcttgtctc tcatcatggg gtgtctgacc atccaacctg cagtactcat aatttctcca 120
catgcaataa tcttccaaaa tgtccaatac ccttgtcatt tgactgaaga ttagtactcg 180
tgaaccttgt tcttttaact tagggagcag cttgtctaaa accaccattt tgccactgtt 240
ggttactaga tgcatatctg ttgtataagg tggaccaggt tctgctccat caaagagata 300
tggatgatta caacattttc tcaactgcat taggatgttc aataacctca ttttgtccat 360
cttgcctgct gagttgagta tatctatatc cttcattaat atccgagtat accattccct 420
ttgcattttg ctgaggccca catagatttt tacttccttc tttggaggca aactcttttc 480
aacatcagcc ttaattcgac gaaggaggaa tggacgcaaa accatatgaa gcctc 535

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: 4, 348
<223> OTHER INFORMATION: n = A,T,C or G

<400> SEQUENCE: 292
tacnagcccg tgctgatcga gatcctggtg gaggtgatgg atccttcctt cgtgtgcttg 60
aaaattggag cctgcccctc ggcccataag cccttgttgg gaactgagaa gtgtatatgg 120
ggcccaagct actggtgcca gaacacagag acagcagccc agtgcaatgc tgtcgagcat 180
tgcaaacgcc atgtgtggaa ctaggaggag gaatattcca tcttggcaga aaccacagca 240
ttggtttttt tctacttgtg tgtctggggg aatgaacgca cagatctgtt tgactttgtt 300
ataaaaatag ggctccccca cctcccccat ttttgtgtcc tttattgnag cattgctgtc 360

-continued

```
tgcaagggag ccccta                                                  376

<210> SEQ ID NO 293
<211> LENGTH: 320
<212> TYPE: DNA
<213> ORGANISM: Homo sapiens

<400> SEQUENCE: 293

tcggctgctt cctggtctgg cggggatggg tttgctttgg aaatcctcta ggaggctcct   60

cctcgcatgg cctgcagtct ggcagcagcc ccgagttgtt tcctcgctga tcgatttctt  120

tcctccaggt agagttttct ttgcttatgt tgaattccat tgcctctttt ctcatcacag  180

aagtgatgtt ggaatcgttt cttttgtttg tctgatttat ggttttttta agtataaaca  240

aaagtttttt attagcattc tgaaagaagg aaagtaaaat gtacaagttt aataaaaagg  300

ggccttcccc tttagaatag                                              320

<210> SEQ ID NO 294
<211> LENGTH: 359
<212> TYPE: DNA
<213> ORGANISM: Homo sapiens

<400> SEQUENCE: 294

ctgtcataaa ctggtctgga gtttctgacg actccttgtt caccaaatgc accatttcct   60

gagacttgct ggcctctccg ttgagtccac ttggctttct gtcctccaca gctccattgc  120

cactgttgat cactagcttt ttcttctgcc cacaccttct tcgactgttg actgcaatgc  180

aaactgcaag aatcaaagcc aaggccaaga gggatgccaa gatgatcagc cattctggaa  240

tttggggtgt ccttatagga ccagaggttg tgtttgctcc accttcttga ctcccatgtg  300

agtgtccatc tgattcagat ccatgagtgg tatgggaccc cccactgggg tggaatgtg   359

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: 558
<223> OTHER INFORMATION: n = A,T,C or G

<400> SEQUENCE: 295

cctgagttgg gctgactgcc agagacagac ccctctgggt ctcggtgaac cagccaggca   60

tttacctcag tggttggcac ctggaacctg tccagggccc tcacctgact gaggagccgc  120

cgggcagtga agtaattgtc caggtctatg ctcttggggt ggataccata gccatccaag  180

gtattcctca ggttgtggaa ctgggtctga gtataggcag aactgggccc caggatgatc  240

tcccggagtg ggggaagctg tgaggtcagg taagtatcca cgtccacccg taccccaatc  300

aaactcagca gaatggtgaa ctggagaagt ccttccgtta agtatttctt cagagaaagc  360

attgctgaag gaccagaatg tttatgcttt ttggttttta aaatcttcca aaagacaaat  420

caaggccact gctctgccgc tccagccagc aggttaccct cctcagtgtc aaaccccgta  480

ccccaccctg gcagaacaca agggatgagc tccctgacgg ccccagagga aagcacaccc  540

tgtggagcca aggccaanga cacactccag accacattca cttt                   584

<210> SEQ ID NO 296
<211> LENGTH: 287
<212> TYPE: DNA
```

-continued

<213> ORGANISM: Homo sapiens

<400> SEQUENCE: 296
ccttatcatt cattcttagc tcttaattgt tcattttgag ctgaaatgct gcattttaat 60
tttaaccaaa acatgtctcc tatcctggtt tttgtagcct tcctccacat cctttctaaa 120
caagatttta aagacatgta ggtgtttgtt catctgtaac tctaaaagat cctttttaaa 180
ttcagtccta agaaagagga gtgcttgtcc cctaagagtg tttaatggca aggcagccct 240
gtctgaagga cacttcctgc ctaagggaga gtggtatttg cagacta 287

<210> SEQ ID NO 297
<211> LENGTH: 457
<212> TYPE: DNA
<213> ORGANISM: Homo sapiens

<400> SEQUENCE: 297
ccaattgaaa caaacagttc tgagaccgtt cttccaccac tgattaagag tggggtggca 60
ggtattaggg ataatattca tttagccttc tgagctttct gggcagactt ggtgaccttg 120
ccagctccag cagccttctt gtccactgct ttgatgacac ccaccgcaac tgtctgtctc 180
atatcacgaa cagcaaagcg acccaaaggt ggatagtctg agaagctctc aacacacatg 240
ggcttgccag gaaccatatc aacaatggca gcatcaccag acttcaagaa tttagggcca 300
tcttccagct ttttaccaga acggcgatca atcttttcct tcagctcagc aaacttgcat 360
gcaatgtgag ccgtgtggca atccaataca ggggcatagc cggcgcttat ttggcctgga 420
tggttcagga taatcacctg agcagtgaag ccagacc 457

<210> SEQ ID NO 298
<211> LENGTH: 469
<212> TYPE: DNA
<213> ORGANISM: Homo sapiens

<400> SEQUENCE: 298
tctttgactt tccttgtcta cctcctctgg agatctcaaa ttctccaggt tccatgctcc 60
cagagatctc aatgattcct gattctcctc ttccaggagt ctgaatgtct cttggttcac 120
ttccacagac tccagtggtt cttgaatttc cttttctaga ggattcattg ccccctgatt 180
tatttcttct ggagtccaca gtggtgcttg agtttctgga gatttcagtg tttccaggtt 240
ctcttgtccc gcagacttca gtgattctag gatctctgtt tctaaagatt ttactgcctc 300
tatgctctct tctttgagtg actttaagaa ctcttgattc tcattttcaa gaggtctagc 360
tatctcctgg tcaagagact tcagtggttc tagatccact tttctgggg gtcttaatgt 420 catctgatcc tgttcccca gagacctccg tcgctgttga gtctctttt 469

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: 37, 82, 144
<223> OTHER INFORMATION: n = A,T,C or G

<400> SEQUENCE: 299
tctgtggaga ggatgaggtt gagggaggtg gggtatntcg ctgctctgac cttaggtaga 60
gtcctccaca gaagcatcaa antggactgg cacatatgga ctcccttcac aggccacaat 120
gatgtgtctc tccttcgggc tggnccggta tgcacagttg gggta 165

<210> SEQ ID NO 300
<211> LENGTH: 506
<212> TYPE: DNA
<213> ORGANISM: Homo sapiens

<400> SEQUENCE: 300
tctgaggaaa gtttgggctt attagtattt gctccagcga acctccaagt tttctccatt 60
gcggacaacg taactaccag ctccttggct cagtggttcg cctccactca gaagttccca 120
gtaggttctg tcattattgt tggcacatag gccctgaata caggtgatat agggccccca 180
tgagcgctcc tccattgtga aaccaaatat agtatcattc attttctggg ctttctccat 240
cacactgagg aagacagaac catttagcac agtgacattg gtgaaatatg tttcattgat 300
tctcacagag taattgacgg agatatatga ttgtgagtca ggaggtgtca cagttatagg 360
ctcatcagcg gagatgttga agttacctga agcagagacg caagaagagt ctttgttaat 420
atccaagaag gtctttccca tcagggcagg taagacctgg gctgcagcgt ttggattgct 480
gaatgctcct tgagaaattt ccgtga 506

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: 221, 223, 252, 275, 280
<223> OTHER INFORMATION: n = A,T,C or G

<400> SEQUENCE: 301
tcctaaggca gagcccccat cacctcaggc ttctcagttc ccttagccgt cttactcaac 60
tgcccctttc ctctccctca gaatttgtgt ttgctgcctc tatcttgttt tttgtttttt 120
cttctggggg gggtctagaa cagtgcctgg cacatagtag gcgctcaata aatacttgtt 180
tgttgaatgt ctcctctctc tttccactct gggaaaccta ngnttctgcc attctgggtg 240
accctgtatt tntttctggt gcccattcca tttgnccagn taatacttcc tcttaaaaat 300
ctcc 304

<210> SEQ ID NO 302
<211> LENGTH: 492
<212> TYPE: DNA
<213> ORGANISM: Homo sapiens

<400> SEQUENCE: 302
ttttcagtaa gcaacttttc catgctctta atgtattcct ttttagtagg aatccggaag 60
tattagattg aatggaaaag cacttgccat ctctgtctag gggtcacaaa ttgaaatggc 120
tcctgtatca catacggagg tcttgtgtat ctgtggcaac agggagtttc cttattcact 180
ctttatttgc tgctgtttaa gttgccaacc tcccctccca ataaaaattc acttacacct 240
cctgcctttg tagttctggt attcacttta ctatgtgata gaagtagcat gttgctgcca 300
gaatacaagc attgcttttg gcaaattaaa gtgcatgtca tttcttaata cactagaaag 360
gggaaataaa ttaaagtaca caagtccaag tctaaaactt tagtactttt ccatgcagat 420
ttgtgcacat gtgagagggt gtccagtttg tctagtgatt gttatttaga gagttggacc 480
actattgtgt gt 492

<210> SEQ ID NO 303

-continued

<211> LENGTH: 470
<212> TYPE: DNA
<213> ORGANISM: Homo sapiens

<400> SEQUENCE: 303

```
tctggggcag caggtactcc ctacggcact agtctacagg gggaaggacg ctctgtgctg     60
gcagcggtgg ctcacatggc ctgtctgcac tgtaaccaca ggctgggatg tagccaggac    120
ttggtctcct tggaagacag gtctgatgtt tggccaatcc agtccttcag accctgcctg    180
aaacttgtat cttacgtgaa cttaaagaat aaaatgcatt tctaccccga tctcgccccc    240
aggactggca cgacaggccc acggcagatt agatcttttc ccagtactga tcggtgcgtg    300
gaattccagc caccacttct gattcgattc cacagtgatc ctgtcctctg agtattttaa    360
agaagccatt gtcaccccag tcagtgttcc aggagttggc aaccagccag tagggtgtgc    420
cattctccac tccccagccc aggatgcgga tggcatggac ctcggccgcg                470
```

<210> SEQ ID NO 304
<211> LENGTH: 79
<212> TYPE: DNA
<213> ORGANISM: Homo sapiens

<400> SEQUENCE: 304

```
tgtcccattg ttaactcagc ctcaaatctc aactgtcagg ccctacaaag aaaatggaga     60
gcctcttctg gtggatgcg                                                   79
```

<210> SEQ ID NO 305
<211> LENGTH: 476
<212> TYPE: DNA
<213> ORGANISM: Homo sapiens

<400> SEQUENCE: 305

```
tcactgagcc accctacagc cagaagagat atgaggaaat tgttaaggaa gtcagcactt     60
acattaagaa aattggctac aaccccgaca cagtagcatt tgtgccaatt tctggttgga    120
atggtgacaa catgctggag ccaagtgcta acgtaagtgg ctttcaagac cattgttaaa    180
aagctctggg aatggcgatt tcatgcttac acaaattggc atgcttgtgt ttcagatgcc    240
ttggttcaag ggatggaaag tcacccgtaa ggatggcaat gccagtggaa ccacgctgct    300
tgaggctctg gactgcatcc taccaccaac tcgtccaact gacaagccct tgcgcctgcc    360
tctccaggat gtctacaaaa ttggtggtaa gttggctgta aacaaagttg aatttgagtt    420
gatagagtac tgtctgcctt cataggtatt tagtatgctg taaatatttt taggta        476
```

<210> SEQ ID NO 306
<211> LENGTH: 404
<212> TYPE: DNA
<213> ORGANISM: Homo sapiens

<400> SEQUENCE: 306

```
tctgtctcgg agctcagggc gcagccagca cacacaggag cccacaggac agccacgtct     60
tcacagaaac tacagaagtc aggacccagg cgaggacctc aggaacaagt gccccctgca    120
gacagagaga cgcagtagca acagcttctg aacaactaca taataatgcg gggagaatcc    180
tgaagaccac tgcatcccac aagcactgac aaccacttca ggattttatt tcctccactc    240
taacccccag atccatttat gagaagtgag tgaggatggc aggggcatgg agggtgaagg    300
gacagcaagg atggtctgag ggcctggaaa caatagaaaa tcttcgtcct ttagcatatc    360
ctggactaga aaacaagagt tggagaagag gggggttgat acta                      404
```

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: 10, 255, 257
<223> OTHER INFORMATION: n = A,T,C or G

<400> SEQUENCE: 307
tcctgcctan acatctgtga gggcctcaag ggctgctgcc tcgactttct ccctagctaa 60
gtccacccgt ccagggacac agccagggca ctgctctgtg ctgacttcca ctgcagccaa 120
gggtcaaaat gaagcatctg cggaggccag gactccttgg catcggacac agtcagggga 180
aaagccaccc tgactctgca ggacagaggg tctagggtca tttggcagga gaacactggt 240
gtgccaaggg aagcnancat 260

<210> SEQ ID NO 308
<211> LENGTH: 449
<212> TYPE: DNA
<213> ORGANISM: Homo sapiens

<400> SEQUENCE: 308
tctgtgctcc cgactcctcc atctcaggta ccaccgactg cactgggcgg ggccctctgg 60
ggggaaaggc tccacggggc agggatacat ctcgaggcca gtcatcctct ggaggcagcc 120
caatcaggtc aaagattttg cccaactggt cggcttcaga gtttccacag aagagaggct 180
ttcgacgaaa catctctgca aagatacagc caacactcca catgtccaca ggtgttgcat 240
atgtggactg cagaagaact tcgggagctc ggtaccagag tgtaacaacc ttgatcgttt 300
cggctggcaa gcctggtggg ggtgccttgt ccagatatgt ccttaggtcc tggtctacat 360
gctcaaacac cagggttacc ttgatctccc ggtcagttcg ggatgtggca cagacgtcca 420
tcagccggac aacattggga tgctcaaaa 449

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: 384
<223> OTHER INFORMATION: n = A,T,C or G

<400> SEQUENCE: 309
ctgtggaaac ctggggtgcc gggtaaatgg agaactccag cttggatttc ttgccataat 60
caactgagag acgttccatg agcagggagg tgaacccaga accagttccc ccaccaaagc 120
tgtggaaaac caagaagccc tgaagaccgg tgcactggtc agccagcttg cgaattcggt 180
ccaacacaag gtcaatgatc tccttgccaa tggtgtagtg ccctcgggca tagttattgg 240
cagcatcttc cttgcctgtg atgagctgct cagggtggaa gagctggcgg taggtgccag 300
tgcgaacttc atcaatgact gtgggttcca agtctacaaa cacagcccgg ggcacgtgct 360
tgccagcgcc cgtctcactt gaanaagggt gtttgaagga agtcatctcc t 411

<210> SEQ ID NO 310
<211> LENGTH: 320
<212> TYPE: DNA
<213> ORGANISM: Homo sapiens
<220> FEATURE:

-continued

<221> NAME/KEY: misc_feature
<222> LOCATION: 250
<223> OTHER INFORMATION: n = A,T,C or G

<400> SEQUENCE: 310
tcctcgtcca gcttgactcg attagtcctc ataaggtaag caaggcagat ggtggctgac 60
cgggaaatgc ctgcctggca gtggacaaac acccttcctc cagcattctt gatggagtct 120
atgaagtcaa tggcctcgtt gaaccaggag ctgatgtctg ccttgtggtt gtcctccaca 180
gggatgctct tgtactggta gtgaccctca aaatggttgg gacaattggc tgagacgttg 240
atcaaggcan ttatgcccaa ggcatccagc atgtccttgc gggaagcgtg atacgcactg 300
cccaggtaca gaaagggcag 320

<210> SEQ ID NO 311
<211> LENGTH: 539
<212> TYPE: DNA
<213> ORGANISM: Homo sapiens

<400> SEQUENCE: 311
tctggcccat gaagctgaag ttgggagaga tgatgcttcg cctctgcttc acaaactcaa 60
aggcctcgtc cagcttgact cgattagtcc tcataaggta agcaaggcag atggtggctg 120
accgggaaat gcctgcctgg cagtggacaa acacccttcc tccagcattc ttgatggagt 180
ctatgaagtc aatggcctcg ttgaaccagg agctgatgtc tgccttgtgg ttgtcctcca 240
cagggatgct cttgtactgg tagtgaccct caaaatggtt gggacaattg gctgagacgt 300
tgatcaaggc agttatgccc aaggcatcca gcatgtcctt gcgggaagcg tgatacgcac 360
tgcccaggta cagaaagggc aggatttcca ccgggccacc ctgaaatcca gaaatatcca 420
acattcatca agcttgctca aagccaaggc cagtgcccat acccacaaaa actttctgct 480
ggaaaagtca atttcagata ccgagtgaac tcagttctgt tgctggagga taaataaat 539

<210> SEQ ID NO 312
<211> LENGTH: 475
<212> TYPE: DNA
<213> ORGANISM: Homo sapiens

<400> SEQUENCE: 312
tcaaggatct tcctaaagcc accatgtgag aggattcgga cgagagtctg agctgtatgg 60
cagaccatgt cctgctgttc tagggtcatg actgtgtgta ctctaaagtt gccactctca 120
caggggtcag tgatacccac tgaacctggc aggaacagtc ctgcagccag aatctgcaag 180
cagcgcctgt atgcaacgtt tagggccaaa ggctgtctgg tggggttgtt catcacagca 240
taatggccta gtaggtcaag gatccagggt gtgaggggct caaagccagg aaaacgaatc 300
ctcaagtcct tcagtagtct gatgagaact ttaactgtgg actgagaagc attttcctcg 360
aaccagcggg catgtcggat ggctgctaag gcactctgca atactttgat atccaaatgg 420
agttctggat ccagttttcg aagattgggt ggcactgttg taatgagaat cttca 475

<210> SEQ ID NO 313
<211> LENGTH: 456
<212> TYPE: DNA
<213> ORGANISM: Homo sapiens

<400> SEQUENCE: 313
tccacttaaa gggtgcctct gccaactggt ggaatcatcg ccacttccag caccacgcca 60
agcctaacat cttccacaag gatcccgatg tgaacatgct gcacgtgttt gttctgggcg 120

-continued aatggcagcc catcgagtac ggcaagaaga agctgaaata cctgccctac aatcaccagc 180
acgaatactt cttcctgatt gggccgccgc tgctcatccc catgtatttc cagtaccaga 240
tcatcatgac catgatcgtc cataagaact gggtggacct ggcctgggcc gtcagctact 300
acatccggtt cttcatcacc tacatccctt tctacggcat cctgggagcc ctccttttcc 360
tcaacttcat caggttcctg gagagccact ggtttgtgtg ggtcacacag atgaatcaca 420
tcgtcatgga gattgaccag gaggacctcg gcccgc 456

<210> SEQ ID NO 314
<211> LENGTH: 477
<212> TYPE: DNA
<213> ORGANISM: Homo sapiens

<400> SEQUENCE: 314
tgcgtgggct tctggaagcc tggatctgga atcattcacc agattattct ggaaaactat 60
gcgtaccctg gtgttcttct gattggcact gactcccaca cccccaatgg tggcggcctt 120
gggggcatct gcattggagt tgggggtgcc gatgctgtgg atgtcatggc tgggatcccc 180
tgggagctga agtgccccaa ggtgattggc gtgaagctga cgggctctct ctccggttgg 240
tcctcaccca aagatgtgat cctgaaggtg gcaggcatcc tcacggtgaa aggtggcaca 300
ggtgcaatcg tggaatacca cgggcctggt gtagactcca tctcctgcac tggcatggcg 360
acaatctgca acatgggtgc agaaattggg gccaccactt ccgtgttccc ttacaaccac 420
aggatgaaga agtatctgag caagaccggc cgggaagaca ttgccaatct agctgat 477

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 315
caggtactgg atgtcaggtc tgcgaaactt cttanatttt gacctcagtc cataaaccac 60
actatcacct cggccatcat atgtgtctac tgtggggaca actggagtga aaacttcggt 120
tgctgcaggt ccgtgggaaa atcagtgacc agttcatcag attcatcaga atggtgagac 180
tcatcagact ggtgagaatc atcagtgtca tctacatcat cagagtcgtt cgagtcaatg 240
g 241

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: 1, 4, 32, 39, 68, 77, 82, 94, 166, 172, 195, 196
<223> OTHER INFORMATION: n = A,T,C or G

<400> SEQUENCE: 316
nttntgtgat agtgtggttt atggactgag gncaaaatnt aagaagtttc gcagacctga 60
catccaancc tgcccgngcg gncgctcgaa aggncgaatt ctgcagatat ccatcacact 120
ggcggccgct cgagcatgca tctagagggc ccaattcgcc ctatantgag tnatattaca 180
attcactggc cgtcnnttta caacgtcgtg actgggaaaa ccctggcgtt acccaactta 240

-continued

```
a                                                                     241


<210> SEQ ID NO 317
<211> LENGTH: 241
<212> TYPE: DNA
<213> ORGANISM: Homo sapiens
<220> FEATURE:
<221> NAME/KEY: misc_feature
<222> LOCATION: 15, 25, 135, 154, 193
<223> OTHER INFORMATION: n = A,T,C or G

<400> SEQUENCE: 317

aggtaccctg ctcancagcc tgggngcctg ggttgtctcc ttgtccatcc actggtccat      60

tctgctctgc attttttgt tcctcttttg gaggttccac tttgggtttg ggctttgaaa      120

ttatagggct acaantacct cggccgaaac cacnctaagg gcgaattctg cagatatcca     180

tcacactggc ggncgctcga gcatgcatct agagggccca attcgcccta tagtgagtcg     240

t                                                                     241


<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: 3, 5, 10, 11, 24, 28, 31, 34, 40, 42, 47, 53, 74, 80,
      96, 101, 127, 129, 136, 138, 205, 241
<223> OTHER INFORMATION: n = A,T,C or G

<400> SEQUENCE: 318

cgngnacaan ntacattgat gganggtntg nggntctgan tntttantta cantggagca      60

ttaatatttt cttnaacgtn cctcaccttc ctgaantaaa nactctgggt tgtagcgctc     120

tgtgctnana accacntnaa ctttacatcc ctcttttgga ttaatccact gcgcggccac     180

ctctgccgcg accacgctaa gggcnaattc tgcagatatc catcacactg gcggccgctc     240

n                                                                     241


<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: 24, 36, 39
<223> OTHER INFORMATION: n = A,T,C or G

<400> SEQUENCE: 319

caggtactga tcggtgcgtg gaantccagc caccanttnt gattcgattc cacagtgatc      60

ctgtcctctg agtattttaa agaagccatt gtcaccccag tcagtgttcc aggagttggc     120

aaccagccag tagggtgtgc cattctccac tccccagccc aggatgcgga tggcatggcc     180

acccatcatc tctccggtga cgtgttggta cctcggccgc gaccacgcta agggcgaatt     240

c                                                                     241


<210> SEQ ID NO 320
<211> LENGTH: 241
<212> TYPE: DNA
<213> ORGANISM: Homo sapiens
<220> FEATURE:
<221> NAME/KEY: misc_feature
<222> LOCATION: 27, 215, 216, 217, 220, 222, 235
<223> OTHER INFORMATION: n = A,T,C or G
```

-continued

<400> SEQUENCE: 320
ggcaggtacc aacagagctt agtaatntct aaaaagaaaa aatgatcttt ttccgacttc 60
taaacaagtg actatactag cataaatcat tctagtaaaa cagctaaggt atagacattc 120
taataatttg ggaaaaccta tgattacaag tgaaaactca gaaatgcaaa gatgttggtt 180
ttttgtttct cagtctgctt tagcttttaa ctctnnnaan cncatgcaca cttgnaactc 240
t 241

<210> SEQ ID NO 321
<211> LENGTH: 241
<212> TYPE: DNA
<213> ORGANISM: Homo sapiens
<220> FEATURE:
<221> NAME/KEY: misc_feature
<222> LOCATION: 2, 25, 26, 228
<223> OTHER INFORMATION: n = A,T,C or G

<400> SEQUENCE: 321
angtaccaac agagcttagt aattnntaaa aagaaaaaat gatctttttc cgacttctaa 60
acaagtgact atactagcat aaatcattct agtaaaacag ctaaggtata gacattctaa 120
taatttggga aaacctatga ttacaagtga aaactcagaa atgcaaagat gttggttttt 180
tgtttctcag tctgctttag cttttaactc tggaagcgca tgcacacntg aactctgctc 240
a 241

<210> SEQ ID NO 322
<211> LENGTH: 241
<212> TYPE: DNA
<213> ORGANISM: Homo sapiens

<400> SEQUENCE: 322
ggtaccaaca gagcttagta atttctaaaa agaaaaaatg atctttttcc gacttctaaa 60
caagtgacta tactagcata aatcattctt ctagtaaaac agctaaggta tagacattct 120
aataatttgg gaaaacctat gattacaagt aaaaactcag aaatgcaaag atgttggttt 180
tttgtttctc agtctgcttt agcttttaac tctggaagcg catgcacact gaactctgct 240
c 241

<210> SEQ ID NO 323
<211> LENGTH: 241
<212> TYPE: DNA
<213> ORGANISM: Homo sapiens

<400> SEQUENCE: 323
cgaggtactg tcgtatcctc agccttgttc tatttcttta ttttagcttt acagagatta 60
ggtctcaagt tatgagaatc tccatggctt tcaggggcta aacttttctg ccattctttt 120
gctcttaccg ggctcagaag gacatgtcag gtgggatacg tgtttctctt tcagagctga 180
agaaagggtc tgagctgcgg aatcagtaga gaaagccttg gtctcagtga ctccttggct 240
t 241

<210> SEQ ID NO 324
<211> LENGTH: 241
<212> TYPE: DNA
<213> ORGANISM: Homo sapiens

<400> SEQUENCE: 324
aggtactgtc gtatcctcag ccttgttcta tttctttatt ttagctttac agagattagg 60

-continued

```
tctcaagtta tgagaatctc catggctttc aggggctaaa cttttctgcc attcttttgc    120

tcttaccggg ctcagaagga catgtcaggt gggatacgtg tttctctttc agagctgaag    180

aaagggtctg agctgcggaa tcagtagaga aagccttggt ctcagtgact ccttggcttt    240

c                                                                    241
```

<210> SEQ ID NO 325
<211> LENGTH: 241
<212> TYPE: DNA
<213> ORGANISM: Homo sapiens

<400> SEQUENCE: 325

```
ggcaggtaca tttgttttgc ccagccatca ctctttttg tgaggagcct aaatacattc      60

ttcctggggt ccagagtccc cattcaaggc agtcaagtta agacactaac ttggcccttt    120

cctgatggaa atatttcctc catagcagaa gttgtgttct gacaagactg agagagttac    180

atgttgggaa aaaaaaagaa gcattaactt agtagaactg aaccaggagc attaagttct    240

g                                                                    241
```

<210> SEQ ID NO 326
<211> LENGTH: 241
<212> TYPE: DNA
<213> ORGANISM: Homo sapiens

<400> SEQUENCE: 326

```
gcaggtacat ttgttttgcc cagccatcac tctttttgt gaggagccta aatacattct      60

tcctggggtc cagagtcccc attcaaggca gtcaagttaa gacactaact tggccctttc    120

ctgatggaaa tatttcctcc atagcagaag ttgtgttctg acaagactga gagagttaca    180

tgttgggaaa aaaaagaagc attaacttag tagaactgat ccaggagcat taagttctga    240

a                                                                    241
```

<210> SEQ ID NO 327
<211> LENGTH: 241
<212> TYPE: DNA
<213> ORGANISM: Homo sapiens

<400> SEQUENCE: 327

```
ggtaccagac caagtgaatg cgacagggaa ttatttcctg tgttgataat tcatgaagta     60

gaacagtata atcaaaatca attgtatcat cattagtttt ccactgcctc acactagtga    120

gctgtgccaa gtagtagtgt gacacctgtg ttgtcatttc ccacatcacg taagagcttc    180

caaggaaagc caaatcccag atgagtctca gagagggatc aatatgtcca tgattatcag    240

g                                                                    241
```

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: 6, 19, 66, 232, 240
<223> OTHER INFORMATION: n = A,T,C or G

<400> SEQUENCE: 328

```
ggtacnagac caaatgaang ccacagggaa ttatttcctg tgttgataat tcatgaagta     60

gaacantata atcaaaatca attgtatcat cattagtttt ccactgcctc acactagtga    120
```

-continued

```
gctgtgccaa gtagtagtgt gacacctgtg ttgtcatttc ccacatcacg taagagcttc    180

caaggaaagc caaatcccag atgagtctca gagagggatc aatatgtcca tnatcatcan    240

g                                                                    241


<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: 33, 61, 220, 228, 229, 240, 241
<223> OTHER INFORMATION: n = A,T,C or G

<400> SEQUENCE: 329

ttcaggtcga gttggctgca gatttgtggt gcnttctgag ccgtctgtcc tgcgccaaaa     60

ngcttcaaag tattattaaa aacatatgga tccccatgaa gccctactac accaaagttt    120

accaggagat ttggatagga atggggctga tgggcttcat cgtttataaa atccgggctg    180

ctgataagaa gtaaggcttt gaaagcttca gcgcctgctn ctggtcanna ctaaccatan    240

n                                                                    241


<210> SEQ ID NO 330
<211> LENGTH: 241
<212> TYPE: DNA
<213> ORGANISM: Homo sapiens

<400> SEQUENCE: 330

ttttgtgcag atttgtggtg cgttctgagc cgtctgtcct gcgccaagat gcttcaaagt     60

attattaaaa acatatggat ccccatgaag ccctactaca ccaaagttta ccaggagatt    120

tggataggaa tggggctgat gggcttcatc gtttataaaa tccgggctgc tgataaaaga    180

agtaaggctt tgaaagcttc agcgcctgct cctggtcatc actaaccaga tttacttgga    240

g                                                                    241


<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: 1, 9, 41, 60, 61, 119, 124, 132, 139, 141, 153, 168
<223> OTHER INFORMATION: n = A,T,C or G

<400> SEQUENCE: 331

nttttaggna ctttgggctc cagacttcac tggtcttagg nattgaaacc atcacctggn     60

ntgcattcct catgactgag gttaacttaa aacaaaaatg gtaggaaagc tttcctatnc    120

ttcnggtaag anacaaatnt nctttaaaaa aangtggaag gcatgacnta cgtgagaact    180

gcacaaactg gccactgaca aaaatgaccc ccatttgtgt gacttcattg agacacatta    240

c                                                                    241


<210> SEQ ID NO 332
<211> LENGTH: 241
<212> TYPE: DNA
<213> ORGANISM: Homo sapiens

<400> SEQUENCE: 332

tgtgaggaga gggaacatgc tgagaaactg atgaagctgc agaaccaacg aggtggccga     60

atcttccttc aggatatcaa gaaaccagac tgtgatgact gggagagcgg gctgaatgca    120
```

-continued

```
atggagtgtg cattacattt ggaaaaaaat gtgaatcagt cactactgga actgcacaaa    180

ctggccactg acaaaaatga cccccatttg tgtgacttca ttgagacaca ttacctgaat    240

g                                                                    241
```

<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: 44, 52, 60, 98, 104, 108, 124, 126, 190, 198, 206, 214
<223> OTHER INFORMATION: n = A,T,C or G

<400> SEQUENCE: 333

```
caggtacaag cttttttttt tttttttttt tttttttttt ttgnaaatac tntttattgn     60

aaatattcta tcctaaattc catatagcca attaattntt acanaatntt ttgttaattt    120

ttgngngtat aaattttaca aaaataaagg gtatgtttgt tgcacacaac ttacaaataa    180

taataaactn tttattgnaa atattnttta ttgnaaatat tctttatcct aaattccata    240

t                                                                    241
```

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: 10, 16, 22, 24, 49, 158, 159, 237
<223> OTHER INFORMATION: n = A,T,C or G

<400> SEQUENCE: 334

```
tacctgctgn aggggntgaa gncntctctg ctgccccagg catctgcanc ccctgctgct     60

ggttctgccc ctgctgcagc agaggagaag aaagatgaga agaaggagga gtctgaagag    120

tcagatgatg acatgggatt tggccttttt gattaaannc ctgctcccct gcaaataaag    180

ccttttttaca caaaaaaaaa aaaaaaaaaa aaaaaaaaaa aagcttgtac ctgcccnggc    240

g                                                                    241
```

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: 39
<223> OTHER INFORMATION: n = A,T,C or G

<400> SEQUENCE: 335

```
ctatgtgctg ggatgactat ggagacccaa atgtctcana atgtatgtcc cagaaacctg     60

tggctgcttc aaccattgac agttttgctg ctgctggctt ctgcagacag tcaagctgca    120

gctcccccaa aggctgtgct gaaacttgag cccccgtgga tcaacgtgct ccaggaggac    180

tctgtgactc tgacatgcca gggggctcgc agccctgaga gcgactccat tcagtggttc    240

c                                                                    241
```

<210> SEQ ID NO 336
<211> LENGTH: 241
<212> TYPE: DNA
<213> ORGANISM: Homo sapiens -continued

<400> SEQUENCE: 336
taccaaccta tgcagccaag caacctcagc agttcccatc aaggccacct ccaccacaac 60
cgaaagtatc atctcaggga aacttaattc ctgcccgtcc tgctcctgca cctcctttat 120
atagttccct cacttgattt ttttaacctt ctttttgcaa atgtcttcag ggaactgagc 180
taatactttt tttttcttg atgttttctt gaaaagcctt tctgttgcaa ctatgaatga 240
a 241

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: 47, 56, 69, 228
<223> OTHER INFORMATION: n = A,T,C or G

<400> SEQUENCE: 337
ggtactgtat gtagctgcac tacaacagat tcttaccgtc tccacanagg tcatanattg 60
taaatggtna atactgactt ttttttatt cccttgactc aagacagcta acttcatttt 120
cagaactgtt ttaaaccttt gtgtgctggt ttataaaata atgtgtgtaa tccttgttgc 180
tttcctgata ccagactgtt tcccgtggtt ggttagaata tattttgntt tgatgcttat 240
a 241

<210> SEQ ID NO 338
<211> LENGTH: 241
<212> TYPE: DNA
<213> ORGANISM: Homo sapiens

<400> SEQUENCE: 338
aggtacaggt gtgcgctgag ccgagtttac acggaaagga taaagcccat ttagtttctt 60
ctcaaatgga gttttccact ttcctttgaa gtagacagca ttcaccagga tcatcctggt 120
atccccatct acagaacctt caggtaacaa gtttgggatt ttgcctttgg tttgagtctt 180
gacccaggaa ttaatctttt ttctagcttc ttctgcacat tctaggaagt ctactgcctg 240
g 241

<210> SEQ ID NO 339
<211> LENGTH: 241
<212> TYPE: DNA
<213> ORGANISM: Homo sapiens

<400> SEQUENCE: 339
taccgacggc tcctggaggg agagagtgaa gggacacggg aagaatcaaa gtcgagcatg 60
aaagtgtctg caactccaaa gatcaaggcc ataacccagg agaccatcaa cggaagatta 120
gttctttgtc aagtgaatga aatccaaaag cacgcatgag accaatgaaa gtttccgcct 180
gttgtaaaat ctattttccc ccaaggaaag tccttgcaca gacaccagtg agtgagttct 240
a 241

<210> SEQ ID NO 340
<211> LENGTH: 241
<212> TYPE: DNA
<213> ORGANISM: Homo sapiens

<400> SEQUENCE: 340
gtagccctca cacacacatg cccgtaacag gatttatcac aagacacgcc tgcatgtaga 60

-continued ccagacacag ggcgtatgga aagcacgtcc tcaagactgt agtattccag atgagctgca 120
gatgcttacc taccacggcc gtctccacca gaaaaccatc gccaactcct gcgatcagct 180
tgtgacttac aaaccttgtt taaaagctgc ttacatggac ttctgtcctt taaaagcttc 240
c 241

<210> SEQ ID NO 341
<211> LENGTH: 241
<212> TYPE: DNA
<213> ORGANISM: Homo sapiens

<400> SEQUENCE: 341
gtaccgccta ctttcgtctc atgtctccga acttcttgct gatggccgtt ccaacgttgc 60
tgaaagctgc agttgccttt tgccctgcgt gactcagggt ttcatgtgtt ttcttgtagg 120
cagtggtagt ctgcatgtca tgccagcttt tgctgaagtt ctgttttaat tcattcatca 180
ggttcatgcc gagttttgtt ttatctcaac tagatgcctt tctttcgctg acaaaacttg 240
t 241

<210> SEQ ID NO 342
<211> LENGTH: 241
<212> TYPE: DNA
<213> ORGANISM: Homo sapiens

<400> SEQUENCE: 342
gtacattggt gctataaata taaatgctac ttatgaagca tgaaattaag cttcttttt 60 cttcaagttt tttctcttgt ctagcaatct gttaggcttc tgaaccaaga ccaaatgttt 120
acgttcctct gctgcatacc aacgttactc caaacaataa aaatctatca tttctgctct 180
gtgctgagga atggaaaatg aaaccccac cccctgaccc ctaggactat acagtggaaa 240
c 241

<210> SEQ ID NO 343
<211> LENGTH: 241
<212> TYPE: DNA
<213> ORGANISM: Homo sapiens

<400> SEQUENCE: 343
gtacatgtgg tagcagtaat ttttttgaag caactgcact gacattcatt tgagttttct 60
ctcattatca gattctgttc caaacaagta ttctgtagat ccaaatggat taccagtgtg 120
ctacagactt cttattatag aacagcattc tattctacat caaaaatagt ttgtgtaagt 180
tagttttggt taccatctaa aatattttta aatgttcttt acataaaaat ttatgttgtg 240
t 241

<210> SEQ ID NO 344
<211> LENGTH: 241
<212> TYPE: DNA
<213> ORGANISM: Homo sapiens

<400> SEQUENCE: 344
ggtacaaaat tgttggaatt tagctaatag aaaaacatag taaatattta caaaaacgtt 60
gataacatta ctcaagtcac acacatataa caatgtagac aggtcttaac aaagtttaca 120
aattgaaatt atggagattt cccaaaatga atctaatagc tcattgctga gcatggttat 180
caatataaca tttaagatct tggatcaaat gttgtccccg agtcttctgc aatccagtcc 240

-continued t 241

<210> SEQ ID NO 345
<211> LENGTH: 241
<212> TYPE: DNA
<213> ORGANISM: Homo sapiens

<400> SEQUENCE: 345
ggtacgaagc tgagcgcacg ggggttgccc cagcgtggag cctggacctc aaacttcacg 60
gaaaatgctc tctctctttg acaggcttcc agctgtctcc taatttcctg gatgaactct 120
ccccggcgat ttaactgatc ctgaaaagtg gtgagaggac tgaggaagac aaccaggtca 180
gcgttagatc ggcctctgag ggtggtgccc ttgcctgagg agccaccctt taccaccttg 240
g 241

<210> SEQ ID NO 346
<211> LENGTH: 241
<212> TYPE: DNA
<213> ORGANISM: Homo sapiens

<400> SEQUENCE: 346
caggtaccac tgagcctgag atggggatga gggcagagag aggggagccc cctcttccac 60
tcagttgttc ctactcagac tgttgcactc taaacctagg gaggttgaag aatgagaccc 120
ttaggtttta acacgaatcc tgacaccacc atctataggg tcccaacttg gttattgtag 180
gcaaccttcc ctctctcctt ggtgaagaac atcccaagcc agaaagaagt taactacagt 240
g 241

<210> SEQ ID NO 347
<211> LENGTH: 241
<212> TYPE: DNA
<213> ORGANISM: Homo sapiens

<400> SEQUENCE: 347
aggtacatct aaaggcatga agcactcaat tgggcaatta acattagtgt ttgttctctg 60
atggtatctc tgagaatact ggttgtagga ctggccagta gtgccttcgg gactgggttc 120
acccccaggt ctgcggcagt tgtcacagcg ccagccccgc tggcctccaa agcatgtgca 180
ggagcaaatg gcaccgagat attccttctg ccactgttct cctacgtggt atgtcttccc 240
a 241

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: 2, 18, 29, 35, 56, 57, 64, 76, 77, 85, 102, 103, 104,
189, 232
<223> OTHER INFORMATION: n = A,T,C or G

<400> SEQUENCE: 348
angtacttgg caagattnga tgctcttgng ctcantgaca tcattcataa cttgtnngtg 60
tgancagagg aggagnncat catcntgtcc tcattcgtca gnnncctctc ctctctgaat 120
ctcaaacaag ttgataatgg agaaaaattt gaattctcag gattgaggct ggactggttc 180
cgcctacang catacactag cgtggctaag gcccctctgc accctgcatg anaaccctga 240
c 241

-continued

<210> SEQ ID NO 349
<211> LENGTH: 241
<212> TYPE: DNA
<213> ORGANISM: Homo sapiens

<400> SEQUENCE: 349
gcaggtacca tttgtctgac ctctgtaaaa aatgtgatcc tacagaagtg gagctggata 60
atcagatagt tactgctacc cagagcaata tctgtgatga agacagtgct acagagacct 120
gctacactta tgacagaaac aagtgctaca cagctgtggt cccactcgta tatggtggtg 180
agaccaaaat ggtggaaaca gccttaaccc cagatgcctg ctatcctgac taatttaagt 240
c 241

<210> SEQ ID NO 350
<211> LENGTH: 241
<212> TYPE: DNA
<213> ORGANISM: Homo sapiens

<400> SEQUENCE: 350
aggtactgtg gatatttaaa atatcacagt aacaagatca tgcttgttcc tacagtattg 60
cgggccagac acttaagtga aagcagaagt gtttgggtga ctttcctact taaaattttg 120
gtcatatcat ttcaaaacat ttgcatcttg gttggctgca tatgctttcc tattgatccc 180
aaaccaaatc ttagaatcac ttcatttaaa atactgagcg gtattgaata cttcgaagca 240
g 241

<210> SEQ ID NO 351
<211> LENGTH: 241
<212> TYPE: DNA
<213> ORGANISM: Homo sapiens

<400> SEQUENCE: 351
tacagaaatc atttggagcc gttttgagac agaagtagag gctctgtcaa gtcaatactg 60
cattgcagct tggtccactg aagaagccac gcctgagata caaaagatgc actacacttg 120
acccgcttta tgttcgcttc ctctcccctt ctctctcatc aactttatta ggttaaaaca 180
ccacatacag gctttctcca aatgactccc tatgtctggg gtttggttag aattttatgc 240
c 241

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: 10, 28, 29, 49, 54, 59, 72, 127, 148, 150, 160, 166, 182
<223> OTHER INFORMATION: n = A,T,C or G

<400> SEQUENCE: 352
gtaccctgtn gagctgcacc aagattannt ggggccatca tgactgcanc cacnacgang 60
acgcaggcgt gnagtgcatc gtctgacccg gaaacccttt cacttctctg ctcccgaggt 120
gtcctcnggc tcatatgtgg gaaggcanan gatctctgan gagttncctg gggacaactg 180
ancagcctct ggagaggggc cattaataaa gctcaacatc attggcaaaa aaaaaaaaaa 240
a 241

<210> SEQ ID NO 353

-continued

<211> LENGTH: 241
<212> TYPE: DNA
<213> ORGANISM: Homo sapiens

<400> SEQUENCE: 353
aggtaccagt gcattaattt gggcaaggaa agtgtcataa tttgatactg tatctgtttt 60
ccttcaaagt atagagcttt tggggaagga aagtattgaa ctgggggttg gtctggccta 120
ctgggctgac attaactaca attatgggaa atgcaaaagt tgtttggata tggtagtgtg 180
tggttctctt ttggaatttt tttcaggtga tttaataata atttaaaact actataaaaa 240
c 241

<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 354
ngcaggtccg ggcaggtacc aagattcatt ctcatcaaaa actagaaaca gaagggcaaa 60
ttccagtttc cttctgggat tgaatacttt caagtaaggt cttcgacaaa caatcagggg 120
gccaattaat ccactgtaga ggtccttaac ttgatccaca gttgaataat aagcccatgg 180
aatacaagca gaatcctctg ttccagctcc agatctttct gggattttcc atacgtaagt 240
g 241

<210> SEQ ID NO 355
<211> LENGTH: 241
<212> TYPE: DNA
<213> ORGANISM: Homo sapiens

<400> SEQUENCE: 355
ggtacccacc ctaaatttga actcttatca agaggctgat gaatctgacc atcaaatagg 60
ataggatgga cctttttttg agttcattgt ataaacaaat tttctgattt ggacttaatt 120
cccaaaggat taggtctact cctgctcatt cactctttca aagctctgtc cactctaact 180
tttctccagt gtcatagata gggaattgct cactgcgtgc ctagtctttc ttcacttacc 240
t 241

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: 27
<223> OTHER INFORMATION: n = A,T,C or G

<400> SEQUENCE: 356
aggtactgta attgagcatc cggaatntgg agaagtaatt tagctacagg gtgaccaacg 60
caagaacata tgccagttcc tcgtagagat tggactggct aaggacgatc agctgaaggt 120
tcatgggttt taagtgcttg tggctcactg aagcttaagt gaggatttcc ttgcaatgag 180
tagaatttcc cttctctccc ttgtcacagg tttaaaaacc tcacagcttg tataatgtaa 240
c 241

-continued

<210> SEQ ID NO 357
<211> LENGTH: 241
<212> TYPE: DNA
<213> ORGANISM: Homo sapiens

<400> SEQUENCE: 357
ttttgtacca ccgatatgat caaggaaaat tctgcccatt tttatggctg aagttctaaa 60
aacctaattc aaagttcttc catgatccta cactgcctcc aagatggtcc aggctggcat 120
aaggcctgag cggcggtgag atccgcggct gccagcagct tgtcgctctt cagctggtat 180
gaagcccctc ggccacccga gtctccagga cctgcccggg cgccgctcga aagggcgaat 240
t 241

<210> SEQ ID NO 358
<211> LENGTH: 241
<212> TYPE: DNA
<213> ORGANISM: Homo sapiens
<220> FEATURE:
<221> NAME/KEY: misc_feature
<222> LOCATION: 25, 57
<223> OTHER INFORMATION: n = A,T,C or G

<400> SEQUENCE: 358
aggtacgggg agtgggggtg aagcntgttc tctacatagg caacacagcc gcctaantca 60
caaagtcagt ggtcggccgc ttcgaccaac atgtggtgag cattccacgg gcgcatgaag 120
tctgggtgct gtgctcgagt ctctgaatat tttgatagga agcgacaaga aaattcaaac 180
tgctctttgc tgactactgg aaagtgaaaa gatgctcaag tttaccattc aaagaaacca 240
t 241

<210> SEQ ID NO 359
<211> LENGTH: 241
<212> TYPE: DNA
<213> ORGANISM: Homo sapiens

<400> SEQUENCE: 359
gaggtacaca aaaggaatac cttctgagag ccagggagtg aggaaagggg aaggagactt 60
gacgtcaagg gtgcttttga ggaacatgac gggccagcca gcctgcccca actttgaggc 120
cctgctgggc tcttgtgact ataaatatac tgtctatttc taatgcaatc cgtctttcct 180
gaaagatctt gttatctttt actattgaga catgctttca tttttgtggt cctgtttcca 240
a 241

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 360
ngtactctat actaattctg cctttttata cttaattcta aatttctccc ctctaattta 60
caacaaattt tgtgattttt ataagaatct atgcctcccc aattctcaga ttcttctctt 120
ttctccttta tttctttgct taaattcagt ataagctttc ttggtatttt aggcttcatg 180
cacattctta ttcctaaaca ccagcagttc ttcagagacc taaaatccag tataggaata 240
a 241

-continued

<210> SEQ ID NO 361
<211> LENGTH: 241
<212> TYPE: DNA
<213> ORGANISM: Homo sapiens

<400> SEQUENCE: 361
aggtactctc cgtgccccga cactgaacat tatccagcca gatctgccca gtgccagctc 60
ccactttgta cttttcttac tatcctgtct agaatcatgt cttatgattt taacagatat 120
agaaccactc ctagaaaatg ttctttcact ttctcgtttc ctttttaatc tatcatcctg 180
actactgaac ttaaaatctt tttcttccct tttttgtttc tcttttcttt tatcctgttc 240
a 241

<210> SEQ ID NO 362
<211> LENGTH: 241
<212> TYPE: DNA
<213> ORGANISM: Homo sapiens
<220> FEATURE:
<221> NAME/KEY: misc_feature
<222> LOCATION: 17, 23
<223> OTHER INFORMATION: n = A,T,C or G

<400> SEQUENCE: 362
aggtactttt atacctngct tangtcagtg acagatttac caatgacaac acaattttaa 60
aattccaaca catatattac tttgtcctat gaagggcaaa aagtcaatat attttaaatt 120
ttaaaaacag aatggatata atgacctttt tacacatcag tgatatttaa aagacttaaa 180
gagacaatac tatggttgag acactggctt cctattccag ccctaattaa agaaaaaata 240
g 241

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: 4
<223> OTHER INFORMATION: n = A,T,C or G

<400> SEQUENCE: 363
ttangtacta aaaacaaaat cctaattctg ttttaaagag ctgggagatg ttaatcatat 60
gctcagtttt tccacgttat aatttcctaa atgcaaactt ttcaatcagg gcagttcaaa 120
ttcattacat cacagtaaat aacagtagcc aactttgatt ttatgcttat aggaaaaaaa 180
atcctgtaga tataaaaaca gcaaattttg acaaataaaa ctcaaaccat tcatccctaa 240
a 241

<210> SEQ ID NO 364
<211> LENGTH: 241
<212> TYPE: DNA
<213> ORGANISM: Homo sapiens

<400> SEQUENCE: 364
ggtacaagca gttagtcctg aaggcccctg ataagaatgt catcttctcc ccactgagca 60
tctccaccgc cttggccttc ctgtctctgg gggcccataa taccaccctg acagagattc 120
tcaaaggcct caagttcaac ctcacggaga cttctgaggc agaaattcac cagagcttcc 180
agcacctcct gcgcaccctc aatcagtcca gcgatgagct gcagctgagt atgggaaatg 240
c 241

-continued

<210> SEQ ID NO 365
<211> LENGTH: 241
<212> TYPE: DNA
<213> ORGANISM: Homo sapiens

<400> SEQUENCE: 365
cgaggtactg agattacagg catgagccac cacgcccggc caaaaacatt taaaaaatga 60
ctgtccctgc tcaaatactg cagtaggaaa tgtaatttga catatatcac ttccagaaaa 120
aaactttaaa tctttctata aaatgaattt gatacatcat cagcatgaag tgaagttaaa 180
atctcttaca aagtaaattc aggtatatca acaatgagat ccaaaagtat cggttcaaga 240
t 241

<210> SEQ ID NO 366
<211> LENGTH: 241
<212> TYPE: DNA
<213> ORGANISM: Homo sapiens

<400> SEQUENCE: 366
ggcaggtaca catcaaacac ttcattgcct aaatgcaggg acatgcttcc atctgaccac 60
ttgactatcc gagcattgct ttctttaatt tcatttcctt cttcatctcg gcgtatcctc 120
catcttatag tattttctac ctttaatttt aacctggttc taccttcttc atccagcatt 180
tcttcatctt caaattcatc ttcataatac tgggctctac acttgagaaa gttgggcagt 240
t 241

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: 25
<223> OTHER INFORMATION: n = A,T,C or G

<400> SEQUENCE: 367
gcaggtacaa ataattcctg ttgtnacatt tagtggacgc gattatctgt atacctcaaa 60
ttttaattta agaaagtatc acttaaagag catctcattt tctatagatt gaggcttaat 120
tactgaaaag tgactcaacc aaaaagcaca taacctttta aaggagctac acctaccgca 180
gaaagtcaga tgccctgtaa ataactttgg tctttcaaaa tagtggcaat gcttaagata 240
c 241

<210> SEQ ID NO 368
<211> LENGTH: 241
<212> TYPE: DNA
<213> ORGANISM: Homo sapiens

<400> SEQUENCE: 368
tttgtacatt gttaatagtg accctcggag gaaatggatt tctcttctat taaaaactct 60
atggtatata agcattacat aataatgcta cttaaccacc ttttgtctca agaattatca 120
ccaaagtttt ctggaaataa gtccacataa gaattaaata tttaaaaggt gaaatgttcc 180
ttattttaac tttagcaaga tcttttcttt ttcattaaga aacactttaa taattttaaa 240
g 241

<210> SEQ ID NO 369

-continued

<211> LENGTH: 241
<212> TYPE: DNA
<213> ORGANISM: Homo sapiens

<400> SEQUENCE: 369
gcaggtactt tattcttatt tcttatccta tattctgtgt tacagaaaaa ctactaccat 60
aaacaaaaca ccaaccagcc acagcagttg tgtcaagcat gacaattggt ctagtcttca 120
cattttatta gtaagtctat caagtaagag atgaagggtc tagaaaacta gacacaaagc 180
aaccagggtc caaatcacca aggtagatct gtgcttagct aaagggaaac acccgaagat 240
t 241

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 370
ngttcacagt gcccctccgg cctcgccatg aggctcttcc tgtcgctccc ggtcctggtg 60
gtggttctgt cgatcgtctt ggaaggccca gccccagccc aggggacccc agacgtctcc 120
agtgccttgg ataagctgaa ggagtttgga aacacactgg aggacaaggc tcgggaactc 180
atcagccgca tcaaacagag tgaactttct gccaagatgc gggagtggtt ttcagaagac 240
a 241

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: 227
<223> OTHER INFORMATION: n = A,T,C or G

<400> SEQUENCE: 371
ggcaggtcat cttgagcctt gcacatgata ctcagattcc tcacccttgc ttaggagtaa 60
aacaatatac tttacagggt gataataatc tccatagtta tttgaagtgg cttgaaaaag 120
gcaagattga cttttatgac attggataaa atctacaaat cagccctcga gttattcaat 180
gataactgac aaactaaatt atttccctag aaaggaagat gaaaggnagt ggagtgtggt 240
t 241

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: 26, 27, 59
<223> OTHER INFORMATION: n = A,T,C or G

<400> SEQUENCE: 372
aggtacagca aagcgaccct tggtgnnata gatcagacgg aaattctctc ccgtcttgnc 60
aatgctgatg acatccatga atccagcagg gtaggttata tcagttcgga ccttgccatc 120
gattttaatg aaccgctgca tgcaaatctt ctttacttca tctcctgtca gggcatactt 180
aagtctgttc ctcaggaaaa tgatgagggg gagacactct ctcaacttgt ggggaccggt 240

-continued g 241

<210> SEQ ID NO 373
<211> LENGTH: 241
<212> TYPE: DNA
<213> ORGANISM: Homo sapiens

<400> SEQUENCE: 373
tactgaaaca gaaaaaatgt attcccacaa aagctgttac acagcggttt cccgtcccca 60
gaagcagtag aaaatcttag cattccaatg gaaggcatgt atttgtaaaa tattctaaaa 120
tcagctctat agtttccttg tcctctttga taagggatca gacagagggt gtgtcccccct 180 tcagcagcta cccttcttga caaactggtc tccaataata cctttcagaa acttacaaga 240
c 241

<210> SEQ ID NO 374
<211> LENGTH: 241
<212> TYPE: DNA
<213> ORGANISM: Homo sapiens

<400> SEQUENCE: 374
caggtactaa aacttacaat aaatatcaga gaagccgtta gtttttacag catcgtctgc 60
ttaaaagcta agttgaccag gtgcataatt tcccatcagt ctgtccttgt agtaggcagg 120
gcaatttctg ttttcatgat cggaatactc aaatatatcc aaacatcttt ttaaaacttt 180
gatttatagc tcctagaaag ttatgttttt taatagtcac tctactctaa tcaggcctag 240
c 241

<210> SEQ ID NO 375
<211> LENGTH: 241
<212> TYPE: DNA
<213> ORGANISM: Homo sapiens

<400> SEQUENCE: 375
aggtacaaag gaccagtatc cctacctgaa gtctgtgtgt gagatggcag agaacggtgt 60
gaagaccatc acctccgtgg ccatgaccag tgctctgccc atcatccaga agctagagcc 120
gcaaattgca gttgccaata cctatgcctg taaggggcta gacaggattg aggagagact 180
gcctattctg aatcagccat caactcagat tgttgccaat gccaaaggcg ctgtgactgg 240
g 241

<210> SEQ ID NO 376
<211> LENGTH: 241
<212> TYPE: DNA
<213> ORGANISM: Homo sapiens

<400> SEQUENCE: 376
ggtacatttt actttccttc tttcagaatg ctaataaaaa acttttgttt atacttaaaa 60
aaaccataaa tcagacaaac aaaagaaacg attccaacat cacttctgtg atgagaaaag 120
aggcaatgga attcaacata agcaaagaaa actctacctg gaggaaagaa atcgatcagc 180
gaagaaacaa ctcggggctg ctgccagact gcaggccatg cgaggaggag cctcctagag 240
g 241

<210> SEQ ID NO 377
<211> LENGTH: 241
<212> TYPE: DNA

-continued

<213> ORGANISM: Homo sapiens
<220> FEATURE:
<221> NAME/KEY: misc_feature
<222> LOCATION: 234
<223> OTHER INFORMATION: n = A,T,C or G

<400> SEQUENCE: 377
tcctttctgt ccaggtgatt cacagactag acctttctta tcctcctcct agagttttga 60
cttgggactc tagtgttaag atgatgagcc cgtgcatcag gtccttctgc actttggtgg 120
aagtctccca gggtaggttt cctatttgaa acagtggaat catgtttcca gtgataaagt 180
ttaatgacct catccttttt ttttttttc tcatctgcca tttgtgtgtc ttanatgggt 240
t 241

<210> SEQ ID NO 378
<211> LENGTH: 241
<212> TYPE: DNA
<213> ORGANISM: Homo sapiens

<400> SEQUENCE: 378
aggtcagcga tcaggtcctt tatgggcagc tgctgggcag ccccacaagc ccagggccag 60
ggcactatct ccgctgcgac tccactcagc ccctcttggc gggcctcacc cccagcccca 120
agtcctatga gaacctctgg ttccaggcca gccccttggg gaccctggta accccagccc 180
caagccagga ggacgactgt gtctttgggc cactgctcaa cttccccctc ctgcagggga 240
t 241

<210> SEQ ID NO 379
<211> LENGTH: 241
<212> TYPE: DNA
<213> ORGANISM: Homo sapiens

<400> SEQUENCE: 379
tacggagcaa tcgaagaggc atatccacac ttggggtggc tatagggctg gaaaatgctg 60
aagatgactg ctttcactga ggtcaaggat tgtaatattg ccagctttgt aaagccatta 120
aagcagaagt ttcttcagtg atcttctctc taagaaacac catcacctcc atgtgcctta 180
cagaggcccc ctgcgttctg ctgcattgct tttgcgcaat cccttgatga tgaagatggt 240
c 241

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: 24, 25, 26, 34, 36, 56, 113, 129, 137, 184, 185, 208, 210, 237, 240
<223> OTHER INFORMATION: n = A,T,C or G

<400> SEQUENCE: 380
acgtacacgc agaccgacat gggnnnttca ggcntnagat caaactcaaa acctgnaatg 60
atatccactc tctttttctt aagctcaggg aaatattcca agtagaagtc canaaagtca 120
tcggctaana tgcttcngaa tttgaattca tgcacatagg ccttgaaaaa actgtcaaac 180
tgannctgat cacccaccaa gtgggccntn tatgacacaa agcagaaacc tttctcntan 240
g 241

<210> SEQ ID NO 381

<211> LENGTH: 241
<212> TYPE: DNA
<213> ORGANISM: Homo sapiens

<400> SEQUENCE: 381

```
aggtacaact taatggatta gcttttgggt ttaactgaat atatgaagaa attgggtctg    60
tctaaagaga gggtatttca tatggctttt agttcacttg tttgtatttc atcttgattt   120
ttttctttgg aaaataaagc attctatttg gttcagattt ctcagatttg aaaaaggctc   180
tatctcagat gtagtaaatt atttcctttc agtttgtgaa agcaggattt gactctgaaa   240
g                                                                   241
```

<210> SEQ ID NO 382
<211> LENGTH: 241
<212> TYPE: DNA
<213> ORGANISM: Homo sapiens

<400> SEQUENCE: 382

```
gtactgctat aatcaatacg tctgatagac aggtttatcc actatattga ccctacctct    60
aaaaggattg tcataattta tatgctttat gtttacacct atgatacagt tgccttggaa   120
cacaaaattt ttcattgtaa ttaaaaaaag aagagttgtg cagacagaag aaatcaaatc   180
taagaaaatc acaggagtag ataaatactc tagaattcat atacccttgg aagatgggtt   240
t                                                                   241
```

<210> SEQ ID NO 383
<211> LENGTH: 241
<212> TYPE: DNA
<213> ORGANISM: Homo sapiens

<400> SEQUENCE: 383

```
ggcaggtaca aagtcttctc tttgcttttt ataattttaa agcaaataac acatttaact    60
gtatttaagt ctgtgcaaat aatccttcag aagaaatatc caagattctg tttgcagagg   120
tcattttgtc tctcaaagat gattaaatga gtttgtcttc agataaagtg ctcctgtcca   180
gcagaactca aaaggccttc aagctgttca gtaagtgtag ttcagataag actccgtcat   240
a                                                                   241
```

<210> SEQ ID NO 384
<211> LENGTH: 241
<212> TYPE: DNA
<213> ORGANISM: Homo sapiens

<400> SEQUENCE: 384

```
ggtacacaaa atacacttgc aagcttgctt acagagacct gttaaacaaa gaacagacag    60
attctataaa atcagttata tcaacatata aaggagtgtg attttcagtt tgttttttta   120
agtaaatatg accaaactga ctaaataaga aggcaaaaca aaaaattatg cttccttgac   180
aaggcctttg gagtaaacaa aatgctttaa ggctcctggt gaatggggtt gcaaggatga   240
a                                                                   241
```

<210> SEQ ID NO 385
<211> LENGTH: 241
<212> TYPE: DNA
<213> ORGANISM: Homo sapiens

<400> SEQUENCE: 385

```
ggcaggtcta caatggctct gtcccttctg tggaatcgtt acaccaagag gtctcagtcc    60
```

-continued tggtccctga ccccacagtg agctgtttag atgatccttc acatcttcct gatcaactgg 120
aagacactcc aatcctcagt gaagactctc tggagccctt caactctctg gcaccaggta 180
ggtttggagg ctatgtccct ttaacttatc catgcagagt agccaaactt tacctgaaag 240
a 241

<210> SEQ ID NO 386
<211> LENGTH: 241
<212> TYPE: DNA
<213> ORGANISM: Homo sapiens

<400> SEQUENCE: 386
aggtaccttt ttcctctcca aaggaacagt ttctaaagtt ttctgggggg aaaaaaaact 60
tacatcaaat ttaaaccata tgttaaactg catattagtt gtgttacacc aaaaaattgc 120
ctcagctgat ctacacaagt ttcaaagtca ttaatgcttg atataaattt actcaacatt 180
aaattatctt aaattattaa ttaaaaaaaa aactttctaa gggaaaaata aacaaatgta 240
g 241

<210> SEQ ID NO 387
<211> LENGTH: 241
<212> TYPE: DNA
<213> ORGANISM: Homo sapiens

<400> SEQUENCE: 387
accccactgg ccgctgtgga gtatctccac tctcccctcg tgagggccgc tcccaccgac 60
cagtcgaact ttcgtaaatg gagttaatgt gtttccactc cccttttccc ctttctggcc 120
ttttggtcca gaatttcctg gccttccggc atatcctggg agtcctcgac ttccaggaaa 180
gccaattgct ccccgatcac ctttaagacc cggaggacct attggacctg gaaatcctcg 240
t 241

<210> SEQ ID NO 388
<211> LENGTH: 241
<212> TYPE: DNA
<213> ORGANISM: Homo sapiens

<400> SEQUENCE: 388
tttgtactct tgtccacagc agagacattg agtataccat tggcatcaat gtcaaaagtg 60
acttcaatct gaggaacacc tcggggtgca ggaggtatgc ctgtgagttc aaacttgcca 120
agcaggttgt tatcctttgt catggcacgc tcgccttcat aaacctgaat aagtacacca 180
ggctggttgt cagaataggt agtgaaggtc tgtgtctgct tggtaggaat ggtggtatta 240
c 241

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: 6, 28, 38, 43
<223> OTHER INFORMATION: n = A,T,C or G

<400> SEQUENCE: 389
tacctntgtt agtgagcacc ttgtcttntg tgcttatntc ttnaagataa atacatggaa 60
ggatgtgaaa atcggaacac caactatgtg tctcactgca tctaagtgaa gcagccacag 120

-continued

```
ctgtgagagt tttcaaagca gaaagatgct gatgtgacct ctggaattca gacatactga    180

gctatgggtc agaagtgttt tacttaaaaa gcaaacaatc cccaggaaat actgaatagg    240

a                                                                    241


<210> SEQ ID NO 390
<211> LENGTH: 241
<212> TYPE: DNA
<213> ORGANISM: Homo sapiens

<400> SEQUENCE: 390

gcaggtacat ccacatgttc ctccaaatga cgtttggggt cctgcttgcc aacattcttt     60

attgccagct gttcaggtgt catcttatct tcttcttcta cagccttatt gtaattcttg    120

gctaattcca acatctcttt taccactgat tcattgcgtt tacaatgttc actgtagtcc    180

tgaagtgtca aaccttccat ccaactcttc ttatgcaaat ttagcaacat cttctgttcc    240

a                                                                    241


<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: 2, 10, 14, 22, 23, 25, 40, 50, 57, 59, 65, 71, 72, 73,
      76, 77, 78, 82, 83, 84, 95, 98, 100, 101, 102, 107, 148, 152,
      155, 158, 163, 169, 170, 172, 180, 182, 192, 193, 198, 200,
      202, 203, 206, 207, 208, 213, 214, 218, 220, 224, 225
<223> OTHER INFORMATION: n = A,T,C or G
<220> FEATURE:
<221> NAME/KEY: misc_feature
<222> LOCATION: 235, 236
<223> OTHER INFORMATION: n = A,T,C or G

<400> SEQUENCE: 391

cnggcacaan cttntgtttt tnntnttttt tttttttttn tctttatttn tttttantnt     60

taaanaaaaa nnntannnaa annngggttt aaatnctntn nncagancat taaaactgaa    120

ggggaaaaaa aaaccaaaaa cgagcttntt anttnacntg ggnttgggnn gntgctgatn    180

tnaagaagca anntttanan cnngcnnnat ganngagngn tcannttgaa atttnnaccc    240

t                                                                    241


<210> SEQ ID NO 392
<211> LENGTH: 241
<212> TYPE: DNA
<213> ORGANISM: Homo sapiens

<400> SEQUENCE: 392

gaggtactaa atggtatcct tagattaaaa ttttgtgctt gataacagct gttttttcta     60

cattagaaat aagatgccac acaaggaact acattccaga tttaaagaaa tgaaaggata    120

ccattagtgt gtataacaga ttattgttca tacttgtaaa gcatcttatg tcattgagaa    180

tataaagaac agtgccttag aagacagtga aaggtaagct ctagcttaat gtctatgatt    240

t                                                                    241


<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: 57, 75, 224
```

-continued

<223> OTHER INFORMATION: n = A,T,C or G

<400> SEQUENCE: 393
ggcaggtaca taagcataat cagttatgga cagcttcttg tataaattgc tattcancaa 60
tacataaact gcctnaaaga tttatgctta caggtagaca ttcaatttac caataaaaca 120
gcatgttctg aaaatatggg cacattttaa aacatattaa gacagttctg ttaaccataa 180
tagtcccaca gtatgactga gtaataagaa tctacttcaa aagnaaaaaa aaaattaatc 240
a 241

<210> SEQ ID NO 394
<211> LENGTH: 241
<212> TYPE: DNA
<213> ORGANISM: Homo sapiens

<400> SEQUENCE: 394
aggtacagca gcagtagatg gctgcaacaa ccttcctcct accccagccc agaaaatatt 60
tctgccccac cccaggatcc gggaccaaaa taaagagcaa gcaggccccc ttcactgagg 120
tgctgggtag ggctcagtgc cacattactg tgctttgaga aagaggaagg ggatttgttt 180
ggcactttaa aaatagagga gtaagcagga ctggagaggc cagagaagat accaaaattg 240
g 241

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: 1, 5, 8, 9, 14, 24, 26, 28, 32, 42, 54
<223> OTHER INFORMATION: n = A,T,C or G

<400> SEQUENCE: 395
nggcnggnnc caanatatga aatntnanta tnatacatga tnaaaagctt tatntatttt 60
agtgagtaat taagtttaca ctgtgaataa ggattaattc ccagatgacc atctacagtt 120
actaccacat agagggtata cacggatgga tcgattacaa gaatataaaa cttattttcc 180
ttcctgtatc cacatttctt tgcaatgtga atttgcaggc cctctcaaga agtggagtct 240
a 241

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: 26
<223> OTHER INFORMATION: n = A,T,C or G

<400> SEQUENCE: 396
gaggtacacc ttgaatgaca atgctnggag cccccctgtg gtcatcgacg cctccactgc 60
cattgatgca ccatccaacc tgcgtttcct ggccaccaca cccaattcct tgctggtatc 120
atggcagccg ccacgtgcca ggattaccgg ctacatcatc aagtatgaga agcctgggtc 180
tcctcccaga gaagtggtcc ctcggccccg ccctggtgtc acagaggcta ctattactgg 240
c 241

<210> SEQ ID NO 397
<211> LENGTH: 241

-continued

<212> TYPE: DNA
<213> ORGANISM: Homo sapiens
<220> FEATURE:
<221> NAME/KEY: misc_feature
<222> LOCATION: 90
<223> OTHER INFORMATION: n = A,T,C or G

<400> SEQUENCE: 397
ggcaggtacc agcaggggga tgtgtttctg gggaattgtg gctctggaag cttcacggtt 60
tcccagaatg tggaaaatat atctgtgcan gatagaaatc ctgcccagag gctgtttctg 120
tctcatttga gctctccttc atgtggcaga gctgactgtg gcggtttagg agcctacatt 180
ttagaaaagc ttacctcaaa gttctgcatt gagcctgagc actggaaagg agataaaata 240
a 241

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: 3, 11, 22, 27, 38, 41, 53, 59, 63, 69, 77, 78, 94, 131,
133, 137, 149, 154, 162, 166, 167, 172, 175, 176, 179, 191, 230
<223> OTHER INFORMATION: n = A,T,C or G

<400> SEQUENCE: 398
gangtgacca ngacatcacc tnacacntgg aaagcganga nttgaatggt gcntacaang 60
ccntacccnt tgcccannac ctgaacgcgc cttntgattg ggacagccgt gggaaggaca 120
gttatgaaac nantcanctg gatgaccana gtgntgaaac cnacanncac angcnntcna 180
cattatataa ncggaaagct aatgatgaga gcaatgatca ttccgatgtn attgatagtc 240
a 241

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: 212, 226
<223> OTHER INFORMATION: n = A,T,C or G

<400> SEQUENCE: 399
cagagtgaga tgggagtggg agggccaatc tgatacagaa gggggtgaag ggtagggccc 60
ctgagcagcc caccccttac cctgacgaag gcaatcctcc tctggaatgt ctcttccctc 120
ttcagtctgg gttctgcctc agccacgaac tgggaaggag tgaggaacat cccaacggca 180
atgagagtat cccagtgact ccaaacagga angaatcagt gttcanaaag tcagggccct 240
t 241

<210> SEQ ID NO 400
<211> LENGTH: 241
<212> TYPE: DNA
<213> ORGANISM: Homo sapiens

<400> SEQUENCE: 400
ggtactcttg ctcttttagc tagagtgtat gtgaaaataa agaaatacat cattgtattc 60
acaaccatgt gtcttcattt ataacttttt gtttaaaaaa tttttagttc aagtttagtt 120
cattgatatt atcctctgaa tgcagttaag gctgggcaga aattctactc atgtgacatc 180
tgccacaggt ctattttgaa gcttttcttc taatgggcaa tgtttgtcct taccaggatt 240

-continued t 241

<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: 1, 2
<223> OTHER INFORMATION: n = A,T,C or G

<400> SEQUENCE: 401
nncaggtact ttgtagagca gagagaggct ttggttcctc ctttcttcaa tcacgtggag 60
atgtgtcatc acctgggatt tcatctgggc cgccttttct gggtcaacag ccaacacatg 120
ctggtaatga cggatggtat gtaagcgatc tttgttctca gcacggacat aacgccgtaa 180
ggcctggaga atgcgatgag gccgtggcgg gtcagactgc aaggcagcca ggtagttctc 240
c 241

<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: 26, 27
<223> OTHER INFORMATION: n = A,T,C or G

<400> SEQUENCE: 402
ggcaggtcca aaaaaaacct aaaaanngtt tcaggaatgt agagaaatat ccaacttaaa 60
tagcgaaaaa gtgcaccata attactgctg cactgcagtc atttctgcaa ttcccatgtt 120
tcttaaataa ctatcttgtc agataacaca caatataaag agcaattatg aaaaacagac 180
atttacatat acttctaaag tcttattggg aatatcctgt ttggccattg ggataaccaa 240
t 241

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: 49
<223> OTHER INFORMATION: n = A,T,C or G

<400> SEQUENCE: 403
aggtgttaac tacccgctcc gagacgggat tgatgacgag tcctatgang ccattttcaa 60
gccggtcatg tccaaagtaa tggagatgtt ccagcctagt gcggtggtct tacagtgtgg 120
ctcagactcc ctatctgggg atcggttagg ttgcttcaat ctaactatca aaggacacgc 180
caagtgtgtg gaatttgtca agagctttaa cctgcctatg ctgatgctgg gaggcggtgg 240
t 241

<210> SEQ ID NO 404
<211> LENGTH: 241
<212> TYPE: DNA
<213> ORGANISM: Homo sapiens

<400> SEQUENCE: 404
caggtactgc aacccataaa atactgtttc ctcatatttc accttcctta atttggagtt 60

-continued

```
ttctgtcttc ttttcacggc attcaaagta ggaataaact ttgcttgtgt tgggtggata    120

ttgtttatag tgagtaacct tgtaggagtc ggtggccagg aggatgttga actcggcttc    180

tgccgcagga ttcatctcgg gccggaggac aaggggcccg cgcgccgcga gctccctgac    240

c                                                                    241
```

<210> SEQ ID NO 405
<211> LENGTH: 266
<212> TYPE: DNA
<213> ORGANISM: Homo sapiens

<400> SEQUENCE: 405

```
ttctgggctg gggagtggag agaaagaagt tgcagggctt acaggaaatc ccagagcctg     60

aggttttctc ccagatttga gaactctaga ttctgcatca ttatctttga gtctatattc    120

tcttgggctg taagaagatg aggaatgtaa taggtctgcc ccaagccttt catgccttct    180

gtaccaagct tgtttccttg tgcatccttc ccaggctctg gctgcccctt attggagaat    240

gtgatttcca agacaatcaa tccaca                                         266
```

<210> SEQ ID NO 406
<211> LENGTH: 231
<212> TYPE: DNA
<213> ORGANISM: Homo sapiens

<400> SEQUENCE: 406

```
ttggtgaaga accattcctc ggcatccttg cggttcttct ctgccatctt ctcatactgg     60

tcacgcatct cgttcagaat gcggctcagg tccacgccag gtgcagcgtc catctccaca    120

ttgacatctc cacccacctg gcctctcagg gcattcatct cctcctcgtg gttcttcttc    180

aggtaggcca gctcctcctt caggctctca atctgcatct ccaggtcagc t             231
```

<210> SEQ ID NO 407
<211> LENGTH: 266
<212> TYPE: DNA
<213> ORGANISM: Homo sapiens

<400> SEQUENCE: 407

```
cagcatcatt gtttataatc agaaactctg gtccttctgt ctggtggcac ttagagtctt     60

ttgtgccata atgcagcagt atggagggag gattttatgg agaaatgggg atagtcttca    120

tgaccacaaa taaataaagg aaaactaagc tgcattgtgg gttttgaaaa ggttattata    180

cttcttaaca attctttttt tcagggactt ttctagctgt atgactgtta cttgaccttc    240

tttgaaaagc attcccaaaa tgctct                                         266
```

<210> SEQ ID NO 408
<211> LENGTH: 261
<212> TYPE: DNA
<213> ORGANISM: Homo sapiens

<400> SEQUENCE: 408

```
ctgtgtcagc gagcctcggt acactgattt ccgatcaaaa gaatcatcat ctttaccttg     60

acttttcagg gaattactga actttcttct cagaagatag ggcacagcca ttgccttggc    120

ctcacttgaa gggtctgcat ttgggtcctc tggtctcttg ccaagtttcc cagccactcg    180

agggagtaat atctggaggg caaagaagag acttatgtta ttgttgaacc tccagccaca    240

gggaggagca tgggcatggg t                                              261
```

-continued

<210> SEQ ID NO 409
<211> LENGTH: 266
<212> TYPE: DNA
<213> ORGANISM: Homo sapiens

<400> SEQUENCE: 409
gctgacagta atacactgcc acatcttcag cctgcaggct gctgatggtg agagtgaaat 60
ctgtcccaga cccgctgcca ctgaatcggt cagggatccc ggattcccgg gtagatgccc 120
agtaaatgag cagtttagga ggctgtcctg gtttctgctg gtaccaagct aagtagttct 180
tattgttgga gctgtctaaa acactctggc tggtcttgca gttgatggtg gccctctcgc 240
ccagagacac agccagggag tgtgga 266

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: 9, 17, 24, 26, 65, 97, 98, 99, 100, 103, 105, 106, 107, 108, 120, 121, 123, 142, 145, 149, 162, 177
<223> OTHER INFORMATION: n = A,T,C or G

<400> SEQUENCE: 410
caaaaggtnc tttttgntca aaancnattt ttattccttg atatttttct tttttttttt 60
tttgnggatg gggacttgtg aatttttcta aaggggnnnn ttnannnngg aagaaaaccn 120
ngntccggtt ccagccaaac cngtngctna ctttccacct tntttccacc tccctcnggt 180
t 181

<210> SEQ ID NO 411
<211> LENGTH: 261
<212> TYPE: DNA
<213> ORGANISM: Homo sapiens

<400> SEQUENCE: 411
gcccctgcag tacttggccg atgtggacac ctctgatgag gaaagcatcc gggctcacgt 60
gatggcctcc caccattcca agcggagagg ccgggcgtct tctgagagtc agggtctagg 120
tgctggagtg cgcacggagg ccgatgtaga ggaggaggcc ctgaggagga agctggagga 180
gctggccagc aacgtcagtg accaggagac ctcgtccgag gaggaggaag ccaaggacga 240
aaaggcagag cccaacaggg a 261

<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: 1, 6, 53, 79, 91, 96, 114, 132
<223> OTHER INFORMATION: n = A,T,C or G

<400> SEQUENCE: 412
nttttntctt tacaattcag tcttcaacaa cttgagagct ttcttcatgt tgncaagcaa 60
cagagctgta tctgcaggnt cgtaagcata nagacngttt gaatatcttc cagngatatc 120
ggctctaact gncagagatg ggtcaacaaa cataatcctg gggacatact g 171

<210> SEQ ID NO 413
<211> LENGTH: 266
<212> TYPE: DNA
<213> ORGANISM: Homo sapiens -continued

<400> SEQUENCE: 413
ttaggaccaa agatagcatc aactgtattt gaaggaactg tagtttgcgc attttatgac 60
atttttataa agtactgtaa ttctttcatt gaggggctat gtgatggaga cagactaact 120
cattttgtta tttgcattaa aattattttg ggtctctgtt caaatgagtt tggagaatgc 180
ttgacttgtt ggtctgtgta aatgtgtata tatatatacc tgaatacagg aacatcggag 240
acctattcac tcccacacac tctgct 266

<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: 86, 153, 162, 178, 184, 205
<223> OTHER INFORMATION: n = A,T,C or G

<400> SEQUENCE: 414
tttgccataa ttgagtgaaa agtggcagat ggcattaact ctgctccgct tcaagctggc 60
tccatgacca ctcaaggcct ccccancctg ttcgtcaagt tgtcctcaag tccaagcaat 120
ggaatccatg tgtttgcaaa aaaagtgtgc tanttttaag gnctttcgta taagaatnaa 180
tganacaatt ttcctaccaa aggangaaca aaaggataaa tataatacaa aatatatgta 240
tatggttgtt tgacaaatta tataac 266

<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: 37, 103, 223
<223> OTHER INFORMATION: n = A,T,C or G

<400> SEQUENCE: 415
cctccatcca gtctattaat tgttgccggg aagctanagt aagtagttcg ccagttaata 60
gtttgcgcaa cgttgttgcc attgctacag gcatcgtggt gtnacgctcg tcgattggta 120
tggcttcatt cagctccggt tcccaacgat caaggcgagt tacatgatcc cccatgttgt 180
gcaaaaaagc ggttagctcc ttcggtcctc cgatcgttgt canaagtaag ttggccgcag 240
tgttatcact catggttatg gcagca 266

<210> SEQ ID NO 416
<211> LENGTH: 878
<212> TYPE: DNA
<213> ORGANISM: Homo sapiens

<400> SEQUENCE: 416
cctgacgata gccatggctg taccacttaa ctatgattct attccaactg ttcagaatca 60
tatcacaaaa tgacttgtac acagtagttt acaacgactc ccaagagagg aaaaaaaaaa 120
aaaaagacgc ctcaaaattc actcaacttt tgagacagca atggcaatag gcagcagaga 180
agctatgctg caactgaggg cacatatcat tgaagatgtc acaggagttt aagagacagg 240
ctggaaaaaa tctcatacta agcaaacagt agtatctcat accaagcaaa accaagtagt 300
atctgctcag cctgccgcta acagatctca caatcaccaa ctgtgcttta ggactgtcac 360
caaagtcaga ttcggtgcta accaggtggc atctatgatc aacgtcgccc ctcttattta 420

-continued

```
acaaagggct ctgaaggagg tgttctccaa gcaacaagga gactgcttca gtacaagact    480

ttgcaccttg aattcaattg catcaagtgt ggatagcaaa ataagtatct taccattgaa    540

atatgtgttc agcctaagat tttacccacc agcagaacaa aagtgagggt gagagggatg    600

ggccagtgag gggatggggg agaaaaaaaa atcacaggat taccaccaaa gccttgtttt    660

aaaagggctc ccttcactat tcaggaaggg aagtggaagg agaaattaac caattcctgc    720

cacagcagcc ctttttggct gcttccacaa tagatacttt atggagtggc acagccaacc    780

ctatctgtga cctgccctgc ggataaacac agccaagcag gtttaattag atcaaagaca    840

caaagggcta ttccctcctt tcataacaac gcagacct                            878


<210> SEQ ID NO 417
<211> LENGTH: 514
<212> TYPE: DNA
<213> ORGANISM: Homo sapiens

<400> SEQUENCE: 417

ttctgacttc tagaagacta aggctggtct gtgtttgctt gtttgcccac ctttggctga     60

tacccagaga acctgggcac ttgctgcctg atgcccaccc ctgccagtca ttcctccatt    120

cacccagcgg gaggtgggat gtgagacagc ccacattgga aaatccagaa aaccgggaac    180

agggatttgc ccttcacaat tctactcccc agatcctctc ccctggacac aggagaccca    240

cagggcagga ccctaagatc tggggaaagg aggtcctgag aaccttgagg tacccttaga    300

tccttttcta cccactttcc tatggaggat tccaagtcac cacttctctc accggcttct    360

accagggtcc aggactaagg cgttttctcc atagcctcaa cattttggga atcttccctt    420

aatcaccctt gctcctcctg ggtgcctgga agatggactg gcagagacct ctttgttgcg    480

ttttgtgctt tgatgccagg aatgccgcct agtt                                514


<210> SEQ ID NO 418
<211> LENGTH: 352
<212> TYPE: DNA
<213> ORGANISM: Homo sapiens

<400> SEQUENCE: 418

ctgcaccagc gattaccagt ggcattcaaa tactgtgtga ctaaggattt tgtatgctcc     60

ccagtagaac cagaatcaga caggtatgag ctagtcaaca gcaagtcttt gttggattcg    120

agtaggctca ggatctgctg aaggtcggag gagttagtcc ccgcaatcaa gagcctgtct    180

tcctgaagcc cttggtgata ttttgccact cagccaagaa tgaggatgca tccttcagat    240

tctctatgtc ccgaacctgg aacccatcca cgccagcttg cagccaaaac tccagagcat    300

ccttcacctt ggtggaaaaa aaaaaaaaaa aaaaaaaaaa aaaaaaaaaa aa            352


<210> SEQ ID NO 419
<211> LENGTH: 344
<212> TYPE: DNA
<213> ORGANISM: Homo sapiens

<400> SEQUENCE: 419

ctggacacca taatcccttt taagtggctg gatggtcaca cctctcccat tgacaagctg     60

ggttaagtca ataggttgac taggatcaac acgacccaaa tcaataagat actgcagtct    120

attgagactc aaaggcttat actggcgtct gaaactatgt ccttcgttaa acccgtattt    180

tgggattcgg atgtaaaatg gagtctggcc tccctcaaag cccaagcggg gccgggttcc    240

tctttgcctt tctcctttat ggcctctgcc acattttcta cctcttctcc gacctcttgg    300
```

-continued tcttctctcc ggtttcttgg agccgggatt cggctttaag ttgg 344

<210> SEQ ID NO 420
<211> LENGTH: 935
<212> TYPE: DNA
<213> ORGANISM: Homo sapiens

<400> SEQUENCE: 420
cgaaagtcaa cgttaagggg ctcaggtgaa ccatgatgat gaccttctgt tgactttgaa 60
atattggctc ttgtgggtga caaaagccag acaagctgtg gctgtggtcc gattttaaga 120
cgaggttctc aaagatccaa aggagggaaa gggtattgga aacactgtgt atcatctgag 180
acacacgtgt cctcatgatc ttaaatgcct actttaaagc cacctaatac tgcccttcat 240
tgtggtcaga agagatttct acaaaagcac tcagaattct ggaggcagtt gtgattttgc 300
catgtggcag ttggtttgtg gagttgggca ggtgtgaaag ggtaaaactc cacttctgaa 360
tgctgcttct gccccctggg acccagcaca ttgttagacc atcttcttga ctgaaaattc 420
tctcctgatg ctgagccctg caccaccacc ttccttttcc taactatgaa ttgatggcaa 480
agtccactca aaacaaccag ttaagtgctc acgagagagt agtcaagcac ctccagaaag 540
aaaccgggtt tttgttcaca tagcaggaag tgactccctg ggtggtaatt tatcttggaa 600
acacaggtag attggcagaa aaacgggaac atgtaggtac cgcgatgttg gtgcatgtcc 660
attactttgg gataggcttt ctcagtcttt cctcaaatga tagttgagcc agttttccag 720
tggcaattct gagtgacttg cgcttgtctt atggtgtggt caagggacgt tcagaactac 780
ggaaaacttt tactgaaaca gcgaagcaga gtataccggc atgagaggga agatgaacac 840
tcacctatgt accactcttt gacaataaat atagtatttc tcaaaaaaaa aaaaaaaaaa 900
agtaaaaaaa ctgaaatcgc aagtcaaaaa atcca 935

<210> SEQ ID NO 421
<211> LENGTH: 745
<212> TYPE: DNA
<213> ORGANISM: Homo sapiens

<400> SEQUENCE: 421
ggcttcgagc ggccgcccgg gcaggtccta gatgtcattt gggacccttc acaaccattt 60
tgaagccctg tttgagtccc tgggatatgt gagctgtttc tatgcataat ggatattcgg 120
ggttaacaac agtcccctgc ttggcttcta ttctgaatcc ttttctttca ccatggggtg 180
cctgaagggt ggctgatgca tatggtacaa tggcacccag tgtaaagcag ctacaattag 240
gagtggatgt gttctgtagc atcctattta aataagccta ttttatcctt tggcccgtca 300
actctgttat ctgctgcttg tactggtgcc tgtacttttc tgactctcat tgaccatatt 360
ccacgaccat ggttgtcatc cattacttga tcctacttta catgtctagt ctgtgtggtt 420
ggtggtgaat aggcttcttt ttacatggtg ctgccagccc agctaattaa tggtgcacgt 480
ggacttttag caagcgggct cactggaaga gactgaacct ggcatggaat tcctgaagat 540
gtttggggtt tttttctttc ttaatcgaaa gttaacattg tctgaaaagt tttgttagaa 600
ctactgcgga acctcaaaat cagtagattt ggaagtgatt caaagctaaa ctttttcctt 660
ggccctcctt gtgttctaat tgcttgcaag tgtaatacta ggatgtccaa gatgccagtt 720
tttgcttctt tgttagttgt cagac 745

<210> SEQ ID NO 422

-continued

<211> LENGTH: 764
<212> TYPE: DNA
<213> ORGANISM: Homo sapiens

<400> SEQUENCE: 422
gagttcagta gcaaagtcac acctgtccaa ttccctgagc tttgctcact cagctaatgg 60
gatggcaaag gtggtggtgc tttcatcttc aggcagaagc ctctgcccat ccccctcaag 120
ggctgcaggc ccagttctca tgctgccctt gggtgggcat ctgttaacag aggagaacgt 180
ctgggtggcg gcagcagctt tgctctgagt gcctacaaag ctaatgcttg gtgctagaaa 240
catcatcatt attaaacttc agaaaagcag cagccatgtt cagtcaggct catgctgcct 300
cactgcttaa gtgcctgcag gagccgcctg ccaagctccc cttcctacac ctggcacact 360
ggggtctgca caaggctttg tcaaccaaag acagcttccc ccttttgatt gcctgtagac 420
tttggagcca agaaacactc tgtgtgactc tacacacact tcaggtggtt tgtgcttcaa 480
agtcattgat gcaacttgaa aggaaacagt ttaatggtgg aaatgaacta ccatttataa 540
cttctgtttt tttattgaga aaatgattca cgaattccaa atcagattgc caggaagaaa 600
taggacgtga cggtactggg ccctgtgatt ctcccagccc ttgcagtccg ctaggtgaga 660
ggaaaagctc tttacttccg cccctggcag ggacttctgg gttatgggag aaaccagaga 720
tgggaatgag gaaaatatga actacagcag aagcccctgg gcag 764

<210> SEQ ID NO 423
<211> LENGTH: 1041
<212> TYPE: DNA
<213> ORGANISM: Homo sapiens

<400> SEQUENCE: 423
ctcagagagg ttgaaagatt tgcctacgaa agggacagtg atgaagctaa gctctagatc 60
caggatgtct gacttcaaat tgaaactccc aaagtaatga gtttggaagg gtggggtgtg 120
gcctttccag gatgggggtc ttttctgctc ccagcggata gtgaaacccc tgtctgcacc 180
tggttgggcg tgttgctttc ccaaaggttt ttttttagg tccgtcgctg tcttgtggat 240
taggcattat tatctttact ttgtctccaa ataacctgga gaatggagag agtagtgacc 300
agctcagggc cacagtgcga tgaggaccat cttctcacct ctctaaatgc aggaagaaac 360
gcagagtaac gtggaagtgg tccacaccta ccgccagcac attgtgaatg acatgaaccc 420
cggcaacctg cacctgttca tcaatgccta caacaggtat tgggatgtag ttcagccaca 480
tcattgctat tttatgaggtg tcttctgtag atccgaaatg tgggacagat gagagggaga 540
gtataaaatg agcggaagag gcaggctctg agtttgagca aatagattaa taggacaggt 600
gtccccagga aggacacctg gcctgtaagc tggttcctgg cattcagctc gccttgcagg 660
gatctgaaca aacactccag accactgggg gtgcagacgt gagagggacg cagtcgcaca 720
ctcagagggt tgagagtaaa tatgtgtgcc cgctgctgac cttcacgaaa ggccaaatgt 780
aagaagagct aagtgagaga gcagcaaagc actcctggag gccggggata atccaggcag 840
gcttctggga gtttgtcatt ccaaggataa ggaggacctg aacatggcct ttgcctaagg 900
cgtggccctc tcaaccagca ctaggtgctt atctggagct cagctagggg aggagacagc 960
tcagggccat tggtgtcagc cagagactct gtaatcttcc agggagctcg ctcaacctgc 1020
tgagctcgct ctgccacgca c 1041

<210> SEQ ID NO 424
<211> LENGTH: 1288

-continued

<212> TYPE: DNA
<213> ORGANISM: Homo sapiens

<400> SEQUENCE: 424
ctaagaactg agacttgtga cacaaggcca acgacctaag attagcccag ggttgtagct 60
ggaagaccta caacccaagg atggaaggcc cctgtcacaa agcctaccta gatggataga 120
ggacccaagc gaaaaaggta tctcaagact aacggccgga atctggaggc ccatgaccca 180
gaacccagga aggatagaag cttgaagacc tggggaaatc ccaagatgag aaccctaaac 240
cctacctctt ttctattgtt tacacttctt actcttagat atttccagtt ctcctgttta 300
tctttaagcc tgattctttt gagatgtact ttttgatgtt gccggttacc tttagattga 360
cagtattatg cctgggccag tcttgagcca gctttaaatc acagctttta cctatttgtt 420
aggctatagt gttttgtaaa cttctgtttc tattcacatc ttctccactt gagagagaca 480
ccaaaatcca gtcagtatct aatctggctt ttgttaactt ccctcaggag cagacattca 540
tataggtgat actgtatttc agtcctttct tttgacccca gaagccctag actgagaaga 600
taaaatggtc aggttgttgg ggaaaaaaaa gtgccaggct ctctagagaa aaatgtgaag 660
agatgctcca ggccaatgag aagaattaga caagaaatac acagatgtgc cagacttctg 720
agaagcacct gccagcaaca gcttccttct ttgagcttag tccatccctc atgaaaaatg 780
actgaccact gctgggcagc aggagggatg atgaccaact aattcccaaa ccccagtctc 840
attggtacca gccttgggga accacctaca cttgagccac aattggtttt gaagtgcatt 900
tacaagtttc tggcatcact accactactg attaaacaag aataagagaa cattttatca 960
tcatctgctt tattcacata aatgaagttg tgatgaataa atctgctttt atgcagacac 1020
aaggaattaa gtggcttcgt cattgtcctt ctacctcaaa gataatttat tccaaaagct 1080
aagataaatg gaagactctt gaacttgtga actgatgtga aatgcagaat ctcttttgag 1140
tctttgctgt ttggaagatt gaaaaatatt gttcagcatg ggtgaccacc agaaagtaat 1200
cttaagccat ctagatgtca caattgaaac aaactgggga gttggttgct attgtaaaat 1260
aaaatatact gttttgaaaa aaaaaaac 1288

<210> SEQ ID NO 425
<211> LENGTH: 446
<212> TYPE: DNA
<213> ORGANISM: Homo sapiens

<400> SEQUENCE: 425
ccacttaaag ggtgcctctg ccaactggtg gaatcatcgc cacttccagc accacgccaa 60
gcctaacatc ttccacaagg atcccgatgt gaacatgctg cacgtgtttg ttctgggcga 120
atggcagccc atcgagtacg gcaagaagaa gctgaaatac ctgccctaca atcaccagca 180
cgaatacttc ttcctgattg ggccgccgct gctcatcccc atgtatttcc agtaccagat 240
catcatgacc atgatcgtcc ataagaactg ggtggacctg gcctgggccg tcagctacta 300
catccggttc ttcatcacct acatcccttt ctacggcatc ctgggagccc tccttttcct 360
caacttcatc aggttcctgg agagccactg gtttgtgtgg gtcacacaga tgaatcacat 420
cgtcatggag attgaccagg aggacc 446

<210> SEQ ID NO 426
<211> LENGTH: 874
<212> TYPE: DNA
<213> ORGANISM: Homo sapiens -continued

<400> SEQUENCE: 426 ttttttttt ttttttttt ttttttcaat taaagatttg atttattcaa gtatgtgaaa 60
acattctaca atggaaactt ttattaaatg ctgcatgtac tgtgctatgg accacgcaca 120
tacagccatg ctgtttcaga agacttgaaa tgccattgat agtttaaaaa ctctacaccc 180
gatggagaat cgaggaagac aatttaatgt ttcatctgaa tccagaggtg catcaaatta 240
aatgacagct ccacttggca aataatagct gttacttgat ggtatccaag aagaaatggt 300
tggtgatgga taaattcaga aatgcttccc caaaggtggg tggtttttaa aaagttttca 360
ggtcacaacc cttgcagaaa acactgatgc ccaacacact gattcgcggt ccaggaaaca 420
cgggtcttcc aagttccaag gggctggggt tccccaacga tcaagttcct gtgctgtaat 480
caagagggtc ctttggactg gatagggagc acttgggagc tgtacaccat cagtcataat 540
ggatggcagt gtaaaagatg atccaaatga cctgagatgc tcctgaggag tggtgcacca 600
gacccaggag tgccactgta gggctgcttc tttgctttag tcatcacaca cacacacagc 660
tccagagcag caatggcctt tcctgtaaca ggaaaaaagc ctcctgctat tcccaagaac 720
cctcgtaatg gcaaaactcc ccaaatgaca cccaggacca cagcaatgat ctgtcggaac 780
cagtagatca catctaaaaa ttcatcctta tcctcccagg ccgcgtcgct ccgcagcacc 840
ttactccaga cggagacttt gagggccccg ttgg 874

<210> SEQ ID NO 427
<211> LENGTH: 638
<212> TYPE: DNA
<213> ORGANISM: Homo sapiens

<400> SEQUENCE: 427
acttgtaatt agcacttggt gaaagctgga aggaagataa ataacactaa actatgctat 60
ttgatttttc ttcttgaaag agtaaggttt acctgttaca ttttcaagtt aattcatgta 120
aaaaatgata gtgattttga tgtaatttat ctcttgtttg aatctgtcat tcaaaggcca 180
ataatttaag ttgctatcag ctgatattag tagctttgca accctgatag agtaaataaa 240
ttttatgggc gggtgccaaa tactgctgtg aatctatttg tatagtatcc atgaatgaat 300
ttatggaaat agatatttgt gcagctcaat ttatgcagag attaaatgac atcataatac 360
tggatgaaaa cttgcataga attctgatta aatagtgggt ctgtttcaca tgtgcagttt 420
gaagtattta aataaccact cctttcacag tttattttct tctcaagcgt tttcaagatc 480
tagcatgtgg attttaaaag atttgccctc attaacaaga ataacattta aaggagattg 540
tttcaaaata tttttgcaaa ttgagataag gacagaaaga ttgagaaaca ttgtatattt 600
tgcaaaaaca agatgtttgt agctgtttca gagagagt 638

<210> SEQ ID NO 428
<211> LENGTH: 535
<212> TYPE: DNA
<213> ORGANISM: Homo sapiens

<400> SEQUENCE: 428
acaagatgat tcttcctcct caatttgaca gatcaaagaa gtatcccttg ctaattcaag 60
tgtatggtgg tccctgcagt cagagtgtaa ggtctgtatt tgctgttaat tggatatctt 120
atcttgcaag taaggaaggg atggtcattg ccttggtgga tggtcgagga acagctttcc 180
aaggtgacaa actcctctat gcagtgtatc gaaagctggg tgtttatgaa gttgaagacc 240
agattacagc tgtcagaaaa ttcatagaaa tgggtttcat tgatgaaaaa agaatagcca 300

-continued tatggggctg gtcctatgga ggatacgttt catcactggc ccttgcatct ggaactggtc 360
ttttcaaatg tggtatagca gtggctccag tctccagctg ggaatattac gcgtctgtct 420
acacagagag attcatgggt ctcccaacaa aggatgataa tcttgagcac tataagaatt 480
caactgtgat ggcaagagca gaatatttca gaaatgtaga ctatcttctc atcca 535

<210> SEQ ID NO 429
<211> LENGTH: 675
<212> TYPE: DNA
<213> ORGANISM: Homo sapiens

<400> SEQUENCE: 429
actattttca accctgagca ttaacactgc ataccaaggg ggggtgggtc aagaagctgg 60
ttagatcgaa gcacaagcac aagccactga tattctctat gtgatcaggt ttttacaaaa 120
aaatacatag ttttcaataa ataatgctta attttacaac tttgatacag caatgtcata 180
caccgtttca acacactaca ctctgcatgc tagatagtct acgagaagac gaaactttgc 240
catgcatttt ctttcccccc tagtgctatc aaacacttca tcctccagcg cactgcctca 300
ggtagcttta ccttctctct gtttcacagc aataggccgt gcgctggcat gcaaactcta 360
aaaaaggtcc cccccacaaa ccactcagac ttctacacaa aagggttttt cagcttttct 420
gctcccaaac ctggagtggc taagaaagta agtttcatgt ggccttggaa aatacacact 480
tgttaacagt gtcatgctga aaactgctct aaaacatcag gtggttctgt cctggtggcc 540
gtcacgaagc attatgggat gccataacca ctaggagtcc caaaccggaa aaaataggcc 600
tccgttttaa aacagtcaat tcaaaaaagg tgtcacagaa caaatgcaaa agactcttaa 660
acccacaaca tatgt 675

<210> SEQ ID NO 430
<211> LENGTH: 434
<212> TYPE: DNA
<213> ORGANISM: Homo sapiens

<400> SEQUENCE: 430
acctctgcca gaagtccagc gagaggacct cacagtagag cacaggccac tccgggagtg 60
catcagaaga ttcatcctca tggaggaaga aggcttcaaa cgtgaatggg taggagaagt 120
gagccacctt gtccattgcc agggacttgg tggtgcaggt ctgtgttact cctgagagct 180
gctggaatgc tgggcttgac cagtgagcag ttggcaattc tacaaagaag tggacgtaga 240
gattgtcata ctcatagcct tgggctgaaa cgacctctcc atttacaaag agccggaggg 300
cacctgggac agtcatctca aagtcggtgc ctacgaggct gctgagatac tccttgtgcc 360
ggccataaag atccttgaac actcgccgtt cccgctcctc ctcctccggc tgtgcgtggg 420
gggaaacatt gtcg 434

<210> SEQ ID NO 431
<211> LENGTH: 581
<212> TYPE: DNA
<213> ORGANISM: Homo sapiens

<400> SEQUENCE: 431
acacaagcct ccagcccgac ccagcggcct aatgaaactc tggcaaccta tcctgggcgt 60
ggccacgagt atccagctcc aagcccaagt gaggcgggga gtcaacttcc ccatgattgc 120
caagtgacca agaccagaag cagggacgat taggctagtt ctgcggcaag gtgaactgga 180

-continued

```
gaccctgtct ctgccctcct tccctggcct gtcccacaga catcccgttg tttaacccac    240

tgcctttgca aggacctgct ctgtccactc caaatcaaag gatacttgca tccttcttac    300

acagactccc atctctctgc tcatagtggt cccaggctgc ccgagaaaaa gaaacttggg    360

tcagtagaag gctcattagt gtgaaggagt gagaggccag gccttcctgt gacataatgc    420

ttctatgctt gtttcctaaa cacttggtcc acacacaata cctgggcagg aagagagaac    480

caagcaccac tggatggctc tggagccagg ggacttctat gcacatacaa ccaacatcac    540

cccactctgc tcatctgtgc ctccaccctg aacagcagag t                        581
```

```
<210> SEQ ID NO 432
<211> LENGTH: 532
<212> TYPE: DNA
<213> ORGANISM: Homo sapiens

<400> SEQUENCE: 432

actccaactc aagtttacaa gttacacctt tgccacagcc ttggctaaat cttgaactag     60

tgcagaattc agctgtggta gagtgctgat cttagcatgc ttcgatgtgg catacttgtt    120

cttgacagtc atgtgctttg taagtccttg atttaccatg actacattct tagccaggtg    180

ctgcataact ggaagaagag attcttcagt atatgacagg taatgttgta gagttggtgt    240

ccattcacca ttatccagaa ttttcagtgc taagcaaaaa gctcctgctg caatttgaga    300

aggaggaaag tgcaccatgt catagtccaa catagttagt tccatcaggt atttggccaa    360

agtatgttgc tcgacatcaa cctctccaat cttagatgct ctccgaagga agtgcaaagg    420

tagaggccga cccagaccaa agtttaaagc tcttagaatc ttcatttcca tctgtctgat    480

ttggtgctta gtataagtgt tgtcagtcac aaaagcaaag tcaccaattt ct            532
```

```
<210> SEQ ID NO 433
<211> LENGTH: 531
<212> TYPE: DNA
<213> ORGANISM: Homo sapiens

<400> SEQUENCE: 433

acttggtttt acagctcctt tgaaaactct gtgtttggaa tatctctaaa aacatagaaa     60

acactacagt ggtttagaaa ttactaattt tacttctaag tcattcataa accttgtcta    120

tgaaatgact tcttaaatat ttagttgata gactgctaca ggtaataggg acttagcaag    180

ctcttttata tgctaaagga gcatctatca gattaagtta gaacatttgc tgtcagccac    240

atattgagat gacactaggt gcaatagcag ggatagattt tgttggtgag tagtctcatg    300

ccttgagatc tgtggtggtc ttcaaaatgg tggccagcca gatcaaggat gtagtatctc    360

atagttccca ggtgatattt ttcttattag aaaaatatta taactcattt gttgtttgac    420

acttatagat tgaaatttcc taatttattc taaattttaa gtggttcttt ggttccagtg    480

ctttatgttg ttgttgtttt tggatggtgt tacatattat atgttctaga a             531
```

```
<210> SEQ ID NO 434
<211> LENGTH: 530
<212> TYPE: DNA
<213> ORGANISM: Homo sapiens

<400> SEQUENCE: 434

acaagagaaa acccctaaaa aaaggatggc tttagatgac aagctctacc agagagactt     60

agaagttgca ctagctttat cagtgaagga acttccaaca gtcaccacta atgtgcagaa    120

ctctcaagat aaaagcattg aaaaacatgg cagtagtaaa atagaaacaa tgaataagtc    180
```

-continued

```
tcctcatatc tctaattgca gtgtagccag tgattattta gatttggata agattactgt    240

ggaagatgat gttggtggtg ttcaagggaa aagaaaagca gcatctaaag ctgcagcaca    300

gcagaggaag attcttctgg aaggcagtga tggtgatagt gctaatgaca ctgaaccaga    360

ctttgcacct ggtgaagatt ctgaggatga ttctgatttt tgtgagagtg aggataatga    420

cgaagacttc tctatgagaa aaagtaaagt taaagaaatt aaaaagaaag aagtgaaggt    480

aaaatcccca gtagaaaaga aagagaagaa atctaaatcc aaatgtaatg               530
```

<210> SEQ ID NO 435
<211> LENGTH: 677
<212> TYPE: DNA
<213> ORGANISM: Homo sapiens

<400> SEQUENCE: 435

```
accttatgat ctaattaata gatattagaa acagtagaaa gacaagttac acgtcaatgc     60

ccaatgacta gagtcaacat taaagagttg taatttaagt aatccaaact gacatctaat    120

tccaaaatca tttataaaat gtatttggct ttggaatcca caggacttca aacaagcaaa    180

gtttcactgc agatagtcac aaagatgcag atacactgaa atacttaaga gccttattaa    240

tgatttttgt tattttggat cttctgtttt tttcttatta tggtccgaag cctccttaat    300

accaatttat cagacagaag catgtcatct tgttgttcaa gataatccag taaattttca    360

gtccattcaa gtgccgcttt atggctaata cgcttctctg gattcagttc tgtttttcta    420

ctcttactgg aaggcttttg ctcagcagcc ttggtctggt cctcagcact ttcactgtca    480

gtcagcacct gacagcttga gtcactgctc cgagagtcga accactgatc aatattctca    540

atgtcaacat gttcacattc ttctgtgttc tgtaaaactg ttgctaaatt agctgctaaa    600

atggctcctt catcaatgtt catacctgaa ttctcttcat tgccagggaa aagtttttc     660

catgctttgg ttatggt                                                   677
```

<210> SEQ ID NO 436
<211> LENGTH: 573
<212> TYPE: DNA
<213> ORGANISM: Homo sapiens

<400> SEQUENCE: 436

```
acctcttagg gtgggagaaa tggtgaagag ttgttcctac aacttgctaa cctagtggac     60

agggtagtag attagcatca tccggataga tgtgaagagg acggctgttt ggataataat    120

taaggataaa atttggccag ttgacagatt ctgtttccag cagtttttac agcaacagtg    180

gagtgcttca gtattgtgtt cctgtaaatt taattttgat ccgcaatcat ttggtataca    240

atgctgtttg aagttttgtc ctattggaaa agtcttgtgt tgcaggggtg cagttaagat    300

ctttgtgatg aggaatggga tggctaatt ttttgccgtt ttcttggaat tgggggcatg     360

gcaaatacag tagggtagtt tagttcttta cacagaacat gataaactac acctgttgat    420

gtcaccgtct gtcaatgaat attatagaag gtatgaaggt gtaattacca taataacaaa    480

acaccctgtc tttagggctg acctttcgtc ctttgacctc ctcagcctcc attcccatct    540

tcgctcagac tgcaagtatg tttgtattaa tgt                                 573
```

<210> SEQ ID NO 437
<211> LENGTH: 645
<212> TYPE: DNA
<213> ORGANISM: Homo sapiens
<220> FEATURE:

-continued

<221> NAME/KEY: misc_feature
<222> LOCATION: 605
<223> OTHER INFORMATION: n = A,T,C or G

<400> SEQUENCE: 437
acaattggta tccatatctt gttgaaattg taatgggaaa acaatatatt tcaatctcta 60
tgtagatagt gggtttttgt tttcataata tattctttta gtttactgta tgagttttgc 120
aggactgcat aatagatcac cacaatcata acatcttagg accacagaca tttatgagat 180
catggcttct gtgggttaga agtatgctca tgtcttaact gggtcctctg ctcagtctta 240
tctggctgca atcaaggtgt cagctgggct gaattttcat ttggaatctt gactgggaaa 300
gagtctgctt ccaaggtcat gaagtttgct ggcaaaatgt atgtttttat gacagtatga 360
ctgaaatccc aagctatctc ctgactttta gctgggtaat ctcaggccct aaatgttgcc 420
tacagttcct agaggctggt cacagttctt agccatgtgg atttcctcaa catggctgct 480
tgcttcatca agtcagcaag aatagcctgt catatcagtg tatatcaggc tcactcagga 540
taatttccct actgatgagc caaacactaa ctgattttag agcttaacta catctgcaaa 600
attcngttca ccagaggcaa gtcatattca gggaaggaga agtgt 645

<210> SEQ ID NO 438
<211> LENGTH: 485
<212> TYPE: DNA
<213> ORGANISM: Homo sapiens

<400> SEQUENCE: 438
acagaattga gagacaagat tgcttgtaat ggagatgctt ctagctctca gataatacat 60
atttctgatg aaaatgaagg aaaagaaatg tgtgttctgc gaatgactcg agctagacgt 120
tcccaggtag aacagcagca gctcatcact gttgaaaagg ctttggcaat tctttctcag 180
cctacaccct cacttgttgt ggatcatgag cgattaaaaa atcttttgaa gactgttgtt 240
aaaaaaagtc aaaactacaa catatttcag ttggaaaatt tgtatgcagt aatcagccaa 300
tgtatttatc ggcatcgcaa ggaccatgat aaaacatcac ttattcagaa aatggagcaa 360
gaggtagaaa acttcagttg ttccagatga tgatgtcatg gtatcgagta ttctttatat 420
tcagttccta tttaagtcat ttttgtcatg tccgcctaat tgatgtagta tgaaaccctg 480
catct 485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc 60
aggttcaaca gtatggctcc aaatgatgaa atttcattct gattttctgg ctgaagacta 120
ttctgtttgt gtatgtccac cacagttact ttatcccttc atctgtggat gggcagaatg 180
aaacatatat ggaaatgttc tgtgcaataa aaacagcagt ggtaacacag atgtaggctc 240
tgagtgtctc actggagact gaagtccaca gatatgcaac aaagcctttg tctccctgat 300
gtttttgcct cctgctggtc atgtgctttc acacatcaag agaggacatt taacatttga 360
gccacagtgt catttgctgt tgtctgatgg ttggttggca gagaatttga actggagatg 420
aactttatta tccaggacgc tgagagtata acatgcatga cagagctttt agagcactgt 480
gatgtaacat gtcaagcaga aatagggagc atgtttacag ccattctatg aaa 533

-continued

<210> SEQ ID NO 440
<211> LENGTH: 341
<212> TYPE: DNA
<213> ORGANISM: Homo sapiens

<400> SEQUENCE: 440
catggggtag gggggtcggg gattcattga attgtggttg gcaggagcaa gccctgctca 60
cactctcaca ctcgcaccca gaattgtcaa agatacagat tgtaaaaatc tacgatccct 120
cagtctcact cacaaaaaat aaaatctcat gtccccaacg aacccagagt cagacgacag 180
ctggagcatt ggcagggaca gtcagaaagg agacaagtga aaacggtcag atggacacag 240
gcggaggaga aaagacagag ggagagagac catcgggaac aatcagaggg gccgagacga 300
tcagaaaagg gtcagcccga gacaggctga gccagagttt c 341

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: 53, 84, 132, 138, 148
<223> OTHER INFORMATION: n = A,T,C or G

<400> SEQUENCE: 441
aagtttgggg ataatttatt atgcagcaag agataataca caggacttct canagcactt 60
aatatgttaa tataaatctc caanaaaaaa gatatacaat gaaacattcc tcttagttat 120
ctggccaagg anactttntt tttttganaa tattcttcaa aaagctgatc taatgatatg 180
gctctggtcc tacaattcca tgtaacttct aaccttgatt ttatctcatg agcaaatcat 240
ttatccttcc agaacctcaa cttttccctt ttacaaagta gaaataaacc atctgccttt 300
acataaatca ttaatacagc cctggatggg cagattctga gctatttttg gctgggggt 360 gggaaatagc ctgtggaggt cctaaaaaga tctacggggc tcgagatggt tctctgcaag 420
gtagcaggtg ggctcagggc ccatttcagt ctttgttccc caggccattt ccacaaaatg 480
gtgagaaata gtgtcttctt ttagcttgct cataactcaa agatgggggg catggacctg 540
ggcctttcta ggctagggca tgaacctcct cc 572

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: 34, 67
<223> OTHER INFORMATION: n = A,T,C or G

<400> SEQUENCE: 442
tcccagctgc actgcttaca cgtcttcctt cgtnttcacc taccccgagg ctgactcctt 60
ccccagntgt gcagctgccc accgcaaggg cagcagcagc aatgagcctt cctctgactc 120
gctcagctca cccacgctgc tggccctgtg agggggcagg gaaggggagg cagccggcac 180
ccacaagtgc cactgcccga gctggtgcat tacagagagg agaaacacat cttccctaga 240
gggttcctgt agacctaggg aggaccttat ctgtgcgtga aacacaccag gctgtgggcc 300
tcaaggactt gaaagcatcc atgtgtggac tcaagtcctt acctcttccg gagatgtagc 360
aaaacgcatg gagtgtgta 379

-continued

<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: 444
<223> OTHER INFORMATION: n = A,T,C or G

<400> SEQUENCE: 443
acatgccccc aaaggctcgc ttcattgcta cgattctcta cttaaatcca cattcacagc 60
tattgcctca gaccctctgg aggaggggcc aggggttagc tggctttgaa tagcatgtag 120
agcacaggca gtgtggccac aaatgtcaca caggtgacca gggtgctata gatggtgttc 180
ctgttgactt gggcttctag tctctgctcc gtgtctgaca gtgccaagat catgctcccc 240
tgctccagca agaagctggg catagccccg tctgctggtt ccaccaggcc tgggtgtgct 300
gcagacttta caagctgaac caccccagcc atttggctac aagtcttttc taggccatca 360
agctgctctc gtaagccttc tagacatgaa tggacttgcc tggaatgact aagctgctct 420
ttcaaggcag ctgaaaggac atcnacatct ctgtctctgg tcgggggact acctgcctgt 480
gacccagagt cctgccctgg cccagcagca t 511

<210> SEQ ID NO 444
<211> LENGTH: 612
<212> TYPE: DNA
<213> ORGANISM: Homo sapiens
<220> FEATURE:
<221> NAME/KEY: misc_feature
<222> LOCATION: 547
<223> OTHER INFORMATION: n = A,T,C or G

<400> SEQUENCE: 444
acaggaagaa ttctacagtt aatctatcac agtgttccag caaagcatat gttgaaaact 60
acagttttca atctaacatc taaattttaa aaagtagcat ttcagcaaca aacaagctca 120
gagaggctca tggcaaaagt gaaataacag aactattgct cagatgtctg caaagtcaag 180
ctgctgccct cagctccgcc cacttgaagg cttaggcaga cacgtaaggt ggcggtggct 240
ccttggcagc accattcaca gtggcatcat catacggagg tagcagcacc gtagtgtcat 300
tgctggtaac ataaaccagg acatcagagg agttcctacc attgatgtat cggtagcagt 360
tccaaacaca gctaatcaag taacccttaa aagtcaagat aatgctaata aacagaagaa 420
taataaggac caaacaggta ggattcactg acatgacatc atctctgtag ggaaaattag 480
gaggcagttg ccgtatgtat tcctgaatgg agtttggata aataagcaca gtgattgcaa 540
ccaacanctt cagggcaaag tcaaagatct ggtaacagaa gaatgggatg atccaggctg 600
cgcgttgctt gt 612

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: 643, 676
<223> OTHER INFORMATION: n = A,T,C or G

<400> SEQUENCE: 445
accatcctgt tccaacagag ccattgccta ttcctaaatt gaatctgact gggtgtgccc 60
ctcctcggaa cacaacagta gaccttaata gtggaaacat cgatgtgcct cccaacatga 120

-continued caagctgggc cagctttcat aatggtgtgg ctgctggcct gaagatagct cctgcctccc 180
agatcgactc agcttggatt gtttacaata agcccaagca tgctgagttg gccaatgagt 240
atgctggctt tctcatggct ctgggtttga atgggcacct taccaagctg gcgactctca 300
atatccatga ctacttgacc aagggccatg aaatgacaag cattggactg ctacttggtg 360
tttctgctgc aaaactaggc accatggata tgtctattac tcggcttgtt agcattcgca 420
ttcctgctct cttacccca acgtccacag agttggatgt tcctcacaat gtccaagtgg 480
ctgcagtggt tggcattggc cttgtatatc aagggacagc tcacagacat actgcagaag 540
tcctgttggc tgagatagga cggcctcctg gtcctgaaat ggaatactgc actgacagag 600
agtcatactc cttagctgct ggcttggccc tgggcatggt ctncttgggg catggcagca 660
atttgatagg tatgtntgat ctcaatgtgc ctgagcagct ctatcagt 708

<210> SEQ ID NO 446
<211> LENGTH: 612
<212> TYPE: DNA
<213> ORGANISM: Homo sapiens

<400> SEQUENCE: 446
acaagcaacg cgcagcctgg atcatcccat tcttctgtta ccagatcttt gactttgccc 60
tgaacatgtt ggttgcaatc actgtgctta tttatccaaa ctccattcag gaatacatac 120
ggcaactgcc tcctaatttt ccctacagag atgatgtcat gtcagtgaat cctacctgtt 180
tggtccttat tattcttctg tttattagca ttatcttgac ttttaagggt tacttgatta 240
gctgtgtttg gaactgctac cgatacatca atggtaggaa ctcctctgat gtcctggttt 300
atgttaccag caatgacact acggtgctgc tacccccgta tgatgatgcc actgtgaatg 360
gtgctgccaa ggagccaccg ccaccttacg tgtctgccta agccttcaag tgggcggagc 420
tgagggcagc agcttgactt tgcagacatc tgagcaatag ttctgttatt tcacttttgc 480
catgagcctc tctgagcttg tttgttgctg aaatgctact ttttaaaatt tagatgttag 540
attgaaaact gtagttttca acatatgctt tgctggaaca ctgtgataga ttaactgtag 600
aattcttcct gt 612

<210> SEQ ID NO 447
<211> LENGTH: 642
<212> TYPE: DNA
<213> ORGANISM: Homo sapiens

<400> SEQUENCE: 447
actgaaagaa ttaaagtcag aagtcttccc aaaacaaaaa gaactgccca cagagaaaat 60
cctttctgat acttttcatt gctaaaataa aacaggcggg aaatgtggaa aagaaattca 120
acaaaataat gtagcaccag aagaacaagt cctagatgat tcaagttcaa aaggtaagct 180
ccagcaatgt ggaagaggta aagaccaatg tagacaagct gacgaggaat atcttctttt 240
ttggttttct ggaagtagag ttcaggaaaa gcatgaagcc agtaagccag ctgtgatatg 300
tagaaaaact tcatttgaaa tgtcatcagg ttatggggat aagccctcca taagatagtt 360
gggtctgaga tgtagttttc agagatgaga atgaatgtgc cccaaacaca ggcaaaaagg 420
tagaacgcac taagctgacc agattcatta aacttgctgt gttttgtttt ggagaagtgc 480
attcgcctgt taattttatc caacatatac tcttgaatta cggcatgaat aattatcgcc 540
actagcatgt agaagaaaac agtagccaaa tctttgatgc catagtaata aagggacact 600

-continued gattcagtag cttgttcttc tgttgctggg agggtgacat tg 642

<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 448
accagaagac cttagaaaaa ggaggaaagg aggagaggca gataatttgg atgaattcct 60
caaagngttt gaaaatccag aggttcctag agaggaccag caacagcagc atcagcagcg 120
tgatgttatc gatgagccca ttattgaaga gccaagccgc ctccaggagt cagtgatgga 180
ggccagcaga acaaacatag atgagtcagc tatgcctcca ccaccacctc agggagttaa 240
gcgaaaagct ggacaaattg acccagagcc tgtgatgcct cctcagcagg tagagcagat 300
ggaaatacca cctgtagagc ttcccccaga agaacctcca aatatctgtc agctaatacc 360
agagttagaa cttctgccag aaaaagagaa ggag 394

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 449
acaaaaaaca caaggaatac aacccaatag aaaatagtcc tgggaatgtg gtcagaagca 60
aaggcntgag tgtctttctc aaccgtgcaa aagccgtgtt cttcccggga aaccaggaaa 120
aggatccgct actcaaaaac caagaattta aaggagtttc ttaaatttcg accttgtttc 180
tgaagctcac ttttcagtgc cattgatgtg agatgtgctg gagtggctat taaccttttt 240
ttcctaaaga ttattgttaa atagatattg tggtttgggg aagttgaatt ttttataggt 300
taaatgtcat tttagagatg gggagaggga ttatactgca ggcagcttca gccatgttgt 360
gaaactgata aaagcaactt agcaaggctt cttttcatta ttttttatgt ttcacttata 420
aagtcttagg taactagtag gatagaaaca ctgtgtcccg agagtaagga gagaagctac 480
tattgattag agcc 494

<210> SEQ ID NO 450
<211> LENGTH: 547
<212> TYPE: DNA
<213> ORGANISM: Homo sapiens

<400> SEQUENCE: 450
actttgggct ccagacttca ctgtccttag gcattgaaac catcacctgg tttgcattct 60
tcatgactga ggttaactta aaacaaaaat ggtaggaaag ctttcctatg cttcgggtaa 120
gagacaaatt tgcttttgta gaattggtgg ctgagaaagg cagacagggc ctgattaaag 180
aagacatttg tcaccactag ccaccaagtt aagttgtgga acccaaaggt gacggccatg 240
gaaacgtaga tcatcagctc tgctaagtag ttaggggaag aaacatattc aaaccagtct 300
ccaaatggga tcctgtggtt acagtgaatg gccactcctg ctttattttt cctgagattg 360
ccgagaataa catggcactt atactgatgg gcagatgacc agatgaacat catcatccca 420

-continued agaatatgga accaccgtgc ttgcatcaat agatttttcc ctgttatgta ggcattcctg 480
ccatccattg gcacttggct cagcacagtt aggccaacaa ggacataata gacaagtcca 540
aaacagt 547

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: 8, 9, 19, 41
<223> OTHER INFORMATION: n = A,T,C or G

<400> SEQUENCE: 451
actacttnnt ggttaaaang ccactggtag agtcatctga ntgtaaacaa tgtccctgca 60
ctgctggaaa aatccactgg ctcccaagaa aagaaaatgg tctgaagcct ctgttgtggc 120
tctcacaact catctttccc taagtcatca agctccacat cactgaggtc aatgtcatcc 180
tccacgggaa gctcgccatc cctgccgtcc caaggctctc tctcaacgat ggtagggaaa 240
gccccgcctc ctacaggtgc cgtggagcca cgcccaaaag agagctccct gagaaactcg 300
ttgatgcctt gctcactgaa ggagcctttt agcagagcaa atttcatctt gcgtgcattg 360
atggcggcca tggcggggta ccca 384

<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: 291, 341, 368
<223> OTHER INFORMATION: n = A,T,C or G

<400> SEQUENCE: 452
actctaaagt tgccactctc acaggggtca gtgataccca ctgaacctgg caggaacagt 60
cctgcagcca gaatctgcaa gcagcgcctg tatgcaacgt ttagggccaa aggctgtctg 120
gtggggttgt tcatcacagc ataatggcct agtaggtcaa ggatccaggg tgtgaggggc 180
tcaaagccag gaaaacgaat cctcaagtcc ttcagtagtc tgatgagaac tttaactgtg 240
gactgagaag cattttcctc gaaccagcgg gcatgtcgga tggctgctaa ngcactctgc 300
aatactttga tatccaaatg gagttctgga tccagttttc naagattggg tggcactgtt 360
gtaatganaa tcttcactgt a 381

<210> SEQ ID NO 453
<211> LENGTH: 455
<212> TYPE: DNA
<213> ORGANISM: Homo sapiens

<400> SEQUENCE: 453
actgtgctaa acagcctata gccaagtttt aaagagttac aggaacaact gctacacatt 60
caaagaacag gcattcactg cagcctcctg atttgacctg atgggaggga caggagaatg 120
agtcactctg ccaccacttt tcctgccttg gatttgtaga ggatttgttt tgctctaatt 180
tgtttttcct atatctgccc tactaaggta cacagtctgg gcactttgaa aatgttaaag 240
tttttaacgt ttgactgaca gaagcagcac ttaaaggctt catgaatcta ttttccaaaa 300
aaagtatgct ttcagtaaaa cattttacca ttttatctaa ctatgcactg acatttttgt 360

-continued

```
tcttcctgaa aaggggattt atgctaacac tgtattttta atgtaaaaat atacgtgtag    420

agatatttta acttcctgag tgacttatac ctcaa                               455
```

<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: 9
<223> OTHER INFORMATION: n = A,T,C or G

<400> SEQUENCE: 454

```
acagagcanc tttacaagtt gtcacatttc tttataaatt tttttaaagc tacagtttaa     60

tacaaaatga attgcggttt tattacatta ataacctttc acctcagggt tttatgaaga    120

ggaaagggtt ttatgcaaaa gaaagtgcta caattcctaa tcattttaga cactttagga    180

gggggtgaag ttgtatgata aagcagatat tttaattatt tgttatcttt ttgtattgca    240

agaaatttct tgctagtgaa tcaagaaaac atccagattg acagtctaaa atggctactg    300

gtattttagt taattcaaaa atgaaacttt tcagtgattc actttactaa cattctattt    360

gagaaggctt attggtaaag ttt                                            383
```

<210> SEQ ID NO 455
<211> LENGTH: 383
<212> TYPE: DNA
<213> ORGANISM: Homo sapiens
<220> FEATURE:
<221> NAME/KEY: misc_feature
<222> LOCATION: 10
<223> OTHER INFORMATION: n = A,T,C or G

<400> SEQUENCE: 455

```
actcctttan gacaaggaaa caggtatcag catgatggta gcagaaacct tatcaccaag     60

gtgcaggagc tgacttcttc caaagagttg tggttccggg cagcggtcat tgccgtgccc    120

attgctggag ggctgatttt agtgttgctt attatgttgg ccctgaggat gcttcgaagt    180

gaaaataaga ggctgcagga tcagcggcaa cagatgctct cccgtttgca ctacagcttt    240

cacggacacc attccaaaaa ggggcaggtt gcaaagttag acttggaatg catggtgccg    300

gtcagtgggc acgagaactg ctgtctgacc tgtgataaaa tgagacaagc agacctcagc    360

aacgataaga tcctctcgct tgt                                            383
```

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: 64
<223> OTHER INFORMATION: n = A,T,C or G

<400> SEQUENCE: 456

```
acaaacattt tacaaaaaag aacattacca atatcagtgg cagtaagggc aagctgaaga     60

atangtagac tgagtttccg ggcaatgtct gtcctcaaag acatccaaac tgcgttcagg    120

cagctgaaac aggcttcttt cccagtgaca agcatatgtg gtcagtaata caaacgatgg    180

taaatgaggc tactacatag gcccagttaa caaactcctc ttctcctcgg gtaggccatg    240

atacaagtgg aactcatcaa ataatttaaa cccaaggcga taacaacact atttcccatc    300

taaactcatt taagccttca caatgtcgca atggattcag ttacttgcaa acgatcccgg    360
```

-continued

```
gttgtcatac agatacttgt tttttacaca taacgctgtg ccatcccttc cttcactgcc    420

ccagtcaggt ttcctgttgt tggaccgaaa ggggatacat tttagaaatg cttccctcaa    480

gacagaagtg agaaagaaag gagaccctga ggccaggatc tattaaacct ggtgtgtgcg    540

caa                                                                  543
```

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: 17
<223> OTHER INFORMATION: n = A,T,C or G

<400> SEQUENCE: 457

```
actggtgcca atattgncat ggtgagctcc tctctaatgt cttccagggc accaatatct     60

gcccatgtca cattagggac agtgacaaag ccttcccttt tggcagaggg ttggactgag    120

gatagagcaa caatgaaatc attcagttca atgcacagtc cttgcatctg ctcctctgag    180

aggggatctt ggtctcttag caaccccagc agcctttgta attcatcctg tgtttcagaa    240

gtgggctcag ttcccagcct ttcctcctgg actcctttag atggcaaatc ttccatttca    300

ggatttttct tctgctgttc ctgtagcttc attaagactc tattgactgc acacattgct    360

gcctctcggc acagtgccat gagatcagca ccaacaaagc ctggagttag gtgtgctaag    420

tgacagaaat caaaagcttg aggaagcctc agttttctgc acaatgtttg aagtattctt    480

tccctggatg cttcatctgg gatacctagg catatttctc ggtcgaacct tcccgcacgt    540

ctca                                                                 544
```

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: 5, 23
<223> OTHER INFORMATION: n = A,T,C or G

<400> SEQUENCE: 458

```
acctntaggc tcaacggcag aancttcacc acaaaagcga aatgggcaca ccacagggag     60

aaaactggtt gtcctggatg tttgaaaagt tggtcgttgt catggtgtgt tacttcatcc    120

tatctatcat taactccatg gcacaaagtt atgccaaacg aatccagcag cggttgaact    180

cagaggagaa aactaaataa gtagagaaag ttttaaactg cagaaattgg agtggatggg    240

ttctgcctta aattgggagg actccaagcc gggaaggaaa attccctttt ccaacctgta    300

tcaattttta caactttttt cctgaaagca gtttagtcca tactttgcac tgacatactt    360

tttccttctg tgctaaggta ag                                             382
```

<210> SEQ ID NO 459
<211> LENGTH: 168
<212> TYPE: DNA
<213> ORGANISM: Homo sapiens

<400> SEQUENCE: 459

```
ctcgtactct agccaggcac gaaaccatga agtagcctga tccttcttag ccatcctggc     60

cgccttagcg gtagtaactt tgtgttatga atcacatgaa agcatggaat cttatgaact    120
```

-continued

```
taatcccttc attaacagga gaaatgcaaa taccttcata tcccctca                168


<210> SEQ ID NO 460
<211> LENGTH: 190
<212> TYPE: DNA
<213> ORGANISM: Homo sapiens
<220> FEATURE:
<221> NAME/KEY: misc_feature
<222> LOCATION: 4
<223> OTHER INFORMATION: n = A,T,C or G

<400> SEQUENCE: 460

acanctgcta ccagggagcc gagagctgac tatcccagcc tcggctaatg tattctacgc     60

catggatgga gcttcacacg atttcctcct gcggcagcgg cgaaggtcct ctactgctac    120

acctggcgtc accagtggcc cgtctgcctc aggaactcct ccgagtgagg gaggaggggg    180

ctcctttccc                                                           190


<210> SEQ ID NO 461
<211> LENGTH: 495
<212> TYPE: DNA
<213> ORGANISM: Homo sapiens

<400> SEQUENCE: 461

acagacaggc ttctctgcta tcctccaggc agtgtaatag tcaaggaaaa gggcaacagt     60

attggatcat tccttagaca ctaatcagct ggggaaagag ttcattggca aaagtgtcct    120

cccaagaatg gtttacacca agcagagagg acatgtcact gaatggggaa agggaacccc    180

cgtatccaca gtcactgtaa gcatccagta ggcaggaaga tggctttggg cagtggctgg    240

atgaaagcag atttgagata cccagctccg gaacgaggtc atcttctaca ggttcttcct    300

tcactgagac aatgaattca gggtgatcat tctctgaggg gctgagaggt gcttcctcga    360

ttttcactac cacattagct tggctctctg tctcagaggg tatctctaag actaggggct    420

tggtatatat gtggtcaaaa cgaattagtt cattaatggc ttccagcttg gctgatgacg    480

tccccactga cagag                                                     495


<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: 68
<223> OTHER INFORMATION: n = A,T,C or G

<400> SEQUENCE: 462

acactgaaac ataaatccgc aagtcaccac acatacaaca cccggcagga aaaaaacaaa     60

aacagggngt ttacatgatc cctgtaacag ccatggtctc aaactcagat gcttcctcca    120

tctgccaagt gtgttttgga tacagagcac atcgtggctt ctggggtcac actcagctta    180

ggctgtgggt ccacagagca ctcatctggc tgggctatgg tggtggtggc tctactcaag    240

aagcaaagca gttaccagca cattcaaaca gtgtattgaa catcttttaa atatcaaagt    300

gagaaacaag aaggcaacat aataatgtta tcagaaagat gttaggaagt aaggacagct    360

gtgtaaagct tgaggctgaa aagtagcttg ccagcttcat ttctttggtt tcttgggtag    420

tgggcgccgg aacagcaaga tgtgaggttc tggttcatgg atcatataat ggacccatcc    480

ctgactctgc tga                                                       493
```

-continued

<210> SEQ ID NO 463
<211> LENGTH: 3681
<212> TYPE: DNA
<213> ORGANISM: Homo sapiens

<400> SEQUENCE: 463
tccgagctga ttacagacac caaggaagat gctgtaaaga gtcagcagcc acagccctgg 60
ctagctggcc ctgtgggcat ttattagtaa agttttaatg acaaaagctt tgagtcaaca 120
cacccgtggg taattaacct ggtcatcccc accctggaga gccatcctgc ccatgggtga 180
tcaaagaagg aacatctgca ggaacacctg atgaggctgc acccttggcg gaaagaacac 240
ctgacacagc tgaaagcttg gtggaaaaaa cacctgatga ggctgcaccc ttggtggaaa 300
gaacacctga cacggctgaa agcttggtgg aaaaaacacc tgatgaggct gcatccttgg 360
tggagggaac atctgacaaa attcaatgtt tggagaaagc gacatctgga aagttcgaac 420
agtcagcaga agaaacacct agggaaatta cgagtcctgc aaaagaaaca tctgagaaat 480
ttacgtggcc agcaaaagga agacctagga agatcgcatg ggagaaaaaa gaagacacac 540
ctagggaaat tatgagtccc gcaaaagaaa catctgagaa atttacgtgg gcagcaaaag 600
gaagacctag gaagatcgca tgggagaaaa aagaaacacc tgtaaagact ggatgcgtgg 660
caagagtaac atctaataaa actaaagttt tggaaaaagg aagatctaag atgattgcat 720
gtcctacaaa agaatcatct acaaaagcaa gtgccaatga tcagaggttc ccatcagaat 780
ccaaacaaga ggaagatgaa gaatattctt gtgattctcg gagtctcttt gagagttctg 840
caaagattca agtgtgtata cctgagtcta tatatcaaaa agtaatggag ataaatagag 900
aagtagaaga gcctcctaag aagccatctg ccttcaagcc tgccattgaa atgcaaaact 960
ctgttccaaa taaagccttt gaattgaaga atgaacaaac attgagagca gatccgatgt 1020
tcccaccaga atccaaacaa aaggactatg aagaaaattc ttgggattct gagagtctct 1080
gtgagactgt ttcacagaag gatgtgtgtt tacccaaggc tacacatcaa aaagaaatag 1140
ataaaataaa tggaaaatta gaagagtctc ctaataaaga tggtcttctg aaggctacct 1200
gcggaatgaa agtttctatt ccaactaaag ccttagaatt gaaggacatg caaactttca 1260
aagcagagcc tccggggaag ccatctgcct tcgagcctgc cactgaaatg caaaagtctg 1320
tcccaaataa agccttggaa ttgaaaaatg aacaaacatt gagagcagat gagatactcc 1380
catcagaatc caaacaaaag gactatgaag aaagttcttg ggattctgag agtctctgtg 1440
agactgtttc acagaaggat gtgtgtttac ccaaggctrc rcatcaaaaa gaaatagata 1500
aaataaatgg aaaattagaa gggtctcctg ttaaagatgg tcttctgaag gctaactgcg 1560
gaatgaaagt ttctattcca actaaagcct tagaattgat ggacatgcaa actttcaaag 1620
cagagcctcc cgagaagcca tctgccttcg agcctgccat tgaaatgcaa aagtctgttc 1680
caaataaagc cttggaattg aagaatgaac aaacattgag agcagatgag atactcccat 1740
cagaatccaa acaaaaggac tatgaagaaa gttcttggga ttctgagagt ctctgtgaga 1800
ctgtttcaca gaaggatgtg tgtttaccca aggctrcrca tcaaaaagaa atagataaaa 1860
taaatggaaa attagaagag tctcctgata atgatggttt tctgaaggct ccctgcagaa 1920
tgaaagtttc tattccaact aaagccttag aattgatgga catgcaaact ttcaaagcag 1980
agcctcccga gaagccatct gccttcgagc ctgccattga aatgcaaaag tctgttccaa 2040
ataaagcctt ggaattgaag aatgaacaaa cattgagagc agatcagatg ttcccttcag 2100
aatcaaaaca aaagaasgtt gaagaaaatt cttgggattc tgagagtctc cgtgagactg 2160

-continued

```
tttcacagaa ggatgtgtgt gtacccaagg ctacacatca aaaagaaatg gataaaataa   2220

gtggaaaatt agaagattca actagcctat caaaaatctt ggatacagtt cattcttgtg   2280

aaagagcaag ggaacttcaa aaagatcact gtgaacaacg tacaggaaaa atggaacaaa   2340

tgaaaaagaa gttttgtgta ctgaaaaaga aactgtcaga agcaaaagaa ataaaatcac   2400

agttagagaa ccaaaaagtt aaatgggaac aagagctctg cagtgtgagg tttctcacac   2460

tcatgaaaat gaaaattatc tcttacatga aaattgcatg ttgaaaaagg aaattgccat   2520

gctaaaactg gaaatagcca cactgaaaca ccaataccag gaaaaggaaa ataaatactt   2580

tgaggacatt aagattttaa aagaaaagaa tgctgaactt cagatgaccc taaaactgaa   2640

agaggaatca ttaactaaaa gggcatctca atatagtggg cagcttaaag ttctgatagc   2700

tgagaacaca atgctcactt ctaaattgaa ggaaaaacaa gacaaagaaa tactagaggc   2760

agaaattgaa tcacaccatc ctagactggc ttctgctgta caagaccatg atcaaattgt   2820

gacatcaaga aaaagtcaag aacctgcttt ccacattgca ggagatgctt gtttgcaaag   2880

aaaaatgaat gttgatgtga gtagtacgat atataacaat gaggtgctcc atcaaccact   2940

ttctgaagct caaaggaaat ccaaaagcct aaaaattaat ctcaattatg cmggagatgc   3000

tctaagagaa aatacattgg tttcagaaca tgcacaaaga gaccaacgtg aaacacagtg   3060

tcaaatgaag gaagctgaac acatgtatca aaacgaacaa gataatgtga acaaacacac   3120

tgaacagcag gagtctctag atcagaaatt atttcaacta caaagcaaaa atatgtggct   3180

tcaacagcaa ttagttcatg cacataagaa agctgacaac aaaagcaaga taacaattga   3240

tattcatttt cttgagagga aaatgcaaca tcatctccta aaagagaaaa atgaggagat   3300

atttaattac aataaccatt taaaaaaccg tatatatcaa tatgaaaaag agaaagcaga   3360

aacagaaaac tcatgagaga caagcagtaa gaaacttctt ttggagaaac aacagaccag   3420

atctttactc acaactcatg ctaggaggcc agtcctagca tcaccttatg ttgaaaatct   3480

taccaatagt ctgtgtcaac agaatactta ttttagaaga aaaattcatg atttcttcct   3540

gaagcctaca gacataaaat aacagtgtga agaattactt gttcacgaat tgcataaagc   3600

tgcacaggat tcccatctac cctgatgatg cagcagacat cattcaatcc aaccagaatc   3660

tcgctctgtc actcaggctg g                                               3681
```

<210> SEQ ID NO 464
<211> LENGTH: 1424
<212> TYPE: DNA
<213> ORGANISM: Homo sapiens

<400> SEQUENCE: 464

```
tccgagctga ttacagacac caaggaagat gctgtaaaga gtcagcagcc acagccctgg     60

ctagctggcc ctgtgggcat ttattagtaa agttttaatg acaaaagctt tgagtcaaca    120

cacccgtggg taattaacct ggtcatcccc accctggaga gccatcctgc ccatgggtga    180

tcaaagaagg aacatctgca ggaacacctg atgaggctgc acccttggcg gaaagaacac    240

ctgacacagc tgaaagcttg gtggaaaaaa cacctgatga ggctgcaccc ttggtggaaa    300

gaacacctga cacggctgaa agcttggtgg aaaaaacacc tgatgaggct gcatccttgg    360

tggagggaac atctgacaaa attcaatgtt tggagaaagc gacatctgga aagttcgaac    420

agtcagcaga agaaacacct agggaaatta cgagtcctgc aaaagaaaca tctgagaaat    480

ttacgtggcc agcaaaagga agacctagga agatcgcatg ggagaaaaaa gaagacacac    540

ctagggaaat tatgagtccc gcaaaagaaa catctgagaa atttacgtgg gcagcaaaag    600
```

-continued

```
gaagacctag gaagatcgca tgggagaaaa aagaaacacc tgtaaagact ggatgcgtgg    660
caagagtaac atctaataaa actaaagttt tggaaaaagg aagatctaag atgattgcat    720
gtcctacaaa agaatcatct acaaaagcaa gtgccaatga tcagaggttc ccatcagaat    780
ccaaacaaga ggaagatgaa gaatattctt gtgattctcg gagtctcttt gagagttctg    840
caaagattca agtgtgtata cctgagtcta tatatcaaaa agtaatggag ataaatagag    900
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta gaaggtaaga accgtttttt atttaaaaat cagttgaccg   1200
aatatttctc taaactgatg aggagggata tcctctagta gctgaagaaa attacctcct   1260
aaatgcaaac catggaaaaa aagagaagtg caatggtcgt aagttgtatg tctcatcagg   1320
tgttggcaac agactatatt gagagtgctg aaaaggagct gaattattag tttgaattca   1380
agatattgca agacctgaga gaaaaaaaaa aaaaaaaaaa aaaa                    1424
```

<210> SEQ ID NO 465
<211> LENGTH: 674
<212> TYPE: DNA
<213> ORGANISM: Homo sapiens

<400> SEQUENCE: 465

```
attccgagct gattacagac accaaggaag atgctgtaaa gagtcagcag ccacagccct     60
ggctagctgg ccctgtgggc atttattagt aaagttttaa tgacaaaagc tttgagtcaa    120
cacacccgtg ggtaattaac ctggtcatcc ccaccctgga gagccatcct gcccatgggt    180
gatcaaagaa ggaacatctg caggaacacc tgatgaggct gcacccttgg cggaaagaac    240
acctgacaca gctgaaagct tggtggaaaa aacacctgat gaggctgcac ccttggtgga    300
aagaacacct gacacggctg aaagcttggt ggaaaaaaca cctgatgagg ctgcatcctt    360
ggtggaggga acatctgaca aaattcaatg tttggagaaa gcgacatctg gaaagttcga    420
acagtcagca gaagaaacac ctagggaaat tacgagtcct gcaaaagaaa catctgagaa    480
atttacgtgg ccagcaaaag gaagacctag gaagatcgca tgggagaaaa aagatgactc    540
agttaaggca aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaa                                                      674
```

<210> SEQ ID NO 466
<211> LENGTH: 1729
<212> TYPE: DNA
<213> ORGANISM: Homo sapiens
<220> FEATURE:
<221> NAME/KEY: misc_feature
<222> LOCATION: 11, 1128
<223> OTHER INFORMATION: n = A,T,C or G

<400> SEQUENCE: 466

```
gaaagttcga ncagtcagca gaagaaacac ctagggaaat tacgagtcct gcaaaagaaa     60
catctgagaa atttacgtgg ccagcaaaag gaagacctag gaagatcgca tgggagaaaa    120
aagaagacac acctagggaa attatgagtc ccgcaaaaga aacatctgag aaatttacgt    180
```

-continued

```
gggcagcaaa aggaagacct aggaagatcg catgggagaa aaaagaaaca cctgtaaaga    240

ctggatgcgt ggcaagagta acatctaata aaactaaagt tttggaaaaa ggaagatcta    300

agatgattgc atgtcctaca aaagaatcat ctacaaaagc aagtgccaat gatcagaggt    360

tcccatcaga atccaaacaa gaggaagatg aagaatattc ttgtgattct cggagtctct    420

ttgagagttc tgcaaagatt caagtgtgta tacctgagtc tatatatcaa aaagtaatgg    480

agataaatag agaagtagaa gagcctccta agaagccatc tgccttcaag cctgccattg    540

aaatgcaaaa ctctgttcca aataaagcct ttgaattgaa gaatgaacaa acattgagag    600

cagatccgat gttcccacca gaatccaaac aaaaggacta tgaagaaaat tcttgggatt    660

ctgagagtct ctgtgagact gtttcacaga aggatgtgtg tttacccaag gctacacatc    720

aaaaagaaat agataaaata aatggaaaat tagaagagtc tcctaataaa gatggtcttc    780

tgaaggctac ctgcggaatg aaagtttcta ttccaactaa agccttagaa ttgaaggaca    840

tgcaaacttt caaagcagag cctccgggga agccatctgc cttcgagcct gccactgaaa    900

tgcaaaagtc tgtcccaaat aaagccttgg aattgaaaaa tgaacaaaca ttgagagcag    960

atgagatact cccatcagaa tccaaacaaa aggactatga agaaaattct tgggatactg   1020

agagtctctg tgagactgtt tcacagaagg atgtgtgttt acccaaggct gcgcatcaaa   1080

aagaaataga taaaataaat ggaaaattag aagggtctcc tggtaaaanat ggtcttctga   1140

aggctaactg cggaatgaaa gtttctattc caactaaagc cttagaattg atggacatgc   1200

aaactttcaa agcagagcct cccgagaagc catctgcctt cgagcctgcc attgaaatgc   1260

aaaagtctgt tccaaataaa gccttggaat tgaagaatga acaaacattg agagcagatg   1320

agatactccc atcagaatcc aaacaaaagg actatgaaga aagttcttgg gattctgaga   1380

gtctctgtga gactgtttca cagaaggatg tgtgtttacc caaggctgcg catcaaaaag   1440

aaatagataa aataaatgga aaattagaag gtaagaaccg ttttttattt aaaaatcatt   1500

tgaccaaata tttctctaaa ttgatgagga aggatatcct ctagtagctg aagaaaatta   1560

cctcctaaat gcaaaccatg gaaaaaaaga gaagtgcaat ggtcataagc tatgtgtctc   1620

atcaggcatt ggcaacagac tatattgtga gtgctgaaga ggagctgaat tactagttta   1680

aattcaagat attccaagac gtgaggaaaa tgagaaaaaa aaaaaaaaa               1729
```

<210> SEQ ID NO 467
<211> LENGTH: 1337
<212> TYPE: DNA
<213> ORGANISM: Homo sapiens

<400> SEQUENCE: 467

```
aaaaagaaat agataaaata aatggaaaat tagaagggtc tcctgttaaa gatggtcttc     60

tgaaggctaa ctgcggaatg aaagtttcta ttccaactaa agccttagaa ttgatggaca    120

tgcaaacttt caaagcagag cctcccgaga agccatctgc cttcgagcct gccattgaaa    180

tgcaaaagtc tgttccaaat aaagccttgg aattgaagaa tgaacaaaca ttgagagcag    240

atgagatact cccatcagaa tccaaacaaa aggactatga agaaagttct tgggattctg    300

agagtctctg tgagactgtt tcacagaagg atgtgtgttt acccaaggct gcgcatcaaa    360

aagaaataga taaaataaat ggaaaattag aagagtctcc tgataatgat ggttttctga    420

aggctccctg cagaatgaaa gtttctattc caactaaagc cttagaattg atggacatgc    480

aaactttcaa agcagagcct cccgagaagc catctgcctt cgagcctgcc attgaaatgc    540

aaaagtctgt tccaaataaa gccttggaat tgaagaatga acaaacattg agagcagatc    600
```

-continued agatgttccc ttcagaatca aaacaaaaga aggttgaaga aaattcttgg gattctgaga 660
gtctccgtga gactgtttca cagaaggatg tgtgtgtacc caaggctaca catcaaaaag 720
aaatggataa aataagtgga aaattagaag attcaactag cctatcaaaa atcttggata 780
cagttcattc ttgtgaaaga gcaagggaac ttcaaaaaga tcactgtgaa caacgtacag 840
gaaaaatgga acaaatgaaa aagaagtttt gtgtactgaa aaagaaactg tcagaagcaa 900
aagaaataaa atcacagtta gagaaccaaa aagttaaatg ggaacaagag ctctgcagtg 960
tgagattgac tttaaaccaa gaagaagaga agagaagaaa tgccgatata ttaaatgaaa 1020
aaattaggga agaattagga agaatcgaag agcagcatag gaaagagtta gaagtgaaac 1080
aacaacttga acaggctctc agaatacaag atatagaatt gaagagtgta gaaagtaatt 1140
tgaatcaggt ttctcacact catgaaaatg aaaattatct cttacatgaa aattgcatgt 1200
tgaaaaagga aattgccatg ctaaaactgg aaatagccac actgaaacac caataccagg 1260
aaaaggaaaa taaatacttt gaggacatta agattttaaa agaaaagaat gctgaacttc 1320
agatgacccc tcgtgcc 1337

<210> SEQ ID NO 468
<211> LENGTH: 2307
<212> TYPE: DNA
<213> ORGANISM: Homo sapiens

<400> SEQUENCE: 468
attgagagca gatgagatac tcccatcaga atccaaacaa aaggactatg aagaaagttc 60
ttgggattct gagagtctct gtgagactgt ttcacagaag gatgtgtgtt tacccaaggc 120
tacacatcaa aaagaaatag ataaaataaa tggaaaatta gaagggtctc ctgttaaaga 180
tggtcttctg aaggctaact gcggaatgaa agtttctatt ccaactaaag ccttagaatt 240
gatggacatg caaactttca aagcagagcc tcccgagaag ccatctgcct tcgagcctgc 300
cattgaaatg caaaagtctg ttccaaataa agccttggaa ttgaagaatg aacaaacatt 360
gagagcagat gagatactcc catcagaatc caaacaaaag gactatgaag aaagttcttg 420
ggattctgag agtctctgtg agactgtttc acagaaggat gtgtgtttac ccaaggctac 480
acatcaaaaa gaaatagata aaataaatgg aaaattagaa gagtctcctg ataatgatgg 540
ttttctgaag tctccctgca gaatgaaagt ttctattcca actaaagcct tagaattgat 600
ggacatgcaa actttcaaag cagagcctcc cgagaagcca tctgccttcg agcctgccat 660
tgaaatgcaa aagtctgttc caaataaagc cttggaattg aagaatgaac aaacattgag 720
agcagatcag atgttccctt cagaatcaaa acaaaagaac gttgaagaaa attcttggga 780
ttctgagagt ctccgtgaga ctgtttcaca gaaggatgtg tgtgtaccca aggctacaca 840
tcaaaaagaa atggataaaa taagtggaaa attagaagat tcaactagcc tatcaaaaat 900
cttggataca gttcattctt gtgaaagagc aagggaactt caaaaagatc actgtgaaca 960
acgtacagga aaaatggaac aaatgaaaaa gaagttttgt gtactgaaaa agaaactgtc 1020
agaagcaaaa gaaataaaat cacagttaga gaaccaaaaa gttaaatggg aacaagagct 1080
ctgcagtgtg aggtttctca cactcatgaa aatgaaaatt atctcttaca tgaaaattgc 1140
atgttgaaaa aggaaattgc catgctaaaa ctggaaatag ccacactgaa acaccaatac 1200
caggaaaagg aaaataaata ctttgaggac attaagattt taaaagaaaa gaatgctgaa 1260
cttcagatga ccctaaaact gaaagaggaa tcattaacta aaagggcatc tcaatatagt 1320

-continued

```
gggcagctta aagttctgat agctgagaac acaatgctca cttctaaatt gaaggaaaaa   1380

caagacaaag aaatactaga ggcagaaatt gaatcacacc atcctagact ggcttctgct   1440

gtacaagacc atgatcaaat tgtgacatca agaaaaagtc aagaacctgc tttccacatt   1500

gcaggagatg cttgtttgca aagaaaaatg aatgttgatg tgagtagtac gatatataac   1560

aatgaggtgc tccatcaacc actttctgaa gctcaaagga aatccaaaag cctaaaaatt   1620

aatctcaatt atgcaggaga tgctctaaga gaaaatacat tggtttcaga acatgcacaa   1680

agagaccaac gtgaaacaca gtgtcaaatg aaggaagctg aacacatgta tcaaaacgaa   1740

caagataatg tgaacaaaca cactgaacag caggagtctc tagatcagaa attatttcaa   1800

ctacaaagca aaaatatgtg gcttcaacag caattagttc atgcacataa gaaagctgac   1860

aacaaaagca agataacaat tgatattcat ttttcttgaga ggaaaatgca acatcatctc   1920

ctaaaagaga aaaatgagga gatatttaat tacaataacc atttaaaaaa ccgtatatat   1980

caatatgaaa aagagaaagc agaaacagaa aactcatgag agacaagcag taagaaactt   2040

cttttggaga aacaacagac cagatcttta ctcacaactc atgctaggag gccagtccta   2100

gcatcacctt atgttgaaaa tcttaccaat agtctgtgtc aacagaatac ttattttaga   2160

agaaaaattc atgatttctt cctgaagcct acagacataa aataacagtg tgaagaatta   2220

cttgttcacg aattgcataa agctgcacag gattcccatc taccctgatg atgcagcaga   2280

catcattcaa tccaaccaga atctcgc                                        2307
```

<210> SEQ ID NO 469
<211> LENGTH: 650
<212> TYPE: PRT
<213> ORGANISM: Homo sapiens
<220> FEATURE:
<221> NAME/KEY: VARIANT
<222> LOCATION: 310, 429, 522
<223> OTHER INFORMATION: Xaa = Any Amino Acid

<400> SEQUENCE: 469

```
Met Ser Pro Ala Lys Glu Thr Ser Glu Lys Phe Thr Trp Ala Ala Lys
 1               5                  10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175
```

-continued

```
Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
        515                 520                 525

Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590

Lys Met Glu Gln Met Lys Lys Lys Phe Cys Val Leu Lys Lys Lys Leu
```

-continued

```
        595                 600                 605

Ser Glu Ala Lys Glu Ile Lys Ser Gln Leu Glu Asn Gln Lys Val Lys
    610                 615                 620

Trp Glu Gln Glu Leu Cys Ser Val Arg Phe Leu Thr Leu Met Lys Met
625                 630                 635                 640

Lys Ile Ile Ser Tyr Met Lys Ile Ala Cys
                645                 650


<210> SEQ ID NO 470
<211> LENGTH: 228
<212> TYPE: PRT
<213> ORGANISM: Homo sapiens

<400> SEQUENCE: 470

Met Ser Pro Ala Lys Glu Thr Ser Glu Lys Phe Thr Trp Ala Ala Lys
 1               5                  10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Gly Lys Asn Arg
        195                 200                 205

Phe Leu Phe Lys Asn Gln Leu Thr Glu Tyr Phe Ser Lys Leu Met Arg
    210                 215                 220

Arg Asp Ile Leu
225


<210> SEQ ID NO 471
<211> LENGTH: 154
<212> TYPE: PRT
<213> ORGANISM: Homo sapiens
<220> FEATURE:
<221> NAME/KEY: VARIANT
<222> LOCATION: 148
<223> OTHER INFORMATION: Xaa = Any Amino Acid

<400> SEQUENCE: 471

Met Arg Leu His Pro Trp Arg Lys Glu His Leu Thr Gln Leu Lys Ala
 1               5                  10                  15
```

-continued

```
Trp Trp Lys Lys His Leu Met Arg Leu His Pro Trp Trp Lys Glu His
            20                  25                  30

Leu Thr Arg Leu Lys Ala Trp Trp Lys Lys His Leu Met Arg Leu His
        35                  40                  45

Pro Trp Trp Arg Glu His Leu Thr Lys Phe Asn Val Trp Arg Lys Arg
    50                  55                  60

His Leu Glu Ser Ser Asn Ser Gln Gln Lys Lys His Leu Gly Lys Leu
65                  70                  75                  80

Arg Val Leu Gln Lys Lys His Leu Arg Asn Leu Arg Gly Gln Gln Lys
                85                  90                  95

Glu Asp Leu Gly Arg Ser His Gly Arg Lys Lys Met Thr Gln Leu Arg
            100                 105                 110

Gln Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys Lys
    130                 135                 140

Lys Lys Lys Xaa Lys Lys Lys Lys Lys Lys
145                 150
```

```
<210> SEQ ID NO 472
<211> LENGTH: 466
<212> TYPE: PRT
<213> ORGANISM: Homo sapiens
<220> FEATURE:
<221> NAME/KEY: VARIANT
<222> LOCATION: 329
<223> OTHER INFORMATION: Xaa = Any Amino Acid

<400> SEQUENCE: 472

Met Ser Pro Ala Lys Glu Thr Ser Glu Lys Phe Thr Trp Ala Ala Lys
 1               5                  10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
```

-continued

```
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Asn
        275                 280                 285

Ser Trp Asp Thr Glu Ser Leu Cys Glu Thr Val Ser Gln Lys Asp Val
    290                 295                 300

Cys Leu Pro Lys Ala Ala His Gln Lys Glu Ile Asp Lys Ile Asn Gly
305                 310                 315                 320

Lys Leu Glu Gly Ser Pro Gly Lys Xaa Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Ala His Gln Lys
            420                 425                 430

Glu Ile Asp Lys Ile Asn Gly Lys Leu Glu Gly Lys Asn Arg Phe Leu
        435                 440                 445

Phe Lys Asn His Leu Thr Lys Tyr Phe Ser Lys Leu Met Arg Lys Asp
    450                 455                 460

Ile Leu
465


<210> SEQ ID NO 473
<211> LENGTH: 445
<212> TYPE: PRT
<213> ORGANISM: Homo sapiens

<400> SEQUENCE: 473

Lys Glu Ile Asp Lys Ile Asn Gly Lys Leu Glu Gly Ser Pro Val Lys
 1               5                  10                  15

Asp Gly Leu Leu Lys Ala Asn Cys Gly Met Lys Val Ser Ile Pro Thr
            20                  25                  30

Lys Ala Leu Glu Leu Met Asp Met Gln Thr Phe Lys Ala Glu Pro Pro
        35                  40                  45

Glu Lys Pro Ser Ala Phe Glu Pro Ala Ile Glu Met Gln Lys Ser Val
    50                  55                  60

Pro Asn Lys Ala Leu Glu Leu Lys Asn Glu Gln Thr Leu Arg Ala Asp
65                  70                  75                  80

Glu Ile Leu Pro Ser Glu Ser Lys Gln Lys Asp Tyr Glu Glu Ser Ser
                85                  90                  95

Trp Asp Ser Glu Ser Leu Cys Glu Thr Val Ser Gln Lys Asp Val Cys
            100                 105                 110
```

-continued

```
Leu Pro Lys Ala Ala His Gln Lys Glu Ile Asp Lys Ile Asn Gly Lys
        115                 120                 125

Leu Glu Glu Ser Pro Asp Asn Asp Gly Phe Leu Lys Ala Pro Cys Arg
    130                 135                 140

Met Lys Val Ser Ile Pro Thr Lys Ala Leu Glu Leu Met Asp Met Gln
145                 150                 155                 160

Thr Phe Lys Ala Glu Pro Pro Glu Lys Pro Ser Ala Phe Glu Pro Ala
                165                 170                 175

Ile Glu Met Gln Lys Ser Val Pro Asn Lys Ala Leu Glu Leu Lys Asn
            180                 185                 190

Glu Gln Thr Leu Arg Ala Asp Gln Met Phe Pro Ser Glu Ser Lys Gln
        195                 200                 205

Lys Lys Val Glu Glu Asn Ser Trp Asp Ser Glu Ser Leu Arg Glu Thr
    210                 215                 220

Val Ser Gln Lys Asp Val Cys Val Pro Lys Ala Thr His Gln Lys Glu
225                 230                 235                 240

Met Asp Lys Ile Ser Gly Lys Leu Glu Asp Ser Thr Ser Leu Ser Lys
                245                 250                 255

Ile Leu Asp Thr Val His Ser Cys Glu Arg Ala Arg Glu Leu Gln Lys
            260                 265                 270

Asp His Cys Glu Gln Arg Thr Gly Lys Met Glu Gln Met Lys Lys Lys
        275                 280                 285

Phe Cys Val Leu Lys Lys Lys Leu Ser Glu Ala Lys Glu Ile Lys Ser
    290                 295                 300

Gln Leu Glu Asn Gln Lys Val Lys Trp Glu Gln Glu Leu Cys Ser Val
305                 310                 315                 320

Arg Leu Thr Leu Asn Gln Glu Glu Glu Lys Arg Arg Asn Ala Asp Ile
                325                 330                 335

Leu Asn Glu Lys Ile Arg Glu Glu Leu Gly Arg Ile Glu Glu Gln His
            340                 345                 350

Arg Lys Glu Leu Glu Val Lys Gln Gln Leu Glu Gln Ala Leu Arg Ile
        355                 360                 365

Gln Asp Ile Glu Leu Lys Ser Val Glu Ser Asn Leu Asn Gln Val Ser
    370                 375                 380

His Thr His Glu Asn Glu Asn Tyr Leu Leu His Glu Asn Cys Met Leu
385                 390                 395                 400

Lys Lys Glu Ile Ala Met Leu Lys Leu Glu Ile Ala Thr Leu Lys His
                405                 410                 415

Gln Tyr Gln Glu Lys Glu Asn Lys Tyr Phe Glu Asp Ile Lys Ile Leu
            420                 425                 430

Lys Glu Lys Asn Ala Glu Leu Gln Met Thr Pro Arg Ala
        435                 440                 445
```

<210> SEQ ID NO 474
<211> LENGTH: 3865
<212> TYPE: DNA
<213> ORGANISM: Homo sapiens

<400> SEQUENCE: 474

```
tccgagctga ttacagacac caaggaagat gctgtaaaga gtcagcagcc acagccctgg      60

ctagctggcc ctgtgggcat ttattagtaa agttttaatg acaaaagctt tgagtcaaca     120

cacccgtggg taattaacct ggtcatcccc accctggaga gccatcctgc ccatgggtga     180

tcaaagaagg aacatctgca ggaacacctg atgaggctgc acccttggcg gaaagaacac     240
```

-continued

```
ctgacacagc tgaaagcttg gtggaaaaaa cacctgatga ggctgcaccc ttggtggaaa    300
gaacacctga cacggctgaa agcttggtgg aaaaaacacc tgatgaggct gcatccttgg    360
tggagggaac atctgacaaa attcaatgtt tggagaaagc gacatctgga aagttcgaac    420
agtcagcaga agaaacacct agggaaatta cgagtcctgc aaaagaaaca tctgagaaat    480
ttacgtggcc agcaaaagga agacctagga agatcgcatg ggagaaaaaa gaagacacac    540
ctagggaaat tatgagtccc gcaaaagaaa catctgagaa atttacgtgg gcagcaaaag    600
gaagacctag gaagatcgca tgggagaaaa aagaaacacc tgtaaagact ggatgcgtgg    660
caagagtaac atctaataaa actaaagttt tggaaaaagg aagatctaag atgattgcat    720
gtcctacaaa agaatcatct acaaaagcaa gtgccaatga tcagaggttc ccatcagaat    780
ccaaacaaga ggaagatgaa gaatattctt gtgattctcg gagtctcttt gagagttctg    840
caaagattca agtgtgtata cctgagtcta tatatcaaaa agtaatggag ataaatagag    900
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta gaagagtctc ctaataaaga tggtcttctg aaggctacct   1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aaataaatgg aaaattagaa gggtctcctg ttaaagatgg tcttctgaag gctaactgcg   1560
gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga aatgcaaaag tctgttccaa   2040
ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagcctat caaaaatctt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga aactgtcaga agcaaaagaa ataaaatcac   2400
agttagagaa ccaaaaagtt aaatgggaac aagagctctg cagtgtgaga ttgactttaa   2460
accaagaaga agagaagaga agaaatgccg atatattaaa tgaaaaaatt agggaagaat   2520
taggaagaat cgaagagcag cataggaaag agttagaagt gaaacaacaa cttgaacagg   2580
ctctcagaat acaagatata gaattgaaga gtgtagaaag taatttgaat caggtttctc   2640
```

-continued

```
acactcatga aaatgaaaat tatctcttac atgaaaattg catgttgaaa aaggaaattg   2700

ccatgctaaa actggaaata gccacactga aacaccaata ccaggaaaag gaaaataaat   2760

actttgagga cattaagatt ttaaaagaaa agaatgctga acttcagatg accctaaaac   2820

tgaaagagga atcattaact aaaagggcat ctcaatatag tgggcagctt aaagttctga   2880

tagctgagaa cacaatgctc acttctaaat tgaaggaaaa acaagacaaa gaaatactag   2940

aggcagaaat tgaatcacac catcctagac tggcttctgc tgtacaagac catgatcaaa   3000

ttgtgacatc aagaaaaagt caagaacctg ctttccacat tgcaggagat gcttgtttgc   3060

aaagaaaaat gaatgttgat gtgagtagta cgatatataa caatgaggtg ctccatcaac   3120

cactttctga agctcaaagg aaatccaaaa gcctaaaaat taatctcaat tatgcmggag   3180

atgctctaag agaaaataca ttggtttcag aacatgcaca aagagaccaa cgtgaaacac   3240

agtgtcaaat gaaggaagct gaacacatgt atcaaaacga acaagataat gtgaacaaac   3300

acactgaaca gcaggagtct ctagatcaga aattatttca actacaaagc aaaaatatgt   3360

ggcttcaaca gcaattagtt catgcacata agaaagctga caacaaaagc aagataacaa   3420

ttgatattca ttttcttgag aggaaaatgc aacatcatct cctaaaagag aaaaatgagg   3480

agatatttaa ttacaataac catttaaaaa accgtatata tcaatatgaa aaagagaaag   3540

cagaaacaga aaactcatga gagacaagca gtaagaaact tcttttggag aaacaacaga   3600

ccagatcttt actcacaact catgctagga ggccagtcct agcatcacct tatgttgaaa   3660

atcttaccaa tagtctgtgt caacagaata cttattttag aagaaaaatt catgatttct   3720

tcctgaagcc tacagacata aaataacagt gtgaagaatt acttgttcac gaattgcata   3780

aagctgcaca ggattcccat ctaccctgat gatgcagcag acatcattca atccaaccag   3840

aatctcgctc tgtcactcag gctgg                                          3865
```

<210> SEQ ID NO 475
<211> LENGTH: 1002
<212> TYPE: PRT
<213> ORGANISM: Homo sapiens
<220> FEATURE:
<221> NAME/KEY: VARIANT
<222> LOCATION: 310, 429, 522
<223> OTHER INFORMATION: Xaa = Any Amino Acid

<400> SEQUENCE: 475

```
Met Ser Pro Ala Lys Glu Thr Ser Glu Lys Phe Thr Trp Ala Ala Lys
1               5                   10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125
```

-continued

```
Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
        515                 520                 525

Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
```

-continued

```
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590

Lys Met Glu Gln Met Lys Lys Lys Phe Cys Val Leu Lys Lys Lys Leu
        595                 600                 605

Ser Glu Ala Lys Glu Ile Lys Ser Gln Leu Glu Asn Gln Lys Val Lys
    610                 615                 620

Trp Glu Gln Glu Leu Cys Ser Val Arg Leu Thr Leu Asn Gln Glu Glu
625                 630                 635                 640

Glu Lys Arg Arg Asn Ala Asp Ile Leu Asn Glu Lys Ile Arg Glu Glu
                645                 650                 655

Leu Gly Arg Ile Glu Glu Gln His Arg Lys Glu Leu Glu Val Lys Gln
            660                 665                 670

Gln Leu Glu Gln Ala Leu Arg Ile Gln Asp Ile Glu Leu Lys Ser Val
        675                 680                 685

Glu Ser Asn Leu Asn Gln Val Ser His Thr His Glu Asn Glu Asn Tyr
    690                 695                 700

Leu Leu His Glu Asn Cys Met Leu Lys Lys Glu Ile Ala Met Leu Lys
705                 710                 715                 720

Leu Glu Ile Ala Thr Leu Lys His Gln Tyr Gln Glu Lys Glu Asn Lys
                725                 730                 735

Tyr Phe Glu Asp Ile Lys Ile Leu Lys Glu Lys Asn Ala Glu Leu Gln
            740                 745                 750

Met Thr Leu Lys Leu Lys Glu Glu Ser Leu Thr Lys Arg Ala Ser Gln
        755                 760                 765

Tyr Ser Gly Gln Leu Lys Val Leu Ile Ala Glu Asn Thr Met Leu Thr
    770                 775                 780

Ser Lys Leu Lys Glu Lys Gln Asp Lys Glu Ile Leu Glu Ala Glu Ile
785                 790                 795                 800

Glu Ser His His Pro Arg Leu Ala Ser Ala Val Gln Asp His Asp Gln
                805                 810                 815

Ile Val Thr Ser Arg Lys Ser Gln Glu Pro Ala Phe His Ile Ala Gly
            820                 825                 830

Asp Ala Cys Leu Gln Arg Lys Met Asn Val Asp Val Ser Ser Thr Ile
        835                 840                 845

Tyr Asn Asn Glu Val Leu His Gln Pro Leu Ser Glu Ala Gln Arg Lys
    850                 855                 860

Ser Lys Ser Leu Lys Ile Asn Leu Asn Tyr Ala Gly Asp Ala Leu Arg
865                 870                 875                 880

Glu Asn Thr Leu Val Ser Glu His Ala Gln Arg Asp Gln Arg Glu Thr
                885                 890                 895

Gln Cys Gln Met Lys Glu Ala Glu His Met Tyr Gln Asn Glu Gln Asp
            900                 905                 910

Asn Val Asn Lys His Thr Glu Gln Gln Glu Ser Leu Asp Gln Lys Leu
        915                 920                 925

Phe Gln Leu Gln Ser Lys Asn Met Trp Leu Gln Gln Gln Leu Val His
    930                 935                 940

Ala His Lys Lys Ala Asp Asn Lys Ser Lys Ile Thr Ile Asp Ile His
945                 950                 955                 960

Phe Leu Glu Arg Lys Met Gln His His Leu Leu Lys Glu Lys Asn Glu
                965                 970                 975
```

-continued

Glu Ile Phe Asn Tyr Asn Asn His Leu Lys Asn Arg Ile Tyr Gln Tyr
980 985 990

Glu Lys Glu Lys Ala Glu Thr Glu Asn Ser
995 1000

<210> SEQ ID NO 476
<211> LENGTH: 356
<212> TYPE: DNA
<213> ORGANISM: Homo sapiens

<400> SEQUENCE: 476
aggtctgccg gaaatgttag gcaccccaac tcaagtccca ggccccaggc atctttcctg 60
ccctgccttg cttggcccat ccagtccagg cgcctggagc aagtgctcag ctacttctcc 120
tgcactttga aagacccctc ccactcctgg cctcacattt ctctgtgtga tcccccactt 180
ctgggctctg ccaccccaca gtgggaaagg ccaccctaga aagaagtccg ctggcaccca 240
taggaagggg cctcaggagc aggaagggcc aggaccagaa ccttgcccac ggcaactgcc 300
ttcctgcctc tccccttcct cctctgctct tgatctgtgt ttcaataaat taatgt 356

<210> SEQ ID NO 477
<211> LENGTH: 1876
<212> TYPE: DNA
<213> ORGANISM: Homo sapiens

<400> SEQUENCE: 477
atgacctgcg gatcaggatt tggtgggcgc gccttcagct gcatctcggc ctgcgggccg 60
cgccccggcc gctgctgcat caccgccgcc ccctaccgtg gcatctcctg ctaccgcggc 120
ctcaccgggg gcttcggcag ccacagcgtg tgcggaggct ttcgggccgg ctcctgcgga 180
cgcagcttcg gctaccgctc cgggggcgtg tgcgggccca gtcccccatg catcaccacc 240
gtgtcggtca acgagagcct cctcacgccc ctcaacctgg agatcgaccc caacgcgcag 300
tgcgtgaagc aggaggagaa ggagcagatc aagtccctca acagcaggtt cgcggccttc 360
atcgacaagg tgcgcttcct ggagcagcag aacaaactgc tggagacaaa gctgcagttc 420
taccagaacc gcgagtgttg ccagagcaac ctggagcccc tgtttgaggg ctacatcgag 480
actctgcggc gggaggccga gtgcgtggag gccgacagcg ggaggctggc ctcagagctt 540
aaccacgtgc aggaggtgct ggagggctac aagaagaagt atgaggagga ggtttctctg 600
agagcaacag ctgagaacga gtttgtggct ctgaagaagg atgtggactg cgcctacctc 660
cgcaagtcag acctggaggc caacgtggag gccctgatcc aggagatcga cttcctgagg 720
cggctgtatg aggaggagat ccgcattctc cagtcgcaca tctcagacac ctccgtggtt 780
gtcaagctgg acaacagccg ggacctgaac atggactgca tcattgccga gattaaggca 840
cagtatgacg acattgtcac ccgcagccgg gccgaggccg agtcctggta ccgcagcaag 900
tgtgaggaga tgaaggccac ggtgatcagg cacggggaga ccctgcgccg caccaaggag 960
gagatcaatg agctgaaccg catgatccaa aggctgacgg ccgaggtgga gaatgccaag 1020
tgccagaact ccaagctgga ggccgcggtg gctcagtctg agcagcaggg tgaggcagcc 1080
ctcagtgatg cccgctgcaa gctggccgag ctggagggcg ccctgcagaa ggccaagcag 1140
gacatggcct gcctgatcag ggagtaccag gaggtgatga actccaagct gggcctggac 1200
atcgagatcg ccacctacag gcgcctgctg gagggcgagg agcagaggct atgtgaaggc 1260
attggggctg tgaatgtctg tgtcagcagc tcccggggcg gggtcgtgtg cggggacctc 1320

-continued

```
tgcgtgtcag gctcccggcc agtgactggc agtgtctgca gcgctccgtg caacgggaac   1380

gtggcggtga gcaccggcct gtgtgcgccc tgcggccaat tgaacaccac ctgcggaggg   1440

ggttcctgcg gcgtgggctc ctgtggtatc agctccctgg gtgtggggtc ttgcggcagc   1500

agctgccgga aatgttaggc accccaactc aagtcccagg ccccaggcat ctttcctgcc   1560

ctgccttgct tggcccatcc agtccaggcg cctggagcaa gtgctcagct acttctcctg   1620

cactttgaaa gacccctccc actcctggcc tcacatttct ctgtgtgatc ccccacttct   1680

gggctctgcc accccacagt gggaaaggcc accctagaaa gaagtccgct ggcacccata   1740

ggaaggggcc tcaggagcag gaagggccag gaccagaacc ttgcccacgg caactgcctt   1800

cctgcctctc cccttcctcc tctgctcttg atctgtgttt caataaatta atgtagccaa   1860

aaaaaaaaaa aaaaaa                                                   1876


<210> SEQ ID NO 478
<211> LENGTH: 505
<212> TYPE: PRT
<213> ORGANISM: Homo sapiens

<400> SEQUENCE: 478

Met Thr Cys Gly Ser Gly Phe Gly Gly Arg Ala Phe Ser Cys Ile Ser
 1               5                  10                  15

Ala Cys Gly Pro Arg Pro Gly Arg Cys Cys Ile Thr Ala Ala Pro Tyr
            20                  25                  30

Arg Gly Ile Ser Cys Tyr Arg Gly Leu Thr Gly Gly Phe Gly Ser His
        35                  40                  45

Ser Val Cys Gly Gly Phe Arg Ala Gly Ser Cys Gly Arg Ser Phe Gly
    50                  55                  60

Tyr Arg Ser Gly Gly Val Cys Gly Pro Ser Pro Pro Cys Ile Thr Thr
65                  70                  75                  80

Val Ser Val Asn Glu Ser Leu Leu Thr Pro Leu Asn Leu Glu Ile Asp
                85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
            260                 265                 270
```

-continued

```
Cys Ile Ile Ala Glu Ile Lys Ala Gln Tyr Asp Asp Ile Val Thr Arg
        275                 280                 285

Ser Arg Ala Glu Ala Glu Ser Trp Tyr Arg Ser Lys Cys Glu Glu Met
    290                 295                 300

Lys Ala Thr Val Ile Arg His Gly Glu Thr Leu Arg Arg Thr Lys Glu
305                 310                 315                 320

Glu Ile Asn Glu Leu Asn Arg Met Ile Gln Arg Leu Thr Ala Glu Val
                325                 330                 335

Glu Asn Ala Lys Cys Gln Asn Ser Lys Leu Glu Ala Ala Val Ala Gln
            340                 345                 350

Ser Glu Gln Gln Gly Glu Ala Ala Leu Ser Asp Ala Arg Cys Lys Leu
        355                 360                 365

Ala Glu Leu Glu Gly Ala Leu Gln Lys Ala Lys Gln Asp Met Ala Cys
    370                 375                 380

Leu Ile Arg Glu Tyr Gln Glu Val Met Asn Ser Lys Leu Gly Leu Asp
385                 390                 395                 400

Ile Glu Ile Ala Thr Tyr Arg Arg Leu Leu Glu Gly Glu Glu Gln Arg
                405                 410                 415

Leu Cys Glu Gly Ile Gly Ala Val Asn Val Cys Val Ser Ser Ser Arg
            420                 425                 430

Gly Gly Val Val Cys Gly Asp Leu Cys Val Ser Gly Ser Arg Pro Val
        435                 440                 445

Thr Gly Ser Val Cys Ser Ala Pro Cys Asn Gly Asn Val Ala Val Ser
    450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
                485                 490                 495

Ser Cys Gly Ser Ser Cys Arg Lys Cys
            500                 505
```

<210> SEQ ID NO 479
<211> LENGTH: 221
<212> TYPE: DNA
<213> ORGANISM: Homo sapiens
<220> FEATURE:
<221> NAME/KEY: misc_feature
<222> LOCATION: 22
<223> OTHER INFORMATION: n = A,T,C or G

<400> SEQUENCE: 479

```
ggtccattcc tttcctcgcg tnggggtttc tctgtgtcag cgagcctcgg tacactgatt      60

tccgatcaaa agaatcatca tctttacctt gacttttcag ggaattactg aactttcttc     120

tcagaagata gggcacagcc attgccttgg cctcacttga agggtctgca tttgggtcct     180

ctggtctctt gccaagtttc ccagccactc gagggagaaa t                         221
```

<210> SEQ ID NO 480
<211> LENGTH: 36
<212> TYPE: DNA
<213> ORGANISM: Artificial Sequence
<220> FEATURE:
<223> OTHER INFORMATION: PCR primer

<400> SEQUENCE: 480

```
cggcgaattc accatgggaa caagagctct gcagtg                                36
```

<210> SEQ ID NO 481

-continued

<211> LENGTH: 62
<212> TYPE: DNA
<213> ORGANISM: Artificial Sequence
<220> FEATURE:
<223> OTHER INFORMATION: PCR primer

<400> SEQUENCE: 481
cggcaagctt ttaatggtga tggtgatgat gtataacttc tgtttctgct ttctcttttt 60
ca 62

<210> SEQ ID NO 482
<211> LENGTH: 972
<212> TYPE: DNA
<213> ORGANISM: Homo sapiens

<400> SEQUENCE: 482
atgggaacaa gagctctgca gtgtgaggtt tctcacactc atgaaaatga aaattatctc 60
ttacatgaaa attgcatgtt gaaaaaggaa attgccatgc taaaactgga aatagccaca 120
ctgaaacacc aataccagga aaaggaaaat aaatactttg aggacattaa gattttaaaa 180
gaaaagaatg ctgaacttca gatgacccta aaactgaaag aggaatcatt aactaaaagg 240
gcatctcaat atagtgggca gcttaaagtt ctgatagctg agaacacaat gctcacttct 300
aaattgaagg aaaaacaaga caaagaaata ctagaggcag aaattgaatc acaccatcct 360
agactggctt ctgctgtaca agaccatgat caaattgtga catcaagaaa aagtcaagaa 420
cctgctttcc acattgcagg agatgcttgt ttgcaaagaa aaatgaatgt tgatgtgagt 480
agtacgatat ataacaatga ggtgctccat caaccacttt ctgaagctca aaggaaatcc 540
aaaagcctaa aaattaatct caattatgcc ggagatgctc taagagaaaa tacattggtt 600
tcagaacatg cacaaagaga ccaacgtgaa acacagtgtc aaatgaagga agctgaacac 660
atgtatcaaa acgaacaaga taatgtgaac aaacacactg aacagcagga gtctctagat 720
cagaaattat ttcaactaca aagcaaaaat atgtggcttc aacagcaatt agttcatgca 780
cataagaaag ctgacaacaa aagcaagata acaattgata ttcattttct tgagaggaaa 840
atgcaacatc atctcctaaa agagaaaaat gaggagatat ttaattacaa taaccattta 900
aaaaaccgta tatatcaata tgaaaaagag aaagcagaaa cagaagttat acatcatcac 960
catcaccatt aa 972

<210> SEQ ID NO 483
<211> LENGTH: 323
<212> TYPE: PRT
<213> ORGANISM: Homo sapiens

<400> SEQUENCE: 483

Met Gly Thr Arg Ala Leu Gln Cys Glu Val Ser His Thr His Glu Asn
1 5 10 15

Glu Asn Tyr Leu Leu His Glu Asn Cys Met Leu Lys Lys Glu Ile Ala
20 25 30

Met Leu Lys Leu Glu Ile Ala Thr Leu Lys His Gln Tyr Gln Glu Lys
35 40 45

Glu Asn Lys Tyr Phe Glu Asp Ile Lys Ile Leu Lys Glu Lys Asn Ala
50 55 60

Glu Leu Gln Met Thr Leu Lys Leu Lys Glu Glu Ser Leu Thr Lys Arg
65 70 75 80

Ala Ser Gln Tyr Ser Gly Gln Leu Lys Val Leu Ile Ala Glu Asn Thr
85 90 95

-continued

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300

Tyr Gln Tyr Glu Lys Glu Lys Ala Glu Thr Glu Val Ile His His His
305                 310                 315                 320

His His His

<210> SEQ ID NO 484
<211> LENGTH: 1518
<212> TYPE: DNA
<213> ORGANISM: Homo sapiens

<400> SEQUENCE: 484
atgacctgcg gatcaggatt tggtgggcgc gccttccgct gcatctcggc ctgcgggccg 60
cggcccggcc gctgctgcat caccgccgcc ccctaccgtg gcatctcctg ctaccgcggc 120
ctcaccgggg gcttcggcag ccacagcgtg tgcggaggct ttcgggccgg ctcctgcgga 180
cgcagcttcg gctaccgctc cgggggcgtg tgcgggccca gtcccccatg catcaccacc 240
gtgtcggtca acgagagcct cctcacgccc ctcaacctgg agatcgaccc caacgcgcag 300
tgcgtgaagc aggaggagaa ggagcagatc aagtccctca acagcaggtt cgcggccttc 360
atcgacaagg tgcgcttcct ggagcagcag aacaaactgc tggagacaaa gctgcagttc 420
taccagaacc gcgagtgttg ccagagcaac ctggagcccc tgtttgaggg ctacatcgag 480
actctgcggc gggaggccga gtgcgtggag gccgacagcg ggaggctggc ctcagagctt 540
aaccacgtgc aggaggtgct ggagggctac aagaagaagt atgaggagga ggtttctctg 600
agagcaacag ctgagaacga gtttgtggct ctgaagaagg atgtggactg cgcctacctc 660
cgcaagtcag acctggaggc caacgtggag gccctgatcc aggagatcga cttcctgagg 720
cggctgtatg aggaggagat ccgcattctc cagtcgcaca tctcagacac ctccgtggtt 780

-continued

```
gtcaagctgg acaacagccg ggacctgaac atggactgca tcattgccga gattaaggca    840

cagtatgacg acattgtcac ccgcagccgg gccgaggccg agtcctggta ccgcagcaag    900

tgtgaggaga tgaaggccac ggtgatcagg cacggggaga ccctgcgccg caccaaggag    960

gagatcaatg agctgaaccg catgatccaa aggctgacgg ccgaggtgga gaatgccaag   1020

tgccagaact ccaagctgga ggccgcggtg gcccagtctg agcagcaggg tgaggcagcc   1080

ctcagtgatg cccgctgcaa gctggccgag ctggagggcg ccctgcagaa ggccaagcag   1140

gacatggcct gcctgatcag ggagtaccag gaggtgatga actccaagct gggcctggac   1200

atcgagatcg ccacctacag gcgcctgctg gagggcgagg agcagaggct atgtgaaggc   1260

attggggctg tgaatgtctg tgtcagcagc tcccggggcg gggtcgtgtg cggggacctc   1320

tgcgtgtcag gctcccggcc agtgactggc agtgtctgca gcgctccgtg caacgggaac   1380

gtggcggtga gcaccggcct gtgtgcgccc tgcggccaat tgaacaccac ctgcggaggg   1440

ggttcctgcg gcgtgggctc ctgtggtatc agctccctgg gtgtggggtc ttgcggcagc   1500

agctgccgga aatgttag                                                  1518
```

```
<210> SEQ ID NO 485
<211> LENGTH: 505
<212> TYPE: PRT
<213> ORGANISM: Homo sapiens

<400> SEQUENCE: 485

Met Thr Cys Gly Ser Gly Phe Gly Gly Arg Ala Phe Arg Cys Ile Ser
 1               5                  10                  15

Ala Cys Gly Pro Arg Pro Gly Arg Cys Cys Ile Thr Ala Ala Pro Tyr
            20                  25                  30

Arg Gly Ile Ser Cys Tyr Arg Gly Leu Thr Gly Gly Phe Gly Ser His
        35                  40                  45

Ser Val Cys Gly Gly Phe Arg Ala Gly Ser Cys Gly Arg Ser Phe Gly
    50                  55                  60

Tyr Arg Ser Gly Gly Val Cys Gly Pro Ser Pro Pro Cys Ile Thr Thr
65                  70                  75                  80

Val Ser Val Asn Glu Ser Leu Leu Thr Pro Leu Asn Leu Glu Ile Asp
                85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240
```

-continued

```
Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
            260                 265                 270

Cys Ile Ile Ala Glu Ile Lys Ala Gln Tyr Asp Asp Ile Val Thr Arg
        275                 280                 285

Ser Arg Ala Glu Ala Glu Ser Trp Tyr Arg Ser Lys Cys Glu Glu Met
    290                 295                 300

Lys Ala Thr Val Ile Arg His Gly Glu Thr Leu Arg Arg Thr Lys Glu
305                 310                 315                 320

Glu Ile Asn Glu Leu Asn Arg Met Ile Gln Arg Leu Thr Ala Glu Val
                325                 330                 335

Glu Asn Ala Lys Cys Gln Asn Ser Lys Leu Glu Ala Ala Val Ala Gln
            340                 345                 350

Ser Glu Gln Gln Gly Glu Ala Ala Leu Ser Asp Ala Arg Cys Lys Leu
        355                 360                 365

Ala Glu Leu Glu Gly Ala Leu Gln Lys Ala Lys Gln Asp Met Ala Cys
    370                 375                 380

Leu Ile Arg Glu Tyr Gln Glu Val Met Asn Ser Lys Leu Gly Leu Asp
385                 390                 395                 400

Ile Glu Ile Ala Thr Tyr Arg Arg Leu Leu Glu Gly Glu Glu Gln Arg
                405                 410                 415

Leu Cys Glu Gly Ile Gly Ala Val Asn Val Cys Val Ser Ser Ser Arg
            420                 425                 430

Gly Gly Val Val Cys Gly Asp Leu Cys Val Ser Gly Ser Arg Pro Val
        435                 440                 445

Thr Gly Ser Val Cys Ser Ala Pro Cys Asn Gly Asn Val Ala Val Ser
    450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
                485                 490                 495

Ser Cys Gly Ser Ser Cys Arg Lys Cys
            500                 505
```

```
<210> SEQ ID NO 486
<211> LENGTH: 827
<212> TYPE: DNA
<213> ORGANISM: Homo sapiens

<400> SEQUENCE: 486

gcattctcca gtcgcacatc tcagacacct ccgtggttgt caagctggac aacagccggg      60

acctgaacat ggactgcatc attgccgaga ttaaggcaca gtatgacgac attgtcaccc     120

gcagccgggc cgaggccgag tcctggtacc gcagcaagtg tgaggagatg aaggccacgg     180

tgatcaggca cggggagacc ctgcgccgca ccaaggagga gatcaatgag ctgaaccgca     240

tgatccaaag gctgacggcc gaggtggaga atgccaagtg ccagaactcc aagctggagg     300

ccgcggtggc ccagtctgag cagcagggtg aggcagccct cagtgatgcc cgctgcaagc     360

tggccgagct ggagggcgcc ctgcagaagg ccaagcagga catggcctgc ctgatcaggg     420

agtaccagga ggtgatgaac tccaagctgg gcctggacat cgagatcgcc acctacaggc     480

gcctgctgga gggcgaggag cagaggctat gtgaaggcat tggggctgtg aatgtctgtg     540

tcagcagctc ccggggcggg gtcgtgtgcg gggacctctg cgtgtcaggc tcccggccag     600
```

-continued

```
tgactggcag tgtctgcagc gctccgtgca acgggaacgt ggcggtgagc accggcctgt    660

gtgcgccctg cggccaattg aacaccacct gcggaggggg ttcctgcggc gtgggctcct    720

gtggtatcag ctccctgggt gtggggtctt gcggcagcag ctgccggaaa tgttaggcac    780

cccaactcaa gtcccaggcc ccaggcatct ttcctgccct gccttgc                  827
```

<210> SEQ ID NO 487
<211> LENGTH: 235
<212> TYPE: PRT
<213> ORGANISM: Homo sapiens

<400> SEQUENCE: 487

```
Met Asp Cys Ile Ile Ala Glu Ile Lys Ala Gln Tyr Asp Asp Ile Val
 1               5                  10                  15

Thr Arg Ser Arg Ala Glu Ala Glu Ser Trp Tyr Arg Ser Lys Cys Glu
            20                  25                  30

Glu Met Lys Ala Thr Val Ile Arg His Gly Glu Thr Leu Arg Arg Thr
        35                  40                  45

Lys Glu Glu Ile Asn Glu Leu Asn Arg Met Ile Gln Arg Leu Thr Ala
    50                  55                  60

Glu Val Glu Asn Ala Lys Cys Gln Asn Ser Lys Leu Glu Ala Ala Val
65                  70                  75                  80

Ala Gln Ser Glu Gln Gln Gly Glu Ala Ala Leu Ser Asp Ala Arg Cys
                85                  90                  95

Lys Leu Ala Glu Leu Glu Gly Ala Leu Gln Lys Ala Lys Gln Asp Met
            100                 105                 110

Ala Cys Leu Ile Arg Glu Tyr Gln Glu Val Met Asn Ser Lys Leu Gly
        115                 120                 125

Leu Asp Ile Glu Ile Ala Thr Tyr Arg Arg Leu Leu Glu Gly Glu Glu
    130                 135                 140

Gln Arg Leu Cys Glu Gly Ile Gly Ala Val Asn Val Cys Val Ser Ser
145                 150                 155                 160

Ser Arg Gly Gly Val Val Cys Gly Asp Leu Cys Val Ser Gly Ser Arg
                165                 170                 175

Pro Val Thr Gly Ser Val Cys Ser Ala Pro Cys Asn Gly Asn Val Ala
            180                 185                 190

Val Ser Thr Gly Leu Cys Ala Pro Cys Gly Gln Leu Asn Thr Thr Cys
        195                 200                 205

Gly Gly Gly Ser Cys Gly Val Gly Ser Cys Gly Ile Ser Ser Leu Gly
    210                 215                 220

Val Gly Ser Cys Gly Ser Ser Cys Arg Lys Cys
225                 230                 235
```

<210> SEQ ID NO 488
<211> LENGTH: 9
<212> TYPE: PRT
<213> ORGANISM: Homo sapiens

<400> SEQUENCE: 488

```
Ser Leu Thr Lys Arg Ala Ser Gln Tyr
 1               5
```

<210> SEQ ID NO 489
<211> LENGTH: 27
<212> TYPE: DNA
<213> ORGANISM: Homo sapiens

<400> SEQUENCE: 489

-continued

```
tcattaacta aaagggcatc tcaatat                                          27


<210> SEQ ID NO 490
<211> LENGTH: 3288
<212> TYPE: DNA
<213> ORGANISM: Homo sapiens

<400> SEQUENCE: 490

atgaagttgc tgatggtcct catgctggcg gccctctccc agcactgcta cgcaggctct     60

ggctgcccct tattggagaa tgtgatttcc aagacaatca atccacaagt gtctaagact    120

gaatacaaag aacttcttca agagttcata gacgacaatg ccactacaaa tgccatagat    180

gaattgaagg aatgttttct taaccaaacg gatgaaactc tgagcaatgt tgaggtgttt    240

atgcaattaa tatatgacag cagtctttgt gatttattta tgagtcccgc aaaagaaaca    300

tctgagaaat ttacgtgggc agcaaaagga agacctagga agatcgcatg ggagaaaaaa    360

gaaacacctg taaagactgg atgcgtggca agagtaacat ctaataaaac taaagttttg    420

gaaaaaggaa gatctaagat gattgcatgt cctacaaaag aatcatctac aaaagcaagt    480

gccaatgatc agaggttccc atcagaatcc aaacaagagg aagatgaaga atattcttgt    540

gattctcgga gtctctttga gagttctgca aagattcaag tgtgtatacc tgagtctata    600

tatcaaaaag taatggagat aaatagagaa gtagaagagc ctcctaagaa gccatctgcc    660

ttcaagcctg ccattgaaat gcaaaactct gttccaaata aagcctttga attgaagaat    720

gaacaaacat tgagagcaga tccgatgttc ccaccagaat ccaaacaaaa ggactatgaa    780

gaaaattctt gggattctga gagtctctgt gagactgttt cacagaagga tgtgtgttta    840

cccaaggcta cacatcaaaa agaaatagat aaaataaatg gaaaattaga agagtctcct    900

aataaagatg gtcttctgaa ggctacctgc ggaatgaaag tttctattcc aactaaagcc    960

ttagaattga aggacatgca aactttcaaa gcagagcctc cggggaagcc atctgccttc   1020

gagcctgcca ctgaaatgca aaagtctgtc ccaaataaag ccttggaatt gaaaaatgaa   1080

caaacattga gagcagatga gatactccca tcagaatcca aacaaaagga ctatgaagaa   1140

agttcttggg attctgagag tctctgtgag actgtttcac agaaggatgt gtgtttaccc   1200

aaggctrcrc atcaaaaaga aatagataaa ataaatggaa aattagaagg gtctcctgtt   1260

aaagatggtc ttctgaaggc taactgcgga atgaaagttt ctattccaac taaagcctta   1320

gaattgatgg acatgcaaac tttcaaagca gagcctcccg agaagccatc tgccttcgag   1380

cctgccattg aaatgcaaaa gtctgttcca aataaagcct tggaattgaa gaatgaacaa   1440

acattgagag cagatgagat actcccatca gaatccaaac aaaaggacta tgaagaaagt   1500

tcttgggatt ctgagagtct ctgtgagact gtttcacaga aggatgtgtg tttacccaag   1560

gctrcrcatc aaaaagaaat agataaaata aatggaaaat tagaagagtc tcctgataat   1620

gatggttttc tgaaggctcc ctgcagaatg aaagtttcta ttccaactaa agccttagaa   1680

ttgatggaca tgcaaacttt caaagcagag cctcccgaga agccatctgc cttcgagcct   1740

gccattgaaa tgcaaaagtc tgttccaaat aaagccttgg aattgaagaa tgaacaaaca   1800

ttgagagcag atcagatgtt cccttcagaa tcaaaacaaa agaasgttga agaaaattct   1860

tgggattctg agagtctccg tgagactgtt tcacagaagg atgtgtgtgt acccaaggct   1920

acacatcaaa aagaaatgga taaaataagt ggaaaattag aagattcaac tagcctatca   1980

aaaatcttgg atacagttca ttcttgtgaa agagcaaggg aacttcaaaa agatcactgt   2040
```

-continued

```
gaacaacgta caggaaaaat ggaacaaatg aaaaagaagt tttgtgtact gaaaaagaaa   2100

ctgtcagaag caaaagaaat aaaatcacag ttagagaacc aaaaagttaa atgggaacaa   2160

gagctctgca gtgtgagatt gactttaaac caagaagaag agaagagaag aaatgccgat   2220

atattaaatg aaaaaattag ggaagaatta ggaagaatcg aagagcagca taggaaagag   2280

ttagaagtga aacaacaact tgaacaggct ctcagaatac aagatataga attgaagagt   2340

gtagaaagta atttgaatca ggtttctcac actcatgaaa atgaaaatta tctcttacat   2400

gaaaattgca tgttgaaaaa ggaaattgcc atgctaaaac tggaaatagc cacactgaaa   2460

caccaatacc aggaaaagga aaataaatac tttgaggaca ttaagatttt aaaagaaaag   2520

aatgctgaac ttcagatgac cctaaaactg aaagaggaat cattaactaa aagggcatct   2580

caatatagtg ggcagcttaa agttctgata gctgagaaca caatgctcac ttctaaattg   2640

aaggaaaaac aagacaaaga aatactagag gcagaaattg aatcacacca tcctagactg   2700

gcttctgctg tacaagacca tgatcaaatt gtgacatcaa gaaaaagtca agaacctgct   2760

ttccacattg caggagatgc ttgtttgcaa agaaaaatga atgttgatgt gagtagtacg   2820

atatataaca atgaggtgct ccatcaacca ctttctgaag ctcaaaggaa atccaaaagc   2880

ctaaaaatta atctcaatta tgcmggagat gctctaagag aaaatacatt ggtttcagaa   2940

catgcacaaa gagaccaacg tgaaacacag tgtcaaatga aggaagctga acacatgtat   3000

caaaacgaac aagataatgt gaacaaacac actgaacagc aggagtctct agatcagaaa   3060

ttatttcaac tacaaagcaa aaatatgtgg cttcaacagc aattagttca tgcacataag   3120

aaagctgaca acaaaagcaa gataacaatt gatattcatt ttcttgagag gaaaatgcaa   3180

catcatctcc taaaagagaa aaatgaggag atatttaatt acaataacca tttaaaaaac   3240

cgtatatatc aatatgaaaa agagaaagca gaaacagaaa actcatga                3288
```

<210> SEQ ID NO 491
<211> LENGTH: 2232
<212> TYPE: DNA
<213> ORGANISM: Homo sapiens

<400> SEQUENCE: 491

```
atgaagttgc tgatggtcct catgctggcg gccctctccc agcactgcta cgcaggctct     60

ggctgcccct tattggagaa tgtgatttcc aagacaatca atccacaagt gtctaagact    120

gaatacaaag aacttcttca agagttcata gacgacaatg ccactacaaa tgccatagat    180

gaattgaagg aatgttttct taaccaaacg gatgaaactc tgagcaatgt tgaggtgttt    240

atgcaattaa tatatgacag cagtctttgt gatttattta tgagtcccgc aaaagaaaca    300

tctgagaaat ttacgtgggc agcaaaagga agacctagga agatcgcatg ggagaaaaaa    360

gaaacacctg taaagactgg atgcgtggca agagtaacat ctaataaaac taaagttttg    420

gaaaaaggaa gatctaagat gattgcatgt cctacaaaag aatcatctac aaaagcaagt    480

gccaatgatc agaggttccc atcagaatcc aaacaagagg aagatgaaga atattcttgt    540

gattctcgga gtctctttga gagttctgca aagattcaag tgtgtatacc tgagtctata    600

tatcaaaaag taatggagat aaatagagaa gtagaagagc ctcctaagaa gccatctgcc    660

ttcaagcctg ccattgaaat gcaaaactct gttccaaata aagcctttga attgaagaat    720

gaacaaacat tgagagcaga tccgatgttc ccaccagaat ccaaacaaaa ggactatgaa    780

gaaaattctt gggattctga gagtctctgt gagactgttt cacagaagga tgtgtgttta    840

cccaaggcta cacatcaaaa agaaatagat aaaataaatg gaaaattaga agagtctcct    900
```

-continued

```
aataaagatg gtcttctgaa ggctacctgc ggaatgaaag tttctattcc aactaaagcc    960

ttagaattga aggacatgca aactttcaaa gcagagcctc cggggaagcc atctgccttc   1020

gagcctgcca ctgaaatgca aaagtctgtc ccaaataaag ccttggaatt gaaaaatgaa   1080

caaacattga gagcagatga gatactccca tcagaatcca aacaaaagga ctatgaagaa   1140

agttcttggg attctgagag tctctgtgag actgtttcac agaaggatgt gtgtttaccc   1200

aaggctrcrc atcaaaaaga aatagataaa ataaatggaa aattagaagg gtctcctgtt   1260

aaagatggtc ttctgaaggc taactgcgga atgaaagttt ctattccaac taaagcctta   1320

gaattgatgg acatgcaaac tttcaaagca gagcctcccg agaagccatc tgccttcgag   1380

cctgccattg aaatgcaaaa gtctgttcca aataaagcct tggaattgaa gaatgaacaa   1440

acattgagag cagatgagat actcccatca gaatccaaac aaaaggacta tgaagaaagt   1500

tcttgggatt ctgagagtct ctgtgagact gtttcacaga aggatgtgtg tttacccaag   1560

gctrcrcatc aaaaagaaat agataaaata aatggaaaat tagaagagtc tcctgataat   1620

gatggttttc tgaaggctcc ctgcagaatg aaagtttcta ttccaactaa agccttagaa   1680

ttgatggaca tgcaaacttt caaagcagag cctcccgaga agccatctgc cttcgagcct   1740

gccattgaaa tgcaaaagtc tgttccaaat aaagccttgg aattgaagaa tgaacaaaca   1800

ttgagagcag atcagatgtt cccttcagaa tcaaaacaaa agaasgttga agaaaattct   1860

tgggattctg agagtctccg tgagactgtt tcacagaagg atgtgtgtgt acccaaggct   1920

acacatcaaa aagaaatgga taaaataagt ggaaaattag aagattcaac tagcctatca   1980

aaaatcttgg atacagttca ttcttgtgaa agagcaaggg aacttcaaaa agatcactgt   2040

gaacaacgta caggaaaaat ggaacaaatg aaaaagaagt tttgtgtact gaaaaagaaa   2100

ctgtcagaag caaaagaaat aaaatcacag ttagagaacc aaaaagttaa atgggaacaa   2160

gagctctgca gtgtgaggtt tctcacactc atgaaaatga aaattatctc ttacatgaaa   2220

attgcatgtt ga                                                       2232
```

<210> SEQ ID NO 492
<211> LENGTH: 1233
<212> TYPE: DNA
<213> ORGANISM: Homo sapiens

<400> SEQUENCE: 492

```
atgaagttgc tgatggtcct catgctggcg gccctctccc agcactgcta cgcaggctct     60

ggctgcccct tattggagaa tgtgatttcc aagacaatca atccacaagt gtctaagact    120

gaatacaaag aacttcttca agagttcata gacgacaatg ccactacaaa tgccatagat    180

gaattgaagg aatgttttct taaccaaacg gatgaaactc tgagcaatgt tgaggtgttt    240

atgcaattaa tatatgacag cagtctttgt gatttattta tgggaacaag agctctgcag    300

tgtgaggttt ctcacactca tgaaaatgaa aattatctct tacatgaaaa ttgcatgttg    360

aaaaaggaaa ttgccatgct aaaactggaa atagccacac tgaaacacca ataccaggaa    420

aaggaaaata aatactttga ggacattaag attttaaaag aaaagaatgc tgaacttcag    480

atgaccctaa aactgaaaga ggaatcatta actaaaaggg catctcaata tagtgggcag    540

cttaaagttc tgatagctga gaacacaatg ctcacttcta aattgaagga aaaacaagac    600

aaagaaatac tagaggcaga aattgaatca caccatccta gactggcttc tgctgtacaa    660

gaccatgatc aaattgtgac atcaagaaaa agtcaagaac ctgctttcca cattgcagga    720
```

-continued

```
gatgcttgtt tgcaaagaaa aatgaatgtt gatgtgagta gtacgatata taacaatgag    780

gtgctccatc aaccactttc tgaagctcaa aggaaatcca aaagcctaaa aattaatctc    840

aattatgccg gagatgctct aagagaaaat acattggttt cagaacatgc acaaagagac    900

caacgtgaaa cacagtgtca aatgaaggaa gctgaacaca tgtatcaaaa cgaacaagat    960

aatgtgaaca aacacactga acagcaggag tctctagatc agaaattatt tcaactacaa   1020

agcaaaaata tgtggcttca acagcaatta gttcatgcac ataagaaagc tgacaacaaa   1080

agcaagataa caattgatat tcattttctt gagaggaaaa tgcaacatca tctcctaaaa   1140

gagaaaaatg aggagatatt taattacaat aaccatttaa aaaaccgtat atatcaatat   1200

gaaaaagaga aagcagaaac agaagttata taa                                1233
```

```
<210> SEQ ID NO 493
<211> LENGTH: 1095
<212> TYPE: PRT
<213> ORGANISM: Homo sapiens
<220> FEATURE:
<221> NAME/KEY: VARIANT
<222> LOCATION: 403, 522, 615
<223> OTHER INFORMATION: Xaa = Any Amino Acid

<400> SEQUENCE: 493

Met Lys Leu Leu Met Val Leu Met Leu Ala Ala Leu Ser Gln His Cys
 1               5                  10                  15

Tyr Ala Gly Ser Gly Cys Pro Leu Leu Glu Asn Val Ile Ser Lys Thr
            20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
    50                  55                  60

Cys Phe Leu Asn Gln Thr Asp Glu Thr Leu Ser Asn Val Glu Val Phe
65                  70                  75                  80

Met Gln Leu Ile Tyr Asp Ser Ser Leu Cys Asp Leu Phe Met Ser Pro
                85                  90                  95

Ala Lys Glu Thr Ser Glu Lys Phe Thr Trp Ala Ala Lys Gly Arg Pro
            100                 105                 110

Arg Lys Ile Ala Trp Glu Lys Lys Glu Thr Pro Val Lys Thr Gly Cys
        115                 120                 125

Val Ala Arg Val Thr Ser Asn Lys Thr Lys Val Leu Glu Lys Gly Arg
    130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ser Ala Lys Ile
            180                 185                 190

Gln Val Cys Ile Pro Glu Ser Ile Tyr Gln Lys Val Met Glu Ile Asn
        195                 200                 205

Arg Glu Val Glu Glu Pro Pro Lys Lys Pro Ser Ala Phe Lys Pro Ala
    210                 215                 220

Ile Glu Met Gln Asn Ser Val Pro Asn Lys Ala Phe Glu Leu Lys Asn
225                 230                 235                 240

Glu Gln Thr Leu Arg Ala Asp Pro Met Phe Pro Pro Glu Ser Lys Gln
                245                 250                 255

Lys Asp Tyr Glu Glu Asn Ser Trp Asp Ser Glu Ser Leu Cys Glu Thr
```

-continued

```
            260                 265                 270

Val Ser Gln Lys Asp Val Cys Leu Pro Lys Ala Thr His Gln Lys Glu
        275                 280                 285

Ile Asp Lys Ile Asn Gly Lys Leu Glu Glu Ser Pro Asn Lys Asp Gly
    290                 295                 300

Leu Leu Lys Ala Thr Cys Gly Met Lys Val Ser Ile Pro Thr Lys Ala
305                 310                 315                 320

Leu Glu Leu Lys Asp Met Gln Thr Phe Lys Ala Glu Pro Pro Gly Lys
                325                 330                 335

Pro Ser Ala Phe Glu Pro Ala Thr Glu Met Gln Lys Ser Val Pro Asn
            340                 345                 350

Lys Ala Leu Glu Leu Lys Asn Glu Gln Thr Leu Arg Ala Asp Glu Ile
        355                 360                 365

Leu Pro Ser Glu Ser Lys Gln Lys Asp Tyr Glu Glu Ser Ser Trp Asp
    370                 375                 380

Ser Glu Ser Leu Cys Glu Thr Val Ser Gln Lys Asp Val Cys Leu Pro
385                 390                 395                 400

Lys Ala Xaa His Gln Lys Glu Ile Asp Lys Ile Asn Gly Lys Leu Glu
                405                 410                 415

Gly Ser Pro Val Lys Asp Gly Leu Leu Lys Ala Asn Cys Gly Met Lys
            420                 425                 430

Val Ser Ile Pro Thr Lys Ala Leu Glu Leu Met Asp Met Gln Thr Phe
        435                 440                 445

Lys Ala Glu Pro Pro Glu Lys Pro Ser Ala Phe Glu Pro Ala Ile Glu
    450                 455                 460

Met Gln Lys Ser Val Pro Asn Lys Ala Leu Glu Leu Lys Asn Glu Gln
465                 470                 475                 480

Thr Leu Arg Ala Asp Glu Ile Leu Pro Ser Glu Ser Lys Gln Lys Asp
                485                 490                 495

Tyr Glu Glu Ser Ser Trp Asp Ser Glu Ser Leu Cys Glu Thr Val Ser
            500                 505                 510

Gln Lys Asp Val Cys Leu Pro Lys Ala Xaa His Gln Lys Glu Ile Asp
        515                 520                 525

Lys Ile Asn Gly Lys Leu Glu Glu Ser Pro Asp Asn Asp Gly Phe Leu
    530                 535                 540

Lys Ala Pro Cys Arg Met Lys Val Ser Ile Pro Thr Lys Ala Leu Glu
545                 550                 555                 560

Leu Met Asp Met Gln Thr Phe Lys Ala Glu Pro Pro Glu Lys Pro Ser
                565                 570                 575

Ala Phe Glu Pro Ala Ile Glu Met Gln Lys Ser Val Pro Asn Lys Ala
            580                 585                 590

Leu Glu Leu Lys Asn Glu Gln Thr Leu Arg Ala Asp Gln Met Phe Pro
        595                 600                 605

Ser Glu Ser Lys Gln Lys Xaa Val Glu Glu Asn Ser Trp Asp Ser Glu
    610                 615                 620

Ser Leu Arg Glu Thr Val Ser Gln Lys Asp Val Cys Val Pro Lys Ala
625                 630                 635                 640

Thr His Gln Lys Glu Met Asp Lys Ile Ser Gly Lys Leu Glu Asp Ser
                645                 650                 655

Thr Ser Leu Ser Lys Ile Leu Asp Thr Val His Ser Cys Glu Arg Ala
            660                 665                 670

Arg Glu Leu Gln Lys Asp His Cys Glu Gln Arg Thr Gly Lys Met Glu
        675                 680                 685
```

-continued

```
Gln Met Lys Lys Lys Phe Cys Val Leu Lys Lys Lys Leu Ser Glu Ala
    690                 695                 700

Lys Glu Ile Lys Ser Gln Leu Glu Asn Gln Lys Val Lys Trp Glu Gln
705                 710                 715                 720

Glu Leu Cys Ser Val Arg Leu Thr Leu Asn Gln Glu Glu Glu Lys Arg
                725                 730                 735

Arg Asn Ala Asp Ile Leu Asn Glu Lys Ile Arg Glu Glu Leu Gly Arg
            740                 745                 750

Ile Glu Glu Gln His Arg Lys Glu Leu Glu Val Lys Gln Gln Leu Glu
        755                 760                 765

Gln Ala Leu Arg Ile Gln Asp Ile Glu Leu Lys Ser Val Glu Ser Asn
    770                 775                 780

Leu Asn Gln Val Ser His Thr His Glu Asn Glu Asn Tyr Leu Leu His
785                 790                 795                 800

Glu Asn Cys Met Leu Lys Lys Glu Ile Ala Met Leu Lys Leu Glu Ile
                805                 810                 815

Ala Thr Leu Lys His Gln Tyr Gln Glu Lys Glu Asn Lys Tyr Phe Glu
            820                 825                 830

Asp Ile Lys Ile Leu Lys Glu Lys Asn Ala Glu Leu Gln Met Thr Leu
        835                 840                 845

Lys Leu Lys Glu Glu Ser Leu Thr Lys Arg Ala Ser Gln Tyr Ser Gly
    850                 855                 860

Gln Leu Lys Val Leu Ile Ala Glu Asn Thr Met Leu Thr Ser Lys Leu
865                 870                 875                 880

Lys Glu Lys Gln Asp Lys Glu Ile Leu Glu Ala Glu Ile Glu Ser His
                885                 890                 895

His Pro Arg Leu Ala Ser Ala Val Gln Asp His Asp Gln Ile Val Thr
            900                 905                 910

Ser Arg Lys Ser Gln Glu Pro Ala Phe His Ile Ala Gly Asp Ala Cys
        915                 920                 925

Leu Gln Arg Lys Met Asn Val Asp Val Ser Ser Thr Ile Tyr Asn Asn
    930                 935                 940

Glu Val Leu His Gln Pro Leu Ser Glu Ala Gln Arg Lys Ser Lys Ser
945                 950                 955                 960

Leu Lys Ile Asn Leu Asn Tyr Ala Gly Asp Ala Leu Arg Glu Asn Thr
                965                 970                 975

Leu Val Ser Glu His Ala Gln Arg Asp Gln Arg Glu Thr Gln Cys Gln
            980                 985                 990

Met Lys Glu Ala Glu His Met Tyr Gln Asn Glu Gln Asp Asn Val Asn
        995                 1000                1005

Lys His Thr Glu Gln Gln Glu Ser Leu Asp Gln Lys Leu Phe Gln Leu
    1010                1015                1020

Gln Ser Lys Asn Met Trp Leu Gln Gln Gln Leu Val His Ala His Lys
1025                1030                1035                1040

Lys Ala Asp Asn Lys Ser Lys Ile Thr Ile Asp Ile His Phe Leu Glu
                1045                1050                1055

Arg Lys Met Gln His His Leu Leu Lys Glu Lys Asn Glu Glu Ile Phe
            1060                1065                1070

Asn Tyr Asn Asn His Leu Lys Asn Arg Ile Tyr Gln Tyr Glu Lys Glu
        1075                1080                1085

Lys Ala Glu Thr Glu Asn Ser
    1090                1095
```

-continued

<210> SEQ ID NO 494
<211> LENGTH: 743
<212> TYPE: PRT
<213> ORGANISM: Homo sapiens
<220> FEATURE:
<221> NAME/KEY: VARIANT
<222> LOCATION: 403, 522, 615
<223> OTHER INFORMATION: Xaa = Any Amino Acid

<400> SEQUENCE: 494

```
Met Lys Leu Leu Met Val Leu Met Leu Ala Ala Leu Ser Gln His Cys
 1               5                  10                  15

Tyr Ala Gly Ser Gly Cys Pro Leu Leu Glu Asn Val Ile Ser Lys Thr
            20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
    50                  55                  60

Cys Phe Leu Asn Gln Thr Asp Glu Thr Leu Ser Asn Val Glu Val Phe
65                  70                  75                  80

Met Gln Leu Ile Tyr Asp Ser Ser Leu Cys Asp Leu Phe Met Ser Pro
                85                  90                  95

Ala Lys Glu Thr Ser Glu Lys Phe Thr Trp Ala Ala Lys Gly Arg Pro
            100                 105                 110

Arg Lys Ile Ala Trp Glu Lys Lys Glu Thr Pro Val Lys Thr Gly Cys
        115                 120                 125

Val Ala Arg Val Thr Ser Asn Lys Thr Lys Val Leu Glu Lys Gly Arg
    130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ser Ala Lys Ile
            180                 185                 190

Gln Val Cys Ile Pro Glu Ser Ile Tyr Gln Lys Val Met Glu Ile Asn
        195                 200                 205

Arg Glu Val Glu Glu Pro Pro Lys Lys Pro Ser Ala Phe Lys Pro Ala
    210                 215                 220

Ile Glu Met Gln Asn Ser Val Pro Asn Lys Ala Phe Glu Leu Lys Asn
225                 230                 235                 240

Glu Gln Thr Leu Arg Ala Asp Pro Met Phe Pro Pro Glu Ser Lys Gln
                245                 250                 255

Lys Asp Tyr Glu Glu Asn Ser Trp Asp Ser Glu Ser Leu Cys Glu Thr
            260                 265                 270

Val Ser Gln Lys Asp Val Cys Leu Pro Lys Ala Thr His Gln Lys Glu
        275                 280                 285

Ile Asp Lys Ile Asn Gly Lys Leu Glu Glu Ser Pro Asn Lys Asp Gly
    290                 295                 300

Leu Leu Lys Ala Thr Cys Gly Met Lys Val Ser Ile Pro Thr Lys Ala
305                 310                 315                 320

Leu Glu Leu Lys Asp Met Gln Thr Phe Lys Ala Glu Pro Pro Gly Lys
                325                 330                 335

Pro Ser Ala Phe Glu Pro Ala Thr Glu Met Gln Lys Ser Val Pro Asn
            340                 345                 350

Lys Ala Leu Glu Leu Lys Asn Glu Gln Thr Leu Arg Ala Asp Glu Ile
```

-continued

```
        355                 360                 365

Leu Pro Ser Glu Ser Lys Gln Lys Asp Tyr Glu Glu Ser Ser Trp Asp
    370                 375                 380

Ser Glu Ser Leu Cys Glu Thr Val Ser Gln Lys Asp Val Cys Leu Pro
385                 390                 395                 400

Lys Ala Xaa His Gln Lys Glu Ile Asp Lys Ile Asn Gly Lys Leu Glu
                405                 410                 415

Gly Ser Pro Val Lys Asp Gly Leu Leu Lys Ala Asn Cys Gly Met Lys
            420                 425                 430

Val Ser Ile Pro Thr Lys Ala Leu Glu Leu Met Asp Met Gln Thr Phe
        435                 440                 445

Lys Ala Glu Pro Pro Glu Lys Pro Ser Ala Phe Glu Pro Ala Ile Glu
    450                 455                 460

Met Gln Lys Ser Val Pro Asn Lys Ala Leu Glu Leu Lys Asn Glu Gln
465                 470                 475                 480

Thr Leu Arg Ala Asp Glu Ile Leu Pro Ser Glu Ser Lys Gln Lys Asp
                485                 490                 495

Tyr Glu Glu Ser Ser Trp Asp Ser Glu Ser Leu Cys Glu Thr Val Ser
            500                 505                 510

Gln Lys Asp Val Cys Leu Pro Lys Ala Xaa His Gln Lys Glu Ile Asp
        515                 520                 525

Lys Ile Asn Gly Lys Leu Glu Glu Ser Pro Asp Asn Asp Gly Phe Leu
    530                 535                 540

Lys Ala Pro Cys Arg Met Lys Val Ser Ile Pro Thr Lys Ala Leu Glu
545                 550                 555                 560

Leu Met Asp Met Gln Thr Phe Lys Ala Glu Pro Pro Glu Lys Pro Ser
                565                 570                 575

Ala Phe Glu Pro Ala Ile Glu Met Gln Lys Ser Val Pro Asn Lys Ala
            580                 585                 590

Leu Glu Leu Lys Asn Glu Gln Thr Leu Arg Ala Asp Gln Met Phe Pro
        595                 600                 605

Ser Glu Ser Lys Gln Lys Xaa Val Glu Glu Asn Ser Trp Asp Ser Glu
    610                 615                 620

Ser Leu Arg Glu Thr Val Ser Gln Lys Asp Val Cys Val Pro Lys Ala
625                 630                 635                 640

Thr His Gln Lys Glu Met Asp Lys Ile Ser Gly Lys Leu Glu Asp Ser
                645                 650                 655

Thr Ser Leu Ser Lys Ile Leu Asp Thr Val His Ser Cys Glu Arg Ala
            660                 665                 670

Arg Glu Leu Gln Lys Asp His Cys Glu Gln Arg Thr Gly Lys Met Glu
        675                 680                 685

Gln Met Lys Lys Lys Phe Cys Val Leu Lys Lys Lys Leu Ser Glu Ala
    690                 695                 700

Lys Glu Ile Lys Ser Gln Leu Glu Asn Gln Lys Val Lys Trp Glu Gln
705                 710                 715                 720

Glu Leu Cys Ser Val Arg Phe Leu Thr Leu Met Lys Met Lys Ile Ile
                725                 730                 735

Ser Tyr Met Lys Ile Ala Cys
            740
```

<210> SEQ ID NO 495
<211> LENGTH: 410
<212> TYPE: PRT
<213> ORGANISM: Homo sapiens

<400> SEQUENCE: 495

Met Lys Leu Leu Met Val Leu Met Leu Ala Ala Leu Ser Gln His Cys
1               5                   10                  15

Tyr Ala Gly Ser Gly Cys Pro Leu Leu Glu Asn Val Ile Ser Lys Thr
            20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
    50                  55                  60

Cys Phe Leu Asn Gln Thr Asp Glu Thr Leu Ser Asn Val Glu Val Phe
65                  70                  75                  80

Met Gln Leu Ile Tyr Asp Ser Ser Leu Cys Asp Leu Phe Met Gly Thr
                85                  90                  95

Arg Ala Leu Gln Cys Glu Val Ser His Thr His Glu Asn Glu Asn Tyr
            100                 105                 110

Leu Leu His Glu Asn Cys Met Leu Lys Lys Glu Ile Ala Met Leu Lys
        115                 120                 125

Leu Glu Ile Ala Thr Leu Lys His Gln Tyr Gln Glu Lys Glu Asn Lys
    130                 135                 140

Tyr Phe Glu Asp Ile Lys Ile Leu Lys Glu Lys Asn Ala Glu Leu Gln
145                 150                 155                 160

Met Thr Leu Lys Leu Lys Glu Glu Ser Leu Thr Lys Arg Ala Ser Gln
                165                 170                 175

Tyr Ser Gly Gln Leu Lys Val Leu Ile Ala Glu Asn Thr Met Leu Thr
            180                 185                 190

Ser Lys Leu Lys Glu Lys Gln Asp Lys Glu Ile Leu Glu Ala Glu Ile
        195                 200                 205

Glu Ser His His Pro Arg Leu Ala Ser Ala Val Gln Asp His Asp Gln
    210                 215                 220

Ile Val Thr Ser Arg Lys Ser Gln Glu Pro Ala Phe His Ile Ala Gly
225                 230                 235                 240

Asp Ala Cys Leu Gln Arg Lys Met Asn Val Asp Val Ser Ser Thr Ile
                245                 250                 255

Tyr Asn Asn Glu Val Leu His Gln Pro Leu Ser Glu Ala Gln Arg Lys
            260                 265                 270

Ser Lys Ser Leu Lys Ile Asn Leu Asn Tyr Ala Gly Asp Ala Leu Arg
        275                 280                 285

Glu Asn Thr Leu Val Ser Glu His Ala Gln Arg Asp Gln Arg Glu Thr
    290                 295                 300

Gln Cys Gln Met Lys Glu Ala Glu His Met Tyr Gln Asn Glu Gln Asp
305                 310                 315                 320

Asn Val Asn Lys His Thr Glu Gln Gln Glu Ser Leu Asp Gln Lys Leu
                325                 330                 335

Phe Gln Leu Gln Ser Lys Asn Met Trp Leu Gln Gln Gln Leu Val His
            340                 345                 350

Ala His Lys Lys Ala Asp Asn Lys Ser Lys Ile Thr Ile Asp Ile His
        355                 360                 365

Phe Leu Glu Arg Lys Met Gln His His Leu Leu Lys Glu Lys Asn Glu
    370                 375                 380

Glu Ile Phe Asn Tyr Asn Asn His Leu Lys Asn Arg Ile Tyr Gln Tyr
385                 390                 395                 400

Glu Lys Glu Lys Ala Glu Thr Glu Val Ile 405 410

<210> SEQ ID NO 496
<211> LENGTH: 20
<212> TYPE: PRT
<213> ORGANISM: Homo sapiens

<400> SEQUENCE: 496

Ile Asp Glu Leu Lys Glu Cys Phe Leu Asn Gln Thr Asp Glu Thr Leu
1 5 10 15

Ser Asn Val Glu
20

<210> SEQ ID NO 497
<211> LENGTH: 15
<212> TYPE: PRT
<213> ORGANISM: Homo sapiens

<400> SEQUENCE: 497

Thr Thr Asn Ala Ile Asp Glu Leu Lys Glu Cys Phe Leu Asn Gln
1 5 10 15

<210> SEQ ID NO 498
<211> LENGTH: 21
<212> TYPE: PRT
<213> ORGANISM: Homo sapiens

<400> SEQUENCE: 498

Ser Gln His Cys Tyr Ala Gly Ser Gly Cys Pro Leu Leu Glu Asn Val
1 5 10 15

Ile Ser Lys Thr Ile
20

<210> SEQ ID NO 499
<211> LENGTH: 20
<212> TYPE: PRT
<213> ORGANISM: Homo sapiens

<400> SEQUENCE: 499

Glu Tyr Lys Glu Leu Leu Gln Glu Phe Ile Asp Asp Asn Ala Thr Thr
1 5 10 15

Asn Ala Ile Asp
20

<210> SEQ ID NO 500
<211> LENGTH: 9
<212> TYPE: PRT
<213> ORGANISM: Homo sapiens

<400> SEQUENCE: 500

Lys Leu Leu Met Val Leu Met Leu Ala
1 5

<210> SEQ ID NO 501
<211> LENGTH: 13
<212> TYPE: PRT
<213> ORGANISM: Homo sapiens

<400> SEQUENCE: 501

Gln Glu Phe Ile Asp Asp Asn Ala Thr Thr Asn Ala Ile
1 5 10

<210> SEQ ID NO 502

-continued

<211> LENGTH: 13
<212> TYPE: PRT
<213> ORGANISM: Homo sapiens

<400> SEQUENCE: 502

Leu Lys Glu Cys Phe Leu Asn Gln Thr Asp Glu Thr Leu
1 5 10

<210> SEQ ID NO 503
<211> LENGTH: 93
<212> TYPE: PRT
<213> ORGANISM: Homo sapiens

<400> SEQUENCE: 503

Met Lys Leu Leu Met Val Leu Met Leu Ala Ala Leu Ser Gln His Cys
1 5 10 15

Tyr Ala Gly Ser Gly Cys Pro Leu Leu Glu Asn Val Ile Ser Lys Thr
20 25 30

Ile Asn Pro Gln Val Ser Lys Thr Glu Tyr Lys Glu Leu Leu Gln Glu
35 40 45

Phe Ile Asp Asp Asn Ala Thr Thr Asn Ala Ile Asp Glu Leu Lys Glu
50 55 60

Cys Phe Leu Asn Gln Thr Asp Glu Thr Leu Ser Asn Val Glu Val Phe
65 70 75 80

Met Gln Leu Ile Tyr Asp Ser Ser Leu Cys Asp Leu Phe
85 90

<210> SEQ ID NO 504
<211> LENGTH: 1964
<212> TYPE: DNA
<213> ORGANISM: Homo sapiens

<400> SEQUENCE: 504
gcatgctcga cgccccatgt gctgaaaggg cgaggagcct cctgcggcgg cccctgtgtc 60
cctgcctcta cctgcgcacc tgcatgtgtt caacccccgg gagaacacct ggcggcccct 120
gacccaggtg cccgaggagg ccccgcttcg gggctgcggt ctctgcacca tgcacaacta 180
cctgtttctg gcggggggca tccgtggctc cggtgccaag gccgtctgct ccaacgaggt 240
cttctgctac aaccctctga ccaacatctg gagccaggtt cggcccatgc agcaggcccg 300
agcccagctc aagctggtgg ccctggacgg gctgctctat gccatcggtg gcgaatgcct 360
gtacagcatg gagtgctacg acccgcgaac agacgcctgg accccacgcg cgccactccc 420
cgcaggcacc ttccctgtgg cccacgaggc tgtggcctgc cgtggggaca tctacgtcac 480
cgggggtcac ctcttctacc gcctgctcag gtacagcccc gtgaaggatg cttgggacga 540
gtgcccatac agtgccagcc accggcgttc cagcgacatc gttgcactgg ggggcttcct 600
gtaccgcttc gacctgctgc ggggcgtggg cgccgccgtg atgcgctaca acacagtgac 660
cggctcctgg agcagggctg cctccctgcc cctgcccgcc cccgccccac tgcgctgcac 720
caccctgggc aacaccattt actgcctcaa cccccaggtc actgccacct tcacggtctc 780 tgggggggact gcccagttcc aggccaagga gctgcagccc ttccccttgg ggagcaccgg 840
ggtcctcagt ccattcatcc tgactctgcc ccctgaggac cggctgcaga cctcactctg 900
agtggcaggc agagaaccaa agctgcttcg ctgctctcca gggagaccct cctgggatgg 960
gcctgagagg ccggggctca gggaaggggc tgggatcgga acttcctgct cttgtttctg 1020
gacaactttc cccttctgct ttaaaggttg tcgattattt tgaagcccag actccctcag 1080

-continued

```
cctctttctg cccctcactc cacacccaga ctgtttcctg actcaattcc gtacctactt   1140

acagaccctc tcagcttgct gacacccccc tgtctgtggg actccctatt ccctagagcc   1200

agggactgat gcgtctccac agacaaggac ttggctcgct ggagctctgc tgagccgaga   1260

gaggaggggg tagaaaacat tcacacttcc tatgctctgt cagcaggaca gggagcaaaa   1320

acgtccccag gcaacgccct cgcctctggg actttctgcc tgtcctaagg cctccccagg   1380

taccaacccc gtagctatct gggtctgttt ggcactgtgg attctcaagg gcctagaacc   1440

cttgcctctg aaactggtcc gctggtgcag ccctgctgtc tgcagctcct gcccataccc   1500

ccagcccaca ccaggccagg cccactccgg gctcaccacc ctctgcagcc ttgtggggct   1560

ctcccagccc ctccagaagc ccaccccact tctcgccaac ccccgatctc taaatgaggc   1620

ctgagcgtca ccctagttct gccccttttt agctgtgtag acttggacga gacatttgac   1680

ttccctttct ccttgtctat aaaatgtgga cagtggacgt ctgtcaccca agagagttgt   1740

gggagacaag atcacagcta tgagcacctc gcacggtgtc caggatgcac agcacaatcc   1800

atgatgcgtt ttctcccctt acgcactttg aaacccatgc tagaaaagtg aatacatctg   1860

actgtgctcc actccaacct ccagcctgga tgtccctgtc tgggcccttt ttctgttttt   1920

tattctatgt tcagcaccac tggcaccaaa tacattttaa ttca                    1964
```

<210> SEQ ID NO 505
<211> LENGTH: 732
<212> TYPE: DNA
<213> ORGANISM: Homo sapiens

<400> SEQUENCE: 505

```
atgcacaact acctgtttct ggcggggggc atccgtggct ccggtgccaa ggccgtctgc     60

tccaacgagg tcttctgcta caaccctctg accaacatct ggagccaggt tcggcccatg    120

cagcaggccc gagcccagct caagctggtg gccctggacg ggctgctcta tgccatcggt    180

ggcgaatgcc tgtacagcat ggagtgctac gacccgcgaa cagacgcctg gaccccacgc    240

gcgccactcc ccgcaggcac cttccctgtg gcccacgagg ctgtggcctg ccgtggggac    300

atctacgtca ccgggggtca cctcttctac cgcctgctca ggtacagccc cgtgaaggat    360

gcttgggacg agtgcccata cagtgccagc caccggcgtt ccagcgacat cgttgcactg    420

gggggcttcc tgtaccgctt cgacctgctg cggggcgtgg gcgccgccgt gatgcgctac    480

aacacagtga ccggctcctg gagcagggct gcctccctgc ccctgcccgc ccccgcccca    540

ctgcgctgca ccaccctggg caacaccatt tactgcctca acccccaggt cactgccacc    600

ttcacggtct ctgggggac tgcccagttc caggccaagg agctgcagcc cttccccttg    660

gggagcaccg gggtcctcag tccattcatc ctgactctgc cccctgagga ccggctgcag    720

acctcactct ga                                                        732
```

<210> SEQ ID NO 506
<211> LENGTH: 729
<212> TYPE: DNA
<213> ORGANISM: Homo sapiens

<400> SEQUENCE: 506

```
atgcacaact acctgtttct ggcgggggc atccgtggct ccggtgccaa ggccgtctgc     60

tccaacgagg tcttctgcta caaccctctg accaacatct ggagccaggt tcggcccatg    120

cagcaggccc gagcccagct caagctggtg gccctggacg ggctgctcta tgccatcggt    180

ggcgaatgcc tgtacagcat ggagtgctac gacccgcgaa cagacgcctg gaccccacgc    240
```

-continued

```
gcgccactcc ccgcaggcac cttccctgtg gcccacgagg ctgtggcctg ccgtggggac    300

atctacgtca ccgggggtca cctcttctac cgcctgctca ggtacagccc cgtgaaggat    360

gcttgggacg agtgcccata cagtgccagc caccggcgtt ccagcgacat cgttgcactg    420

gggggcttcc tgtaccgctt cgacctgctg cggggcgtgg gcgccgccgt gatgcgctac    480

aacacagtga ccggctcctg gagcagggct gcctccctgc ccctgcccgc ccccgcccca    540

ctgcgctgca ccaccctggg caacaccatt tactgcctca acccccaggt cactgccacc    600

ttcacggtct ctgggggac tgcccagttc caggccaagg agctgcagcc cttccccttg    660

gggagcaccg gggtcctcag tccattcatc ctgactctgc cccctgagga ccggctgcag    720

acctcactc                                                            729
```

```
<210> SEQ ID NO 507
<211> LENGTH: 243
<212> TYPE: PRT
<213> ORGANISM: Homo sapiens

<400> SEQUENCE: 507

Met His Asn Tyr Leu Phe Leu Ala Gly Gly Ile Arg Gly Ser Gly Ala
 1               5                  10                  15

Lys Ala Val Cys Ser Asn Glu Val Phe Cys Tyr Asn Pro Leu Thr Asn
            20                  25                  30

Ile Trp Ser Gln Val Arg Pro Met Gln Gln Ala Arg Ala Gln Leu Lys
        35                  40                  45

Leu Val Ala Leu Asp Gly Leu Leu Tyr Ala Ile Gly Gly Glu Cys Leu
    50                  55                  60

Tyr Ser Met Glu Cys Tyr Asp Pro Arg Thr Asp Ala Trp Thr Pro Arg
65                  70                  75                  80

Ala Pro Leu Pro Ala Gly Thr Phe Pro Val Ala His Glu Ala Val Ala
                85                  90                  95

Cys Arg Gly Asp Ile Tyr Val Thr Gly Gly His Leu Phe Tyr Arg Leu
            100                 105                 110

Leu Arg Tyr Ser Pro Val Lys Asp Ala Trp Asp Glu Cys Pro Tyr Ser
        115                 120                 125

Ala Ser His Arg Arg Ser Ser Asp Ile Val Ala Leu Gly Gly Phe Leu
    130                 135                 140

Tyr Arg Phe Asp Leu Leu Arg Gly Val Gly Ala Ala Val Met Arg Tyr
145                 150                 155                 160

Asn Thr Val Thr Gly Ser Trp Ser Arg Ala Ala Ser Leu Pro Leu Pro
                165                 170                 175

Ala Pro Ala Pro Leu Arg Cys Thr Thr Leu Gly Asn Thr Ile Tyr Cys
            180                 185                 190

Leu Asn Pro Gln Val Thr Ala Thr Phe Thr Val Ser Gly Gly Thr Ala
        195                 200                 205

Gln Phe Gln Ala Lys Glu Leu Gln Pro Phe Pro Leu Gly Ser Thr Gly
    210                 215                 220

Val Leu Ser Pro Phe Ile Leu Thr Leu Pro Pro Glu Asp Arg Leu Gln
225                 230                 235                 240

Thr Ser Leu


<210> SEQ ID NO 508
<211> LENGTH: 158
<212> TYPE: PRT
<213> ORGANISM: Homo sapiens
```

-continued

<400> SEQUENCE: 508

Met His Asn Tyr Leu Phe Leu Ala Gly Gly Ile Arg Gly Ser Gly Ala
1               5                   10                  15

Lys Ala Val Cys Ser Asn Glu Val Phe Cys Tyr Asn Pro Leu Thr Asn
            20                  25                  30

Ile Trp Ser Gln Val Arg Pro Met Gln Gln Ala Arg Ala Gln Leu Lys
        35                  40                  45

Leu Val Ala Leu Asp Gly Leu Leu Tyr Ala Ile Gly Gly Glu Cys Leu
    50                  55                  60

Tyr Ser Met Glu Cys Tyr Asp Pro Arg Thr Asp Ala Trp Thr Pro Arg
65                  70                  75                  80

Ala Pro Leu Pro Ala Gly Thr Phe Pro Val Ala His Glu Ala Val Ala
                85                  90                  95

Cys Arg Gly Asp Ile Tyr Val Thr Gly Gly His Leu Phe Tyr Arg Leu
            100                 105                 110

Leu Arg Tyr Ser Pro Val Lys Asp Ala Trp Asp Glu Cys Pro Tyr Ser
        115                 120                 125

Ala Ser His Arg Arg Ser Ser Asp Ile Val Ala Leu Gly Gly Phe Leu
    130                 135                 140

Tyr Arg Phe Asp Leu Leu Arg Gly Val Gly Ala Ala Val Met
145                 150                 155

<210> SEQ ID NO 509
<211> LENGTH: 85
<212> TYPE: PRT
<213> ORGANISM: Homo sapiens

<400> SEQUENCE: 509

Arg Tyr Asn Thr Val Thr Gly Ser Trp Ser Arg Ala Ala Ser Leu Pro
1               5                   10                  15

Leu Pro Ala Pro Ala Pro Leu Arg Cys Thr Thr Leu Gly Asn Thr Ile
            20                  25                  30

Tyr Cys Leu Asn Pro Gln Val Thr Ala Thr Phe Thr Val Ser Gly Gly
        35                  40                  45

Thr Ala Gln Phe Gln Ala Lys Glu Leu Gln Pro Phe Pro Leu Gly Ser
    50                  55                  60

Thr Gly Val Leu Ser Pro Phe Ile Leu Thr Leu Pro Pro Glu Asp Arg
65                  70                  75                  80

Leu Gln Thr Ser Leu
                85

<210> SEQ ID NO 510
<211> LENGTH: 732
<212> TYPE: DNA
<213> ORGANISM: Homo sapiens

<400> SEQUENCE: 510
atgcgacccc agggccccgc cgcctccccg cagcggctcc gcggcctcct gctgctcctg 60
ctgctgcagc tgcccgcgcc gtcgagcgcc tctgagatcc ccaaggggaa gcaaaaggcg 120
cagctccggc agagggaggt ggtggacctg tataatggaa tgtgcttaca agggccagca 180
ggagtgcctg gtcgagacgg gagccctggg gccaatgtta ttccgggtac acctgggatc 240
ccaggtcggg atggattcaa aggagaaaag gggaatgtc tgagggaaag ctttgaggag 300
tcctggacac ccaactacaa gcagtgttca tggagttcat tgaattatgg catagatctt 360

-continued

```
gggaaaattg cggagtgtac atttacaaag atgcgttcaa atagtgctct aagagttttg    420

ttcagtggct cacttcggct aaaatgcaga aatgcatgct gtcagcgttg gtatttcaca    480

ttcaatggag ctgaatgttc aggacctctt cccattgaag ctataattta tttggaccaa    540

ggaagccctg aaatgaattc aacaattaat attcatcgca cttcttctgt ggaaggactt    600

tgtgaaggaa ttggtgctgg attagtggat gttgctatct gggttggcac ttgttcagat    660

tacccaaaag gagatgcttc tactggatgg aattcagttt ctcgcatcat tattgaagaa    720

ctaccaaaat aa                                                        732
```

<210> SEQ ID NO 511
<211> LENGTH: 729
<212> TYPE: DNA
<213> ORGANISM: Homo sapiens

<400> SEQUENCE: 511

```
atgcgacccc agggccccgc cgcctccccg cagcggctcc gcggcctcct gctgctcctg     60

ctgctgcagc tgcccgcgcc gtcgagcgcc tctgagatcc ccaaggggaa gcaaaaggcg    120

cagctccggc agagggaggt ggtggacctg tataatggaa tgtgcttaca agggccagca    180

ggagtgcctg gtcgagacgg gagccctggg gccaatgtta ttccgggtac acctgggatc    240

ccaggtcggg atggattcaa aggagaaaag ggggaatgtc tgagggaaag ctttgaggag    300

tcctggacac ccaactacaa gcagtgttca tggagttcat tgaattatgg catagatctt    360

gggaaaattg cggagtgtac atttacaaag atgcgttcaa atagtgctct aagagttttg    420

ttcagtggct cacttcggct aaaatgcaga aatgcatgct gtcagcgttg gtatttcaca    480

ttcaatggag ctgaatgttc aggacctctt cccattgaag ctataattta tttggaccaa    540

ggaagccctg aaatgaattc aacaattaat attcatcgca cttcttctgt ggaaggactt    600

tgtgaaggaa ttggtgctgg attagtggat gttgctatct gggttggcac ttgttcagat    660

tacccaaaag gagatgcttc tactggatgg aattcagttt ctcgcatcat tattgaagaa    720

ctaccaaaa                                                            729
```

<210> SEQ ID NO 512
<211> LENGTH: 837
<212> TYPE: DNA
<213> ORGANISM: Homo sapiens

<400> SEQUENCE: 512

```
atgcagcctg cggcggcctc ggagcgcggc ggagcagacg ctgaccacgt tcctctcctc     60

ggtctcctcc gcctccagct ccgcgctgcc cggcagccgg gagccatgcg accccagggc    120

cccgccgcct ccccgcagcg gctccgcggc ctcctgctgc tcctgctgct gcagctgccc    180

gcgccgtcga gcgcctctga gatccccaag gggaagcaaa aggcgcagct ccggcagagg    240

gaggtggtgg acctgtataa tggaatgtgc ttacaagggc cagcaggagt gcctggtcga    300

gacgggagcc ctggggccaa tgttattccg ggtacacctg ggatcccagg tcgggatgga    360

ttcaaaggag aaaaggggga atgtctgagg gaaagctttg aggagtcctg gacacccaac    420

tacaagcagt gttcatggag ttcattgaat tatggcatag atcttgggaa aattgcggag    480

tgtacattta caaagatgcg ttcaaatagt gctctaagag ttttgttcag tggctcactt    540

cggctaaaat gcagaaatgc atgctgtcag cgttggtatt tcacattcaa tggagctgaa    600

tgttcaggac ctcttcccat tgaagctata atttatttgg accaaggaag ccctgaaatg    660

aattcaacaa ttaatattca tcgcacttct tctgtggaag gactttgtga aggaattggt    720
```

gctggattag tggatgttgc tatctgggtt ggcacttgtt cagattaccc aaaaggagat 780
gcttctactg gatggaattc agtttctcgc atcattattg aagaactacc aaaataa 837

<210> SEQ ID NO 513
<211> LENGTH: 837
<212> TYPE: DNA
<213> ORGANISM: Homo sapiens

<400> SEQUENCE: 513
atgcagcctg cggcggcctc ggagcgcggc ggagcagacg ctgaccacgt tcctctcctc 60
ggtctcctcc gcctccagct ccgcgctgcc cggcagccgg gagccatgcg accccagggc 120
cccgccgcct ccccgcagcg gctccgcggc ctcctgctgc tcctgctgct gcagctgccc 180
gcgccgtcga gcgcctctga gatccccaag gggaagcaaa aggcgcagct ccggcagagg 240
gaggtggtgg acctgtataa tggaatgtgc ttacaagggc cagcaggagt gcctggtcga 300
gacgggagcc ctggggccaa tgttattccg ggtacacctg ggatcccagg tcgggatgga 360
ttcaaaggag aaaaggggga atgtctgagg gaaagctttg aggagtcctg gacacccaac 420
tacaagcagt gttcatggag ttcattgaat tatggcatag atcttgggaa aattgcggag 480
tgtacattta caaagatgcg ttcaaatagt gctctaagag ttttgttcag tggctcactt 540
cggctaaaat gcagaaatgc atgctgtcag cgttggtatt tcacattcaa tggagctgaa 600
tgttcaggac ctcttcccat tgaagctata atttatttgg accaaggaag ccctgaaatg 660
aattcaacaa ttaatattca tcgcacttct tctgtggaag gactttgtga aggaattggt 720
gctggattag tggatgttgc tatctgggtt ggcacttgtt cagattaccc aaaaggagat 780
gcttctactg gatggaattc agtttctcgc atcattattg aagaactacc aaaataa 837

<210> SEQ ID NO 514
<211> LENGTH: 243
<212> TYPE: PRT
<213> ORGANISM: Homo sapiens

<400> SEQUENCE: 514

Met Arg Pro Gln Gly Pro Ala Ala Ser Pro Gln Arg Leu Arg Gly Leu
1 5 10 15

Leu Leu Leu Leu Leu Leu Gln Leu Pro Ala Pro Ser Ser Ala Ser Glu
20 25 30

Ile Pro Lys Gly Lys Gln Lys Ala Gln Leu Arg Gln Arg Glu Val Val
35 40 45

Asp Leu Tyr Asn Gly Met Cys Leu Gln Gly Pro Ala Gly Val Pro Gly
50 55 60

Arg Asp Gly Ser Pro Gly Ala Asn Val Ile Pro Gly Thr Pro Gly Ile
65 70 75 80

Pro Gly Arg Asp Gly Phe Lys Gly Glu Lys Gly Glu Cys Leu Arg Glu
85 90 95

Ser Phe Glu Glu Ser Trp Thr Pro Asn Tyr Lys Gln Cys Ser Trp Ser
100 105 110

Ser Leu Asn Tyr Gly Ile Asp Leu Gly Lys Ile Ala Glu Cys Thr Phe
115 120 125

Thr Lys Met Arg Ser Asn Ser Ala Leu Arg Val Leu Phe Ser Gly Ser
130 135 140

Leu Arg Leu Lys Cys Arg Asn Ala Cys Cys Gln Arg Trp Tyr Phe Thr
145 150 155 160

-continued

```
Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
225                 230                 235                 240

Leu Pro Lys


<210> SEQ ID NO 515
<211> LENGTH: 278
<212> TYPE: PRT
<213> ORGANISM: Homo sapiens

<400> SEQUENCE: 515

Met Gln Pro Ala Ala Ala Ser Glu Arg Gly Gly Ala Asp Ala Asp His
                5                   10                  15

Val Pro Leu Leu Gly Leu Leu Arg Leu Gln Leu Arg Ala Ala Arg Gln
            20                  25                  30

Pro Gly Ala Met Arg Pro Gln Gly Pro Ala Ala Ser Pro Gln Arg Leu
        35                  40                  45

Arg Gly Leu Leu Leu Leu Leu Leu Leu Gln Leu Pro Ala Pro Ser Ser
    50                  55                  60

Ala Ser Glu Ile Pro Lys Gly Lys Gln Lys Ala Gln Leu Arg Gln Arg
65                  70                  75                  80

Glu Val Val Asp Leu Tyr Asn Gly Met Cys Leu Gln Gly Pro Ala Gly
                85                  90                  95

Val Pro Gly Arg Asp Gly Ser Pro Gly Ala Asn Val Ile Pro Gly Thr
            100                 105                 110

Pro Gly Ile Pro Gly Arg Asp Gly Phe Lys Gly Glu Lys Gly Glu Cys
        115                 120                 125

Leu Arg Glu Ser Phe Glu Glu Ser Trp Thr Pro Asn Tyr Lys Gln Cys
    130                 135                 140

Ser Trp Ser Ser Leu Asn Tyr Gly Ile Asp Leu Gly Lys Ile Ala Glu
145                 150                 155                 160

Cys Thr Phe Thr Lys Met Arg Ser Asn Ser Ala Leu Arg Val Leu Phe
                165                 170                 175

Ser Gly Ser Leu Arg Leu Lys Cys Arg Asn Ala Cys Cys Gln Arg Trp
            180                 185                 190

Tyr Phe Thr Phe Asn Gly Ala Glu Cys Ser Gly Pro Leu Pro Ile Glu
        195                 200                 205

Ala Ile Ile Tyr Leu Asp Gln Gly Ser Pro Glu Met Asn Ser Thr Ile
    210                 215                 220

Asn Ile His Arg Thr Ser Ser Val Glu Gly Leu Cys Glu Gly Ile Gly
225                 230                 235                 240

Ala Gly Leu Val Asp Val Ala Ile Trp Val Gly Thr Cys Ser Asp Tyr
                245                 250                 255

Pro Lys Gly Asp Ala Ser Thr Gly Trp Asn Ser Val Ser Arg Ile Ile
            260                 265                 270

Ile Glu Glu Leu Pro Lys
        275
```

<210> SEQ ID NO 516
<211> LENGTH: 197
<212> TYPE: PRT
<213> ORGANISM: Homo sapiens

<400> SEQUENCE: 516

```
Met Arg Pro Gln Gly Pro Ala Ala Ser Pro Gln Arg Leu Arg Gly Leu
                5                   10                  15

Leu Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
        35                  40                  45

Asp Leu Tyr Asn Gly Met Cys Leu Gln Gly Pro Ala Gly Val Pro Gly
    50                  55                  60

Arg Asp Gly Ser Pro Gly Ala Asn Val Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val
        195
```

<210> SEQ ID NO 517
<211> LENGTH: 232
<212> TYPE: PRT
<213> ORGANISM: Homo sapiens

<400> SEQUENCE: 517

```
Met Gln Pro Ala Ala Ala Ser Glu Arg Gly Gly Ala Asp Ala Asp His
                5                   10                  15

Val Pro Leu Leu Gly Leu Leu Arg Leu Gln Leu Arg Ala Ala Arg Gln
            20                  25                  30

Pro Gly Ala Met Arg Pro Gln Gly Pro Ala Ala Ser Pro Gln Arg Leu
        35                  40                  45

Arg Gly Leu Leu Leu Leu Leu Leu Leu Gln Leu Pro Ala Pro Ser Ser
    50                  55                  60

Ala Ser Glu Ile Pro Lys Gly Lys Gln Lys Ala Gln Leu Arg Gln Arg
65                  70                  75                  80

Glu Val Val Asp Leu Tyr Asn Gly Met Cys Leu Gln Gly Pro Ala Gly
                85                  90                  95

Val Pro Gly Arg Asp Gly Ser Pro Gly Ala Asn Val Ile Pro Gly Thr
            100                 105                 110

Pro Gly Ile Pro Gly Arg Asp Gly Phe Lys Gly Glu Lys Gly Glu Cys
        115                 120                 125
```

-continued

```
Leu Arg Glu Ser Phe Glu Glu Ser Trp Thr Pro Asn Tyr Lys Gln Cys
    130                 135                 140

Ser Trp Ser Ser Leu Asn Tyr Gly Ile Asp Leu Gly Lys Ile Ala Glu
145                 150                 155                 160

Cys Thr Phe Thr Lys Met Arg Ser Asn Ser Ala Leu Arg Val Leu Phe
                165                 170                 175

Ser Gly Ser Leu Arg Leu Lys Cys Arg Asn Ala Cys Cys Gln Arg Trp
            180                 185                 190

Tyr Phe Thr Phe Asn Gly Ala Glu Cys Ser Gly Pro Leu Pro Ile Glu
        195                 200                 205

Ala Ile Ile Tyr Leu Asp Gln Gly Ser Pro Glu Met Asn Ser Thr Ile
    210                 215                 220

Asn Ile His Arg Thr Ser Ser Val
225                 230


<210> SEQ ID NO 518
<211> LENGTH: 46
<212> TYPE: PRT
<213> ORGANISM: Homo sapiens

<400> SEQUENCE: 518

Glu Gly Leu Cys Glu Gly Ile Gly Ala Gly Leu Val Asp Val Ala Ile
                5                   10                  15

Trp Val Gly Thr Cys Ser Asp Tyr Pro Lys Gly Asp Ala Ser Thr Gly
            20                  25                  30

Trp Asn Ser Val Ser Arg Ile Ile Ile Glu Glu Leu Pro Lys
        35                  40                  45


<210> SEQ ID NO 519
<211> LENGTH: 26
<212> TYPE: PRT
<213> ORGANISM: Homo sapiens

<400> SEQUENCE: 519

Cys Ser Asp Tyr Pro Lys Gly Asp Ala Ser Thr Gly Trp Asn Ser Val
                5                   10                  15

Ser Arg Ile Ile Ile Glu Glu Leu Pro Lys
            20                  25


<210> SEQ ID NO 520
<211> LENGTH: 60
<212> TYPE: DNA
<213> ORGANISM: Homo sapiens

<400> SEQUENCE: 520

aaaaatgagg agatatttaa ttacaataac catttaaaaa accgtatata tcaatatgaa     60


<210> SEQ ID NO 521
<211> LENGTH: 60
<212> TYPE: DNA
<213> ORGANISM: Homo sapiens

<400> SEQUENCE: 521

atgcaacatc atctcctaaa agagaaaaat gaggagatat ttaattacaa taaccattta     60


<210> SEQ ID NO 522
<211> LENGTH: 60
<212> TYPE: DNA
<213> ORGANISM: Homo sapiens

<400> SEQUENCE: 522
```

-continued gacaacaaaa gcaagataac aattgatatt cattttcttg agaggaaaat gcaacatcat 60

<210> SEQ ID NO 523
<211> LENGTH: 60
<212> TYPE: DNA
<213> ORGANISM: Homo sapiens

<400> SEQUENCE: 523
aaaaatatgt ggcttcaaca gcaattagtt catgcacata agaaagctga caacaaaagc 60

<210> SEQ ID NO 524
<211> LENGTH: 63
<212> TYPE: DNA
<213> ORGANISM: Homo sapiens

<400> SEQUENCE: 524
gatcagaaat tatttcaact acaaagcaaa aatatgtggc ttcaacagca attagttcat 60
gca 63

<210> SEQ ID NO 525
<211> LENGTH: 60
<212> TYPE: DNA
<213> ORGANISM: Homo sapiens

<400> SEQUENCE: 525
actgaacagc aggagtctct agatcagaaa ttatttcaac tacaaagcaa aaatatgtgg 60

<210> SEQ ID NO 526
<211> LENGTH: 63
<212> TYPE: DNA
<213> ORGANISM: Homo sapiens

<400> SEQUENCE: 526
gctcaaagga aatccaaaag cctaaaaatt aatctcaatt atgccggaga tgctctaaga 60
gaa 63

<210> SEQ ID NO 527
<211> LENGTH: 60
<212> TYPE: DNA
<213> ORGANISM: Homo sapiens

<400> SEQUENCE: 527
agtacgatat ataacaatga ggtgctccat caaccacttt ctgaagctca aaggaaatcc 60

<210> SEQ ID NO 528
<211> LENGTH: 60
<212> TYPE: DNA
<213> ORGANISM: Homo sapiens

<400> SEQUENCE: 528
agaaaaatga atgttgatgt gagtagtacg atatataaca atgaggtgct ccatcaacca 60

<210> SEQ ID NO 529
<211> LENGTH: 60
<212> TYPE: DNA
<213> ORGANISM: Homo sapiens

<400> SEQUENCE: 529
attgcaggag atgcttgttt gcaaagaaaa atgaatgttg atgtgagtag tacgatatat 60

<210> SEQ ID NO 530

-continued

<211> LENGTH: 60
<212> TYPE: DNA
<213> ORGANISM: Homo sapiens

<400> SEQUENCE: 530
aaaagtcaag aacctgcttt ccacattgca ggagatgctt gtttgcaaag aaaaatgaat 60

<210> SEQ ID NO 531
<211> LENGTH: 60
<212> TYPE: DNA
<213> ORGANISM: Homo sapiens

<400> SEQUENCE: 531
gaaaataaat actttgagga cattaagatt ttaaaagaaa agaatgctga acttcagatg 60

<210> SEQ ID NO 532
<211> LENGTH: 60
<212> TYPE: DNA
<213> ORGANISM: Homo sapiens

<400> SEQUENCE: 532
ctgaaacacc aataccagga aaaggaaaat aaatactttg aggacattaa gattttaaaa 60

<210> SEQ ID NO 533
<211> LENGTH: 63
<212> TYPE: DNA
<213> ORGANISM: Homo sapiens

<400> SEQUENCE: 533
aattgcatgt tgaaaaagga aattgccatg ctaaaactgg aaatagccac actgaaacac 60
caa 63

<210> SEQ ID NO 534
<211> LENGTH: 21
<212> TYPE: PRT
<213> ORGANISM: Homo sapiens

<400> SEQUENCE: 534

Asn Cys Met Leu Lys Lys Glu Ile Ala Met Leu Lys Leu Glu Ile Ala
1 5 10 15

Thr Leu Lys His Gln
20

<210> SEQ ID NO 535
<211> LENGTH: 20
<212> TYPE: PRT
<213> ORGANISM: Homo sapiens

<400> SEQUENCE: 535

Leu Lys His Gln Tyr Gln Glu Lys Glu Asn Lys Tyr Phe Glu Asp Ile
1 5 10 15

Lys Ile Leu Lys
20

<210> SEQ ID NO 536
<211> LENGTH: 20
<212> TYPE: PRT
<213> ORGANISM: Homo sapiens

<400> SEQUENCE: 536

Glu Asn Lys Tyr Phe Glu Asp Ile Lys Ile Leu Lys Glu Lys Asn Ala
1 5 10 15

-continued

Glu Leu Gln Met
20

<210> SEQ ID NO 537
<211> LENGTH: 20
<212> TYPE: PRT
<213> ORGANISM: Homo sapiens

<400> SEQUENCE: 537

Lys Ser Gln Glu Pro Ala Phe His Ile Ala Gly Asp Ala Cys Leu Gln
5 10 15

Arg Lys Met Asn
20

<210> SEQ ID NO 538
<211> LENGTH: 20
<212> TYPE: PRT
<213> ORGANISM: Homo sapiens

<400> SEQUENCE: 538

Ile Ala Gly Asp Ala Cys Leu Gln Arg Lys Met Asn Val Asp Val Ser
5 10 15

Ser Thr Ile Tyr
20

<210> SEQ ID NO 539
<211> LENGTH: 20
<212> TYPE: PRT
<213> ORGANISM: Homo sapiens

<400> SEQUENCE: 539

Arg Lys Met Asn Val Asp Val Ser Ser Thr Ile Tyr Asn Asn Glu Val
5 10 15

Leu His Gln Pro
20

<210> SEQ ID NO 540
<211> LENGTH: 20
<212> TYPE: PRT
<213> ORGANISM: Homo sapiens

<400> SEQUENCE: 540

Ser Thr Ile Tyr Asn Asn Glu Val Leu His Gln Pro Leu Ser Glu Ala
5 10 15

Gln Arg Lys Ser
20

<210> SEQ ID NO 541
<211> LENGTH: 21
<212> TYPE: PRT
<213> ORGANISM: Homo sapiens

<400> SEQUENCE: 541

Ala Gln Arg Lys Ser Lys Ser Leu Lys Ile Asn Leu Asn Tyr Ala Gly
5 10 15

Asp Ala Leu Arg Glu
20

<210> SEQ ID NO 542
<211> LENGTH: 20
<212> TYPE: PRT
<213> ORGANISM: Homo sapiens -continued

```
<400> SEQUENCE: 542

Thr Glu Gln Gln Glu Ser Leu Asp Gln Lys Leu Phe Gln Leu Gln Ser
              5                   10                  15
Lys Asn Met Trp
            20

<210> SEQ ID NO 543
<211> LENGTH: 21
<212> TYPE: PRT
<213> ORGANISM: Homo sapiens

<400> SEQUENCE: 543

Asp Gln Lys Leu Phe Gln Leu Gln Ser Lys Asn Met Trp Leu Gln Gln
              5                   10                  15
Gln Leu Val His Ala
            20

<210> SEQ ID NO 544
<211> LENGTH: 20
<212> TYPE: PRT
<213> ORGANISM: Homo sapiens

<400> SEQUENCE: 544

Lys Asn Met Trp Leu Gln Gln Gln Leu Val His Ala His Lys Lys Ala
              5                   10                  15
Asp Asn Lys Ser
            20

<210> SEQ ID NO 545
<211> LENGTH: 20
<212> TYPE: PRT
<213> ORGANISM: Homo sapiens

<400> SEQUENCE: 545

Asp Asn Lys Ser Lys Ile Thr Ile Asp Ile His Phe Leu Glu Arg Lys
              5                   10                  15
Met Gln His His
            20

<210> SEQ ID NO 546
<211> LENGTH: 20
<212> TYPE: PRT
<213> ORGANISM: Homo sapiens

<400> SEQUENCE: 546

Met Gln His His Leu Leu Lys Glu Lys Asn Glu Glu Ile Phe Asn Tyr
              5                   10                  15
Asn Asn His Leu
            20

<210> SEQ ID NO 547
<211> LENGTH: 20
<212> TYPE: PRT
<213> ORGANISM: Homo sapiens

<400> SEQUENCE: 547

Lys Asn Glu Glu Ile Phe Asn Tyr Asn Asn His Leu Lys Asn Arg Ile
              5                   10                  15
Tyr Gln Tyr Glu
            20
```

-continued

<210> SEQ ID NO 548
<211> LENGTH: 3045
<212> TYPE: DNA
<213> ORGANISM: Homo sapiens

<400> SEQUENCE: 548
atgcagcatc accaccatca ccacgtcggc tccatgagtc ccgcaaaaga aacatctgag 60
aaatttacgt gggcagcaaa aggaagacct aggaagatcg catgggagaa aaaagaaaca 120
cctgtaaaga ctggatgcgt ggcaagagta acatctaata aaactaaagt tttggaaaaa 180
ggaagatcta agatgattgc atgtcctaca aaagaatcat ctacaaaagc aagtgccaat 240
gatcagaggt tcccatcaga atccaaacaa gaggaagatg aagaatattc ttgtgattct 300
cggagtctct ttgagagttc tgcaaagatt caagtgtgta tacctgagtc tatatatcaa 360
aaagtaatgg agataaatag agaagtagaa gagcctccta agaagccatc tgccttcaag 420
cctgccattg aaatgcaaaa ctctgttcca aataaagcct ttgaattgaa gaatgaacaa 480
acattgagag cagatccgat gttcccacca gaatccaaac aaaaggacta tgaagaaaat 540
tcttgggatt ctgagagtct ctgtgagact gtttcacaga aggatgtgtg tttacccaag 600
gctacacatc aaaaagaaat agataaaata aatggaaaat tagaagagtc tcctaataaa 660
gatggtcttc tgaaggctac ctgcggaatg aaagtttcta ttccaactaa agccttagaa 720
ttgaaggaca tgcaaacttt caaagcagag cctccgggga agccatctgc cttcgagcct 780
gccactgaaa tgcaaaagtc tgtcccaaat aaagccttgg aattgaaaaa tgaacaaaca 840
ttgagagcag atgagatact cccatcagaa tccaaacaaa aggactatga agaaaattct 900
tgggatactg agagtctctg tgagactgtt tcacagaagg atgtgtgttt acccaaggct 960
gcgcatcaaa aagaaataga taaaataaat ggaaaattag aagggtctcc tggtaaagat 1020
ggtcttctta aggctaactg cggaatgaaa gtttctattc caactaaagc cttagaattg 1080
atggacatgc aaactttcaa agcagagcct cccgagaagc catctgcctt cgagcctgcc 1140
attgaaatgc aaaagtctgt tccaaataaa gccttggaat tgaagaatga acaaacattg 1200
agagcagatg agatactccc atcagaatcc aaacaaaagg actatgaaga aagttcttgg 1260
gattctgaga gtctctgtga gactgtttca cagaaggatg tgtgtttacc caaggctgcg 1320
catcaaaaag aaatagataa aataaatgga aaattagaag agtctcctga taatgatggt 1380
tttctgaagt ctccctgcag aatgaaagtt tctattccaa ctaaagcctt agaattgatg 1440
gacatgcaaa ctttcaaagc agagcctccc gagaagccat ctgccttcga gcctgccatt 1500
gaaatgcaaa agtctgttcc aaataaagcc ttggaattga agaatgaaca aacattgaga 1560
gcagatcaga tgttcccttc agaatcaaaa caaaagaacg ttgaagaaaa ttcttgggat 1620
tctgagagtc tccgtgagac tgtttcacag aaggatgtgt gtgtacccaa ggctacacat 1680
caaaaagaaa tggataaaat aagtggaaaa ttagaagatt caactagcct atcaaaaatc 1740
ttggatacag ttcattcttg tgaaagagca agggaacttc aaaaagatca ctgtgaacaa 1800
cgtacaggaa aaatggaaca aatgaaaaag aagttttgtg tactgaaaaa gaaactgtca 1860
gaagcaaaag aaataaaatc acagttagag aaccaaaaag ttaaatggga acaagagctc 1920
tgcagtgtga gattgacttt aaaccaagaa gaagagaaga gaagaaatgc cgatatatta 1980
aatgaaaaaa ttagggaaga attaggaaga atcgaagagc agcataggaa agagttagaa 2040
gtgaaacaac aacttgaaca ggctctcaga atacaagata tagaattgaa gagtgtagaa 2100
agtaatttaa atcaggtttc tcacactcat gaaaatgaaa attatctctt acatgaaaat 2160

-continued

```
tgcatgttga aaaaggaaat tgccatgcta aaactggaaa tagccacact gaaacaccaa   2220

taccaggaaa aggaaaataa atactttgag gacattaaga ttttaaaaga aaagaatgct   2280

gaacttcaga tgaccctaaa actgaaagag gaatcattaa ctaaaagggc atctcaatat   2340

agtgggcagc ttaaagttct gatagctgag aacacaatgc tcacttctaa attgaaggaa   2400

aaacaagaca aagaaatact agaggcagaa attgaatcac accatcctag actggcttct   2460

gctgtacaag accatgatca aattgtgaca tcaagaaaaa gtcaagaacc tgctttccac   2520

attgcaggag atgcttgttt gcaaagaaaa atgaatgttg atgtgagtag tacgatatat   2580

aacaatgagg tgctccatca accactttct gaagctcaaa ggaaatccaa aagcctaaaa   2640

attaatctca attatgccgg agatgctcta agagaaaata cattggtttc agaacatgca   2700

caaagagacc aacgtgaaac acagtgtcaa atgaaggaag ctgaacacat gtatcaaaac   2760

gaacaagata atgtgaacaa acacactgaa cagcaggagt ctctagatca gaaattattt   2820

caactacaaa gcaaaaatat gtggcttcaa cagcaattag ttcatgcaca taagaaagct   2880

gacaacaaaa gcaagataac aattgatatt cattttcttg agaggaaaat gcaacatcat   2940

ctcctaaaag agaaaaatga ggagatattt aattacaata accatttaaa aaaccgtata   3000

tatcaatatg aaaaagagaa agcagaaaca gaagttatat aatag                  3045
```

<210> SEQ ID NO 549
<211> LENGTH: 1953
<212> TYPE: DNA
<213> ORGANISM: Homo sapiens
<220> FEATURE:
<221> NAME/KEY: misc_feature
<222> LOCATION: 985
<223> OTHER INFORMATION: n = A,T,C or G

<400> SEQUENCE: 549

```
atgagtcccg caaaagaaac atctgagaaa tttacgtggg cagcaaaagg aagacctagg     60

aagatcgcat gggagaaaaa agaaacacct gtaaagactg gatgcgtggc aagagtaaca    120

tctaataaaa ctaaagtttt ggaaaaagga agatctaaga tgattgcatg tcctacaaaa    180

gaatcatcta caaaagcaag tgccaatgat cagaggttcc catcagaatc caaacaagag    240

gaagatgaag aatattcttg tgattctcgg agtctctttg agagttctgc aaagattcaa    300

gtgtgtatac ctgagtctat atatcaaaaa gtaatggaga taaatagaga agtagaagag    360

cctcctaaga agccatctgc cttcaagcct gccattgaaa tgcaaaactc tgttccaaat    420

aaagcctttg aattgaagaa tgaacaaaca ttgagagcag atccgatgtt cccaccagaa    480

tccaaacaaa aggactatga agaaaattct tgggattctg agagtctctg tgagactgtt    540

tcacagaagg atgtgtgttt acccaaggct acacatcaaa aagaaataga taaaataaat    600

ggaaaattag aagagtctcc taataaagat ggtcttctga aggctacctg cggaatgaaa    660

gtttctattc caactaaagc cttagaattg aaggacatgc aaactttcaa agcagagcct    720

ccggggaagc catctgcctt cgagcctgcc actgaaatgc aaaagtctgt cccaaataaa    780

gccttggaat tgaaaaatga acaaacattg agagcagatg agatactccc atcagaatcc    840

aaacaaaagg actatgaaga aaattcttgg gatactgaga gtctctgtga gactgtttca    900

cagaaggatg tgtgtttacc caaggctgcg catcaaaaag aaatagataa aataaatgga    960

aaattagaag ggtctcctgg taaanatggt cttctgaagg ctaactgcgg aatgaaagtt   1020

tctattccaa ctaaagcctt agaattgatg gacatgcaaa ctttcaaagc agagcctccc   1080

gagaagccat ctgccttcga gcctgccatt gaaatgcaaa agtctgttcc aaataaagcc   1140
```

-continued

```
ttggaattga agaatgaaca aacattgaga gcagatgaga tactcccatc agaatccaaa   1200

caaaaggact atgaagaaag ttcttgggat tctgagagtc tctgtgagac tgtttcacag   1260

aaggatgtgt gtttacccaa ggctgcgcat caaaaagaaa tagataaaat aaatggaaaa   1320

ttagaagagt ctcctgataa tgatggtttt ctgaagtctc cctgcagaat gaaagtttct   1380

attccaacta aagccttaga attgatggac atgcaaactt tcaaagcaga gcctcccgag   1440

aagccatctg ccttcgagcc tgccattgaa atgcaaaagt ctgttccaaa taaagccttg   1500

gaattgaaga atgaacaaac attgagagca gatcagatgt tcccttcaga atcaaaacaa   1560

aagaacgttg aagaaaattc ttgggattct gagagtctcc gtgagactgt ttcacagaag   1620

gatgtgtgtg tacccaaggc tacacatcaa aaagaaatgg ataaaataag tggaaaatta   1680

gaagattcaa ctagcctatc aaaaatcttg gatacagttc attcttgtga aagagcaagg   1740

gaacttcaaa aagatcactg tgaacaacgt acaggaaaaa tggaacaaat gaaaaagaag   1800

ttttgtgtac tgaaaaagaa actgtcagaa gcaaaagaaa taaaatcaca gttagagaac   1860

caaaaagtta aatgggaaca agagctctgc agtgtgaggt ttctcacact catgaaaatg   1920

aaaattatct cttacatgaa aattgcatgt tga                                1953
```

<210> SEQ ID NO 550
<211> LENGTH: 978
<212> TYPE: DNA
<213> ORGANISM: Homo sapiens

<400> SEQUENCE: 550

```
atgcagcatc accaccatca ccacggcaca agagctctgc agtgtgaggt ttctcacact     60

catgaaaatg aaaattatct cttacatgaa aattgcatgt tgaaaaagga aattgccatg    120

ctaaaactgg aaatagccac actgaaacac caataccagg aaaaggaaaa taaatacttt    180

gaggacatta agattttaaa agaaaagaat gctgaacttc agatgaccct aaaactgaaa    240

gaggaatcat taactaaaag ggcatctcaa tatagtgggc agcttaaagt tctgatagct    300

gagaacacaa tgctcacttc taaattgaag gaaaaacaag acaaagaaat actagaggca    360

gaaattgaat cacaccatcc tagactggct tctgctgtac aagaccatga tcaaattgtg    420

acatcaagaa aaagtcaaga acctgctttc cacattgcag gagatgcttg tttgcaaaga    480

aaaatgaatg ttgatgtgag tagtacgata tataacaatg aggtgctcca tcaaccactt    540

tctgaagctc aaaggaaatc caaaagccta aaaattaatc tcaattatgc cggagatgct    600

ctaagagaaa atacattggt ttcagaacat gcacaaagag accaacgtga aacacagtgt    660

caaatgaagg aagctgaaca catgtatcaa aacgaacaag ataatgtgaa caaacacact    720

gaacagcagg agtctctaga tcagaaatta tttcaactac aaagcaaaaa tatgtggctt    780

caacagcaat tagttcatgc acataagaaa gctgacaaca aaagcaagat aacaattgat    840

attcattttc ttgagaggaa aatgcaacat catctcctaa aagagaaaaa tgaggagata    900

tttaattaca ataaccattt aaaaaaccgt atatatcaat atgaaaaaga gaaagcagaa    960

acagaagtta tataatag                                                  978
```

<210> SEQ ID NO 551
<211> LENGTH: 324
<212> TYPE: PRT
<213> ORGANISM: Homo sapiens

<400> SEQUENCE: 551

-continued

```
Met Gln His His His His His His Gly Thr Arg Ala Leu Gln Cys Glu
1               5                   10                  15

Val Ser His Thr His Glu Asn Glu Asn Tyr Leu Leu His Glu Asn Cys
            20                  25                  30

Met Leu Lys Lys Glu Ile Ala Met Leu Lys Leu Glu Ile Ala Thr Leu
        35                  40                  45

Lys His Gln Tyr Gln Glu Lys Glu Asn Lys Tyr Phe Glu Asp Ile Lys
    50                  55                  60

Ile Leu Lys Glu Lys Asn Ala Glu Leu Gln Met Thr Leu Lys Leu Lys
65                  70                  75                  80

Glu Glu Ser Leu Thr Lys Arg Ala Ser Gln Tyr Ser Gly Gln Leu Lys
                85                  90                  95

Val Leu Ile Ala Glu Asn Thr Met Leu Thr Ser Lys Leu Lys Glu Lys
            100                 105                 110

Gln Asp Lys Glu Ile Leu Glu Ala Glu Ile Glu Ser His His Pro Arg
        115                 120                 125

Leu Ala Ser Ala Val Gln Asp His Asp Gln Ile Val Thr Ser Arg Lys
    130                 135                 140

Ser Gln Glu Pro Ala Phe His Ile Ala Gly Asp Ala Cys Leu Gln Arg
145                 150                 155                 160

Lys Met Asn Val Asp Val Ser Ser Thr Ile Tyr Asn Asn Glu Val Leu
                165                 170                 175

His Gln Pro Leu Ser Glu Ala Gln Arg Lys Ser Lys Ser Leu Lys Ile
            180                 185                 190

Asn Leu Asn Tyr Ala Gly Asp Ala Leu Arg Glu Asn Thr Leu Val Ser
        195                 200                 205

Glu His Ala Gln Arg Asp Gln Arg Glu Thr Gln Cys Gln Met Lys Glu
    210                 215                 220

Ala Glu His Met Tyr Gln Asn Glu Gln Asp Asn Val Asn Lys His Thr
225                 230                 235                 240

Glu Gln Gln Glu Ser Leu Asp Gln Lys Leu Phe Gln Leu Gln Ser Lys
                245                 250                 255

Asn Met Trp Leu Gln Gln Gln Leu Val His Ala His Lys Lys Ala Asp
            260                 265                 270

Asn Lys Ser Lys Ile Thr Ile Asp Ile His Phe Leu Glu Arg Lys Met
        275                 280                 285

Gln His His Leu Leu Lys Glu Lys Asn Glu Glu Ile Phe Asn Tyr Asn
    290                 295                 300

Asn His Leu Lys Asn Arg Ile Tyr Gln Tyr Glu Lys Glu Lys Ala Glu
305                 310                 315                 320

Thr Glu Val Ile
```

<210> SEQ ID NO 552
<211> LENGTH: 661
<212> TYPE: PRT
<213> ORGANISM: Homo sapiens

<400> SEQUENCE: 552

```
Met Gln His His His His His His Val Gly Ser Met Ser Pro Ala Lys
1               5                   10                  15

Glu Thr Ser Glu Lys Phe Thr Trp Ala Ala Lys Gly Arg Pro Arg Lys
            20                  25                  30

Ile Ala Trp Glu Lys Lys Glu Thr Pro Val Lys Thr Gly Cys Val Ala
        35                  40                  45
```

-continued

```
Arg Val Thr Ser Asn Lys Thr Lys Val Leu Glu Lys Gly Arg Ser Lys
    50                  55                  60

Met Ile Ala Cys Pro Thr Lys Glu Ser Ser Thr Lys Ala Ser Ala Asn
65                  70                  75                  80

Asp Gln Arg Phe Pro Ser Glu Ser Lys Gln Glu Glu Asp Glu Glu Tyr
                85                  90                  95

Ser Cys Asp Ser Arg Ser Leu Phe Glu Ser Ser Ala Lys Ile Gln Val
            100                 105                 110

Cys Ile Pro Glu Ser Ile Tyr Gln Lys Val Met Glu Ile Asn Arg Glu
        115                 120                 125

Val Glu Glu Pro Pro Lys Lys Pro Ser Ala Phe Lys Pro Ala Ile Glu
    130                 135                 140

Met Gln Asn Ser Val Pro Asn Lys Ala Phe Glu Leu Lys Asn Glu Gln
145                 150                 155                 160

Thr Leu Arg Ala Asp Pro Met Phe Pro Pro Glu Ser Lys Gln Lys Asp
                165                 170                 175

Tyr Glu Glu Asn Ser Trp Asp Ser Glu Ser Leu Cys Glu Thr Val Ser
            180                 185                 190

Gln Lys Asp Val Cys Leu Pro Lys Ala Thr His Gln Lys Glu Ile Asp
        195                 200                 205

Lys Ile Asn Gly Lys Leu Glu Glu Ser Pro Asn Lys Asp Gly Leu Leu
    210                 215                 220

Lys Ala Thr Cys Gly Met Lys Val Ser Ile Pro Thr Lys Ala Leu Glu
225                 230                 235                 240

Leu Lys Asp Met Gln Thr Phe Lys Ala Glu Pro Pro Gly Lys Pro Ser
                245                 250                 255

Ala Phe Glu Pro Ala Thr Glu Met Gln Lys Ser Val Pro Asn Lys Ala
            260                 265                 270

Leu Glu Leu Lys Asn Glu Gln Thr Leu Arg Ala Asp Glu Ile Leu Pro
        275                 280                 285

Ser Glu Ser Lys Gln Lys Asp Tyr Glu Glu Asn Ser Trp Asp Thr Glu
    290                 295                 300

Ser Leu Cys Glu Thr Val Ser Gln Lys Asp Val Cys Leu Pro Lys Ala
305                 310                 315                 320

Ala His Gln Lys Glu Ile Asp Lys Ile Asn Gly Lys Leu Glu Gly Ser
                325                 330                 335

Pro Gly Lys Asp Gly Leu Leu Lys Ala Asn Cys Gly Met Lys Val Ser
            340                 345                 350

Ile Pro Thr Lys Ala Leu Glu Leu Met Asp Met Gln Thr Phe Lys Ala
        355                 360                 365

Glu Pro Pro Glu Lys Pro Ser Ala Phe Glu Pro Ala Ile Glu Met Gln
    370                 375                 380

Lys Ser Val Pro Asn Lys Ala Leu Glu Leu Lys Asn Glu Gln Thr Leu
385                 390                 395                 400

Arg Ala Asp Glu Ile Leu Pro Ser Glu Ser Lys Gln Lys Asp Tyr Glu
                405                 410                 415

Glu Ser Ser Trp Asp Ser Glu Ser Leu Cys Glu Thr Val Ser Gln Lys
            420                 425                 430

Asp Val Cys Leu Pro Lys Ala Ala His Gln Lys Glu Ile Asp Lys Ile
        435                 440                 445

Asn Gly Lys Leu Glu Glu Ser Pro Asp Asn Asp Gly Phe Leu Lys Ser
    450                 455                 460

Pro Cys Arg Met Lys Val Ser Ile Pro Thr Lys Ala Leu Glu Leu Met
```

-continued 465 470 475 480

Asp Met Gln Thr Phe Lys Ala Glu Pro Pro Glu Lys Pro Ser Ala Phe
485 490 495

Glu Pro Ala Ile Glu Met Gln Lys Ser Val Pro Asn Lys Ala Leu Glu
500 505 510

Leu Lys Asn Glu Gln Thr Leu Arg Ala Asp Gln Met Phe Pro Ser Glu
515 520 525

Ser Lys Gln Lys Asn Val Glu Glu Asn Ser Trp Asp Ser Glu Ser Leu
530 535 540

Arg Glu Thr Val Ser Gln Lys Asp Val Cys Val Pro Lys Ala Thr His
545 550 555 560

Gln Lys Glu Met Asp Lys Ile Ser Gly Lys Leu Glu Asp Ser Thr Ser
565 570 575

Leu Ser Lys Ile Leu Asp Thr Val His Ser Cys Glu Arg Ala Arg Glu
580 585 590

Leu Gln Lys Asp His Cys Glu Gln Arg Thr Gly Lys Met Glu Gln Met
595 600 605

Lys Lys Lys Phe Cys Val Leu Lys Lys Lys Leu Ser Glu Ala Lys Glu
610 615 620

Ile Lys Ser Gln Leu Glu Asn Gln Lys Val Lys Trp Glu Gln Glu Leu
625 630 635 640

Cys Ser Val Arg Phe Leu Thr Leu Met Lys Met Lys Ile Ile Ser Tyr
645 650 655

Met Lys Ile Ala Cys
660

<210> SEQ ID NO 553
<211> LENGTH: 1013
<212> TYPE: PRT
<213> ORGANISM: Homo sapiens

<400> SEQUENCE: 553

Met Gln His His His His His His Val Gly Ser Met Ser Pro Ala Lys
5 10 15

Glu Thr Ser Glu Lys Phe Thr Trp Ala Ala Lys Gly Arg Pro Arg Lys
20 25 30

Ile Ala Trp Glu Lys Lys Glu Thr Pro Val Lys Thr Gly Cys Val Ala
35 40 45

Arg Val Thr Ser Asn Lys Thr Lys Val Leu Glu Lys Gly Arg Ser Lys
50 55 60

Met Ile Ala Cys Pro Thr Lys Glu Ser Ser Thr Lys Ala Ser Ala Asn
65 70 75 80

Asp Gln Arg Phe Pro Ser Glu Ser Lys Gln Glu Glu Asp Glu Glu Tyr
85 90 95

Ser Cys Asp Ser Arg Ser Leu Phe Glu Ser Ser Ala Lys Ile Gln Val
100 105 110

Cys Ile Pro Glu Ser Ile Tyr Gln Lys Val Met Glu Ile Asn Arg Glu
115 120 125

Val Glu Glu Pro Pro Lys Lys Pro Ser Ala Phe Lys Pro Ala Ile Glu
130 135 140

Met Gln Asn Ser Val Pro Asn Lys Ala Phe Glu Leu Lys Asn Glu Gln
145 150 155 160

Thr Leu Arg Ala Asp Pro Met Phe Pro Pro Glu Ser Lys Gln Lys Asp
165 170 175

-continued

```
Tyr Glu Glu Asn Ser Trp Asp Ser Glu Ser Leu Cys Glu Thr Val Ser
            180                 185                 190

Gln Lys Asp Val Cys Leu Pro Lys Ala Thr His Gln Lys Glu Ile Asp
        195                 200                 205

Lys Ile Asn Gly Lys Leu Glu Glu Ser Pro Asn Lys Asp Gly Leu Leu
    210                 215                 220

Lys Ala Thr Cys Gly Met Lys Val Ser Ile Pro Thr Lys Ala Leu Glu
225                 230                 235                 240

Leu Lys Asp Met Gln Thr Phe Lys Ala Glu Pro Pro Gly Lys Pro Ser
                245                 250                 255

Ala Phe Glu Pro Ala Thr Glu Met Gln Lys Ser Val Pro Asn Lys Ala
            260                 265                 270

Leu Glu Leu Lys Asn Glu Gln Thr Leu Arg Ala Asp Glu Ile Leu Pro
        275                 280                 285

Ser Glu Ser Lys Gln Lys Asp Tyr Glu Glu Asn Ser Trp Asp Thr Glu
    290                 295                 300

Ser Leu Cys Glu Thr Val Ser Gln Lys Asp Val Cys Leu Pro Lys Ala
305                 310                 315                 320

Ala His Gln Lys Glu Ile Asp Lys Ile Asn Gly Lys Leu Glu Gly Ser
                325                 330                 335

Pro Gly Lys Asp Gly Leu Leu Lys Ala Asn Cys Gly Met Lys Val Ser
            340                 345                 350

Ile Pro Thr Lys Ala Leu Glu Leu Met Asp Met Gln Thr Phe Lys Ala
        355                 360                 365

Glu Pro Pro Glu Lys Pro Ser Ala Phe Glu Pro Ala Ile Glu Met Gln
    370                 375                 380

Lys Ser Val Pro Asn Lys Ala Leu Glu Leu Lys Asn Glu Gln Thr Leu
385                 390                 395                 400

Arg Ala Asp Glu Ile Leu Pro Ser Glu Ser Lys Gln Lys Asp Tyr Glu
                405                 410                 415

Glu Ser Ser Trp Asp Ser Glu Ser Leu Cys Glu Thr Val Ser Gln Lys
            420                 425                 430

Asp Val Cys Leu Pro Lys Ala Ala His Gln Lys Glu Ile Asp Lys Ile
        435                 440                 445

Asn Gly Lys Leu Glu Glu Ser Pro Asp Asn Asp Gly Phe Leu Lys Ser
    450                 455                 460

Pro Cys Arg Met Lys Val Ser Ile Pro Thr Lys Ala Leu Glu Leu Met
465                 470                 475                 480

Asp Met Gln Thr Phe Lys Ala Glu Pro Pro Glu Lys Pro Ser Ala Phe
                485                 490                 495

Glu Pro Ala Ile Glu Met Gln Lys Ser Val Pro Asn Lys Ala Leu Glu
            500                 505                 510

Leu Lys Asn Glu Gln Thr Leu Arg Ala Asp Gln Met Phe Pro Ser Glu
        515                 520                 525

Ser Lys Gln Lys Asn Val Glu Glu Asn Ser Trp Asp Ser Glu Ser Leu
    530                 535                 540

Arg Glu Thr Val Ser Gln Lys Asp Val Cys Val Pro Lys Ala Thr His
545                 550                 555                 560

Gln Lys Glu Met Asp Lys Ile Ser Gly Lys Leu Glu Asp Ser Thr Ser
                565                 570                 575

Leu Ser Lys Ile Leu Asp Thr Val His Ser Cys Glu Arg Ala Arg Glu
            580                 585                 590

Leu Gln Lys Asp His Cys Glu Gln Arg Thr Gly Lys Met Glu Gln Met
```

-continued

```
        595                 600                 605

Lys Lys Lys Phe Cys Val Leu Lys Lys Lys Leu Ser Glu Ala Lys Glu
    610                 615                 620

Ile Lys Ser Gln Leu Glu Asn Gln Lys Val Lys Trp Glu Gln Glu Leu
625                 630                 635                 640

Cys Ser Val Arg Leu Thr Leu Asn Gln Glu Glu Glu Lys Arg Arg Asn
                645                 650                 655

Ala Asp Ile Leu Asn Glu Lys Ile Arg Glu Glu Leu Gly Arg Ile Glu
            660                 665                 670

Glu Gln His Arg Lys Glu Leu Glu Val Lys Gln Gln Leu Glu Gln Ala
        675                 680                 685

Leu Arg Ile Gln Asp Ile Glu Leu Lys Ser Val Glu Ser Asn Leu Asn
    690                 695                 700

Gln Val Ser His Thr His Glu Asn Glu Asn Tyr Leu Leu His Glu Asn
705                 710                 715                 720

Cys Met Leu Lys Lys Glu Ile Ala Met Leu Lys Leu Glu Ile Ala Thr
                725                 730                 735

Leu Lys His Gln Tyr Gln Glu Lys Glu Asn Lys Tyr Phe Glu Asp Ile
            740                 745                 750

Lys Ile Leu Lys Glu Lys Asn Ala Glu Leu Gln Met Thr Leu Lys Leu
        755                 760                 765

Lys Glu Glu Ser Leu Thr Lys Arg Ala Ser Gln Tyr Ser Gly Gln Leu
    770                 775                 780

Lys Val Leu Ile Ala Glu Asn Thr Met Leu Thr Ser Lys Leu Lys Glu
785                 790                 795                 800

Lys Gln Asp Lys Glu Ile Leu Glu Ala Glu Ile Glu Ser His His Pro
                805                 810                 815

Arg Leu Ala Ser Ala Val Gln Asp His Asp Gln Ile Val Thr Ser Arg
            820                 825                 830

Lys Ser Gln Glu Pro Ala Phe His Ile Ala Gly Asp Ala Cys Leu Gln
        835                 840                 845

Arg Lys Met Asn Val Asp Val Ser Ser Thr Ile Tyr Asn Asn Glu Val
    850                 855                 860

Leu His Gln Pro Leu Ser Glu Ala Gln Arg Lys Ser Lys Ser Leu Lys
865                 870                 875                 880

Ile Asn Leu Asn Tyr Ala Gly Asp Ala Leu Arg Glu Asn Thr Leu Val
                885                 890                 895

Ser Glu His Ala Gln Arg Asp Gln Arg Glu Thr Gln Cys Gln Met Lys
            900                 905                 910

Glu Ala Glu His Met Tyr Gln Asn Glu Gln Asp Asn Val Asn Lys His
        915                 920                 925

Thr Glu Gln Gln Glu Ser Leu Asp Gln Lys Leu Phe Gln Leu Gln Ser
    930                 935                 940

Lys Asn Met Trp Leu Gln Gln Gln Leu Val His Ala His Lys Lys Ala
945                 950                 955                 960

Asp Asn Lys Ser Lys Ile Thr Ile Asp Ile His Phe Leu Glu Arg Lys
                965                 970                 975

Met Gln His His Leu Leu Lys Glu Lys Asn Glu Glu Ile Phe Asn Tyr
            980                 985                 990

Asn Asn His Leu Lys Asn Arg Ile Tyr Gln Tyr Glu Lys Glu Lys Ala
        995                 1000                1005

Glu Thr Glu Val Ile
    1010
```

-continued

<210> SEQ ID NO 554
<211> LENGTH: 25
<212> TYPE: DNA
<213> ORGANISM: Artificial Sequence
<220> FEATURE:
<223> OTHER INFORMATION: PCR primer

<400> SEQUENCE: 554
gtcggctcca tgagtcccgc aaaag 25

<210> SEQ ID NO 555
<211> LENGTH: 36
<212> TYPE: DNA
<213> ORGANISM: Artificial Sequence
<220> FEATURE:
<223> OTHER INFORMATION: PCR primer

<400> SEQUENCE: 555
cgagaattca atacttaaga agaccatctt taccag 36

<210> SEQ ID NO 556
<211> LENGTH: 31
<212> TYPE: DNA
<213> ORGANISM: Artificial Sequence
<220> FEATURE:
<223> OTHER INFORMATION: PCR primer

<400> SEQUENCE: 556
cataagctta aggctaactg cggaatgaaa g 31

<210> SEQ ID NO 557
<211> LENGTH: 35
<212> TYPE: DNA
<213> ORGANISM: Artificial Sequence
<220> FEATURE:
<223> OTHER INFORMATION: PCR primer

<400> SEQUENCE: 557
cccgcagaat tcaacatgca attttcatgt aagag 35

<210> SEQ ID NO 558
<211> LENGTH: 25
<212> TYPE: DNA
<213> ORGANISM: Artificial Sequence
<220> FEATURE:
<223> OTHER INFORMATION: PCR primer

<400> SEQUENCE: 558
ctaaatgccg gcacaagagc tctgc 25

<210> SEQ ID NO 559
<211> LENGTH: 35
<212> TYPE: DNA
<213> ORGANISM: Artificial Sequence
<220> FEATURE:
<223> OTHER INFORMATION: PCR primer

<400> SEQUENCE: 559
cgcgcagaat tctattatat aacttctgtt tctgc 35

<210> SEQ ID NO 560
<211> LENGTH: 26
<212> TYPE: DNA
<213> ORGANISM: Artificial Sequence
<220> FEATURE:

-continued

<223> OTHER INFORMATION: PCR primer

<400> SEQUENCE: 560
ggggaattgt gagcggataa caattc 26

<210> SEQ ID NO 561
<211> LENGTH: 36
<212> TYPE: DNA
<213> ORGANISM: Artificial Sequence
<220> FEATURE:
<223> OTHER INFORMATION: PCR primer

<400> SEQUENCE: 561
cgtagaattc aacctgattt aaattacttt ctacac 36

<210> SEQ ID NO 562
<211> LENGTH: 31
<212> TYPE: DNA
<213> ORGANISM: Artificial Sequence
<220> FEATURE:
<223> OTHER INFORMATION: PCR primer

<400> SEQUENCE: 562
gaaagtaatt taaatcaggt ttctcacact c 31

<210> SEQ ID NO 563
<211> LENGTH: 23
<212> TYPE: DNA
<213> ORGANISM: Artificial Sequence
<220> FEATURE:
<223> OTHER INFORMATION: PCR primer

<400> SEQUENCE: 563
gaggccccaa ggggttatgc tag 23

<210> SEQ ID NO 564
<211> LENGTH: 4458
<212> TYPE: DNA
<213> ORGANISM: Homo sapiens

<400> SEQUENCE: 564
ctagtctata ccagcaacga ctcctacatc gtccactctg gggatcttag aaagatccat 60
aaagctgcct cccggggaca agtccggaag ctggagaaga tgacaaagag gaagaagacc 120
atcaacctta atatacaaga cgcccagaag aggactgctc tacactgggc ctgtgtcaat 180
ggccatgagg aagtagtaac atttctggta gacagaaagt gccagcttga cgtccttgat 240
ggcgaacaca ggacacctct gatgaaggct ctacaatgcc atcaggaggc ttgtgcaaat 300
attctgatag attctggtgc cgatataaat ctcgtagatg tgtatggcaa catggctctc 360
cattatgctg tttatagtga gattttgtca gtggtggcaa aactgctgtc ccatggtgca 420
gtcatcgaag tgcacaacaa ggctagcctc acaccacttt tactatccat aacgaaaaga 480
agtgagcaaa ttgtggaatt tttgctgata aaaaatgcaa atgcgaatgc agttaataag 540
tataaatgca cagccctcat gcttgctgta tgtcatggat catcagagat agttggcatg 600
cttcttcagc aaaatgttga cgtctttgct gcagatatat gtggagtaac tgcagaacat 660
tatgctgtta cttgtggatt tcatcacatt catgaacaaa ttatggaata tatacgaaaa 720
ttatctaaaa atcatcaaaa taccaatcca gaaggaacat ctgcaggaac acctgatgag 780
gctgcaccct tggcggaaag aacacctgac acagctgaaa gcttggtgga aaaaacacct 840
gatgaggctg caccccttggt ggaaagaaca cctgacacgg ctgaaagctt ggtggaaaaa 900

-continued

```
acacctgatg aggctgcatc cttggtggag ggaacatctg acaaaattca atgtttggag    960
aaagcgacat ctggaaagtt cgaacagtca gcagaagaaa cacctaggga aattacgagt   1020
cctgcaaaag aaacatctga gaaatttacg tggccagcaa aaggaagacc taggaagatc   1080
gcatgggaga aaaaagaaga cacacctagg gaaattatga gtcccgcaaa agaaacatct   1140
gagaaattta cgtgggcagc aaaaggaaga cctaggaaga tcgcatggga gaaaaaagaa   1200
acacctgtaa agactggatg cgtggcaaga gtaacatcta ataaaactaa agttttggaa   1260
aaaggaagat ctaagatgat tgcatgtcct acaaaagaat catctacaaa agcaagtgcc   1320
aatgatcaga ggttcccatc agaatccaaa caagaggaag atgaagaata ttcttgtgat   1380
tctcggagtc tctttgagag ttctgcaaag attcaagtgt gtatacctga gtctatatat   1440
caaaaagtaa tggagataaa tagagaagta gaagagcctc ctaagaagcc atctgccttc   1500
aagcctgcca ttgaaatgca aaactctgtt ccaaataaag cctttgaatt gaagaatgaa   1560
caaacattga gagcagatcc gatgttccca ccagaatcca aacaaaagga ctatgaagaa   1620
aattcttggg attctgagag tctctgtgag actgtttcac agaaggatgt gtgtttaccc   1680
aaggctacac atcaaaaaga aatagataaa ataaatggaa aattagaaga gtctcctaat   1740
aaagatggtc ttctgaaggc tacctgcgga atgaaagttt ctattccaac taaagcctta   1800
gaattgaagg acatgcaaac tttcaaagcg gagcctccgg ggaagccatc tgccttcgag   1860
cctgccactg aaatgcaaaa gtctgtccca aataaagcct tggaattgaa aaatgaacaa   1920
acatggagag cagatgagat actcccatca gaatccaaac aaaaggacta tgaagaaaat   1980
tcttgggata ctgagagtct ctgtgagact gtttcacaga aggatgtgtg tttacccaag   2040
gctgcgcatc aaaaagaaat agataaaata aatggaaaat tagaagggtc tcctgttaaa   2100
gatggtcttc tgaaggctaa ctgcggaatg aaagtttcta ttccaactaa agccttagaa   2160
ttgatggaca tgcaaacttt caaagcagag cctcccgaga agccatctgc cttcgagcct   2220
gccattgaaa tgcaaaagtc tgttccaaat aaagccttgg aattgaagaa tgaacaaaca   2280
ttgagagcag atgagatact cccatcagaa tccaaacaaa aggactatga agaaagttct   2340
tgggattctg agagtctctg tgagactgtt tcacagaagg atgtgtgttt acccaaggct   2400
acacatcaaa aagaaataga taaaataaat ggaaaattag aagagtctcc tgataatgat   2460
ggttttctga aggctccctg cagaatgaaa gtttctattc caactaaagc cttagaattg   2520
atggacatgc aaactttcaa agcagagcct cccgagaagc catctgcctt cgagcctgcc   2580
attgaaatgc aaaagtctgt tccaaataaa gccttggaat tgaagaatga acaaacattg   2640
agagcagatc agatgttccc ttcagaatca aaacaaaaga aggttgaaga aaattcttgg   2700
gattctgaga gtctccgtga gactgtttca cagaaggatg tgtgtgtacc caaggctaca   2760
catcaaaaag aaatggataa aataagtgga aaattagaag attcaactag cctatcaaaa   2820
atcttggata cagttcattc ttgtgaaaga gcaagggaac ttcaaaaaga tcactgtgaa   2880
caacgtacag gaaaaatgga acaaatgaaa aagaagtttt gtgtactgaa aaagaaactg   2940
tcagaagcaa aagaaataaa atcacagtta gagaaccaaa aagttaaatg ggaacaagag   3000
ctctgcagtg tgagattgac tttaaaccaa gaagaagaga agagaagaaa tgccgatata   3060
ttaaatgaaa aaattaggga agaattagga agaatcgaag agcagcatag gaaagagtta   3120
gaagtgaaac aacaacttga acaggctctc agaatacaag atatagaatt gaagagtgta   3180
gaaagtaatt tgaatcaggt ttctcacact catgaaaatg aaaattatct cttacatgaa   3240
```

-continued

```
aattgcatgt tgaaaaagga aattgccatg ctaaaactgg aaatagccac actgaaacac   3300

caataccagg aaaaggaaaa taaatacttt gaggacatta agattttaaa agaaaagaat   3360

gctgaacttc agatgaccct aaaactgaaa gaggaatcat taactaaaag ggcatctcaa   3420

tatagtgggc agcttaaagt tctgatagct gagaacacaa tgctcacttc taaattgaag   3480

gaaaaacaag acaaagaaat actagaggca gaaattgaat cacaccatcc tagactggct   3540

tctgctgtac aagaccatga tcaaattgtg acatcaagaa aaagtcaaga acctgctttc   3600

cacattgcag gagatgcttg tttgcaaaga aaaatgaatg ttgatgtgag tagtacgata   3660

tataacaatg aggtgctcca tcaaccactt tctgaagctc aaaggaaatc caaaagccta   3720

aaaattaatc tcaattatgc aggagatgct ctaagagaaa atacattggt ttcagaacat   3780

gcacaaagag accaacgtga aacacagtgt caaatgaagg aagctgaaca catgtatcaa   3840

aacgaacaag ataatgtgaa caaacacact gaacagcagg agtctctaga tcagaaatta   3900

tttcaactac aaagcaaaaa tatgtggctt caacagcaat tagttcatgc acataagaaa   3960

gctgacaaca aaagcaagat aacaattgat attcattttc ttgagaggaa aatgcaacat   4020

catctcctaa aagagaaaaa tgaggagata tttaattaca ataaccattt aaaaaaccgt   4080

atatatcaat atgaaaaaga gaaagcagaa acagaaaact catgagagac aagcagtaag   4140

aaacttcttt tggagaaaca acagaccaga tctttactca caactcatgc taggaggcca   4200

gtcctagcat caccttatgt tgaaaatctt accaatagtc tgtgtcaaca gaatacttat   4260

tttagaagaa aaattcatga tttcttcctg aagcctacag acataaaata acagtgtgaa   4320

gaattacttg ttcacgaatt gcataaagct gcacaggatt cccatctacc ctgatgatgc   4380

agcagacatc attcaatcca accagaatct cgctctgcac tccagcctag gtgacagagt   4440

gagactccac ctcggaaa                                                  4458


<210> SEQ ID NO 565
<211> LENGTH: 1341
<212> TYPE: PRT
<213> ORGANISM: Homo sapiens

<400> SEQUENCE: 565

Met Thr Lys Arg Lys Lys Thr Ile Asn Leu Asn Ile Gln Asp Ala Gln
1               5                   10                  15

Lys Arg Thr Ala Leu His Trp Ala Cys Val Asn Gly His Glu Glu Val
            20                  25                  30

Val Thr Phe Leu Val Asp Arg Lys Cys Gln Leu Asp Val Leu Asp Gly
        35                  40                  45

Glu His Arg Thr Pro Leu Met Lys Ala Leu Gln Cys His Gln Glu Ala
    50                  55                  60

Cys Ala Asn Ile Leu Ile Asp Ser Gly Ala Asp Ile Asn Leu Val Asp
65                  70                  75                  80

Val Tyr Gly Asn Met Ala Leu His Tyr Ala Val Tyr Ser Glu Ile Leu
                85                  90                  95

Ser Val Val Ala Lys Leu Leu Ser His Gly Ala Val Ile Glu Val His
            100                 105                 110

Asn Lys Ala Ser Leu Thr Pro Leu Leu Leu Ser Ile Thr Lys Arg Ser
        115                 120                 125

Glu Gln Ile Val Glu Phe Leu Leu Ile Lys Asn Ala Asn Ala Asn Ala
    130                 135                 140

Val Asn Lys Tyr Lys Cys Thr Ala Leu Met Leu Ala Val Cys His Gly
145                 150                 155                 160
```

-continued

```
Ser Ser Glu Ile Val Gly Met Leu Leu Gln Gln Asn Val Asp Val Phe
                165                 170                 175

Ala Ala Asp Ile Cys Gly Val Thr Ala Glu His Tyr Ala Val Thr Cys
            180                 185                 190

Gly Phe His His Ile His Glu Gln Ile Met Glu Tyr Ile Arg Lys Leu
        195                 200                 205

Ser Lys Asn His Gln Asn Thr Asn Pro Glu Gly Thr Ser Ala Gly Thr
    210                 215                 220

Pro Asp Glu Ala Ala Pro Leu Ala Glu Arg Thr Pro Asp Thr Ala Glu
225                 230                 235                 240

Ser Leu Val Glu Lys Thr Pro Asp Glu Ala Ala Pro Leu Val Glu Arg
                245                 250                 255

Thr Pro Asp Thr Ala Glu Ser Leu Val Glu Lys Thr Pro Asp Glu Ala
            260                 265                 270

Ala Ser Leu Val Glu Gly Thr Ser Asp Lys Ile Gln Cys Leu Glu Lys
        275                 280                 285

Ala Thr Ser Gly Lys Phe Glu Gln Ser Ala Glu Glu Thr Pro Arg Glu
    290                 295                 300

Ile Thr Ser Pro Ala Lys Glu Thr Ser Glu Lys Phe Thr Trp Pro Ala
305                 310                 315                 320

Lys Gly Arg Pro Arg Lys Ile Ala Trp Glu Lys Lys Glu Asp Thr Pro
                325                 330                 335

Arg Glu Ile Met Ser Pro Ala Lys Glu Thr Ser Glu Lys Phe Thr Trp
            340                 345                 350

Ala Ala Lys Gly Arg Pro Arg Lys Ile Ala Trp Glu Lys Lys Glu Thr
        355                 360                 365

Pro Val Lys Thr Gly Cys Val Ala Arg Val Thr Ser Asn Lys Thr Lys
    370                 375                 380

Val Leu Glu Lys Gly Arg Ser Lys Met Ile Ala Cys Pro Thr Lys Glu
385                 390                 395                 400

Ser Ser Thr Lys Ala Ser Ala Asn Asp Gln Arg Phe Pro Ser Glu Ser
                405                 410                 415

Lys Gln Glu Glu Asp Glu Glu Tyr Ser Cys Asp Ser Arg Ser Leu Phe
            420                 425                 430

Glu Ser Ser Ala Lys Ile Gln Val Cys Ile Pro Glu Ser Ile Tyr Gln
        435                 440                 445

Lys Val Met Glu Ile Asn Arg Glu Val Glu Glu Pro Pro Lys Lys Pro
    450                 455                 460

Ser Ala Phe Lys Pro Ala Ile Glu Met Gln Asn Ser Val Pro Asn Lys
465                 470                 475                 480

Ala Phe Glu Leu Lys Asn Glu Gln Thr Leu Arg Ala Asp Pro Met Phe
                485                 490                 495

Pro Pro Glu Ser Lys Gln Lys Asp Tyr Glu Glu Asn Ser Trp Asp Ser
            500                 505                 510

Glu Ser Leu Cys Glu Thr Val Ser Gln Lys Asp Val Cys Leu Pro Lys
        515                 520                 525

Ala Thr His Gln Lys Glu Ile Asp Lys Ile Asn Gly Lys Leu Glu Glu
    530                 535                 540

Ser Pro Asn Lys Asp Gly Leu Leu Lys Ala Thr Cys Gly Met Lys Val
545                 550                 555                 560

Ser Ile Pro Thr Lys Ala Leu Glu Leu Lys Asp Met Gln Thr Phe Lys
                565                 570                 575
```

-continued

```
Ala Glu Pro Pro Gly Lys Pro Ser Ala Phe Glu Pro Ala Thr Glu Met
            580                 585                 590

Gln Lys Ser Val Pro Asn Lys Ala Leu Glu Leu Lys Asn Glu Gln Thr
        595                 600                 605

Trp Arg Ala Asp Glu Ile Leu Pro Ser Glu Ser Lys Gln Lys Asp Tyr
    610                 615                 620

Glu Glu Asn Ser Trp Asp Thr Glu Ser Leu Cys Glu Thr Val Ser Gln
625                 630                 635                 640

Lys Asp Val Cys Leu Pro Lys Ala Ala His Gln Lys Glu Ile Asp Lys
                645                 650                 655

Ile Asn Gly Lys Leu Glu Gly Ser Pro Val Lys Asp Gly Leu Leu Lys
            660                 665                 670

Ala Asn Cys Gly Met Lys Val Ser Ile Pro Thr Lys Ala Leu Glu Leu
        675                 680                 685

Met Asp Met Gln Thr Phe Lys Ala Glu Pro Pro Glu Lys Pro Ser Ala
    690                 695                 700

Phe Glu Pro Ala Ile Glu Met Gln Lys Ser Val Pro Asn Lys Ala Leu
705                 710                 715                 720

Glu Leu Lys Asn Glu Gln Thr Leu Arg Ala Asp Glu Ile Leu Pro Ser
                725                 730                 735

Glu Ser Lys Gln Lys Asp Tyr Glu Glu Ser Ser Trp Asp Ser Glu Ser
            740                 745                 750

Leu Cys Glu Thr Val Ser Gln Lys Asp Val Cys Leu Pro Lys Ala Thr
        755                 760                 765

His Gln Lys Glu Ile Asp Lys Ile Asn Gly Lys Leu Glu Glu Ser Pro
    770                 775                 780

Asp Asn Asp Gly Phe Leu Lys Ala Pro Cys Arg Met Lys Val Ser Ile
785                 790                 795                 800

Pro Thr Lys Ala Leu Glu Leu Met Asp Met Gln Thr Phe Lys Ala Glu
                805                 810                 815

Pro Pro Glu Lys Pro Ser Ala Phe Glu Pro Ala Ile Glu Met Gln Lys
            820                 825                 830

Ser Val Pro Asn Lys Ala Leu Glu Leu Lys Asn Glu Gln Thr Leu Arg
        835                 840                 845

Ala Asp Gln Met Phe Pro Ser Glu Ser Lys Gln Lys Lys Val Glu Glu
    850                 855                 860

Asn Ser Trp Asp Ser Glu Ser Leu Arg Glu Thr Val Ser Gln Lys Asp
865                 870                 875                 880

Val Cys Val Pro Lys Ala Thr His Gln Lys Glu Met Asp Lys Ile Ser
                885                 890                 895

Gly Lys Leu Glu Asp Ser Thr Ser Leu Ser Lys Ile Leu Asp Thr Val
            900                 905                 910

His Ser Cys Glu Arg Ala Arg Glu Leu Gln Lys Asp His Cys Glu Gln
        915                 920                 925

Arg Thr Gly Lys Met Glu Gln Met Lys Lys Lys Phe Cys Val Leu Lys
    930                 935                 940

Lys Lys Leu Ser Glu Ala Lys Glu Ile Lys Ser Gln Leu Glu Asn Gln
945                 950                 955                 960

Lys Val Lys Trp Glu Gln Glu Leu Cys Ser Val Arg Leu Thr Leu Asn
                965                 970                 975

Gln Glu Glu Glu Lys Arg Arg Asn Ala Asp Ile Leu Asn Glu Lys Ile
            980                 985                 990

Arg Glu Glu Leu Gly Arg Ile Glu Glu Gln His Arg Lys Glu Leu Glu
```

-continued

```
        995                 1000                1005

Val Lys Gln Gln Leu Glu Gln Ala Leu Arg Ile Gln Asp Ile Glu Leu
    1010                1015                1020

Lys Ser Val Glu Ser Asn Leu Asn Gln Val Ser His Thr His Glu Asn
1025                1030                1035                1040

Glu Asn Tyr Leu Leu His Glu Asn Cys Met Leu Lys Lys Glu Ile Ala
                1045                1050                1055

Met Leu Lys Leu Glu Ile Ala Thr Leu Lys His Gln Tyr Gln Glu Lys
            1060                1065                1070

Glu Asn Lys Tyr Phe Glu Asp Ile Lys Ile Leu Lys Glu Lys Asn Ala
        1075                1080                1085

Glu Leu Gln Met Thr Leu Lys Leu Lys Glu Glu Ser Leu Thr Lys Arg
    1090                1095                1100

Ala Ser Gln Tyr Ser Gly Gln Leu Lys Val Leu Ile Ala Glu Asn Thr
1105                1110                1115                1120

Met Leu Thr Ser Lys Leu Lys Glu Lys Gln Asp Lys Glu Ile Leu Glu
                1125                1130                1135

Ala Glu Ile Glu Ser His His Pro Arg Leu Ala Ser Ala Val Gln Asp
            1140                1145                1150

His Asp Gln Ile Val Thr Ser Arg Lys Ser Gln Glu Pro Ala Phe His
        1155                1160                1165

Ile Ala Gly Asp Ala Cys Leu Gln Arg Lys Met Asn Val Asp Val Ser
    1170                1175                1180

Ser Thr Ile Tyr Asn Asn Glu Val Leu His Gln Pro Leu Ser Glu Ala
1185                1190                1195                1200

Gln Arg Lys Ser Lys Ser Leu Lys Ile Asn Leu Asn Tyr Ala Gly Asp
                1205                1210                1215

Ala Leu Arg Glu Asn Thr Leu Val Ser Glu His Ala Gln Arg Asp Gln
            1220                1225                1230

Arg Glu Thr Gln Cys Gln Met Lys Glu Ala Glu His Met Tyr Gln Asn
        1235                1240                1245

Glu Gln Asp Asn Val Asn Lys His Thr Glu Gln Gln Glu Ser Leu Asp
    1250                1255                1260

Gln Lys Leu Phe Gln Leu Gln Ser Lys Asn Met Trp Leu Gln Gln Gln
1265                1270                1275                1280

Leu Val His Ala His Lys Lys Ala Asp Asn Lys Ser Lys Ile Thr Ile
                1285                1290                1295

Asp Ile His Phe Leu Glu Arg Lys Met Gln His His Leu Leu Lys Glu
            1300                1305                1310

Lys Asn Glu Glu Ile Phe Asn Tyr Asn Asn His Leu Lys Asn Arg Ile
        1315                1320                1325

Tyr Gln Tyr Glu Lys Glu Lys Ala Glu Thr Glu Asn Ser
    1330                1335                1340


<210> SEQ ID NO 566
<211> LENGTH: 4047
<212> TYPE: DNA
<213> ORGANISM: Homo sapiens

<400> SEQUENCE: 566

atgcagcatc accaccatca ccaccacaca aagaggaaga agaccatcaa ccttaatata      60

caagacgccc agaagaggac tgctctacac tgggcctgtg tcaatggcca tgaggaagta     120

gtaacatttc tggtagacag aaagtgccag cctgacgtcc ttgatggcga acacaggaca     180
```

-continued

```
cctctgatga aggctctaca atgccatcag gaggcttgtg caaatattct gatagattct    240
ggtgccgata taaatctcgt agatgtgtat ggcaacatgg ctctccatta tgctgtttat    300
agtgagattt tgtcagtggt ggcaaaactg ctgtcccatg gtgcagtcat cgaagtgcac    360
aacaaggcta gcctcacacc acttttacta tccataacga aaagaagtga gcaaattgtg    420
gaatttttgc tgataaaaaa tgcaaatgcg aatgcagtta ataagtataa atgcacagcc    480
ctcatgcttg ctgtatgtca tggattatca gagatagttg gcatgcttct tcagcaaaat    540
gttgacgtct ttgctgcaga tatatgtgga gtaactgcag aacattatgc tgttacttgt    600
ggatttcatc acattcatga acaaattatg gaatatatac gaaaattatc taaaaatcat    660
caaaatacca atccagaagg aacatctgca ggaacacctg atgaggctgc acccttggcg    720
gaaagaacac ctgacacagc tgaaagcttg gtggaaaaaa cacctgatga ggctgcaccc    780
ttggtggaaa gaacacctga cacggctgaa agcttggtgg aaaaaacacc tgatgaggct    840
gcatccttgg tggagggaac atctgacaaa attcaatgtt tggagaaagc gacatctgga    900
aagttcgaac agtcagcaga agaaacacct agggaaatta cgagtcctgc aaaagaaaca    960
tctgagaaat ttacgtggcc agcaaaagga agacctagga agatcgcatg ggagaaaaaa   1020
gaagacacac ctagggaaat tatgagtccc gcaaaagaaa catctgagaa atttacgtgg   1080
gcagcaaaag gaagacctag gaagatcgca tgggagaaaa aagaaacacc tgtaaagact   1140
ggatgcgtgg caagagtaac atctaataaa actaaagttt tggaaaaagg aagatctaag   1200
atgattgcat gtcctacaaa agaatcatct acaaaagcaa gtgccaatga tcagaggttc   1260
ccatcagaat ccaaacaaga ggaagatgaa gaatattctt gtgattctcg gagtctcttt   1320
gagagttctg caaagattca agtgtgtata cctgagtcta tatatcaaaa agtaatggag   1380
ataaatagag aagtagaaga gcctcctaag aagccatctg ccttcaagcc tgccattgaa   1440
atgcaaaact ctgttccaaa taaagccttt gaattgaaga atgaacaaac attgagagca   1500
gatccgatgt tcccaccaga atccaaacaa aaggactatg aagaaaattc ttgggattct   1560
gagagtctct gtgagactgt ttcacagaag gatgtgtgtt tacccaaggc tacacatcaa   1620
aaagaaatag ataaaataaa tggaaaatta gaagagtctc ctaataaaga tggtcttctg   1680
aaggctacct gcggaatgaa agtttctatt ccaactaaag ccttagaatt gaaggacatg   1740
caaactttca aagcggagcc tccggggaag ccatctgcct tcgagcctgc cactgaaatg   1800
caaaagtctg tcccaaataa agccttggaa ttgaaaaatg aacaaacatg gagagcagat   1860
gagatactcc catcagaatc caaacaaaag gactatgaag aaaattcttg ggatactgag   1920
agtctctgtg agactgtttc acagaaggat gtgtgtttac ccaaggctgc gcatcaaaaa   1980
gaaatagata aaataaatgg aaaattagaa gggtctcctg ttaaagatgg tcttctgaag   2040
gctaactgcg gaatgaaagt ttctattcca actaaagcct tagaattgat ggacatgcaa   2100
actttcaaag cagagcctcc cgagaagcca tctgccttcg agcctgccat tgaaatgcaa   2160
aagtctgttc caaataaagc cttggaattg aagaatgaac aaacattgag agcagatgag   2220
atactcccat cagaatccaa acaaaaggac tatgaagaaa gttcttggga ttctgagagt   2280
ctctgtgaga ctgtttcaca gaaggatgtg tgtttaccca aggctacaca tcaaaaagaa   2340
atagataaaa taaatggaaa attagaagag tctcctgata atgatggttt tctgaaggct   2400
ccctgcagaa tgaaagtttc tattccaact aaagccttag aattgatgga catgcaaact   2460
ttcaaagcag agcctcccga gaagccatct gccttcgagc ctgccattga aatgcaaaag   2520
tctgttccaa ataaagcctt ggaattgaag aatgaacaaa cattgagagc agatcagatg   2580
```

-continued

```
ttcccttcag aatcaaaaca aaagaaggtt gaagaaaatt cttgggattc tgagagtctc   2640
cgtgagactg tttcacagaa ggatgtgtgt gtacccaagg ctacacatca aaaagaaatg   2700
gataaaataa gtggaaaatt agaagattca actagcctat caaaaatctt ggatacagtt   2760
cattcttgtg aaagagcaag ggaacttcaa aaagatcact gtgaacaacg tacaggaaaa   2820
atggaacaaa tgaaaaagaa gttttgtgta ctgaaaaaga aactgtcaga agcaaaagaa   2880
ataaaatcac agttagagaa ccaaaaagtt aaatgggaac aagagctctg cagtgtgaga   2940
ttgactttaa accaagaaga agagaagaga agaaatgccg atatattaaa tgaaaaaatt   3000
agggaagaat taggaagaat cgaagagcag cataggaaag agttagaagt gaaacaacaa   3060
cttgaacagg ctctcagaat acaagatata gaattgaaga gtgtagaaag taatttgaat   3120
caggtttctc acactcatga aaatgaaaat tatctcttac atgaaaattg catgttgaaa   3180
aaggaaattg ccatgctaaa actggaaata gccacactga aacaccaata ccaggaaaag   3240
gaaaataaat actttgagga cattaagatt ttaaaagaaa agaatgctga acttcagatg   3300
accctaaaac tgaaagagga atcattaact aaaagggcat ctcaatatag tgggcagctt   3360
aaagttctga tagctgagaa cacaatgctc acttctaaat tgaaggaaaa acaagacaaa   3420
gaaatactag aggcagaaat tgaatcacac catcctagac tggcttctgc tgtacaagac   3480
catgatcaaa ttgtgacatc aagaaaaagt caagaacctg ctttccacat tgcaggagat   3540
gcttgtttgc aaagaaaaat gaatgttgat gtgagtagta cgatatataa caatgaggtg   3600
ctccatcaac cactttctga agctcaaagg aaatccaaaa gcctaaaaat taatctcaat   3660
tatgcaggag atgctctaag agaaaataca ttggtttcag aacatgcaca aagagaccaa   3720
cgtgaaacac agtgtcaaat gaaggaagct gaacacatgt atcaaaacga acaagataat   3780
gtgaacaaac acactgaaca gcaggagtct ctagatcaga aattatttca actacaaagc   3840
aaaaatatgt ggcttcaaca gcaattagtt catgcacata agaaagctga caacaaaagc   3900
aagataacaa ttgatattca ttttcttgag aggaaaatgc aacatcatct cctaaaagag   3960
aaaaatgagg agatatttaa ttacaataac catttaaaaa accgtatata tcaatatgaa   4020
aaagagaaag cagaaacaga agttata                                       4047
```

<210> SEQ ID NO 567
<211> LENGTH: 1199
<212> TYPE: DNA
<213> ORGANISM: Homo sapiens

<400> SEQUENCE: 567

```
acaaagagga agaagaccat caaccttaat atacaagacg cccagaagag gactgctcta     60
cactgggcct gtgtcaatgg ccatgaggaa gtagtaacat ttctggtaga cagaaagtgc    120
cagcctgacg tccttgatgg cgaacacagg acacctctga tgaaggctct acaatgccat    180
caggaggctt gtgcaaatat tctgatagat tctggtgccg atataaatct cgtagatgtg    240
tatggcaaca tggctctcca ttatgctgtt tatagtgaga ttttgtcagt ggtggcaaaa    300
ctgctgtccc atggtgcagt catcgaagtg cacaacaagg ctagcctcac accacttttta    360
ctatccataa cgaaaagaag tgagcaaatt gtggaatttt tgctgataaa aaatgcaaat    420
gcgaatgcag ttaataagta taaatgcaca gccctcatgc ttgctgtatg tcatggatta    480
tcagagatag ttggcatgct tcttcagcaa aatgttgacg tctttgctgc agatatatgt    540
ggagtaactg cagaacatta tgctgttact tgtggatttc atcacattca tgaacaaatt    600
```

-continued

```
atggaatata tacgaaaatt atctaaaaat catcaaaata ccaatccaga aggaacatct    660

gcaggaacac ctgatgaggc tgcacccttg gcggaaagaa cacctgacac agctgaaagc    720

ttggtggaaa aaacacctga tgaggctgca cccttggtgg aaagaacacc tgacacggct    780

gaaagcttgg tggaaaaaac acctgatgag gctgcatcct tggtggaggg aacatctgac    840

aaaattcaat gtttggagaa agcgacatct ggaaagttcg aacagtcagc agaagaaaca    900

cctagggaaa ttacgagtcc tgcaaaagaa acatctgaga aatttacgtg gccagcaaaa    960

ggaagaccta ggaagatcgc atgggagaaa aaagaagaca cacctaggga aattatgagt   1020

cccgcaaaag aaacatctga gaaatttacg tgggcagcaa aaggaagacc taggaagatc   1080

gcatgggaga aaaaagaaac acctgtaaag actggatgcg tggcaagagt aacatctaat   1140

aaaactaaag ttttggaaaa aggaagatct aagatgattg catgtcctac aaaagaatc    1199
```

<210> SEQ ID NO 568
<211> LENGTH: 1199
<212> TYPE: DNA
<213> ORGANISM: Homo sapiens

<400> SEQUENCE: 568

```
acaaagagga agaagaccat caaccttaat atacaagacg cccagaagag gactgctcta     60

cactgggcct gtgtcaatgg ccatgaggaa gtagtaacat ttctggtaga cagaaagtgc    120

cagcttgacg tccttgatgg cgaacacagg acacctctga tgaaggctct acaatgccat    180

caggaggctt gtgcaaatat tctgatagat tctggtgccg atataaatct cgtagatgtg    240

tatgacaaca cggctctcca ttatgctgtt tatagtgaga ttttgtcagt ggtggcaaaa    300

ctgctgtccc atggtgcagt catctaagcg cacaacaagg ctagcctcac accactttta    360

ctatccataa cgaaaagaag tgagcaaatt gtggaatttt tgctgataaa aaatgcaaat    420

gcgaatgcag ttaataagta taaatgcaca gccctcatgc ttgctgtatg tcatggatca    480

tcagagatag ttggcatgct tcttcagcaa aatgttgacg tctttgctgc agatatatgt    540

ggagtaactg cagaacatta tgctgttact tgtggatttc atcacattca tgaacaaatt    600

atggaatata tacgaaaatt atctaaaaat catcaaaata ccaatccaga aggaacatct    660

gcaggaacac ctgatgaggc tgcacccttg gcggaaagaa cacctgacac agctgaaagc    720

ttggtggaaa aaacacctga tgaggctgca cccttggtgg aaagaacacc tgacacggct    780

gaaagcttgg tggaaaaaac acctgatgag gctgcatcct tggtggaggg aacatctgac    840

aaaattcaat gtttggagaa agcgacatct ggaaagttcg aacagtcagc agaagaaaca    900

cctagggaaa ttacgagtcc tgcaaaagaa acatctgaga aatttacgtg gccagcaaaa    960

ggaagaccta ggaagatcgc atgggagaaa aaagaagaca cacctaggga aattatgagt   1020

cccgcaaaag aaacatctga gaaatttacg tgggcagcaa aaggaagacc taggaagatc   1080

gcatgggaga aaaaagaaac acctgtaaag actggatgcg tggcaagagt aacatctaat   1140

aaaactaaag ttttggaaaa aggaagatct aagatgattg catgtcctac aaaagaatc    1199
```

<210> SEQ ID NO 569
<211> LENGTH: 1199
<212> TYPE: DNA
<213> ORGANISM: Homo sapiens

<400> SEQUENCE: 569

```
acaaagagga agaagaccat caaccttaat atacaagacg cccagaagag gactgctcta     60

cactgggcct gtgtcaatgg ccatgaggaa gtagtaacat ttctggtaga cagaaagtgc    120
```

-continued

```
cagcttgacg tccttgatgg cgaacacagg acacctctga tgaaggctct acaatgccat    180

caggaggctt gtgcaaatat tctgatagat tctggtgccg atataaatct cgtagatgtg    240

tatggcaaca tggctctcca ttatgctgtt tatagtgaga ttttgtcagt ggtggcaaaa    300

ctgctgtccc atggtgcagt catcgaagtg cacaacaagg ctagcctcac accactttta    360

ctatccataa cgaaaagaag tgagcaaatt gtggaatttt tgctgataaa aaatgcaaat    420

gcgaatgcag ttaataagta taaatgcaca gccctcatgc ttgctgtatg tcatggatca    480

tcagagatag ttggcatgct tcttcagcaa aatgttgacg tctttgctgc agatatatgt    540

ggagtaactg cagaacatta tgctgttact tgtggatttc atcacattca tgaacaaatt    600

atggaatata tacgaaaatt atctaaaaat catcaaaata ccaatccaga aggaacatct    660

gcaggaacac ctgatgaggc tgcacccttg gcggaaagaa cacctgacac agctgaaagc    720

ttggtggaaa aaacacctga tgaggctgca cccttggtgg aaagaacacc tgacacggct    780

gaaagcttgg tggaaaaaac acctgatgag gctgcatcct tggtggaggg aacatctgac    840

aaaattcaat gtttggagaa agcgacatct ggaaagttcg aacagtcagc agaagaaaca    900

cctagggaaa ttacgagtcc tgcaaaagaa acatctgaga aatttacgtg gccagcaaaa    960

ggaagaccta ggaagatcgc atgggagaaa aaagaagaca cacctaggga aattatgagt   1020

cccgcaaaag aaacatctga gaaatttacg tgggcagcaa aaggaagacc taggaagatc   1080

gcatgggaga aaaaagaaac acctgtaaag actggatgcg tggcaagagt aacatctaat   1140

aaaactaaag ttttggaaaa aggaagatct aagatgattg catgtcctac aaaagaatc    1199
```

<210> SEQ ID NO 570
<211> LENGTH: 399
<212> TYPE: PRT
<213> ORGANISM: Homo sapiens

<400> SEQUENCE: 570

```
Thr Lys Arg Lys Lys Thr Ile Asn Leu Asn Ile Gln Asp Ala Gln Lys
                5                   10                  15

Arg Thr Ala Leu His Trp Ala Cys Val Asn Gly His Glu Glu Val Val
            20                  25                  30

Thr Phe Leu Val Asp Arg Lys Cys Gln Leu Asp Val Leu Asp Gly Glu
        35                  40                  45

His Arg Thr Pro Leu Met Lys Ala Leu Gln Cys His Gln Glu Ala Cys
    50                  55                  60

Ala Asn Ile Leu Ile Asp Ser Gly Ala Asp Ile Asn Leu Val Asp Val
65                  70                  75                  80

Tyr Gly Asn Met Ala Leu His Tyr Ala Val Tyr Ser Glu Ile Leu Ser
                85                  90                  95

Val Val Ala Lys Leu Leu Ser His Gly Ala Val Ile Glu Val His Asn
            100                 105                 110

Lys Ala Ser Leu Thr Pro Leu Leu Leu Ser Ile Thr Lys Arg Ser Glu
        115                 120                 125

Gln Ile Val Glu Phe Leu Leu Ile Lys Asn Ala Asn Ala Asn Ala Val
    130                 135                 140

Asn Lys Tyr Lys Cys Thr Ala Leu Met Leu Ala Val Cys His Gly Ser
145                 150                 155                 160

Ser Glu Ile Val Gly Met Leu Leu Gln Gln Asn Val Asp Val Phe Ala
                165                 170                 175

Ala Asp Ile Cys Gly Val Thr Ala Glu His Tyr Ala Val Thr Cys Gly
```

-continued

```
            180                 185                 190

Phe His His Ile His Glu Gln Ile Met Glu Tyr Ile Arg Lys Leu Ser
        195                 200                 205

Lys Asn His Gln Asn Thr Asn Pro Glu Gly Thr Ser Ala Gly Thr Pro
    210                 215                 220

Asp Glu Ala Ala Pro Leu Ala Glu Arg Thr Pro Asp Thr Ala Glu Ser
225                 230                 235                 240

Leu Val Glu Lys Thr Pro Asp Glu Ala Ala Pro Leu Val Glu Arg Thr
                245                 250                 255

Pro Asp Thr Ala Glu Ser Leu Val Glu Lys Thr Pro Asp Glu Ala Ala
            260                 265                 270

Ser Leu Val Glu Gly Thr Ser Asp Lys Ile Gln Cys Leu Glu Lys Ala
        275                 280                 285

Thr Ser Gly Lys Phe Glu Gln Ser Ala Glu Glu Thr Pro Arg Glu Ile
    290                 295                 300

Thr Ser Pro Ala Lys Glu Thr Ser Glu Lys Phe Thr Trp Pro Ala Lys
305                 310                 315                 320

Gly Arg Pro Arg Lys Ile Ala Trp Glu Lys Lys Glu Asp Thr Pro Arg
                325                 330                 335

Glu Ile Met Ser Pro Ala Lys Glu Thr Ser Glu Lys Phe Thr Trp Ala
            340                 345                 350

Ala Lys Gly Arg Pro Arg Lys Ile Ala Trp Glu Lys Lys Glu Thr Pro
        355                 360                 365

Val Lys Thr Gly Cys Val Ala Arg Val Thr Ser Asn Lys Thr Lys Val
    370                 375                 380

Leu Glu Lys Gly Arg Ser Lys Met Ile Ala Cys Pro Thr Lys Glu
385                 390                 395


<210> SEQ ID NO 571
<211> LENGTH: 247
<212> TYPE: PRT
<213> ORGANISM: Homo sapiens

<400> SEQUENCE: 571

Met Leu Ala Val Cys His Gly Ser Ser Glu Ile Val Gly Met Leu Leu
                5                   10                  15

Gln Gln Asn Val Asp Val Phe Ala Ala Asp Ile Cys Gly Val Thr Ala
            20                  25                  30

Glu His Tyr Ala Val Thr Cys Gly Phe His His Ile His Glu Gln Ile
        35                  40                  45

Met Glu Tyr Ile Arg Lys Leu Ser Lys Asn His Gln Asn Thr Asn Pro
    50                  55                  60

Glu Gly Thr Ser Ala Gly Thr Pro Asp Glu Ala Ala Pro Leu Ala Glu
65                  70                  75                  80

Arg Thr Pro Asp Thr Ala Glu Ser Leu Val Glu Lys Thr Pro Asp Glu
                85                  90                  95

Ala Ala Pro Leu Val Glu Arg Thr Pro Asp Thr Ala Glu Ser Leu Val
            100                 105                 110

Glu Lys Thr Pro Asp Glu Ala Ala Ser Leu Val Glu Gly Thr Ser Asp
        115                 120                 125

Lys Ile Gln Cys Leu Glu Lys Ala Thr Ser Gly Lys Phe Glu Gln Ser
    130                 135                 140

Ala Glu Glu Thr Pro Arg Glu Ile Thr Ser Pro Ala Lys Glu Thr Ser
145                 150                 155                 160
```

-continued

```
Glu Lys Phe Thr Trp Pro Ala Lys Gly Arg Pro Arg Lys Ile Ala Trp
                165                 170                 175

Glu Lys Lys Glu Asp Thr Pro Arg Glu Ile Met Ser Pro Ala Lys Glu
            180                 185                 190

Thr Ser Glu Lys Phe Thr Trp Ala Ala Lys Gly Arg Pro Arg Lys Ile
        195                 200                 205

Ala Trp Glu Lys Lys Glu Thr Pro Val Lys Thr Gly Cys Val Ala Arg
    210                 215                 220

Val Thr Ser Asn Lys Thr Lys Val Leu Glu Lys Gly Arg Ser Lys Met
225                 230                 235                 240

Ile Ala Cys Pro Thr Lys Glu
                245


<210> SEQ ID NO 572
<211> LENGTH: 399
<212> TYPE: PRT
<213> ORGANISM: Homo sapiens

<400> SEQUENCE: 572

Thr Lys Arg Lys Lys Thr Ile Asn Leu Asn Ile Gln Asp Ala Gln Lys
                5                   10                  15

Arg Thr Ala Leu His Trp Ala Cys Val Asn Gly His Glu Glu Val Val
            20                  25                  30

Thr Phe Leu Val Asp Arg Lys Cys Gln Pro Asp Val Leu Asp Gly Glu
        35                  40                  45

His Arg Thr Pro Leu Met Lys Ala Leu Gln Cys His Gln Glu Ala Cys
    50                  55                  60

Ala Asn Ile Leu Ile Asp Ser Gly Ala Asp Ile Asn Leu Val Asp Val
65                  70                  75                  80

Tyr Gly Asn Met Ala Leu His Tyr Ala Val Tyr Ser Glu Ile Leu Ser
                85                  90                  95

Val Val Ala Lys Leu Leu Ser His Gly Ala Val Ile Glu Val His Asn
            100                 105                 110

Lys Ala Ser Leu Thr Pro Leu Leu Leu Ser Ile Thr Lys Arg Ser Glu
        115                 120                 125

Gln Ile Val Glu Phe Leu Leu Ile Lys Asn Ala Asn Ala Asn Ala Val
    130                 135                 140

Asn Lys Tyr Lys Cys Thr Ala Leu Met Leu Ala Val Cys His Gly Leu
145                 150                 155                 160

Ser Glu Ile Val Gly Met Leu Leu Gln Gln Asn Val Asp Val Phe Ala
                165                 170                 175

Ala Asp Ile Cys Gly Val Thr Ala Glu His Tyr Ala Val Thr Cys Gly
            180                 185                 190

Phe His His Ile His Glu Gln Ile Met Glu Tyr Ile Arg Lys Leu Ser
        195                 200                 205

Lys Asn His Gln Asn Thr Asn Pro Glu Gly Thr Ser Ala Gly Thr Pro
    210                 215                 220

Asp Glu Ala Ala Pro Leu Ala Glu Arg Thr Pro Asp Thr Ala Glu Ser
225                 230                 235                 240

Leu Val Glu Lys Thr Pro Asp Glu Ala Ala Pro Leu Val Glu Arg Thr
                245                 250                 255

Pro Asp Thr Ala Glu Ser Leu Val Glu Lys Thr Pro Asp Glu Ala Ala
            260                 265                 270

Ser Leu Val Glu Gly Thr Ser Asp Lys Ile Gln Cys Leu Glu Lys Ala
        275                 280                 285
```

-continued

```
Thr Ser Gly Lys Phe Glu Gln Ser Ala Glu Glu Thr Pro Arg Glu Ile
    290                 295                 300

Thr Ser Pro Ala Lys Glu Thr Ser Glu Lys Phe Thr Trp Pro Ala Lys
305                 310                 315                 320

Gly Arg Pro Arg Lys Ile Ala Trp Glu Lys Lys Glu Asp Thr Pro Arg
                325                 330                 335

Glu Ile Met Ser Pro Ala Lys Glu Thr Ser Glu Lys Phe Thr Trp Ala
            340                 345                 350

Ala Lys Gly Arg Pro Arg Lys Ile Ala Trp Glu Lys Lys Glu Thr Pro
        355                 360                 365

Val Lys Thr Gly Cys Val Ala Arg Val Thr Ser Asn Lys Thr Lys Val
    370                 375                 380

Leu Glu Lys Gly Arg Ser Lys Met Ile Ala Cys Pro Thr Lys Glu
385                 390                 395


<210> SEQ ID NO 573
<211> LENGTH: 1349
<212> TYPE: PRT
<213> ORGANISM: Homo sapiens

<400> SEQUENCE: 573

Met Gln His His His His His His His Thr Lys Arg Lys Lys Thr Ile
                5                   10                  15

Asn Leu Asn Ile Gln Asp Ala Gln Lys Arg Thr Ala Leu His Trp Ala
            20                  25                  30

Cys Val Asn Gly His Glu Glu Val Val Thr Phe Leu Val Asp Arg Lys
        35                  40                  45

Cys Gln Pro Asp Val Leu Asp Gly Glu His Arg Thr Pro Leu Met Lys
    50                  55                  60

Ala Leu Gln Cys His Gln Glu Ala Cys Ala Asn Ile Leu Ile Asp Ser
65                  70                  75                  80

Gly Ala Asp Ile Asn Leu Val Asp Val Tyr Gly Asn Met Ala Leu His
                85                  90                  95

Tyr Ala Val Tyr Ser Glu Ile Leu Ser Val Val Ala Lys Leu Leu Ser
            100                 105                 110

His Gly Ala Val Ile Glu Val His Asn Lys Ala Ser Leu Thr Pro Leu
        115                 120                 125

Leu Leu Ser Ile Thr Lys Arg Ser Glu Gln Ile Val Glu Phe Leu Leu
    130                 135                 140

Ile Lys Asn Ala Asn Ala Asn Ala Val Asn Lys Tyr Lys Cys Thr Ala
145                 150                 155                 160

Leu Met Leu Ala Val Cys His Gly Leu Ser Glu Ile Val Gly Met Leu
                165                 170                 175

Leu Gln Gln Asn Val Asp Val Phe Ala Ala Asp Ile Cys Gly Val Thr
            180                 185                 190

Ala Glu His Tyr Ala Val Thr Cys Gly Phe His His Ile His Glu Gln
        195                 200                 205

Ile Met Glu Tyr Ile Arg Lys Leu Ser Lys Asn His Gln Asn Thr Asn
    210                 215                 220

Pro Glu Gly Thr Ser Ala Gly Thr Pro Asp Glu Ala Ala Pro Leu Ala
225                 230                 235                 240

Glu Arg Thr Pro Asp Thr Ala Glu Ser Leu Val Glu Lys Thr Pro Asp
                245                 250                 255

Glu Ala Ala Pro Leu Val Glu Arg Thr Pro Asp Thr Ala Glu Ser Leu
```

-continued

```
            260                 265                 270

Val Glu Lys Thr Pro Asp Glu Ala Ala Ser Leu Val Glu Gly Thr Ser
        275                 280                 285

Asp Lys Ile Gln Cys Leu Glu Lys Ala Thr Ser Gly Lys Phe Glu Gln
    290                 295                 300

Ser Ala Glu Glu Thr Pro Arg Glu Ile Thr Ser Pro Ala Lys Glu Thr
305                 310                 315                 320

Ser Glu Lys Phe Thr Trp Pro Ala Lys Gly Arg Pro Arg Lys Ile Ala
                325                 330                 335

Trp Glu Lys Lys Glu Asp Thr Pro Arg Glu Ile Met Ser Pro Ala Lys
            340                 345                 350

Glu Thr Ser Glu Lys Phe Thr Trp Ala Ala Lys Gly Arg Pro Arg Lys
        355                 360                 365

Ile Ala Trp Glu Lys Lys Glu Thr Pro Val Lys Thr Gly Cys Val Ala
    370                 375                 380

Arg Val Thr Ser Asn Lys Thr Lys Val Leu Glu Lys Gly Arg Ser Lys
385                 390                 395                 400

Met Ile Ala Cys Pro Thr Lys Glu Ser Ser Thr Lys Ala Ser Ala Asn
                405                 410                 415

Asp Gln Arg Phe Pro Ser Glu Ser Lys Gln Glu Glu Asp Glu Glu Tyr
            420                 425                 430

Ser Cys Asp Ser Arg Ser Leu Phe Glu Ser Ser Ala Lys Ile Gln Val
        435                 440                 445

Cys Ile Pro Glu Ser Ile Tyr Gln Lys Val Met Glu Ile Asn Arg Glu
    450                 455                 460

Val Glu Glu Pro Pro Lys Lys Pro Ser Ala Phe Lys Pro Ala Ile Glu
465                 470                 475                 480

Met Gln Asn Ser Val Pro Asn Lys Ala Phe Glu Leu Lys Asn Glu Gln
                485                 490                 495

Thr Leu Arg Ala Asp Pro Met Phe Pro Pro Glu Ser Lys Gln Lys Asp
            500                 505                 510

Tyr Glu Glu Asn Ser Trp Asp Ser Glu Ser Leu Cys Glu Thr Val Ser
        515                 520                 525

Gln Lys Asp Val Cys Leu Pro Lys Ala Thr His Gln Lys Glu Ile Asp
    530                 535                 540

Lys Ile Asn Gly Lys Leu Glu Glu Ser Pro Asn Lys Asp Gly Leu Leu
545                 550                 555                 560

Lys Ala Thr Cys Gly Met Lys Val Ser Ile Pro Thr Lys Ala Leu Glu
                565                 570                 575

Leu Lys Asp Met Gln Thr Phe Lys Ala Glu Pro Pro Gly Lys Pro Ser
            580                 585                 590

Ala Phe Glu Pro Ala Thr Glu Met Gln Lys Ser Val Pro Asn Lys Ala
        595                 600                 605

Leu Glu Leu Lys Asn Glu Gln Thr Trp Arg Ala Asp Glu Ile Leu Pro
    610                 615                 620

Ser Glu Ser Lys Gln Lys Asp Tyr Glu Glu Asn Ser Trp Asp Thr Glu
625                 630                 635                 640

Ser Leu Cys Glu Thr Val Ser Gln Lys Asp Val Cys Leu Pro Lys Ala
                645                 650                 655

Ala His Gln Lys Glu Ile Asp Lys Ile Asn Gly Lys Leu Glu Gly Ser
            660                 665                 670

Pro Val Lys Asp Gly Leu Leu Lys Ala Asn Cys Gly Met Lys Val Ser
        675                 680                 685
```

-continued

```
Ile Pro Thr Lys Ala Leu Glu Leu Met Asp Met Gln Thr Phe Lys Ala
    690                 695                 700

Glu Pro Pro Glu Lys Pro Ser Ala Phe Glu Pro Ala Ile Glu Met Gln
705                 710                 715                 720

Lys Ser Val Pro Asn Lys Ala Leu Glu Leu Lys Asn Glu Gln Thr Leu
                725                 730                 735

Arg Ala Asp Glu Ile Leu Pro Ser Glu Ser Lys Gln Lys Asp Tyr Glu
            740                 745                 750

Glu Ser Ser Trp Asp Ser Glu Ser Leu Cys Glu Thr Val Ser Gln Lys
        755                 760                 765

Asp Val Cys Leu Pro Lys Ala Thr His Gln Lys Glu Ile Asp Lys Ile
    770                 775                 780

Asn Gly Lys Leu Glu Glu Ser Pro Asp Asn Asp Gly Phe Leu Lys Ala
785                 790                 795                 800

Pro Cys Arg Met Lys Val Ser Ile Pro Thr Lys Ala Leu Glu Leu Met
                805                 810                 815

Asp Met Gln Thr Phe Lys Ala Glu Pro Pro Glu Lys Pro Ser Ala Phe
            820                 825                 830

Glu Pro Ala Ile Glu Met Gln Lys Ser Val Pro Asn Lys Ala Leu Glu
        835                 840                 845

Leu Lys Asn Glu Gln Thr Leu Arg Ala Asp Gln Met Phe Pro Ser Glu
    850                 855                 860

Ser Lys Gln Lys Lys Val Glu Glu Asn Ser Trp Asp Ser Glu Ser Leu
865                 870                 875                 880

Arg Glu Thr Val Ser Gln Lys Asp Val Cys Val Pro Lys Ala Thr His
                885                 890                 895

Gln Lys Glu Met Asp Lys Ile Ser Gly Lys Leu Glu Asp Ser Thr Ser
            900                 905                 910

Leu Ser Lys Ile Leu Asp Thr Val His Ser Cys Glu Arg Ala Arg Glu
        915                 920                 925

Leu Gln Lys Asp His Cys Glu Gln Arg Thr Gly Lys Met Glu Gln Met
    930                 935                 940

Lys Lys Lys Phe Cys Val Leu Lys Lys Lys Leu Ser Glu Ala Lys Glu
945                 950                 955                 960

Ile Lys Ser Gln Leu Glu Asn Gln Lys Val Lys Trp Glu Gln Glu Leu
                965                 970                 975

Cys Ser Val Arg Leu Thr Leu Asn Gln Glu Glu Glu Lys Arg Arg Asn
            980                 985                 990

Ala Asp Ile Leu Asn Glu Lys Ile Arg Glu Glu Leu Gly Arg Ile Glu
        995                 1000                1005

Glu Gln His Arg Lys Glu Leu Glu Val Lys Gln Gln Leu Glu Gln Ala
    1010                1015                1020

Leu Arg Ile Gln Asp Ile Glu Leu Lys Ser Val Glu Ser Asn Leu Asn
1025                1030                1035                1040

Gln Val Ser His Thr His Glu Asn Glu Asn Tyr Leu Leu His Glu Asn
                1045                1050                1055

Cys Met Leu Lys Lys Glu Ile Ala Met Leu Lys Leu Glu Ile Ala Thr
            1060                1065                1070

Leu Lys His Gln Tyr Gln Glu Lys Glu Asn Lys Tyr Phe Glu Asp Ile
        1075                1080                1085

Lys Ile Leu Lys Glu Lys Asn Ala Glu Leu Gln Met Thr Leu Lys Leu
    1090                1095                1100
```

-continued

```
Lys Glu Glu Ser Leu Thr Lys Arg Ala Ser Gln Tyr Ser Gly Gln Leu
1105                1110                1115                1120

Lys Val Leu Ile Ala Glu Asn Thr Met Leu Thr Ser Lys Leu Lys Glu
                1125                1130                1135

Lys Gln Asp Lys Glu Ile Leu Glu Ala Glu Ile Glu Ser His His Pro
            1140                1145                1150

Arg Leu Ala Ser Ala Val Gln Asp His Asp Gln Ile Val Thr Ser Arg
        1155                1160                1165

Lys Ser Gln Glu Pro Ala Phe His Ile Ala Gly Asp Ala Cys Leu Gln
    1170                1175                1180

Arg Lys Met Asn Val Asp Val Ser Ser Thr Ile Tyr Asn Asn Glu Val
1185                1190                1195                1200

Leu His Gln Pro Leu Ser Glu Ala Gln Arg Lys Ser Lys Ser Leu Lys
                1205                1210                1215

Ile Asn Leu Asn Tyr Ala Gly Asp Ala Leu Arg Glu Asn Thr Leu Val
            1220                1225                1230

Ser Glu His Ala Gln Arg Asp Gln Arg Glu Thr Gln Cys Gln Met Lys
        1235                1240                1245

Glu Ala Glu His Met Tyr Gln Asn Glu Gln Asp Asn Val Asn Lys His
    1250                1255                1260

Thr Glu Gln Gln Glu Ser Leu Asp Gln Lys Leu Phe Gln Leu Gln Ser
1265                1270                1275                1280

Lys Asn Met Trp Leu Gln Gln Gln Leu Val His Ala His Lys Lys Ala
                1285                1290                1295

Asp Asn Lys Ser Lys Ile Thr Ile Asp Ile His Phe Leu Glu Arg Lys
            1300                1305                1310

Met Gln His His Leu Leu Lys Glu Lys Asn Glu Glu Ile Phe Asn Tyr
        1315                1320                1325

Asn Asn His Leu Lys Asn Arg Ile Tyr Gln Tyr Glu Lys Glu Lys Ala
    1330                1335                1340

Glu Thr Glu Val Ile
1345


<210> SEQ ID NO 574
<211> LENGTH: 24
<212> TYPE: DNA
<213> ORGANISM: Artificial Sequence
<220> FEATURE:
<223> OTHER INFORMATION: PCR primer

<400> SEQUENCE: 574

cacacaaaga ggaagaagac catc                                            24


<210> SEQ ID NO 575
<211> LENGTH: 27
<212> TYPE: DNA
<213> ORGANISM: Artificial Sequence
<220> FEATURE:
<223> OTHER INFORMATION: PCR primer

<400> SEQUENCE: 575

gattcttttg taggacatgc aatcatc                                         27


<210> SEQ ID NO 576
<211> LENGTH: 3720
<212> TYPE: DNA
<213> ORGANISM: Homo sapiens
<220> FEATURE:
<221> NAME/KEY: misc_feature
```

-continued

<222> LOCATION: 1149
<223> OTHER INFORMATION: n = A,T,C or G

<400> SEQUENCE: 576

```
atggtggcaa cactgctgtc ctatggtgca gtcatcgagg tgcaaaacaa ggctagcctc     60
acaccccttt tactggccat acagaaaaga agcaagcaaa ctgtggaatt tttactaaca    120
aaaaatgcaa atgcaaacgc atttaatgag tctaaatgca cagccctcat gcttgccata    180
tgtgaaggct catcagagat agtcggcatg cttcttcagc aaaatgttga cgtctttgct    240
gaagacatac atggaataac tgcagaacgt tatgctgctg ctcgtggagt taattacatt    300
catcaacaac ttttggaaca tatacgaaaa ttacctaaaa atcctcaaaa taccaatcca    360
gaaggaacat ctacaggaac acctgatgag gctgcaccct tggcggaaag aacacctgac    420
acggctgaaa gcttgctgga aaaaacacct gacgaggctg cacgcttggt ggagggaacg    480
tctgccaaaa ttcaatgtct ggggaaagca acatctggaa agtttgaaca gtcaacagaa    540
gaaacaccta ggaaaatttt gaggcctaca aaagaaacat ctgagaaatt ttcatggcca    600
gcaaaagaaa gatctaggaa gatcacatgg gaggaaaaag aaacatctgt aaagactgaa    660
tgcgtggcag gagtaacacc taataaaact gaagttttgg aaaaaggaac atctaatatg    720
attgcatgtc ctacaaaaga aacatctaca aaagcaagta caaatgtgga tgtgagttct    780
gtagagccta tattcagtct tttggcaca cggactattg aaaattcaca gtgtacaaaa     840
gttgaggaag actttaatct tgctaccaag attatctcta agagtgctgc acagaattat    900
acgtgtttac ctgatgctac atatcaaaaa gatatcaaaa caataaatca caaaatagaa    960
gatcagatgt tcccatcaga atccaaacga gaggaagatg aagaatattc ttgggattct   1020
gggagtctct ttgagagttc tgcaaagact caagtgtgta tacctgagtc tatgtatcag   1080
aaagtaatgg agataaatag agaagtagaa gagcttcctg agaagccatc tgccttcaag   1140
cctgccgtng aaatgcaaaa gactgttcca aataaagcct ttgaattgaa gaatgaacaa   1200
acattgagag cagctcagat gttcccatca gaatccaaac aaaaggacga tgaagaaaat   1260
tcttgggatt ctgagagtcc ctgtgagacg gtttcacaga aggatgtgta tttacccaaa   1320
gctacacatc aaaaagaatt cgatacctta agtggaaaat tagaagagtc tcctgttaaa   1380
gatggtcttc tgaagcctac ctgtggaagg aaagtttctc ttccaaataa agccttagaa   1440
ttaaaggaca gagaaacatt caaagcagag tctcctgata aagatggtct tctgaagcct   1500
acctgtggaa ggaaagtttc tcttccaaat aaagccttag aattaaagga cagagaaaca   1560
ctcaaagcag agtctcctga taatgatggt cttctgaagc ctacctgtgg aaggaaagtt   1620
tctcttccaa ataaagcttt agaattgaag gacagagaaa cattcaaagc agctcagatg   1680
ttcccatcag aatccaaaca aaaggatgat gaagaaaatt cttgggattt tgagagtttc   1740
cttgagactc tcttacagaa tgatgtgtgt ttacccaagg ctacacatca aaaagaattc   1800
gataccttaa gtggaaaatt agaagagtct cctgataaag atggtcttct gaagcctacc   1860
tgtggaatga aaatttctct tccaaataaa gccttagaat tgaaggacag agaaacattc   1920
aaagcagagg atgtgagttc tgtagagtcc acattcagtc tttttggcaa accgactact   1980
gaaaattcac agtctacaaa agttgaggaa gactttaatc ttactaccaa ggagggagca   2040
acaaagacag taactggaca acaggaacgt gatattggca ttattgaacg agctccacaa   2100
gatcaaacaa ataagatgcc cacatcagaa ttaggaagaa aagaagatac aaaatcaact   2160
tcagattctg agattatctc tgtgagtgat acacagaatt atgagtgttt acctgaggct   2220
```

-continued

```
acatatcaaa aagaaataaa gacaacaaat ggcaaaatag aagagtctcc tgaaaagcct   2280

tctcactttg agcctgccac tgaaatgcaa aactctgttc caaataaagg cttagaatgg   2340

aagaataaac aaacattgag agcagattca actaccctat caaaaatctt ggatgcactt   2400

ccttcttgtg aaagaggaag ggaacttaaa aaagataact gtgaacaaat tacagcaaaa   2460

atggaacaaa tgaaaaataa gttttgtgta ctacaaaagg aactgtcaga agcgaaagaa   2520

ataaaatcac agttagagaa ccaaaaagct aaatgggaac aagagctctg cagtgtgaga   2580

ttgcctttaa atcaagaaga agagaagaga agaaatgtcg atatattaaa agaaaaaatt   2640

agacccgaag agcaacttag gaaaaagtta gaagtgaaac accaacttga acagactctc   2700

agaatacaag atatagaatt gaaaagtgta acaagtaatt tgaatcaggt ttctcacact   2760

catgaaagtg aaaatgatct ctttcatgaa aattgcatgt tgaaaaagga aattgccatg   2820

ctaaaactgg aagtagccac actgaaacat caacaccagg tgaaggaaaa taaatacttt   2880

gaggacatta agattttaca agaaaagaat gctgaacttc aaatgaccct aaaactgaaa   2940

cagaaaacag taacaaaaag ggcatctcag tatagagagc agcttaaagt tctgacggca   3000

gagaacacga tgctgacttc taaattgaag gaaaaacaag acaaagaaat actggagaca   3060

gaaattgaat cacaccatcc tagactggct tctgctttac aagaccatga tcaaagtgtc   3120

acatcaagaa aaaaccaaga acttgctttc cacagtgcag gagatgctcc tttgcaagga   3180

ataatgaatg ttgatgtgag taatacaata tataacaatg aggtgctcca tcaaccactt   3240

tatgaagctc aaaggaaatc caaaagccca aaaattaatc tcaattatgc aggagatgat   3300

ctaagagaaa atgcattggt ttcagaacat gcacaaagag accgatgtga aacacagtgt   3360

caaatgaaga aagctgaaca catgtatcaa aatgaacaag ataatgtgga caaacacact   3420

gaacagcagg agtctctgga gcagaaatta tttcaactag aaagcaaaaa taggtggctt   3480

cgacagcaat tagtttatgc acataagaaa gttaacaaaa gcaaggtaac aattaatatt   3540

cagtttcctg agatgaaaat gcaacgtcat ctaaaagaga aaaatgagga ggtattcaat   3600

tatggtaacc atttaaaaga acgtatagat caatatgaaa aagagaaagc agaaagagaa   3660

gtaagtatca aaaaatataa atacttttca aacttcctga aagaaagtgg ccttggctaa   3720
```

<210> SEQ ID NO 577
<211> LENGTH: 1239
<212> TYPE: PRT
<213> ORGANISM: Homo sapiens

<400> SEQUENCE: 577

```
Met Val Ala Thr Leu Leu Ser Tyr Gly Ala Val Ile Glu Val Gln Asn
                5                   10                  15

Lys Ala Ser Leu Thr Pro Leu Leu Leu Ala Ile Gln Lys Arg Ser Lys
            20                  25                  30

Gln Thr Val Glu Phe Leu Leu Thr Lys Asn Ala Asn Ala Asn Ala Phe
        35                  40                  45

Asn Glu Ser Lys Cys Thr Ala Leu Met Leu Ala Ile Cys Glu Gly Ser
    50                  55                  60

Ser Glu Ile Val Gly Met Leu Leu Gln Gln Asn Val Asp Val Phe Ala
65                  70                  75                  80

Glu Asp Ile His Gly Ile Thr Ala Glu Arg Tyr Ala Ala Ala Arg Gly
                85                  90                  95

Val Asn Tyr Ile His Gln Gln Leu Leu Glu His Ile Arg Lys Leu Pro
            100                 105                 110
```

-continued

```
Lys Asn Pro Gln Asn Thr Asn Pro Glu Gly Thr Ser Thr Gly Thr Pro
        115                 120                 125

Asp Glu Ala Ala Pro Leu Ala Glu Arg Thr Pro Asp Thr Ala Glu Ser
    130                 135                 140

Leu Leu Glu Lys Thr Pro Asp Glu Ala Ala Arg Leu Val Glu Gly Thr
145                 150                 155                 160

Ser Ala Lys Ile Gln Cys Leu Gly Lys Ala Thr Ser Gly Lys Phe Glu
                165                 170                 175

Gln Ser Thr Glu Glu Thr Pro Arg Lys Ile Leu Arg Pro Thr Lys Glu
            180                 185                 190

Thr Ser Glu Lys Phe Ser Trp Pro Ala Lys Glu Arg Ser Arg Lys Ile
        195                 200                 205

Thr Trp Glu Glu Lys Glu Thr Ser Val Lys Thr Glu Cys Val Ala Gly
    210                 215                 220

Val Thr Pro Asn Lys Thr Glu Val Leu Glu Lys Gly Thr Ser Asn Met
225                 230                 235                 240

Ile Ala Cys Pro Thr Lys Glu Thr Ser Thr Lys Ala Ser Thr Asn Val
                245                 250                 255

Asp Val Ser Ser Val Glu Pro Ile Phe Ser Leu Phe Gly Thr Arg Thr
            260                 265                 270

Ile Glu Asn Ser Gln Cys Thr Lys Val Glu Glu Asp Phe Asn Leu Ala
        275                 280                 285

Thr Lys Ile Ile Ser Lys Ser Ala Ala Gln Asn Tyr Thr Cys Leu Pro
    290                 295                 300

Asp Ala Thr Tyr Gln Lys Asp Ile Lys Thr Ile Asn His Lys Ile Glu
305                 310                 315                 320

Asp Gln Met Phe Pro Ser Glu Ser Lys Arg Glu Glu Asp Glu Glu Tyr
                325                 330                 335

Ser Trp Asp Ser Gly Ser Leu Phe Glu Ser Ser Ala Lys Thr Gln Val
            340                 345                 350

Cys Ile Pro Glu Ser Met Tyr Gln Lys Val Met Glu Ile Asn Arg Glu
        355                 360                 365

Val Glu Glu Leu Pro Glu Lys Pro Ser Ala Phe Lys Pro Ala Val Glu
    370                 375                 380

Met Gln Lys Thr Val Pro Asn Lys Ala Phe Glu Leu Lys Asn Glu Gln
385                 390                 395                 400

Thr Leu Arg Ala Ala Gln Met Phe Pro Ser Glu Ser Lys Gln Lys Asp
                405                 410                 415

Asp Glu Glu Asn Ser Trp Asp Ser Glu Ser Pro Cys Glu Thr Val Ser
            420                 425                 430

Gln Lys Asp Val Tyr Leu Pro Lys Ala Thr His Gln Lys Glu Phe Asp
        435                 440                 445

Thr Leu Ser Gly Lys Leu Glu Glu Ser Pro Val Lys Asp Gly Leu Leu
    450                 455                 460

Lys Pro Thr Cys Gly Arg Lys Val Ser Leu Pro Asn Lys Ala Leu Glu
465                 470                 475                 480

Leu Lys Asp Arg Glu Thr Phe Lys Ala Glu Ser Pro Asp Lys Asp Gly
                485                 490                 495

Leu Leu Lys Pro Thr Cys Gly Arg Lys Val Ser Leu Pro Asn Lys Ala
            500                 505                 510

Leu Glu Leu Lys Asp Arg Glu Thr Leu Lys Ala Glu Ser Pro Asp Asn
        515                 520                 525

Asp Gly Leu Leu Lys Pro Thr Cys Gly Arg Lys Val Ser Leu Pro Asn
```

-continued

```
    530                 535                 540

Lys Ala Leu Glu Leu Lys Asp Arg Glu Thr Phe Lys Ala Ala Gln Met
545                 550                 555                 560

Phe Pro Ser Glu Ser Lys Gln Lys Asp Asp Glu Glu Asn Ser Trp Asp
                565                 570                 575

Phe Glu Ser Phe Leu Glu Thr Leu Leu Gln Asn Asp Val Cys Leu Pro
            580                 585                 590

Lys Ala Thr His Gln Lys Glu Phe Asp Thr Leu Ser Gly Lys Leu Glu
        595                 600                 605

Glu Ser Pro Asp Lys Asp Gly Leu Leu Lys Pro Thr Cys Gly Met Lys
    610                 615                 620

Ile Ser Leu Pro Asn Lys Ala Leu Glu Leu Lys Asp Arg Glu Thr Phe
625                 630                 635                 640

Lys Ala Glu Asp Val Ser Ser Val Glu Ser Thr Phe Ser Leu Phe Gly
                645                 650                 655

Lys Pro Thr Thr Glu Asn Ser Gln Ser Thr Lys Val Glu Glu Asp Phe
            660                 665                 670

Asn Leu Thr Thr Lys Glu Gly Ala Thr Lys Thr Val Thr Gly Gln Gln
        675                 680                 685

Glu Arg Asp Ile Gly Ile Ile Glu Arg Ala Pro Gln Asp Gln Thr Asn
    690                 695                 700

Lys Met Pro Thr Ser Glu Leu Gly Arg Lys Glu Asp Thr Lys Ser Thr
705                 710                 715                 720

Ser Asp Ser Glu Ile Ile Ser Val Ser Asp Thr Gln Asn Tyr Glu Cys
                725                 730                 735

Leu Pro Glu Ala Thr Tyr Gln Lys Glu Ile Lys Thr Thr Asn Gly Lys
            740                 745                 750

Ile Glu Glu Ser Pro Glu Lys Pro Ser His Phe Glu Pro Ala Thr Glu
        755                 760                 765

Met Gln Asn Ser Val Pro Asn Lys Gly Leu Glu Trp Lys Asn Lys Gln
    770                 775                 780

Thr Leu Arg Ala Asp Ser Thr Thr Leu Ser Lys Ile Leu Asp Ala Leu
785                 790                 795                 800

Pro Ser Cys Glu Arg Gly Arg Glu Leu Lys Lys Asp Asn Cys Glu Gln
                805                 810                 815

Ile Thr Ala Lys Met Glu Gln Met Lys Asn Lys Phe Cys Val Leu Gln
            820                 825                 830

Lys Glu Leu Ser Glu Ala Lys Glu Ile Lys Ser Gln Leu Glu Asn Gln
        835                 840                 845

Lys Ala Lys Trp Glu Gln Glu Leu Cys Ser Val Arg Leu Pro Leu Asn
    850                 855                 860

Gln Glu Glu Glu Lys Arg Arg Asn Val Asp Ile Leu Lys Glu Lys Ile
865                 870                 875                 880

Arg Pro Glu Glu Gln Leu Arg Lys Lys Leu Glu Val Lys His Gln Leu
                885                 890                 895

Glu Gln Thr Leu Arg Ile Gln Asp Ile Glu Leu Lys Ser Val Thr Ser
            900                 905                 910

Asn Leu Asn Gln Val Ser His Thr His Glu Ser Glu Asn Asp Leu Phe
        915                 920                 925

His Glu Asn Cys Met Leu Lys Lys Glu Ile Ala Met Leu Lys Leu Glu
    930                 935                 940

Val Ala Thr Leu Lys His Gln His Gln Val Lys Glu Asn Lys Tyr Phe
945                 950                 955                 960
```

-continued

```
Glu Asp Ile Lys Ile Leu Gln Glu Lys Asn Ala Glu Leu Gln Met Thr
                965                 970                 975

Leu Lys Leu Lys Gln Lys Thr Val Thr Lys Arg Ala Ser Gln Tyr Arg
            980                 985                 990

Glu Gln Leu Lys Val Leu Thr Ala Glu Asn Thr Met Leu Thr Ser Lys
        995                 1000                1005

Leu Lys Glu Lys Gln Asp Lys Glu Ile Leu Glu Thr Glu Ile Glu Ser
    1010                1015                1020

His His Pro Arg Leu Ala Ser Ala Leu Gln Asp His Asp Gln Ser Val
1025                1030                1035                1040

Thr Ser Arg Lys Asn Gln Glu Leu Ala Phe His Ser Ala Gly Asp Ala
                1045                1050                1055

Pro Leu Gln Gly Ile Met Asn Val Asp Val Ser Asn Thr Ile Tyr Asn
            1060                1065                1070

Asn Glu Val Leu His Gln Pro Leu Tyr Glu Ala Gln Arg Lys Ser Lys
        1075                1080                1085

Ser Pro Lys Ile Asn Leu Asn Tyr Ala Gly Asp Asp Leu Arg Glu Asn
    1090                1095                1100

Ala Leu Val Ser Glu His Ala Gln Arg Asp Arg Cys Glu Thr Gln Cys
1105                1110                1115                1120

Gln Met Lys Lys Ala Glu His Met Tyr Gln Asn Glu Gln Asp Asn Val
                1125                1130                1135

Asp Lys His Thr Glu Gln Gln Glu Ser Leu Glu Gln Lys Leu Phe Gln
            1140                1145                1150

Leu Glu Ser Lys Asn Arg Trp Leu Arg Gln Gln Leu Val Tyr Ala His
        1155                1160                1165

Lys Lys Val Asn Lys Ser Lys Val Thr Ile Asn Ile Gln Phe Pro Glu
    1170                1175                1180

Met Lys Met Gln Arg His Leu Lys Glu Lys Asn Glu Glu Val Phe Asn
1185                1190                1195                1200

Tyr Gly Asn His Leu Lys Glu Arg Ile Asp Gln Tyr Glu Lys Glu Lys
                1205                1210                1215

Ala Glu Arg Glu Val Ser Ile Lys Lys Tyr Lys Tyr Phe Ser Asn Phe
            1220                1225                1230

Leu Lys Glu Ser Gly Leu Gly
        1235
```

<210> SEQ ID NO 578
<211> LENGTH: 20
<212> TYPE: PRT
<213> ORGANISM: Homo sapiens

<400> SEQUENCE: 578

```
Lys Asn Glu Glu Ile Phe Asn Tyr Asn Asn His Leu Lys Asn Arg Ile
                5                   10                  15

Tyr Gln Tyr Glu
            20
```

<210> SEQ ID NO 579
<211> LENGTH: 20
<212> TYPE: PRT
<213> ORGANISM: Homo sapiens

<400> SEQUENCE: 579

```
Glu Gln Asp Asn Val Asn Lys His Thr Glu Gln Gln Glu Ser Leu Asp
                5                   10                  15
```

-continued

Gln Lys Leu Phe
            20

<210> SEQ ID NO 580
<211> LENGTH: 20
<212> TYPE: PRT
<213> ORGANISM: Homo sapiens

<400> SEQUENCE: 580

Thr Glu Gln Gln Glu Ser Leu Asp Gln Lys Leu Phe Gln Leu Gln Ser
1               5                   10                  15

Lys Asn Met Trp
            20

<210> SEQ ID NO 581
<211> LENGTH: 20
<212> TYPE: PRT
<213> ORGANISM: Homo sapiens

<400> SEQUENCE: 581

Lys Glu Glu Ser Leu Thr Lys Arg Ala Ser Gln Tyr Ser Gly Gln Leu
1               5                   10                  15

Lys Val Leu Ile
            20

<210> SEQ ID NO 582
<211> LENGTH: 20
<212> TYPE: PRT
<213> ORGANISM: Homo sapiens

<400> SEQUENCE: 582

Ile Ala Gly Asp Ala Cys Leu Gln Arg Lys Met Asn Val Asp Val Ser
1               5                   10                  15

Ser Thr Ile Tyr
            20

<210> SEQ ID NO 583
<211> LENGTH: 20
<212> TYPE: PRT
<213> ORGANISM: Homo sapiens

<400> SEQUENCE: 583

Arg Lys Met Asn Val Asp Val Ser Ser Thr Ile Tyr Asn Asn Glu Val
1               5                   10                  15

Leu His Gln Pro
            20

<210> SEQ ID NO 584
<211> LENGTH: 20
<212> TYPE: PRT
<213> ORGANISM: Homo sapiens

<400> SEQUENCE: 584

Met Gly Thr Arg Ala Leu Gln Cys Glu Val Ser His Thr His Glu Asn
1               5                   10                  15

Glu Asn Tyr Leu
            20

<210> SEQ ID NO 585
<211> LENGTH: 20
<212> TYPE: PRT
<213> ORGANISM: Homo sapiens

```
<400> SEQUENCE: 585

Glu Val Ser His Thr His Glu Asn Glu Asn Tyr Leu Leu His Glu Asn
                5                   10                  15
Cys Met Leu Lys
        20

<210> SEQ ID NO 586
<211> LENGTH: 20
<212> TYPE: PRT
<213> ORGANISM: Homo sapiens

<400> SEQUENCE: 586

Glu Asn Tyr Leu Leu His Glu Asn Leu Met Leu Lys Lys Glu Ile Ala
                5                   10                  15
Met Leu Lys Leu
        20

<210> SEQ ID NO 587
<211> LENGTH: 21
<212> TYPE: PRT
<213> ORGANISM: Homo sapiens

<400> SEQUENCE: 587

Asn Cys Met Leu Lys Lys Glu Ile Ala Met Leu Lys Leu Glu Ile Ala
                5                   10                  15
Thr Leu Lys His Gln
        20

<210> SEQ ID NO 588
<211> LENGTH: 20
<212> TYPE: PRT
<213> ORGANISM: Homo sapiens

<400> SEQUENCE: 588

Met Leu Thr Ser Lys Leu Lys Glu Lys Gln Asp Lys Glu Ile Leu Glu
                5                   10                  15
Ala Glu Ile Glu
        20

<210> SEQ ID NO 589
<211> LENGTH: 20
<212> TYPE: PRT
<213> ORGANISM: Homo sapiens

<400> SEQUENCE: 589

Lys Gln Asp Lys Glu Ile Leu Glu Ala Glu Ile Glu Ser His His Pro
                5                   10                  15
Arg Leu Ala Ser
        20

<210> SEQ ID NO 590
<211> LENGTH: 20
<212> TYPE: PRT
<213> ORGANISM: Homo sapiens

<400> SEQUENCE: 590

Ala Glu Ile Glu Ser His His Pro Arg Leu Ala Ser Ala Val Gln Asp
                5                   10                  15
His Asp Gln Ile
        20
```

-continued

<210> SEQ ID NO 591
<211> LENGTH: 20
<212> TYPE: PRT
<213> ORGANISM: Homo sapiens

<400> SEQUENCE: 591

Arg Leu Ala Ser Ala Val Gln Asp His Asp Gln Ile Val Thr Ser Arg
5 10 15

Lys Ser Gln Glu
20

<210> SEQ ID NO 592
<211> LENGTH: 20
<212> TYPE: PRT
<213> ORGANISM: Homo sapiens

<400> SEQUENCE: 592

His Asp Gln Ile Val Thr Ser Arg Lys Ser Gln Glu Pro Ala Phe His
5 10 15

Ile Ala Gly Asp
20

<210> SEQ ID NO 593
<211> LENGTH: 20
<212> TYPE: PRT
<213> ORGANISM: Homo sapiens

<400> SEQUENCE: 593

Lys Ser Gln Glu Pro Ala Phe His Ile Ala Gly Asp Ala Cys Leu Gln
5 10 15

Arg Lys Met Asn
20

<210> SEQ ID NO 594
<211> LENGTH: 20
<212> TYPE: PRT
<213> ORGANISM: Homo sapiens

<400> SEQUENCE: 594

Met Gly Thr Arg Ala Leu Gln Cys Glu Val Ser His Thr His Glu Asn
1 5 10 15

Glu Asn Tyr Leu
20

<210> SEQ ID NO 595
<211> LENGTH: 20
<212> TYPE: PRT
<213> ORGANISM: Homo sapiens

<400> SEQUENCE: 595

Ser His Thr His Glu Asn Glu Asn Tyr Leu Leu His Glu Asn Cys Met
1 5 10 15

Leu Lys Lys Glu
20

<210> SEQ ID NO 596
<211> LENGTH: 20
<212> TYPE: PRT
<213> ORGANISM: Homo sapiens

<400> SEQUENCE: 596

Leu His Glu Asn Cys Met Leu Lys Lys Glu Ile Ala Met Leu Lys Leu

-continued

```
 1               5                   10                  15

Glu Ile Ala Thr
            20


<210> SEQ ID NO 597
<211> LENGTH: 20
<212> TYPE: PRT
<213> ORGANISM: Homo sapiens

<400> SEQUENCE: 597

Ile Ala Met Leu Lys Leu Glu Ile Ala Thr Leu Lys His Gln Tyr Gln
 1               5                   10                  15

Glu Lys Glu Asn
            20


<210> SEQ ID NO 598
<211> LENGTH: 20
<212> TYPE: PRT
<213> ORGANISM: Homo sapiens

<400> SEQUENCE: 598

Leu Lys His Gln Tyr Gln Glu Lys Glu Asn Lys Tyr Phe Glu Asp Ile
 1               5                   10                  15

Lys Ile Leu Lys
            20


<210> SEQ ID NO 599
<211> LENGTH: 20
<212> TYPE: PRT
<213> ORGANISM: Homo sapiens

<400> SEQUENCE: 599

Lys Tyr Phe Glu Asp Ile Lys Ile Leu Lys Glu Lys Asn Ala Glu Leu
 1               5                   10                  15

Gln Met Thr Leu
            20


<210> SEQ ID NO 600
<211> LENGTH: 20
<212> TYPE: PRT
<213> ORGANISM: Homo sapiens

<400> SEQUENCE: 600

Glu Lys Asn Ala Glu Leu Gln Met Thr Leu Lys Leu Lys Glu Glu Ser
 1               5                   10                  15

Leu Thr Lys Arg
            20


<210> SEQ ID NO 601
<211> LENGTH: 20
<212> TYPE: PRT
<213> ORGANISM: Homo sapiens

<400> SEQUENCE: 601

Lys Leu Lys Glu Glu Ser Leu Thr Lys Arg Ala Ser Gln Tyr Ser Gly
 1               5                   10                  15

Gln Leu Lys Val
            20


<210> SEQ ID NO 602
<211> LENGTH: 20
<212> TYPE: PRT
```

-continued

<213> ORGANISM: Homo sapiens

<400> SEQUENCE: 602

Ala Ser Gln Tyr Ser Gly Gln Leu Lys Val Leu Ile Ala Glu Asn Thr
1 5 10 15

Met Leu Thr Ser
20

<210> SEQ ID NO 603
<211> LENGTH: 20
<212> TYPE: PRT
<213> ORGANISM: Homo sapiens

<400> SEQUENCE: 603

Leu Ile Ala Glu Asn Thr Met Leu Thr Ser Lys Leu Lys Glu Lys Gln
1 5 10 15

Asp Lys Glu Ile
20

<210> SEQ ID NO 604
<211> LENGTH: 20
<212> TYPE: PRT
<213> ORGANISM: Homo sapiens

<400> SEQUENCE: 604

Lys Leu Lys Glu Lys Gln Asp Lys Glu Ile Leu Glu Ala Glu Ile Glu
1 5 10 15

Ser His His Pro
20

<210> SEQ ID NO 605
<211> LENGTH: 20
<212> TYPE: PRT
<213> ORGANISM: Homo sapiens

<400> SEQUENCE: 605

Leu Glu Ala Glu Ile Glu Ser His His Pro Arg Leu Ala Ser Ala Val
1 5 10 15

Gln Asp His Asp
20

<210> SEQ ID NO 606
<211> LENGTH: 20
<212> TYPE: PRT
<213> ORGANISM: Homo sapiens

<400> SEQUENCE: 606

Arg Leu Ala Ser Ala Val Gln Asp His Asp Gln Ile Val Thr Ser Arg
1 5 10 15

Lys Ser Gln Glu
20

<210> SEQ ID NO 607
<211> LENGTH: 22
<212> TYPE: PRT
<213> ORGANISM: Homo sapiens

<400> SEQUENCE: 607

Asp Gln Ile Val Thr Ser Arg Lys Ser Gln Glu Pro Ala Phe His Ile
1 5 10 15

Ala Gly Asp Ala Cys Leu
20

-continued

<210> SEQ ID NO 608
<211> LENGTH: 20
<212> TYPE: PRT
<213> ORGANISM: Homo sapiens

<400> SEQUENCE: 608

Pro Ala Phe His Ile Ala Gly Asp Ala Cys Leu Gln Arg Lys Met Asn
1 5 10 15

Val Asp Val Ser
20

<210> SEQ ID NO 609
<211> LENGTH: 20
<212> TYPE: PRT
<213> ORGANISM: Homo sapiens

<400> SEQUENCE: 609

Leu Gln Arg Lys Met Asn Val Asp Val Ser Ser Thr Ile Tyr Asn Asn
1 5 10 15

Glu Val Leu His
20

<210> SEQ ID NO 610
<211> LENGTH: 20
<212> TYPE: PRT
<213> ORGANISM: Homo sapiens

<400> SEQUENCE: 610

Ser Thr Ile Tyr Asn Asn Glu Val Leu His Gln Pro Leu Ser Glu Ala
1 5 10 15

Gln Arg Lys Ser
20

<210> SEQ ID NO 611
<211> LENGTH: 21
<212> TYPE: PRT
<213> ORGANISM: Homo sapiens

<400> SEQUENCE: 611

His Gln Pro Leu Ser Glu Ala Gln Arg Lys Ser Lys Ser Leu Lys Ile
1 5 10 15

Asn Leu Asn Tyr Ala
20

<210> SEQ ID NO 612
<211> LENGTH: 20
<212> TYPE: PRT
<213> ORGANISM: Homo sapiens

<400> SEQUENCE: 612

Lys Ser Leu Lys Ile Asn Leu Asn Tyr Ala Gly Asp Ala Leu Arg Glu
1 5 10 15

Asn Thr Leu Val
20

<210> SEQ ID NO 613
<211> LENGTH: 20
<212> TYPE: PRT
<213> ORGANISM: Homo sapiens

<400> SEQUENCE: 613

-continued

```
Gly Asp Ala Leu Arg Glu Asn Thr Leu Val Ser Glu His Ala Gln Arg
 1               5                  10                  15

Asp Gln Arg Glu
            20


<210> SEQ ID NO 614
<211> LENGTH: 20
<212> TYPE: PRT
<213> ORGANISM: Homo sapiens

<400> SEQUENCE: 614

Ser Glu His Ala Gln Arg Asp Gln Arg Glu Thr Gln Cys Gln Met Lys
 1               5                  10                  15

Glu Ala Glu His
            20


<210> SEQ ID NO 615
<211> LENGTH: 20
<212> TYPE: PRT
<213> ORGANISM: Homo sapiens

<400> SEQUENCE: 615

Thr Gln Cys Gln Met Lys Glu Ala Glu His Met Tyr Gln Asn Glu Gln
 1               5                  10                  15

Asp Asn Val Asn
            20


<210> SEQ ID NO 616
<211> LENGTH: 20
<212> TYPE: PRT
<213> ORGANISM: Homo sapiens

<400> SEQUENCE: 616

Met Tyr Gln Asn Glu Gln Asp Asn Val Asn Lys His Thr Glu Gln Gln
 1               5                  10                  15

Glu Ser Leu Asp
            20


<210> SEQ ID NO 617
<211> LENGTH: 20
<212> TYPE: PRT
<213> ORGANISM: Homo sapiens

<400> SEQUENCE: 617

Lys His Thr Glu Gln Gln Glu Ser Leu Asp Gln Lys Leu Phe Gln Leu
 1               5                  10                  15

Gln Ser Lys Asn
            20


<210> SEQ ID NO 618
<211> LENGTH: 21
<212> TYPE: PRT
<213> ORGANISM: Homo sapiens

<400> SEQUENCE: 618

Asp Gln Lys Leu Phe Gln Leu Gln Ser Lys Asn Met Trp Leu Gln Gln
 1               5                  10                  15

Gln Leu Val His Ala
            20


<210> SEQ ID NO 619
<211> LENGTH: 20
```

-continued

```
<212> TYPE: PRT
<213> ORGANISM: Homo sapiens

<400> SEQUENCE: 619

Met Trp Leu Gln Gln Gln Leu Val His Ala His Lys Lys Ala Asp Asn
 1               5                   10                  15

Lys Ser Lys Ile
            20


<210> SEQ ID NO 620
<211> LENGTH: 20
<212> TYPE: PRT
<213> ORGANISM: Homo sapiens

<400> SEQUENCE: 620

His Lys Lys Ala Asp Asn Lys Ser Lys Ile Thr Ile Asp Ile His Phe
 1               5                   10                  15

Leu Glu Arg Lys
            20


<210> SEQ ID NO 621
<211> LENGTH: 20
<212> TYPE: PRT
<213> ORGANISM: Homo sapiens

<400> SEQUENCE: 621

Thr Ile Asp Ile His Phe Leu Glu Arg Lys Met Gln His His Leu Leu
 1               5                   10                  15

Lys Glu Lys Asn
            20


<210> SEQ ID NO 622
<211> LENGTH: 20
<212> TYPE: PRT
<213> ORGANISM: Homo sapiens

<400> SEQUENCE: 622

Met Gln His His Leu Leu Lys Glu Lys Asn Glu Glu Ile Phe Asn Tyr
 1               5                   10                  15

Asn Asn His Leu
            20


<210> SEQ ID NO 623
<211> LENGTH: 20
<212> TYPE: PRT
<213> ORGANISM: Homo sapiens

<400> SEQUENCE: 623

Glu Glu Ile Phe Asn Tyr Asn Asn His Leu Lys Asn Arg Ile Tyr Gln
 1               5                   10                  15

Tyr Glu Lys Glu
            20


<210> SEQ ID NO 624
<211> LENGTH: 20
<212> TYPE: PRT
<213> ORGANISM: Homo sapiens

<400> SEQUENCE: 624

Asn His Leu Lys Asn Arg Ile Tyr Gln Tyr Glu Lys Glu Lys Ala Glu
 1               5                   10                  15

Thr Glu Val Ile
```

-continued

```
            20


<210> SEQ ID NO 625
<211> LENGTH: 27
<212> TYPE: PRT
<213> ORGANISM: Homo sapiens

<400> SEQUENCE: 625

Leu Thr Leu Asn Gln Glu Glu Glu Lys Arg Arg Asn Ala Asp Ile Leu
 1               5                  10                  15

Asn Glu Lys Ile Arg Glu Glu Leu Gly Cys Gly
            20                  25


<210> SEQ ID NO 626
<211> LENGTH: 29
<212> TYPE: PRT
<213> ORGANISM: Homo sapiens

<400> SEQUENCE: 626

Ile Arg Glu Glu Leu Gly Arg Ile Glu Glu Gln His Arg Lys Glu Leu
 1               5                  10                  15

Glu Val Lys Gln Gln Leu Glu Gln Ala Leu Gly Cys Gly
            20                  25


<210> SEQ ID NO 627
<211> LENGTH: 24
<212> TYPE: PRT
<213> ORGANISM: Homo sapiens

<400> SEQUENCE: 627

Leu Glu Gln Ala Leu Arg Ile Gln Asp Ile Glu Leu Lys Ser Val Glu
 1               5                  10                  15

Ser Asn Leu Asn Gln Gly Cys Gly
            20
```